United States Patent
Hwang et al.

(10) Patent No.: US 10,135,009 B2
(45) Date of Patent: *Nov. 20, 2018

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Kyuyoung Hwang, Ansan-si (KR); Yoonhyun Kwak, Seoul (KR); Ohyun Kwon, Yongin-si (KR); Soyeon Kim, Anyang-si (KR); Jiwhan Kim, Seoul (KR); Sangyeob Lee, Hwaseong-si (KR); Jungin Lee, Seoul (KR); Daeyoung Chung, Seoul (KR); Jongwon Choi, Yongin-si (KR); Hyeonho Choi, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 36 days.

This patent is subject to a terminal disclaimer.

(21) Appl. No.: 15/273,267

(22) Filed: Sep. 22, 2016

(65) Prior Publication Data
US 2017/0012226 A1   Jan. 12, 2017

Related U.S. Application Data

(63) Continuation of application No. 14/568,425, filed on Dec. 12, 2014, now Pat. No. 9,490,437.

(30) Foreign Application Priority Data

Sep. 26, 2014 (KR) .................. 10-2014-0129516

(51) Int. Cl.
| | |
|---|---|
| H01L 51/54 | (2006.01) |
| C09K 11/06 | (2006.01) |
| H01L 51/00 | (2006.01) |
| C07F 15/00 | (2006.01) |
| H01L 51/50 | (2006.01) |
| H01L 51/56 | (2006.01) |
| C09K 11/02 | (2006.01) |
| H01L 51/52 | (2006.01) |

(52) U.S. Cl.
CPC ...... *H01L 51/0094* (2013.01); *C07F 15/0033* (2013.01); *C09K 11/025* (2013.01); *C09K 11/06* (2013.01); *H01L 51/0072* (2013.01); *H01L 51/0085* (2013.01); *H01L 51/50* (2013.01); *H01L 51/5012* (2013.01); *H01L 51/56* (2013.01); *C09K 2211/1007* (2013.01); *C09K 2211/1029* (2013.01); *C09K 2211/185* (2013.01); *H01L 51/5016* (2013.01);
(Continued)

(58) Field of Classification Search
None
See application file for complete search history.

(56) References Cited

U.S. PATENT DOCUMENTS 9,490,437 B2 * 11/2016 Hwang et al. ...... H01L 51/0085
2013/0026452 A1    1/2013 Kottas et al.
(Continued)

FOREIGN PATENT DOCUMENTS

| EP | 1642951 A2 | 4/2006 |
|---|---|---|
| JP | 5546238 B2 | 7/2014 |

(Continued)

OTHER PUBLICATIONS

European Extended Search Report for European Patent Application No. 15186612.6 dated Jan. 26, 2016.

*Primary Examiner* — Marie R. Yamnitzky
(74) *Attorney, Agent, or Firm* — Cantor Colburn LLP

(57) ABSTRACT

An organometallic compound represented by Formula 1:

$$M(L_1)_{n1}(L_2)_{n2},\qquad\text{Formula 1}$$

wherein M is selected from iridium (Ir), platinum (Pt), osmium (Os), titanium (Ti), zirconium (Zr), hafnium (Hf), europium (Eu), terbium (Tb), thulium (Tm), and rhodium (Rd), and wherein $L_1$ is a ligand represented by Formula 2A and $L_2$ is a ligand represented by Formula 2B, and wherein $L_1$ and $L_2$ in Formula 1 are different from each other,

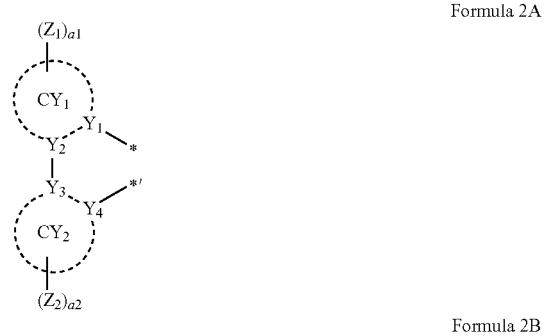

Formula 2A

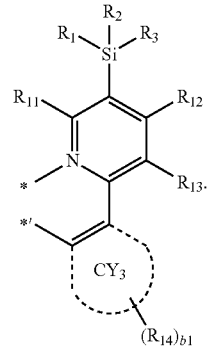

Formula 2B

20 Claims, 1 Drawing Sheet

(52) U.S. Cl.
CPC ...... *H01L 51/5056* (2013.01); *H01L 51/5072* (2013.01); *H01L 51/5088* (2013.01); *H01L 51/5096* (2013.01); *H01L 51/5218* (2013.01)

(56) References Cited

U.S. PATENT DOCUMENTS

2014/0008617 A1   1/2014   Beers et al.
2015/0021585 A1   1/2015   Yu et al.

FOREIGN PATENT DOCUMENTS

| KR | 1020130110934 A | 10/2013 |
| KR | 101344787 B1 | 12/2013 |
| WO | 2013142634 A1 | 9/2013 |
| WO | 2014007564 A1 | 1/2014 |
| WO | 2014007565 A1 | 1/2014 |

\* cited by examiner

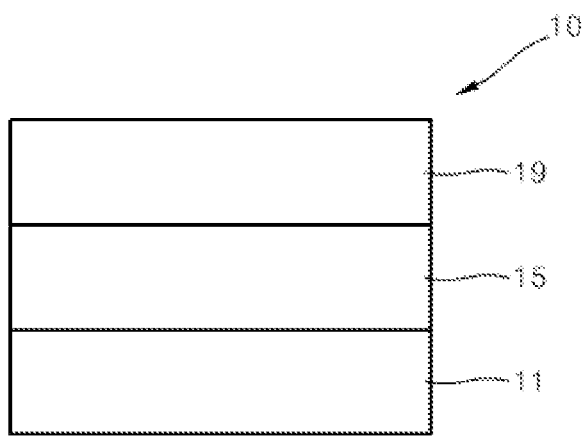

ORGANOMETALLIC COMPOUND AND ORGANIC LIGHT-EMITTING DEVICE INCLUDING THE SAME

CROSS REFERENCE TO RELATED APPLICATION

This application is a continuation of U.S. patent application Ser. No. 14/568,425, filed on Dec. 12, 2014, and claims priority to and the benefit of Korean Patent Application No. 10-2014-0129516, filed on Sep. 26, 2014, in the Korean Intellectual Property Office, and all the benefits accruing therefrom under 35 U.S.C. § 119, the contents of which are incorporated herein in their entirety by reference.

BACKGROUND

1. Field

The present disclosure relates to an organometallic compound and an organic light-emitting device including the same.

2. Description of the Related Art

Organic light-emitting devices are self-emission devices that have wide viewing angles, high contrast ratios, short response times, and excellent brightness, driving voltage, and response speed characteristics, and produce full-color images.

In an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons are recombined in the emission layer to produce excitons. These excitons change from an excited state to a ground state, thereby generating light.

Nonetheless there remains a need for an improved material for the emission layer.

SUMMARY

An embodiment relates to an organometallic compound and an organic light-emitting device including the same.

Additional aspects will be set forth in part in the description which follows and, in part, will be apparent from the description.

An aspect of an exemplary embodiment provides an organometallic compound represented by Formula 1:

$$M(L_1)_{n1}(L_2)_{n2},$$ Formula 1 wherein M in Formula 1 is selected from iridium (Ir), platinum (Pt), osmium (Os), titanium (Ti), zirconium (Zr), hafnium (Hf), europium (Eu), terbium (Tb), thulium (Tm), and rhodium (Rh), wherein $L_1$ is a ligand represented by Formula 2A and $L_2$ is a ligand represented by Formula 2B, and wherein $L_1$ and $L_2$ in Formula 1 are different from each other,

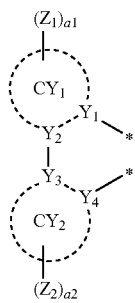
Formula 2A

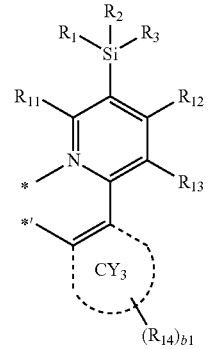
Formula 2B wherein in Formula 2A, $Y_1$ to $Y_4$ are each independently carbon (C) or nitrogen (N), $Y_1$ and $Y_2$ are linked to each other via a single bond or a double bond, and $Y_3$ and $Y_4$ are linked to each other via a single bond or a double bond, wherein in Formulas 2A and 2B, $CY_1$ to $CY_3$ are each independently selected from a $C_5$-$C_{60}$ cyclic group and a $C_1$-$C_{60}$ heterocyclic group, and $CY_1$ and $CY_2$ are optionally further linked to each other via a first linking group, $R_1$ to $R_3$ in Formula 2B are each independently selected from a $C_1$-$C_{10}$ alkyl group; and a $C_1$-$C_{10}$ alkyl group, which is substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group, $Z_1$, $Z_2$, and $R_{11}$ to $R_{14}$ in Formulas 2A and 2B are each independently selected from a hydrogen, a deuterium, —F, —Cl, —Br, —I, —SF$_5$, a hydroxyl group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —P(=O)($Q_8$)($Q_9$), wherein $R_{12}$ in Formula 2B is not a hydrogen or a —$CH_3$, a1 and a2 are each independently selected from 1, 2, 3, 4, and 5, and when a1 is 2 or more, each $Z_1$ of a plurality of $Z_1$ may be identical or different from each other, and when a2 is 2 or more, each $Z_2$ of a plurality of $Z_2$ may be identical or different from each other, and b1 in Formula 2B is selected from 1, 2, 3, and 4, and wherein in Formula 1, n1 and n2 are each independently 1 or 2, with the proviso that the sum of n1 and n2 is 2 or 3;

wherein * and *' in Formulas 2A and 2B are each a binding site to M in Formula 1; and wherein at least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arythio group, the substituted $C_1$-$C_{60}$ heteroaryl group, the substituted a monovalent non-aromatic condensed polycyclic group, and the substituted monovalent non-aromatic condensed heteropolycyclic group is selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$)-B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$)-B($Q_{36}$)($Q_{37}$), and —P(=O)($Q_{38}$)($Q_{39}$);

wherein $Q_1$ to $Q_9$, $Q_{11}$ to $Q_{19}$, $Q_{21}$ to $Q_{29}$, and $Q_{31}$ to $Q_{39}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

Another aspect provides an organic light-emitting device including: a first electrode; a second electrode; and an organic layer that is disposed between the first electrode and the second electrode and which includes an emission layer, wherein the emission layer includes the organometallic compound represented by Formula 1.

The organometallic compound may be included in the emission layer, and the organometallic compound included in the emission layer may act as a dopant, and the emission layer may further include a host.

Also disclosed is a method of manufacturing an organic light-emitting device, the method including: providing a first electrode; a second electrode; and an organic layer that is disposed between the first electrode and the second electrode and which comprises an emission layer, wherein the emission layer comprises the organometallic compound of claim 1.

BRIEF DESCRIPTION OF THE DRAWINGS

These and/or other aspects will become apparent and more readily appreciated from the following description of the exemplary embodiments, taken in conjunction with the FIGURE which is a schematic view of an embodiment of an organic light-emitting device.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the FIGURES, to explain aspects. As used herein, the term "and/or" includes any and all combinations of one or more of the associated listed items. "Or" means "and/or." Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to other elements as illustrated in the FIGURES. It will be understood that relative terms are intended to encompass different orientations of the device in addition to the orientation depicted in the FIGURES. For example, if the device in one of the FIGURES is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the FIGURES is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Alkenyl" means a straight or branched chain, monovalent hydrocarbon group having at least one carbon-carbon double bond (e.g., ethenyl (—HC═CH$_2$)).

"Alkoxy" means an alkyl group that is linked via an oxygen (i.e., alkyl-O—), for example methoxy, ethoxy, and sec-butyloxy groups.

"Alkyl" as used herein means a straight or branched chain, saturated, monovalent hydrocarbon group (e.g., methyl or hexyl).

"Alkynyl" means a straight or branched chain, monovalent hydrocarbon group having at least one carbon-carbon triple bond (e.g., ethynyl).

"Amino" has the general formula —N(R)$_2$, wherein each R is independently hydrogen, a C1 to C6 alkyl, or a C6 to C12 aryl.

"Amidino" means a group of the formula —C(NR$^1$R$^2$)═NR$^3$, wherein each of R$^1$, R$^2$, and R$^3$ is independently hydrogen, a C1 to C8 alkyl, or a C6 to C12 aryl.

"Aryloxy" means an aryl moiety that is linked via an oxygen (i.e., —O-aryl). An aryloxy group includes a C6 to C30 aryloxy group, and specifically a C6 to C18 aryloxy group. Non-limiting examples include phenoxy, naphthyloxy, and tetrahydronaphthyloxy.

"Arylthio" means an aryl moiety that is linked via a sulfur (i.e., —S-aryl). Examples of arylthio groups include phenylthio, naphthylthio.

"Cycloalkenyl" means a monovalent group having one or more rings and one or more carbon-carbon double bond in the ring, wherein all ring members are carbon (e.g., cyclopentyl and cyclohexyl).

"Cycloalkyl" means a monovalent group having one or more saturated rings in which all ring members are carbon (e.g., cyclopentyl and cyclohexyl).

The prefix "hetero" means that the compound or group includes at least one a heteroatom (e.g., 1, 2, or 3 heteroatom(s)), wherein the heteroatom(s) is each independently N, O, S, Si, or P.

An organometallic compound according to an embodiment is represented by Formula 1:

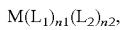

Formula 1 wherein $L_1$ is a ligand represented by Formula 2A, and $L_2$ is a ligand represented by Formula 2B:

Formula 2A

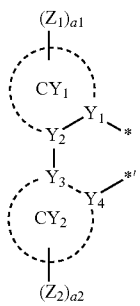

Formula 2B

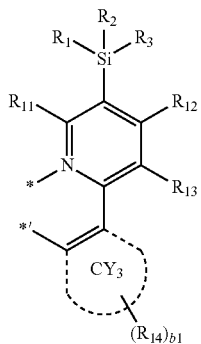

wherein $L_1$ and $L_2$ in Formula 1 are different from each other, and * and *' in Formulas 2A and 2B are binding sites to M in Formula 1.

M in Formula 1 may be selected from iridium (Ir), platinum (Pt), osmium (Os), titanium (Ti), zirconium (Zr), hafnium (Hf), europium (Eu), terbium (Tb), thulium (Tm), and rhodium (Rh).

For example, M in Formula 1 may be Ir or Pt.

In Formula 2A, $Y_1$ to $Y_4$ are each independently carbon (C) or nitrogen (N), $Y_1$ and $Y_2$ are linked to each other via a single bond or a double bond, and $Y_3$ and $Y_4$ are linked to each other via a single bond or a double bond.

In some embodiments, in Formula 2A, $Y_1$ may be N and $Y_2$ to $Y_4$ may be C, but they are not limited thereto.

In Formulas 2A and 2B, $CY_1$ to $CY_3$ may be each independently selected from a $C_5$-$C_{60}$ cyclic group and a $C_1$-$C_{60}$ heterocyclic group, and $CY_1$ and $CY_2$ may be optionally further linked to each other via a first linking group. The $C_5$-$C_{60}$ cyclic group and the $C_1$-$C_{60}$ heterocyclic group may each be "a monocyclic group" or "polycyclic group."

According to an embodiment, $CY_1$ to $CY_3$ in Formulas 2A and 2B may be each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxalaine, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, a dibenzothiophene, and 5, 6, 7, 8-tetrahydroisoquinoline.

In some embodiments, in Formulas 2A and 2B, $CY_1$ may be selected from a pyridine, a pyrimidine, a pyrazine, a triazine, a triazole, an imidazole, a pyrazole, and 5, 6, 7, 8-tetrahydroisoquinoline, $CY_2$ may be selected from a benzene, a pyridine, a pyrimidine, a pyrazine, a triazine, a carbazole, a dibenzofuran, and a dibenzothiophene, and $CY_3$ may be selected from a benzene, a carbazole, a dibenzofuran, and a dibenzothiophene.

$CY_1$ and $CY_2$ in Formula 2A may be optionally further linked to each other via a first linking group, and the first linking group may be selected from linking groups represented by Formula 6:

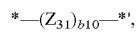

Formula 6 wherein $Z_{31}$ in Formula 6 may be selected from *—O—*', *—S—*', *—N($Q_{41}$)-*', *—C($Q_{42}$)($Q_{43}$)-*', *—C($Q_{44}$)=C($Q_{45}$)-*', and

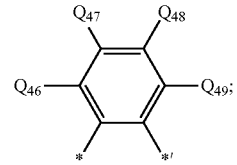

wherein $Q_{41}$ to $Q_{49}$ may be each independently selected from
   a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;
   a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group; and a phenyl group, a naphthyl group, a pyridinyl group, and a pyrimidinyl group; and
   wherein b10 is selected from an integer of 1 to 10, and when b10 is 2 or more, a plurality of $Z_{31}$ may be identical or different.

For example, $Q_{41}$ to $Q_{49}$ in Formula 6 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;
   a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group; and a phenyl group, a naphthyl group, a pyridinyl group, and a pyrimidinyl group, but they are not limited thereto.

For example, $CY_1$ and $CY_2$ in Formula 2 are optionally further linked to each other via a first linking group, and the first linking group is represented by *—$C(Q_{44})$=$C(Q_{45})$-*' or

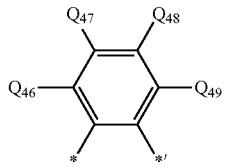

(that is, b10 in Formula 6 is 1), and $Q_{44}$ to $Q_{49}$ may be each independently selected from a hydrogen, a $C_1$-$C_{10}$ alkyl group, and a $C_1$-$C_{10}$ alkoxy group, but they are not limited thereto.

$R_1$ to $R_3$ in Formula 2B are each independently selected from a $C_1$-$C_{10}$ alkyl group; and a $C_1$-$C_{10}$ alkyl group, substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group.

In some embodiments, $R_1$ to $R_3$ in Formula 2B may be each independently selected from a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each of which is unsubstituted; and a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group.

In some embodiments, $R_1$ to $R_3$ in Formula 2B may be each independently selected from a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, and a tert-pentyl group, each of which is unsubstituted; and a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, and a tert-pentyl group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group.

In some embodiments, $R_1$ to $R_3$ in Formula 2B may be each independently selected from a $C_1$-$C_4$ alkyl group, and a $C_1$-$C_4$ alkyl group substituted with at least one deuterium.

In some embodiments, $R_1$ to $R_3$ in Formula 2B may be each independently selected from —$CH_3$, —$CH_2CH_3$, —$CD_3$, —$CD_2H$, —$CDH_2$, —$CH_2CD_3$, and —$CD_2CH_3$, but they are not limited thereto.

In some embodiments, $R_1$ to $R_3$ in Formula 2B may be identical.

$Z_1$, $Z_2$, and $R_{11}$ to $R_{14}$ in Formulas 2A and 2B may be each independently selected from a hydrogen, a deuterium, —F, —Cl, —Br, —I, —$SF_5$, a hydroxyl group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$P(=O)(Q_8)(Q_9)$, and wherein $R_{12}$ in Formula 2B is not a hydrogen or a —$CH_3$.

In some embodiments, $Z_1$, $Z_2$, $R_{11}$, $R_{13}$, and $R_{14}$ in Formulas 2A and 2B are each independently selected from a hydrogen, a deuterium, —F, —Cl, —Br, —I, —$SF_5$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group; and —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ may be each independently selected from a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryl group substituted with at least one selected from a $C_1$-$C_{20}$ alkyl group and a $C_6$-$C_{14}$ aryl group, a $C_1$-$C_{14}$ heteroaryl group, a monovalent non-aromatic condensed polycyclic group, and a monovalent non-aromatic condensed heteropolycyclic group.

In some embodiments, $Z_1$, $Z_2$, $R_{11}$, $R_{13}$, and $R_{14}$ in Formulas 2A and 2B may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, —$CD_3$, —$CD_2H$, —$CDH_2$, —$CF_3$, —$CF_1H$, —$CFH_1$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —$B(Q_6)(Q_7)$ and —$P(=O)(Q_5)(Q_9)$, wherein $Q_6$ to $Q_9$ may be each independently selected from a $C_1$-$C_{20}$ alkyl group, a $C_1$-$C_{20}$ alkoxy group, a phenyl group, a naphthyl group, a pyridinyl group, a pyrimidinyl group, a triazinyl group, and a carbazolyl group; and a phenyl group and a naphthyl group, each substituted with at least one selected from a $C_1$-$C_{20}$ alkyl group, a phenyl group, and a naphthyl group, but they are not limited thereto.

In some embodiments, $Z_1$, $Z_2$, $R_{11}$, $R_{13}$, and $R_{14}$ in Formulas 2A and 2B may be each independently selected from a hydrogen, a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each of which is unsubstituted;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and —B($Q_6$)($Q_7$) and —P(=O)($Q_8$)($Q_9$), wherein $Q_6$ to $Q_9$ may be each independently selected from a $C_1$-$C_{10}$ alkyl group, a $C_1$-$C_{10}$ alkoxy group, a phenyl group, and a naphthyl group;

a phenyl group and a naphthyl group, each substituted with at least one selected from a $C_1$-$C_{10}$ alkyl group, a phenyl group, and a naphthyl group, but they are not limited thereto.

In some embodiments, $R_{12}$ in Formula 2B may be selected from a $C_2$-$C_{20}$ alkyl group and a $C_2$-$C_{20}$ alkoxy group;

a methyl group and a methoxy group, each substituted with at least one selected from a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_2$-$C_{20}$ alkyl group and a $C_2$-$C_{20}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{10}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group, and a monovalent non-aromatic condensed heteropolycyclic group; and —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ may be each independently selected from a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryl group substituted with at least one selected from a $C_1$-$C_{20}$ alkyl group and a $C_6$-$C_{14}$ aryl group, a $C_1$-$C_{14}$ heteroaryl group, a monovalent non-aromatic condensed polycyclic group, and a monovalent non-aromatic condensed heteropolycyclic group.

In some embodiments, $R_{12}$ in Formula 2B may be selected from a $C_2$-$C_{20}$ alkyl group and a $C_2$-$C_{20}$ alkoxy group;

a methyl group and a methoxy group, each substituted with at least one selected from a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;

a $C_2$-$C_{20}$ alkyl group and a $C_2$-$C_{20}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;

a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —B(Q$_6$)(Q$_7$) and —P(=O)(Q$_8$)(Q$_9$), wherein Q$_6$ to Q$_9$ may be each independently selected from a $C_1$-$C_{20}$ alkyl group, a $C_1$-$C_{20}$ alkoxy group, a phenyl group, a naphthyl group, a pyridinyl group, a pyrimidinyl group, a triazinyl group, and a carbazolyl group; and a phenyl group and a naphthyl group, each substituted with at least one selected from a $C_1$-$C_{20}$ alkyl group, a phenyl group, and a naphthyl group, but they are not limited thereto.

In some embodiments, R$_{12}$ in Formula 2B may be selected from an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;

a methyl group and a methoxy group, each substituted with at least one selected from a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group.

In some embodiments, $Z_1$, $Z_2$, $R_{11}$, $R_{13}$, and $R_{14}$ in Formulas 2A and 2B may be each independently selected from a hydrogen, a deuterium, —F, a cyano group, a nitro group, —$SF_5$, —$CH_3$, —$CD_3$, —$CD_2H$, —$CDH_2$, —$CF_3$, —$CF_2H$, —$CFH_2$, groups represented by Formulas 9-1 to 9-17, and groups represented by Formulas 10-1 to 10-16 illustrated, and $R_{12}$ in Formula 2B may be selected from groups represented by Formulas 9-1 to 9-17 and groups represented by Formulas 10-1 to 10-16, but they are not limited thereto:

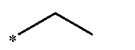

Formula 9-1

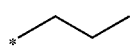

Formula 9-2

Formula 9-3

Formula 9-4

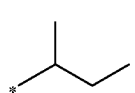

Formula 9-5

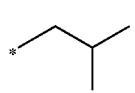

Formula 9-6

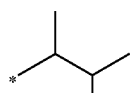

Formula 9-7

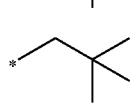

Formula 9-8

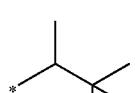

Formula 9-9

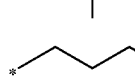

Formula 9-10

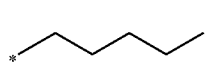

Formula 9-11

-continued

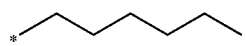

Formula 9-12

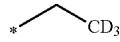

Formula 9-13

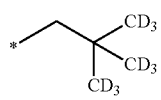

Formula 9-14

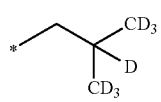

Formula 9-15

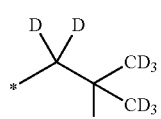

Formula 9-16

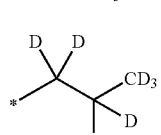

Formula 9-17

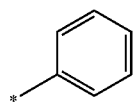

Formula 10-1

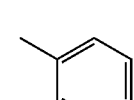

Formula 10-2

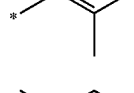

Formula 10-3

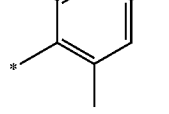

Formula 10-4

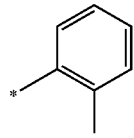

Formula 10-5

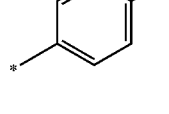

Formula 10-6

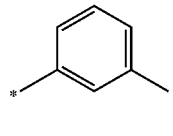

Formula 10-7

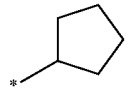

-continued

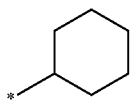
Formula 10-8

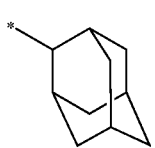
Formula 10-9

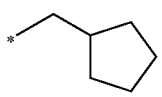
Formula 10-10

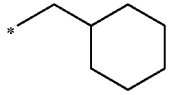
Formula 10-11

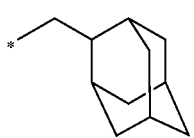
Formula 10-12

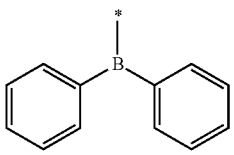
Formula 10-13

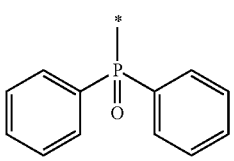
Formula 10-14

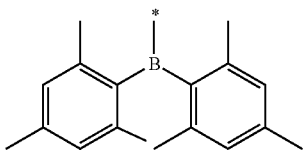
Formula 10-15

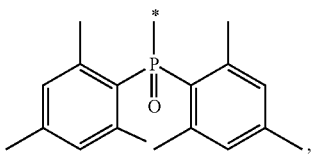
Formula 10-16 wherein a1 and a2 in Formula 2A may be each independently selected from 1, 2, 3, 4, and 5, and when a1 is 2 or more, a plurality of $Z_1$ may be identical or different, and when a2 is 2 or a plurality of $Z_2$ may be identical or different. For example, a1 and a2 may each be 1, 2, or 3, but they are not limited thereto.

In Formula 2B, b1 may be selected from 1, 2, 3, and 4, and when b1 is 2 or more, a plurality of $R_{14}$ may be identical or different. For example, 131 may be 1 or 2, but is not limited thereto.

The descriptions for $R_{15}$ to $R_{17}$ may be the same as defined in connection with $R_{14}$.

In Formula 1, n1 and n2 are each independently 1 or 2, and the sum of n1 and n2 is 2 or 3.

For example, M may be Ir and the sum of n1 and n2 may be 3; or M may be Pt and the sum of n1 and n2 may be 2.

In some embodiments, n2 in Formula 1 may be 1.

The organometallic compound represented by Formula 1 may be neutral, i.e., not a salt consisting of an ionic pair.

For example, $L_1$ in Formula 1 may be selected from ligands represented by Formula 2-1 to ligands represented by Formula 2-112:

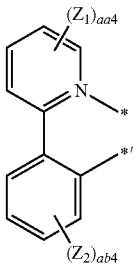
Formula 2-1

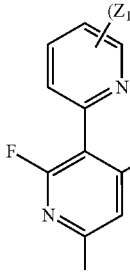
Formula 2-2

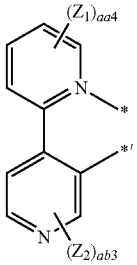
Formula 2-3

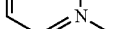
Formula 2-4

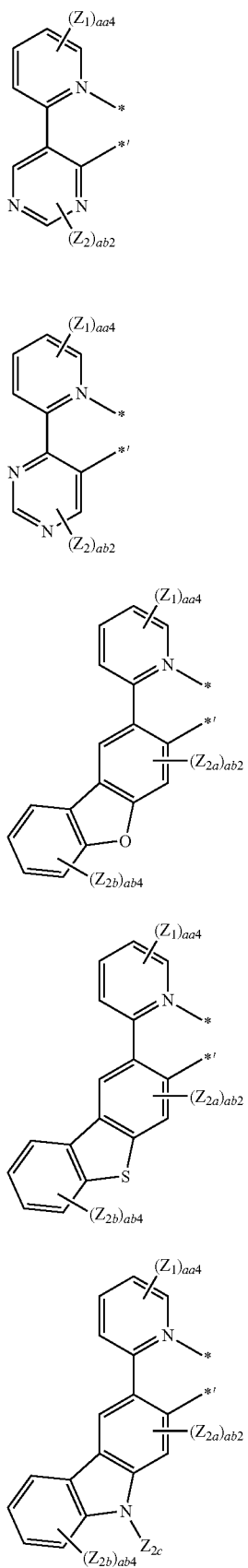
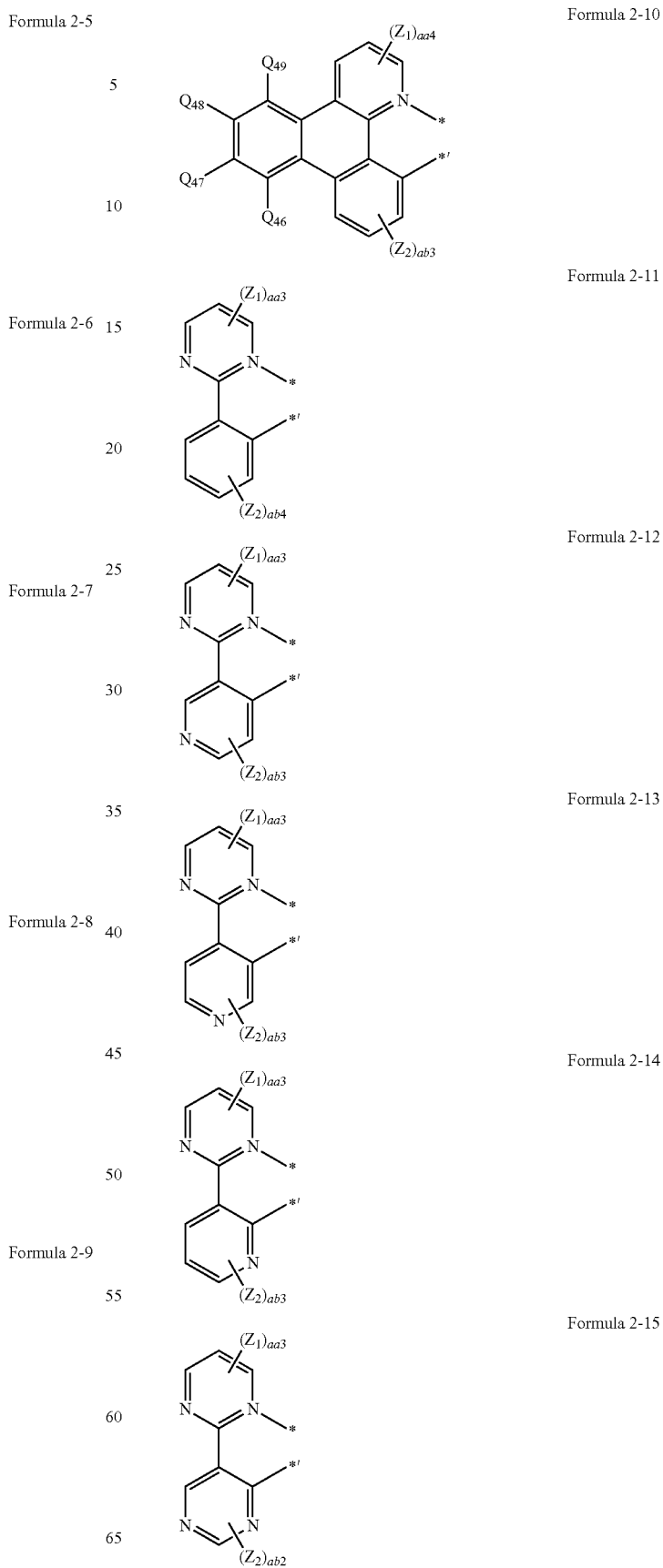

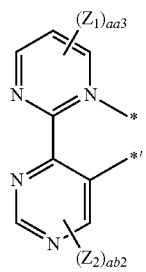
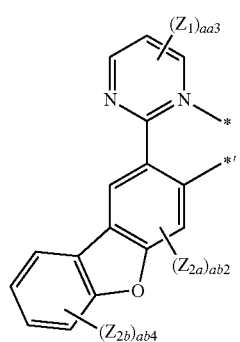
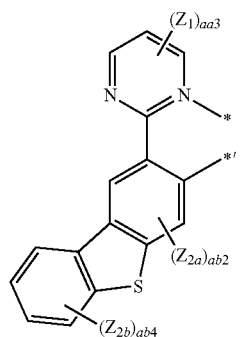
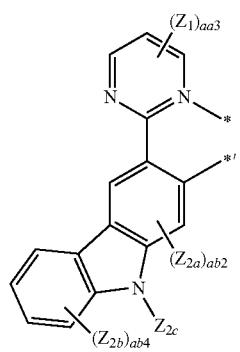
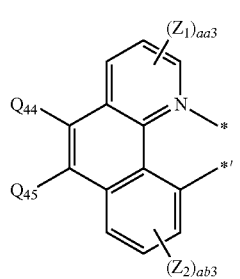
Formula 2-16
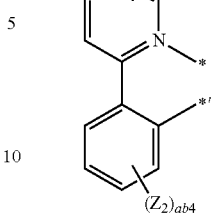
Formula 2-17
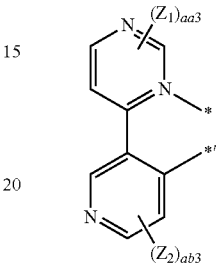
Formula 2-18
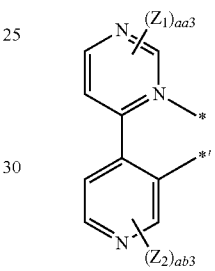
Formula 2-19
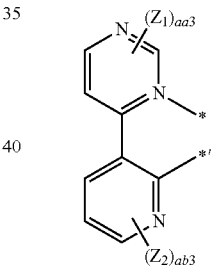
Formula 2-20
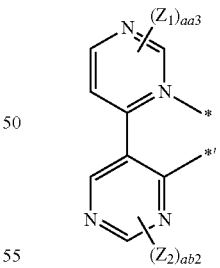
Formula 2-21
Formula 2-22
Formula 2-23
Formula 2-24
Formula 2-25
Formula 2-26
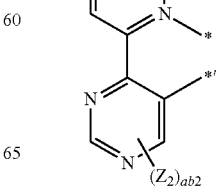

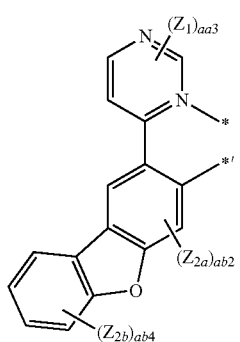
Formula 2-27
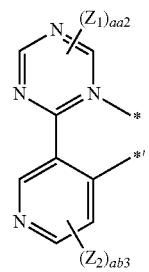
Formula 2-32
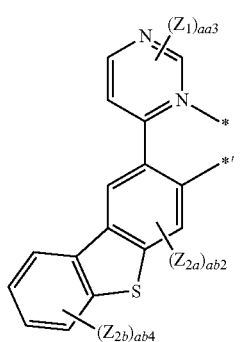
Formula 2-28
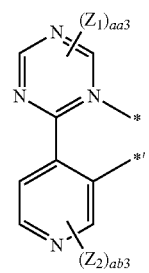
Formula 2-33
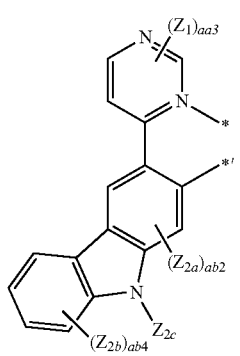
Formula 2-29
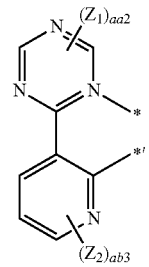
Formula 2-34
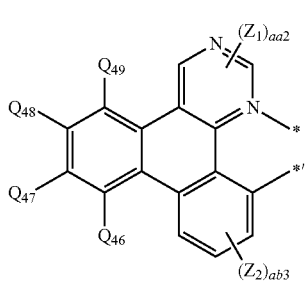
Formula 2-30
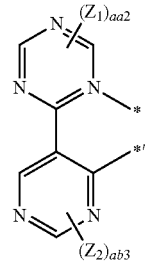
Formula 2-35
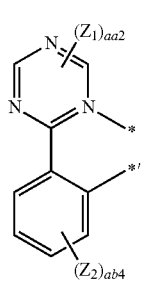
Formula 2-31
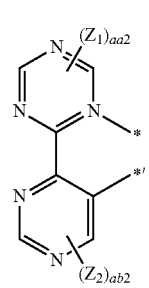
Formula 2-36

-continued
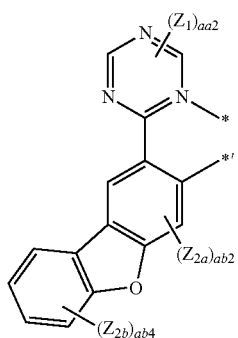
Formula 2-37
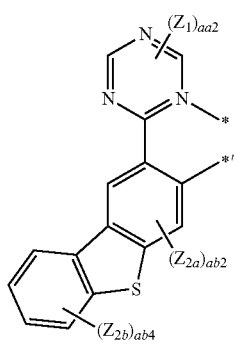
Formula 2-38
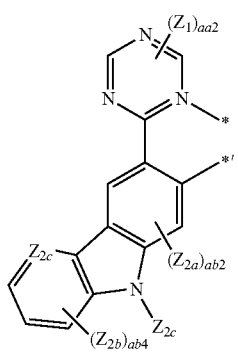
Formula 2-39
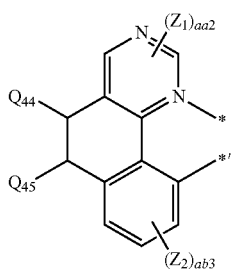
Formula 2-40
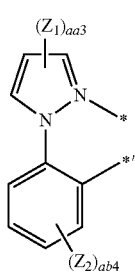
Formula 2-41
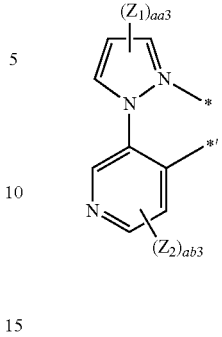
Formula 2-42
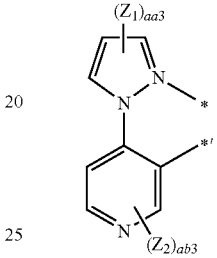
Formula 2-43
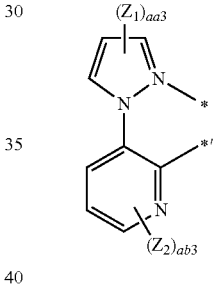
Formula 2-44
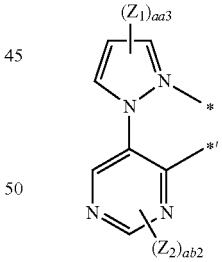
Formula 2-45
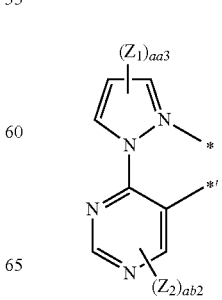
Formula 2-46

-continued
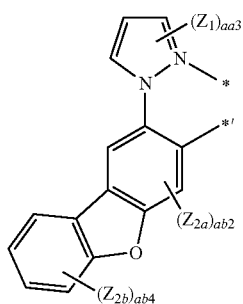
Formula 2-47
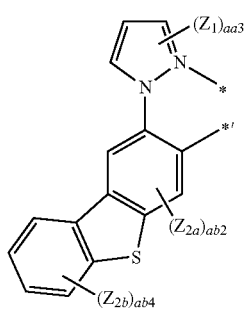
Formula 2-48
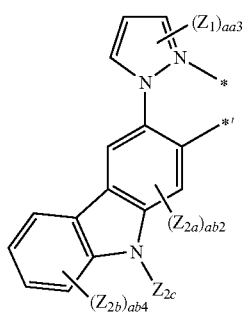
Formula 2-49
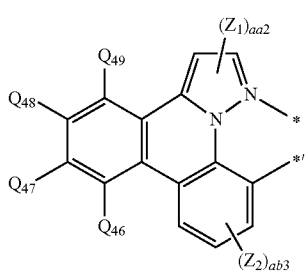
Formula 2-50
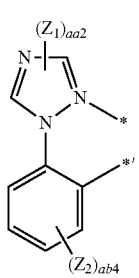
Formula 2-51
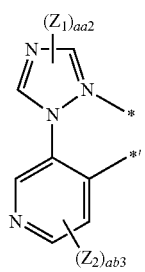
Formula 2-52
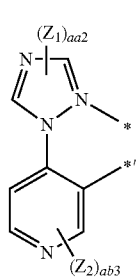
Formula 2-53
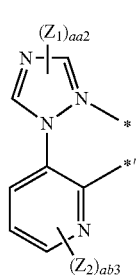
Formula 2-54
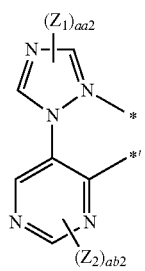
Formula 2-55
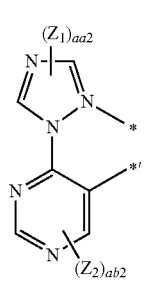
Formula 2-56

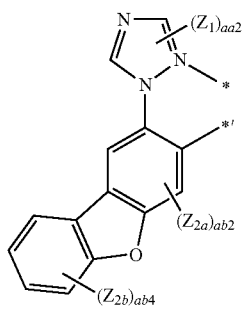
Formula 2-57
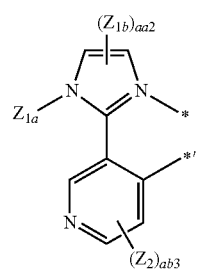
Formula 2-62
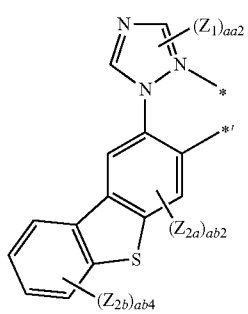
Formula 2-58
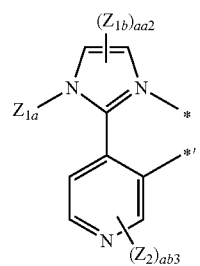
Formula 2-63
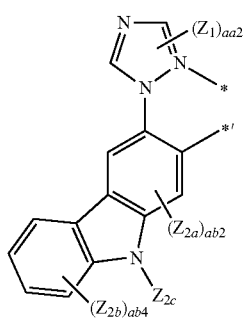
Formula 2-59
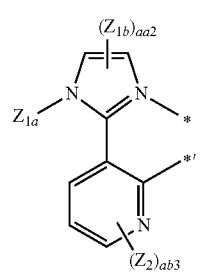
Formula 2-64
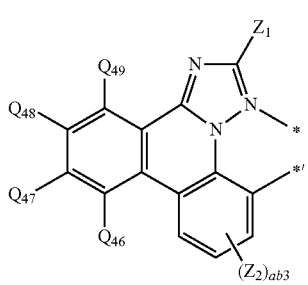
Formula 2-60
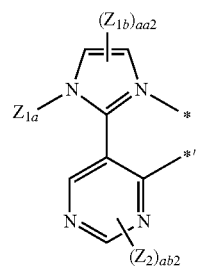
Formula 2-65
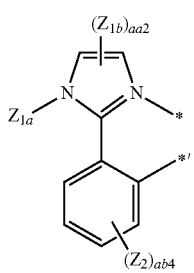
Formula 2-61
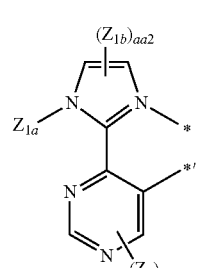
Formula 2-66

Formula 2-67
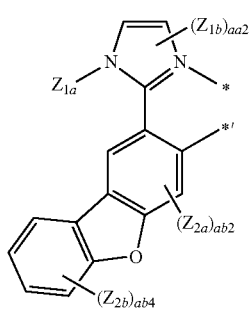
Formula 2-68
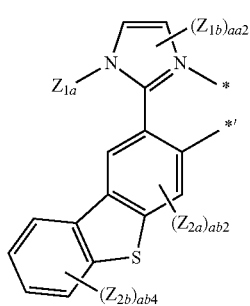
Formula 2-69
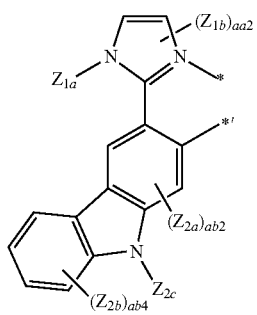
Formula 2-70
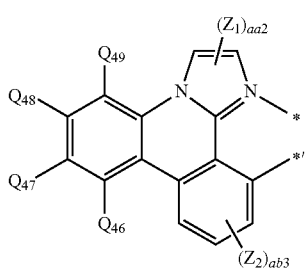
Formula 2-71
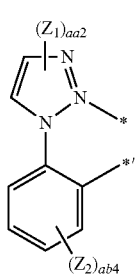
Formula 2-72
Formula 2-73
Formula 2-74
Formula 2-75
Formula 2-76

| | |
|---|---|
| 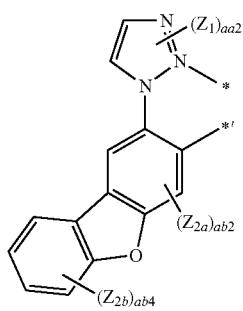 Formula 2-76 (cont.) | 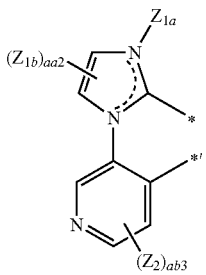 Formula 2-82 |
| 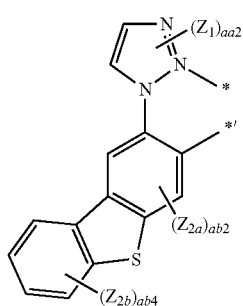 Formula 2-77 | 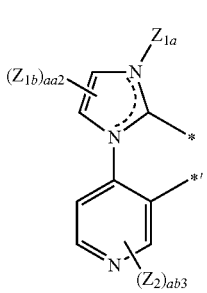 Formula 2-83 |
| 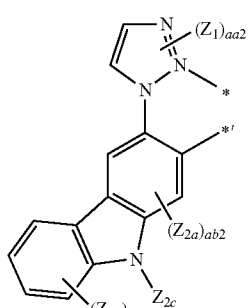 Formula 2-78 | 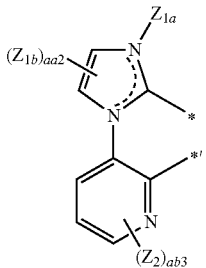 Formula 2-84 |
| 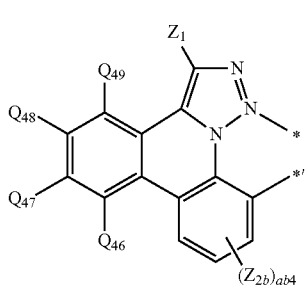 Formula 2-79 | 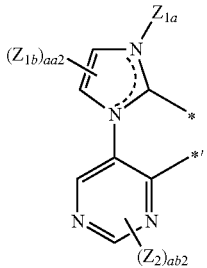 Formula 2-85 |
| 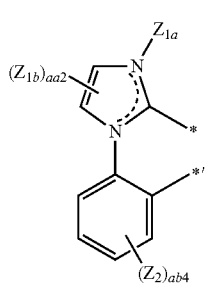 Formula 2-80 | Formula 2-86 |

Formula 2-87 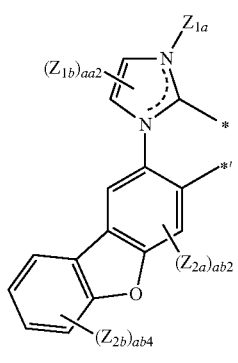
Formula 2-88 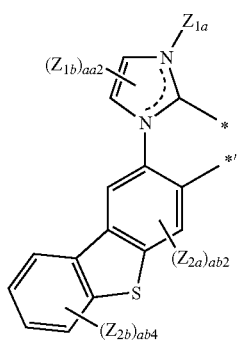
Formula 2-89 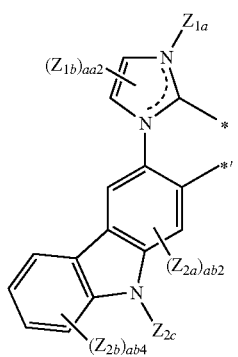
Formula 2-90 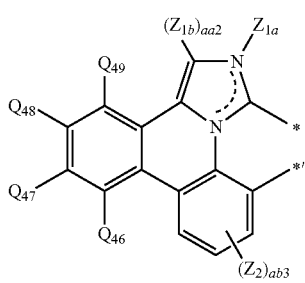
Formula 2-91 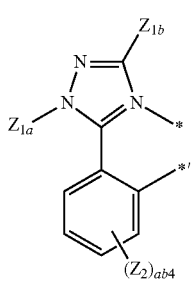
Formula 2-92 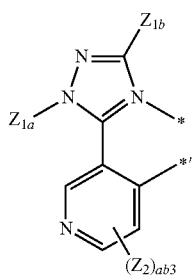
Formula 2-93 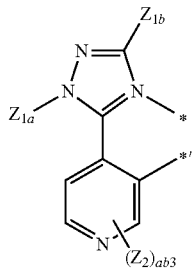
Formula 2-94 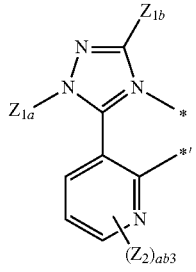
Formula 2-95 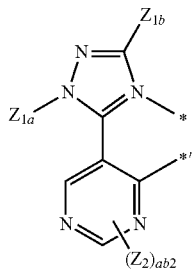
Formula 2-96 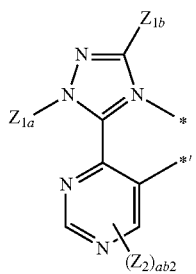

-continued
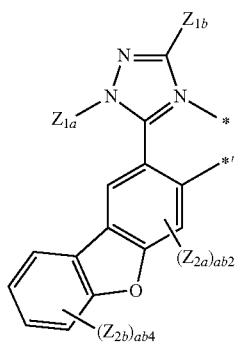
Formula 2-97
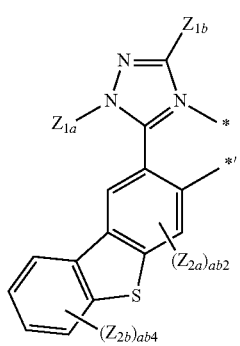
Formula 2-98
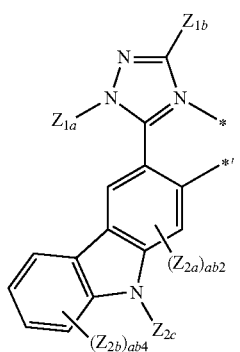
Formula 2-99
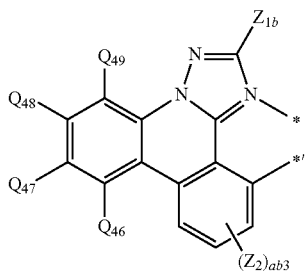
Formula 2-100
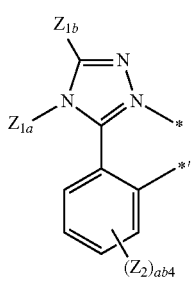
Formula 2-101
-continued
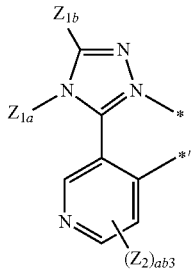
Formula 2-102
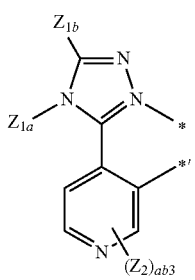
Formula 2-103
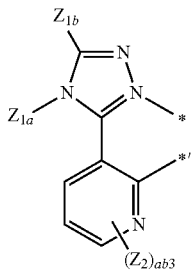
Formula 2-104
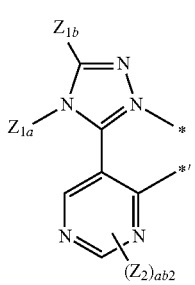
Formula 2-105
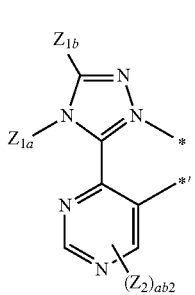
Formula 2-106

Formula 2-107
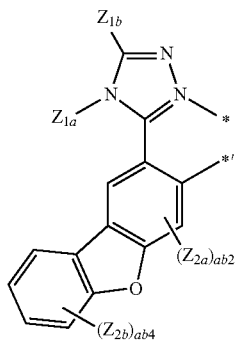

Formula 2-108
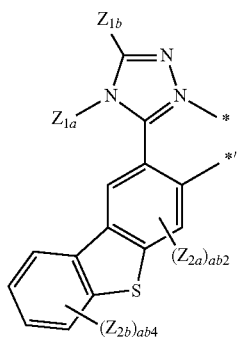

Formula 2-109
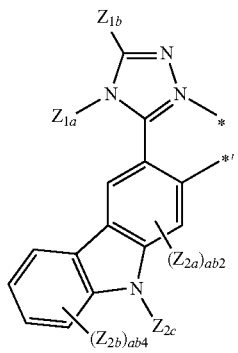

Formula 2-110
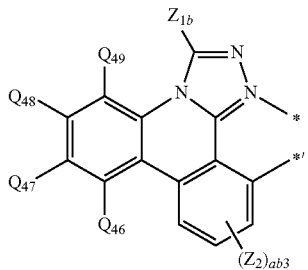

Formula 2-111
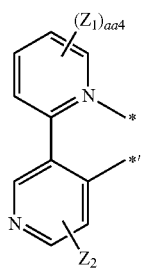

Formula 2-112
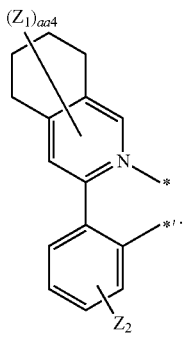

The descriptions for $Z_1$ and $Z_2$ in Formulas 2-1 to 2-112 are the same as defined above.

The descriptions for $Z_{1a}$ and $Z_{1b}$ are the same as explained in connection with $Z_1$, The descriptions for $Z_{2a}$, $Z_{2b}$, and $Z_{2c}$ are the same as explained in connection with $Z_2$, aa2 and ab2 are each independently 1 or 2, aa3 and ab3 are each independently selected from 1, 2, and 3, aa4 and ab4 may be each independently selected from, 1, 2, 3, and 4, and * and *' indicate binding sites to a neighboring atom.

For example, $Z_1$, $Z_2$, $Z_{1a}$, $Z_{1b}$, $Z_{2a}$, $Z_{2b}$, and $Z_{2c}$ in Formulas 2-1 to 2-112 may be each independently selected from a hydrogen, a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, and a pentoxy group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, and a pentoxy group, each substituted with at least one selected from a deuterium, —F, —CD$_3$, —CD$_2$H, —CDH$_2$, —CF$_3$, —CF$_2$H, —CFH$_2$, a cyano group, a nitro group, and a C$_1$-C$_{10}$ alkyl group; and a group represented by one of Formulas 10-1 to 10-16, but they are not limited thereto.

For example, L$_1$ in Formula 1 may be a ligand represented by one of Formulas 2-1 and 2-112, but is not limited thereto.

According an embodiment, L$_1$ in Formula 1 may be selected from ligands represented by Formulas 2-1(1) to 2-1(18), but is not limited thereto:

Formula 2-1(1)
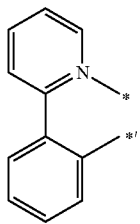
Formula 2-1(2)
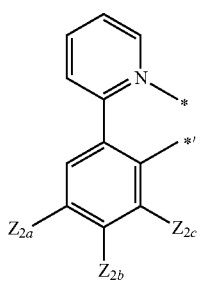
Formula 2-1(3)
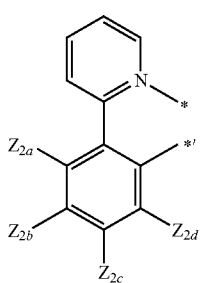
Formula 2-1(4)
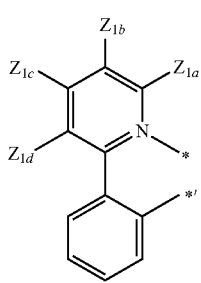
Formula 2-1(5)
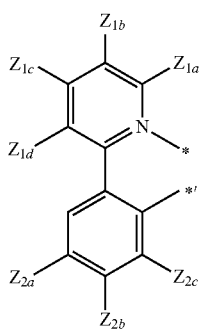
Formula 2-1(6)
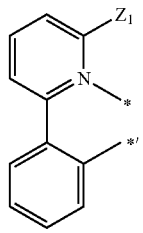
Formula 2-1(7)
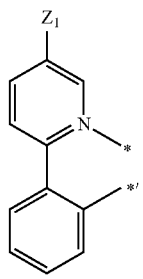
Formula 2-1(8)
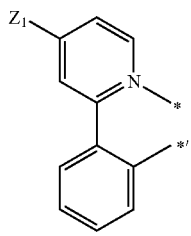
Formula 2-1(9)
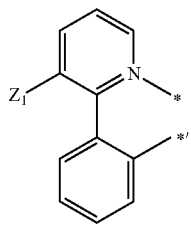
Formula 2-1(10)
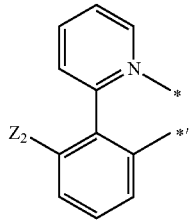
Formula 2-1(11)
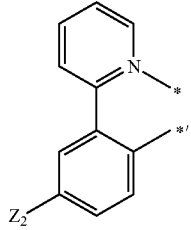

Formula 2-1(12)
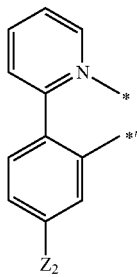

Formula 2-1(13)
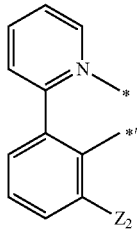

Formula 2-1(14)
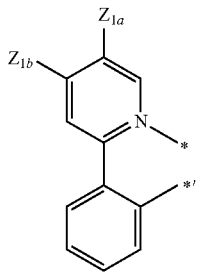

Formula 2-1(15)
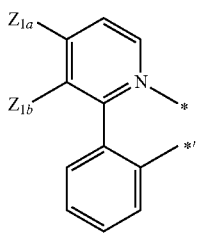

Formula 2-1(16)
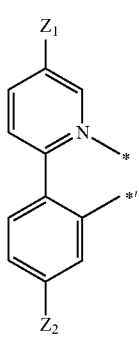

Formula 2-1(17)
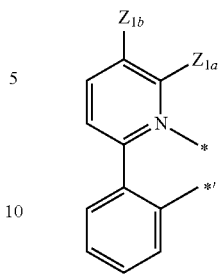

Formula 2-1(18)
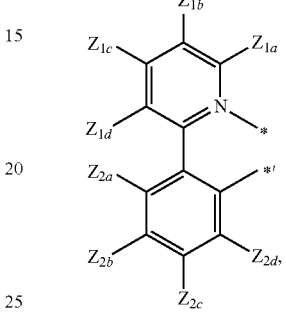

wherein in Formulas 2-1(1) to 2-1(18), the descriptions for $Z_1$ and $Z_2$ are the same as explained above, the descriptions for $Z_{1a}$, $Z_{1b}$, $Z_{1c}$, and $Z_{1d}$ are the same as explained in connection with $Z_1$, and The descriptions for $Z_{2a}$, $Z_{2b}$, $Z_{2c}$, and $Z_{2d}$ are the same as explained in connection with $Z_2$, wherein $Z_1$, $Z_2$, $Z_{1a}$, $Z_{1b}$, $Z_{1c}$, $Z_{1d}$, $Z_{2a}$, $Z_{2b}$, $Z_{2c}$, and $Z_{2d}$ are not hydrogens, and * and *′ indicate binding sites to M.

For example, $Z_1$, $Z_2$, $Z_{1a}$, $Z_{1b}$, $Z_{1c}$, $Z_{1d}$, $Z_{2a}$, $Z_{2b}$, $Z_{2c}$, and $Z_{2d}$ in Formulas 2-1(1) to 2-1(8) may be each independently selected from a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, and a pentoxy group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, and a pentoxy group, each substituted with at least one selected from a deuterium, —F, —CD$_3$, —CD$_2$H, —CDH$_2$, —CF$_3$, —CF$_2$H, —CFH$_2$, a cyano group, a nitro group, and a $C_1$-$C_{10}$ alkyl group; and a group represented by one of Formulas 10-1 to 10-16, but they are not limited thereto.
In some embodiments, $L_2$ in Formula 1 may be selected from ligands represented by Formulas 2B-1 to 2B-12:
Formula 2B-1
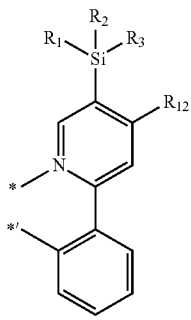
Formula 2B-2
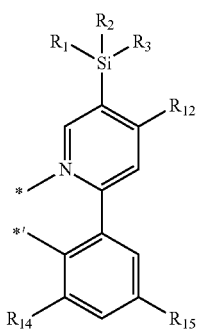
Formula 2B-3
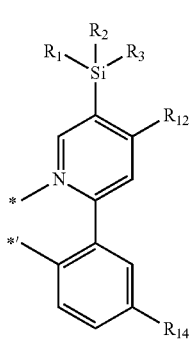
Formula 2B-4
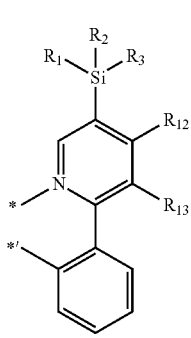
Formula 2B-5
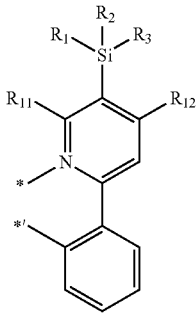
Formula 2B-6
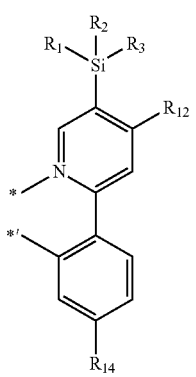
Formula 2B-7
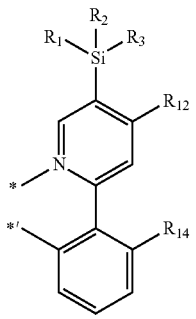
Formula 2B-8
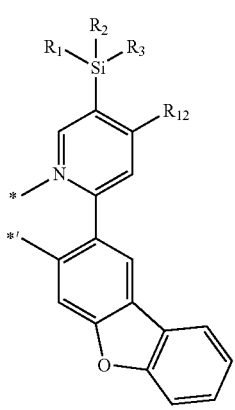

-continued

Formula 2B-9
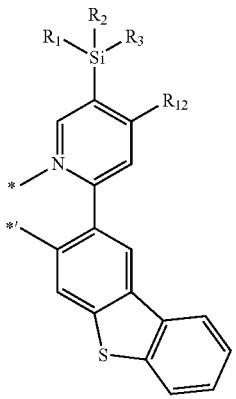

Formula 2B-10
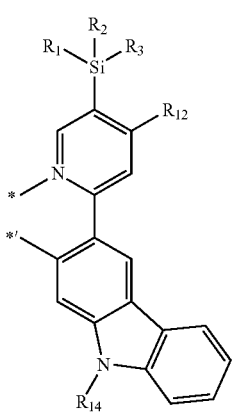

Formula 2B-11
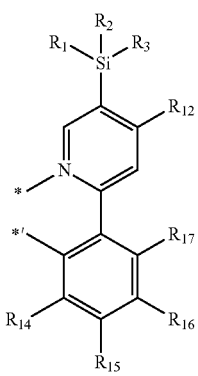

Formula 2B-12
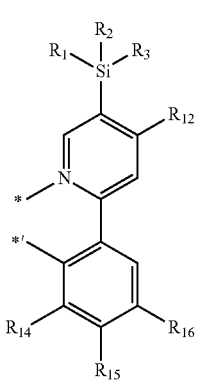

In Formulas 2B-1 to 2B-12, $R_1$, $R_2$, $R_3$, and $R_{11}$ to $R_{14}$ are already explained above, and the descriptions for $R_{15}$ to $R_{17}$ are the same as explained in connection with $R_{14}$. However, $R_{11}$ to $R_{17}$ in Formulas 2B-1 to 2B-12 are not hydrogens.

For example, in Formulas 2B-1 to 2B-12, $R_1$ to $R_3$ may be each independently selected from a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, and a tert-pentyl group; and a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, and a tert-pentyl group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group.

$R_{11}$ and $R_{13}$ to $R_{17}$ may be each independently selected from a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and —B(Q$_6$)(Q$_7$) and —P(=O)(Q$_8$)(Q$_9$), wherein $Q_6$ to $Q_6$ may be each independently selected from a $C_1$-$C_{10}$ alkyl group, a $C_1$-$C_{10}$ alkoxy group, a phenyl group, and a naphthyl group; and a phenyl group and a naphthyl group, each substituted with at least one selected from a $C_1$-$C_{10}$ alkyl group, a phenyl group, and a naphthyl group.

$R_{12}$ may be selected from an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;

a methyl group and a methoxy group, each substituted with at least one selected from a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, but they are not limited thereto.

In some embodiments, in Formulas 2B-1 to 2B-12, $R_1$ to $R_3$ may be each independently selected from —CH$_3$, —CH$_2$CH$_3$, —CD$_3$, —CD$_2$H, —CDH$_2$, —CH$_2$CD$_3$, and —CD$_2$CH$_3$, $R_{11}$, and $R_{13}$ to $R_{17}$ may be each independently selected from a deuterium, —F, a cyano group, a nitro group, —SF$_5$, —CH$_3$, —CD$_3$, —CD$_2$H, —CDH$_2$, —CF$_3$, —CF$_2$H, —CFH$_2$, groups represented by Formulas 9-1 to 9-17, and groups represented by Formulas 10-1 to 10-16, and $R_{12}$ may be selected from groups represented by Formulas 9-1 to 9-17 and groups represented by Formulas 10-1 to 10-16, but they are not limited thereto.

In some embodiments, in Formula 1,

M is Ir and the sum of n1 and n2 is 3; or M is Pt and the sum of n1 and n2 is 2, $L_1$ may be selected from ligands represented by Formulas 2-1 to 2-112 (for example, ligands represented by Formulas 2-1(1) to 2-1(18), $L_2$ may be selected from ligands represented by Formulas 2B-1 to 2B-12, and the organometallic compound represented by Formula 1 may be neutral, but is not limited thereto.

The organometallic compound may be one of Compounds 1 to 388, but is not limited thereto:

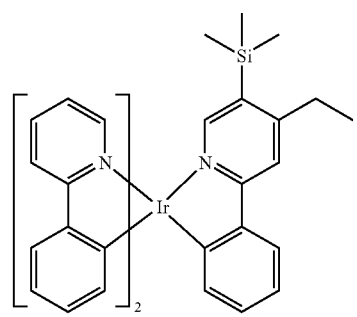

1

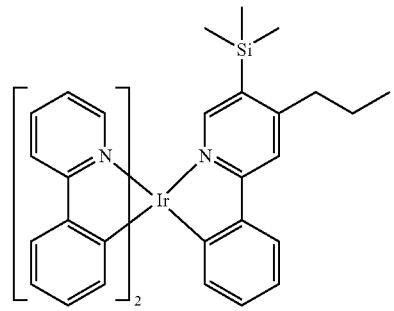

2

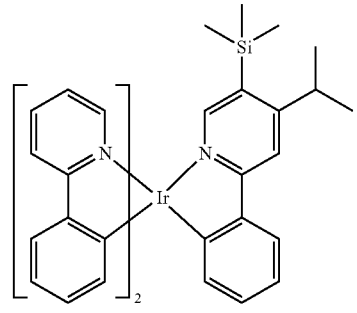

3

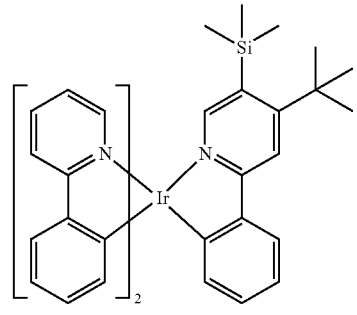

4

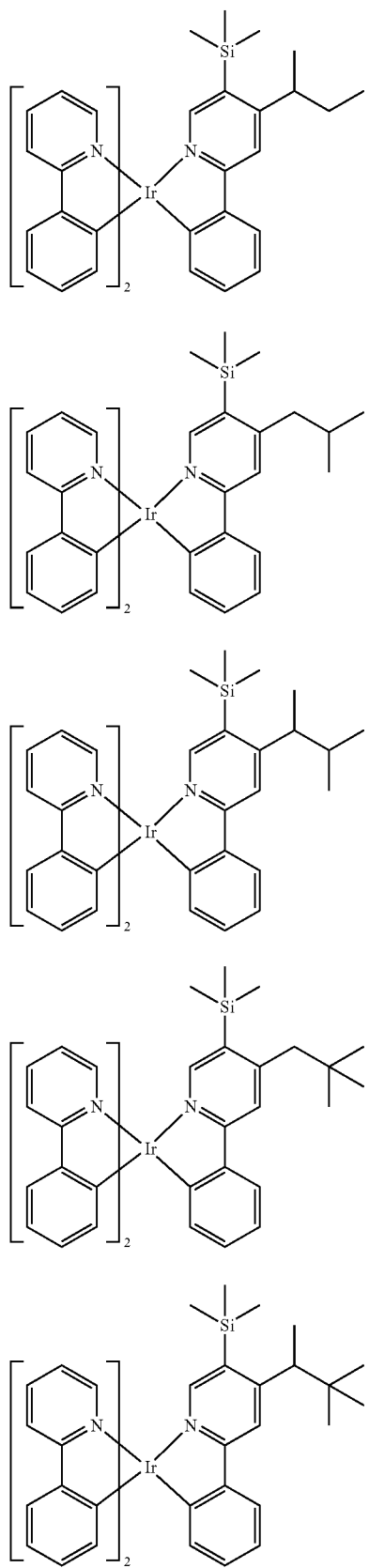
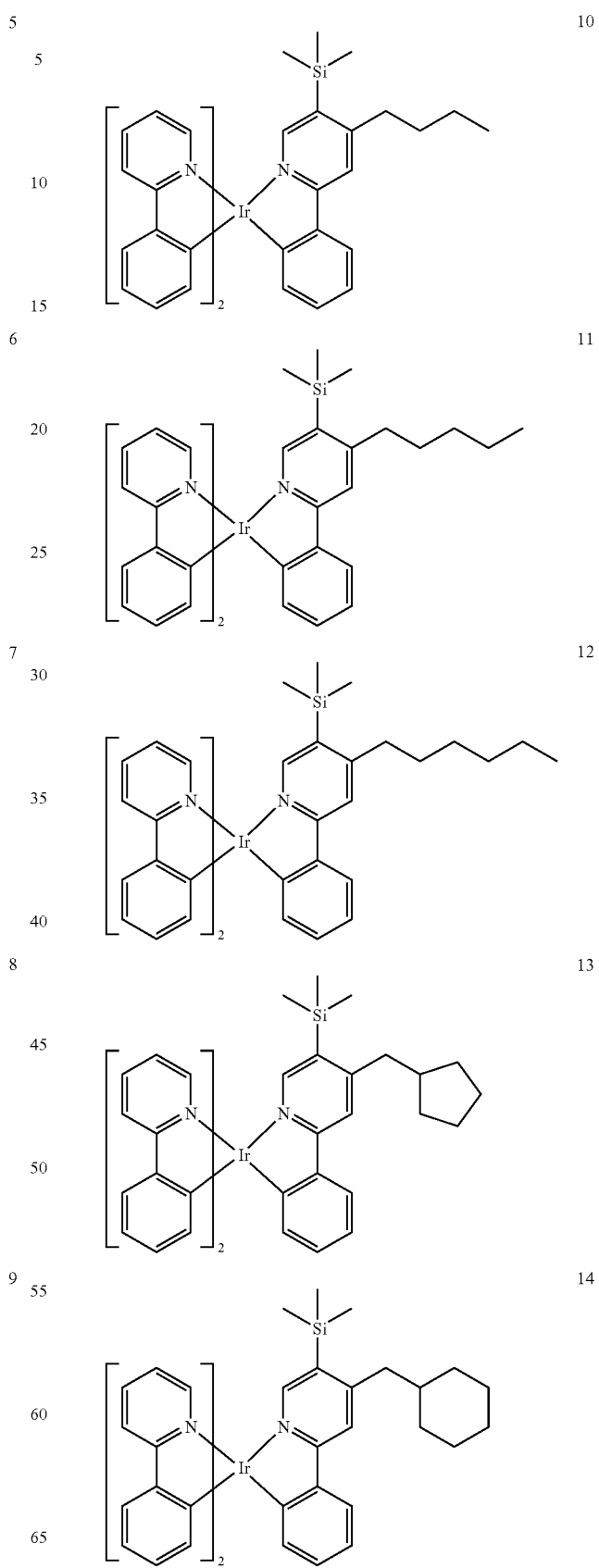

15
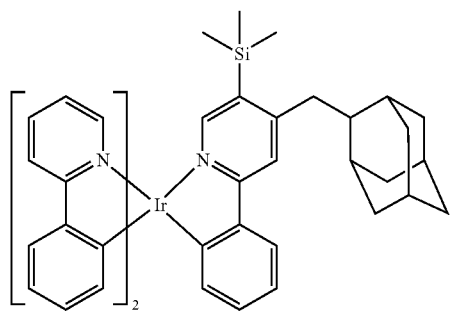
16
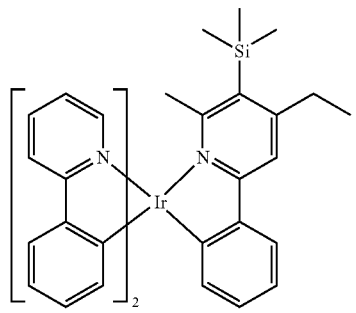
17
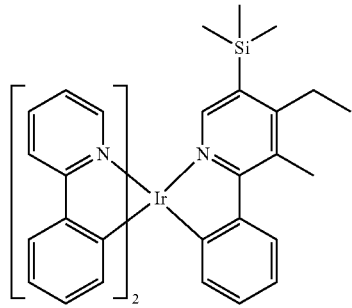
18
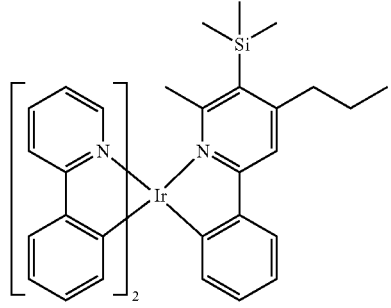
19
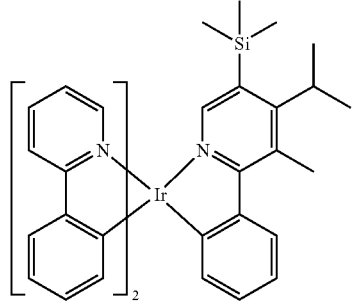
20
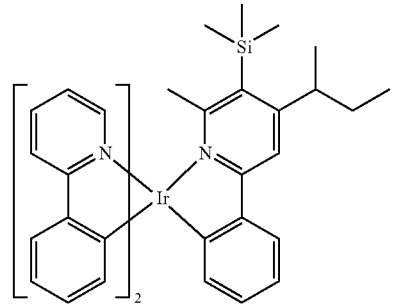
21
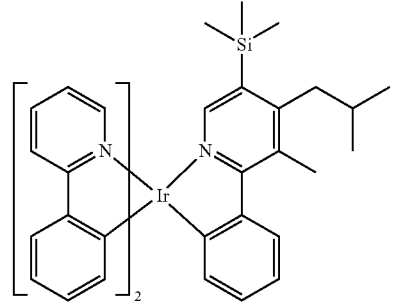
22
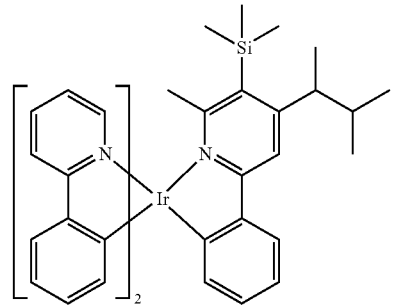
23
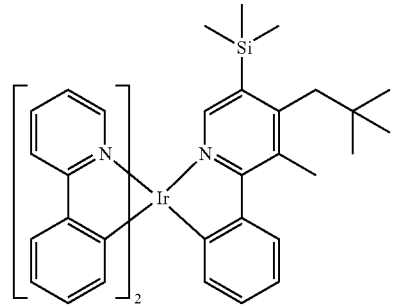
24
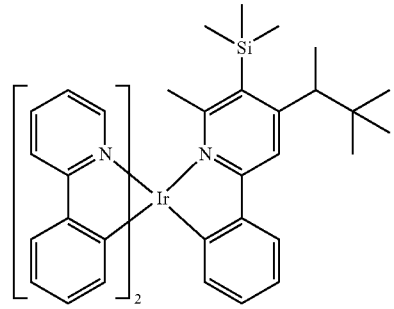

25
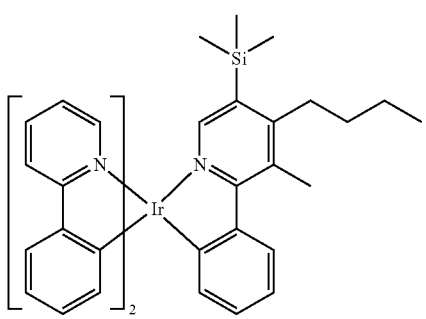
26
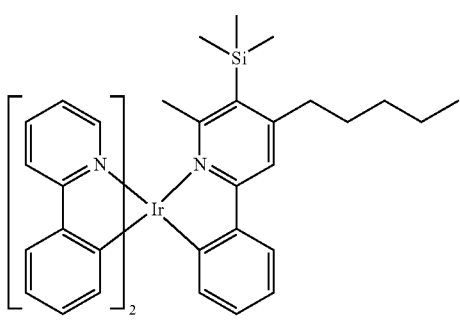
27
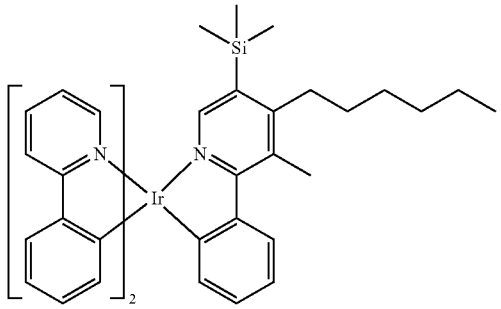
28
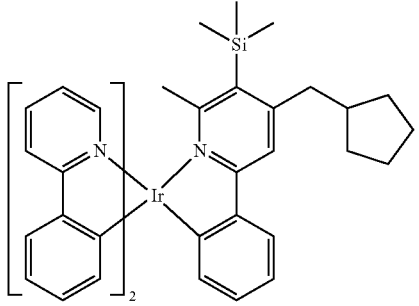
29
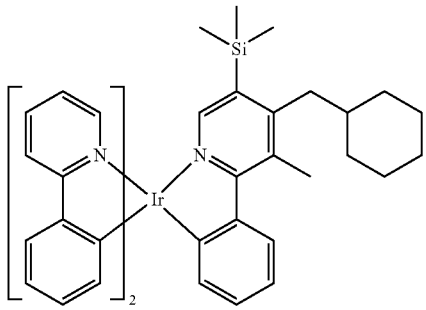
30
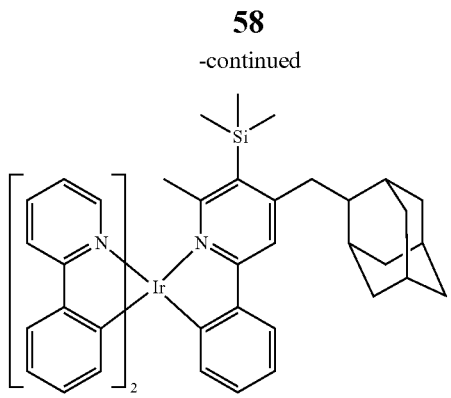
31
32
33

34
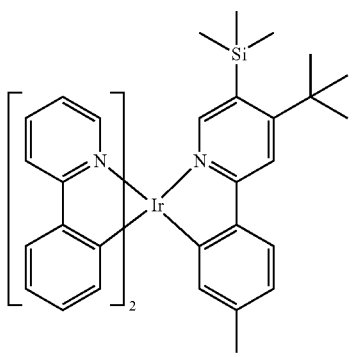
35
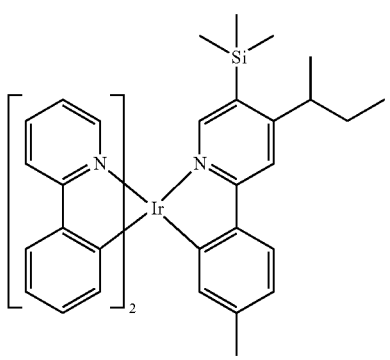
36
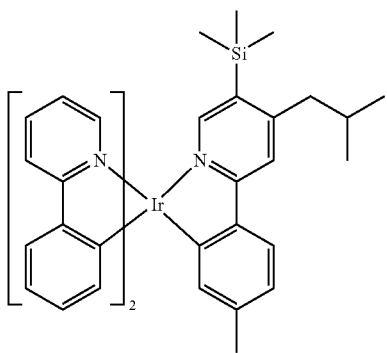
37
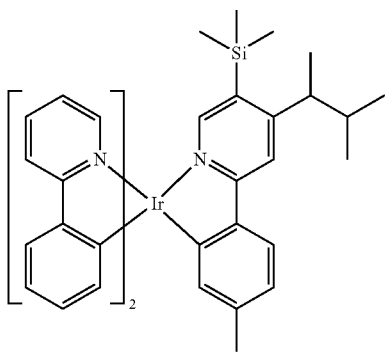
38
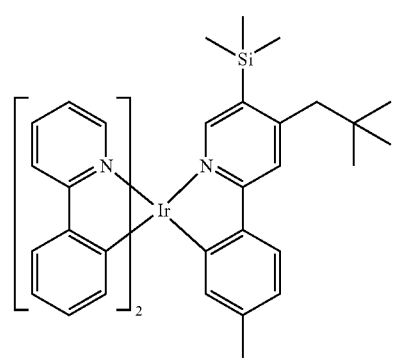
39
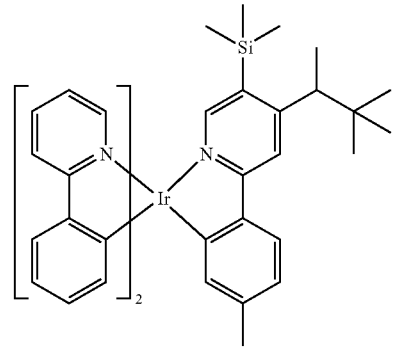
40
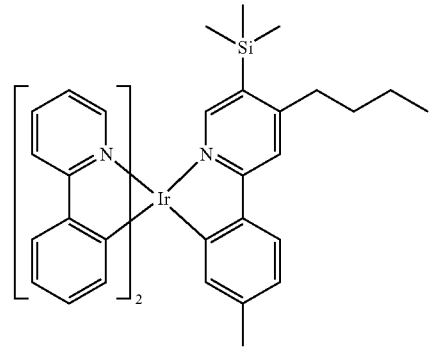
41
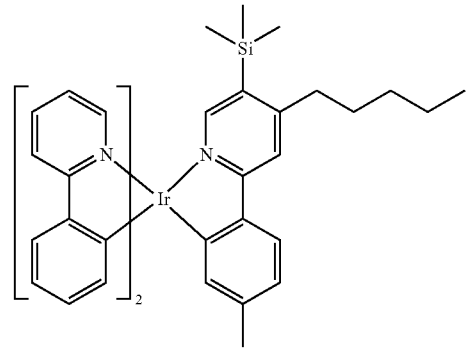

42
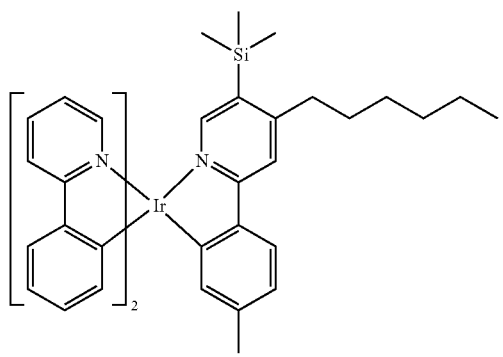
43
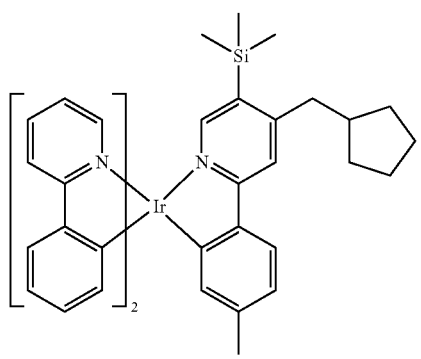
44
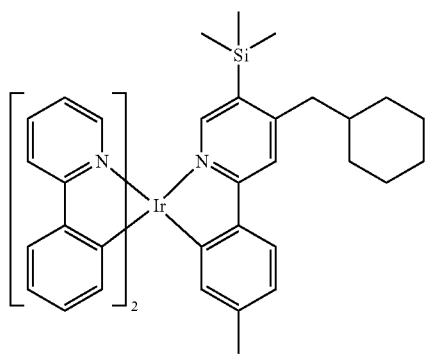
45
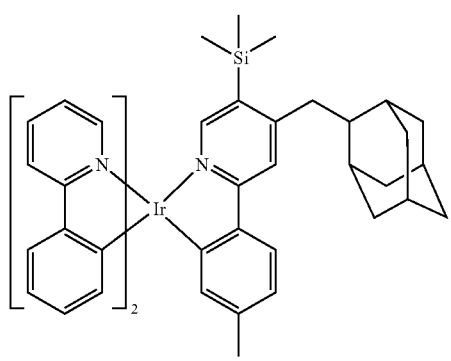
46
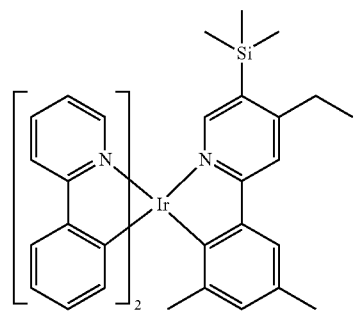
47
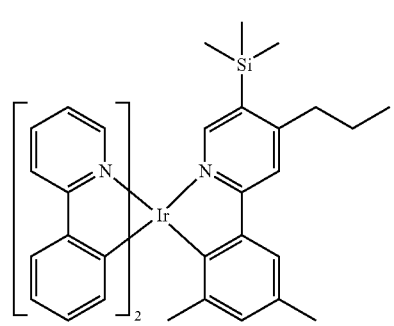
48
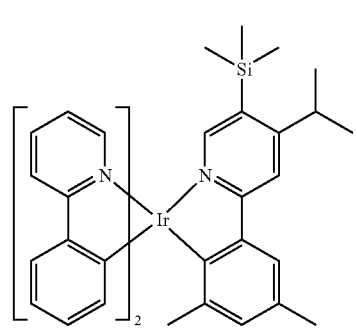
49
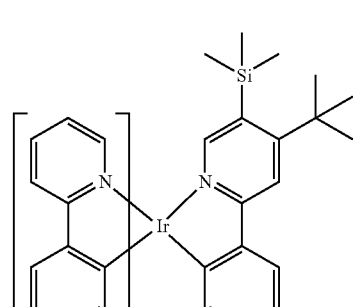
50
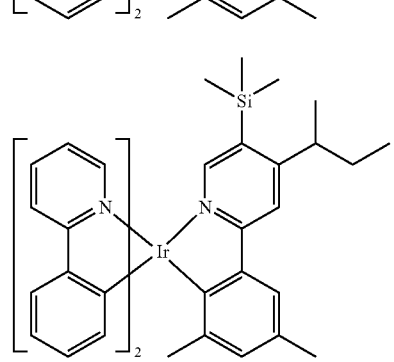

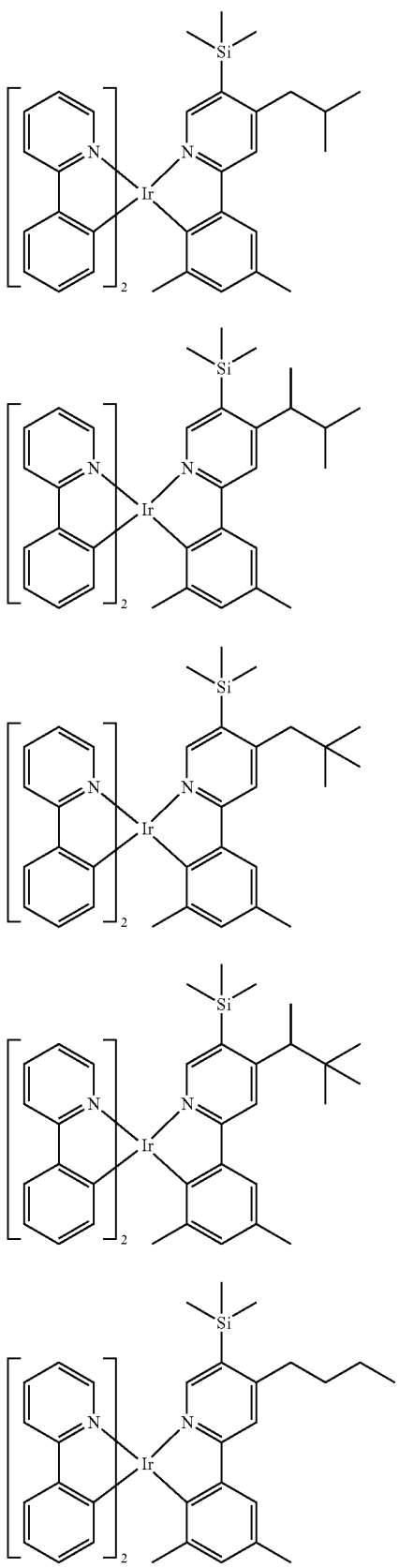
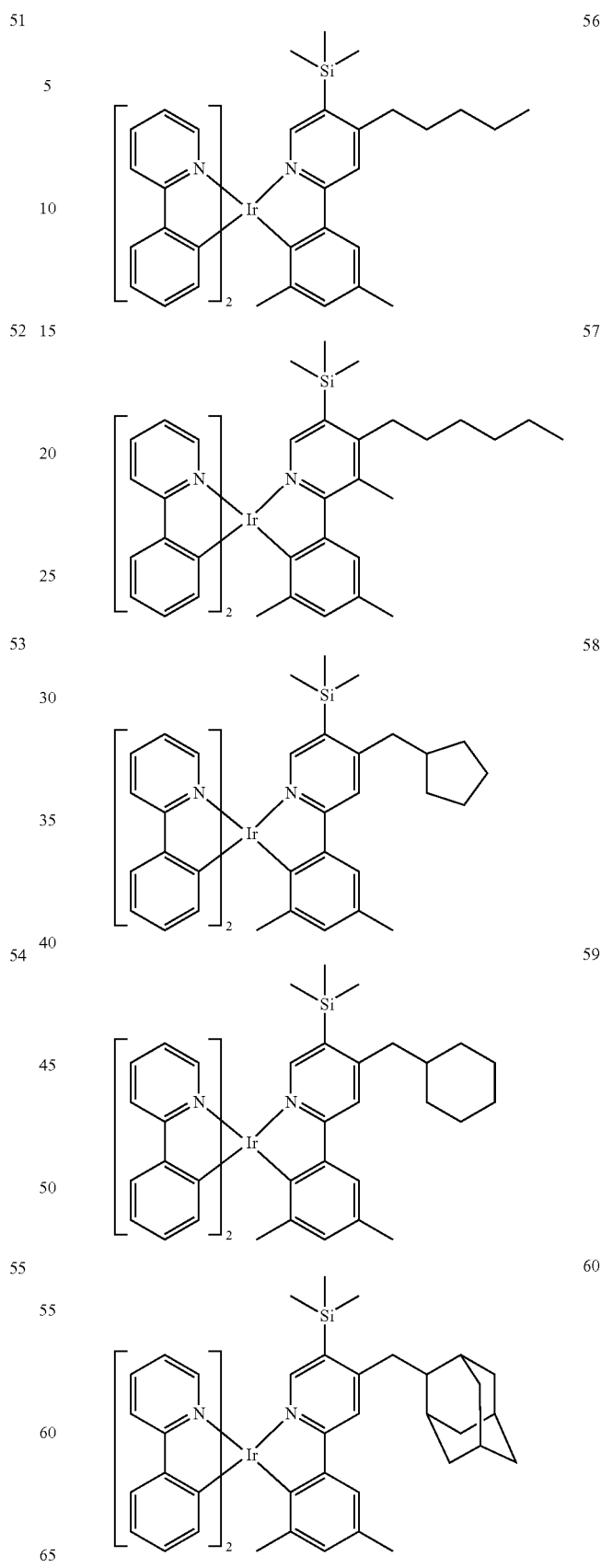

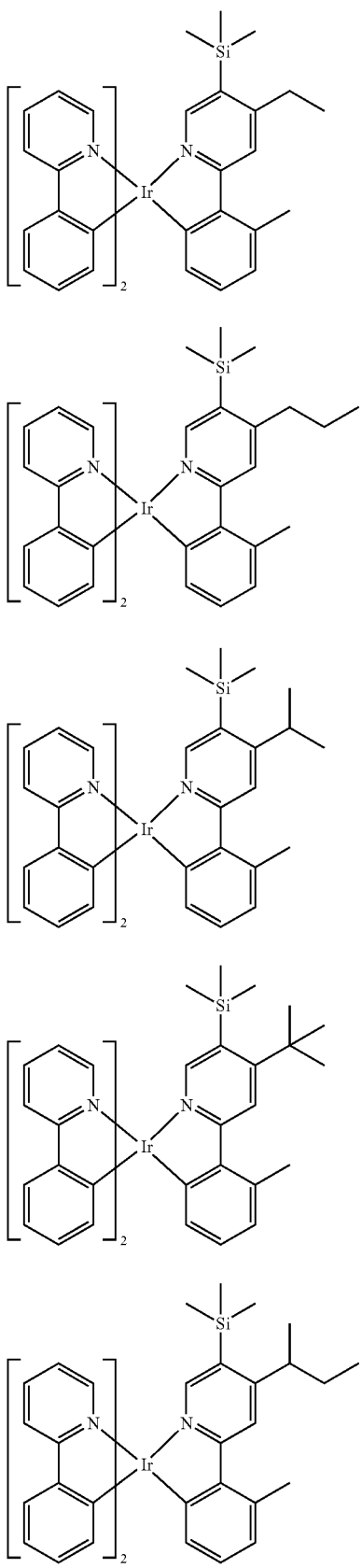
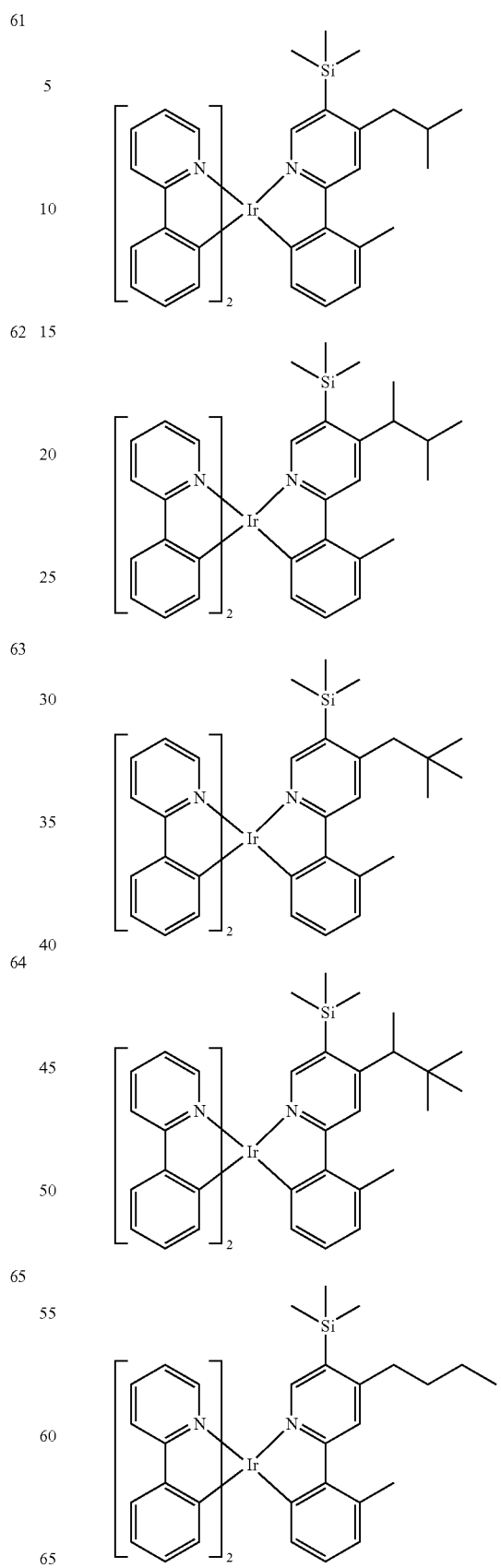

71 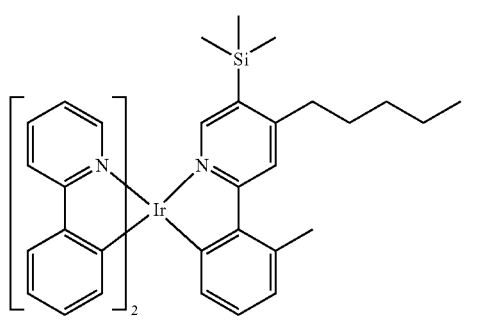
72 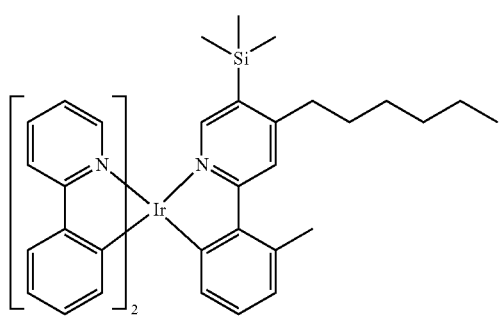
73 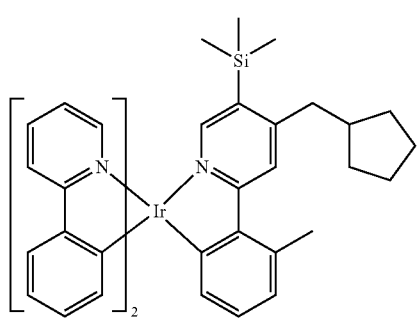
74 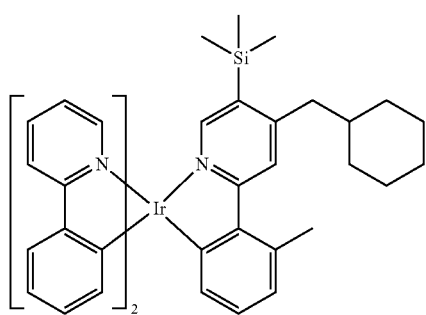
75 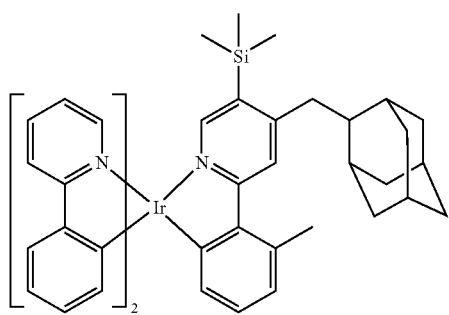
76 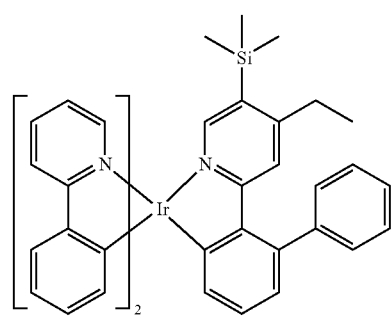
77 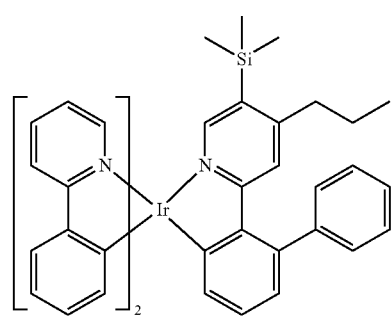
78 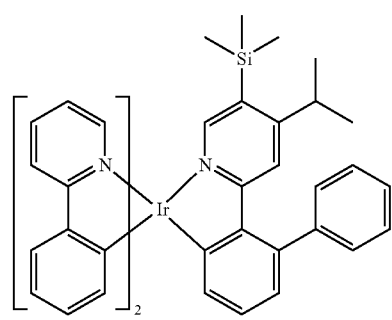
79 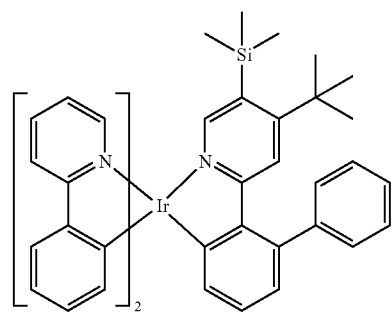
80 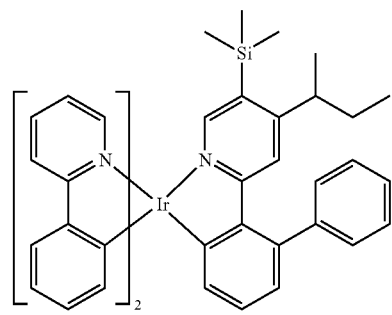

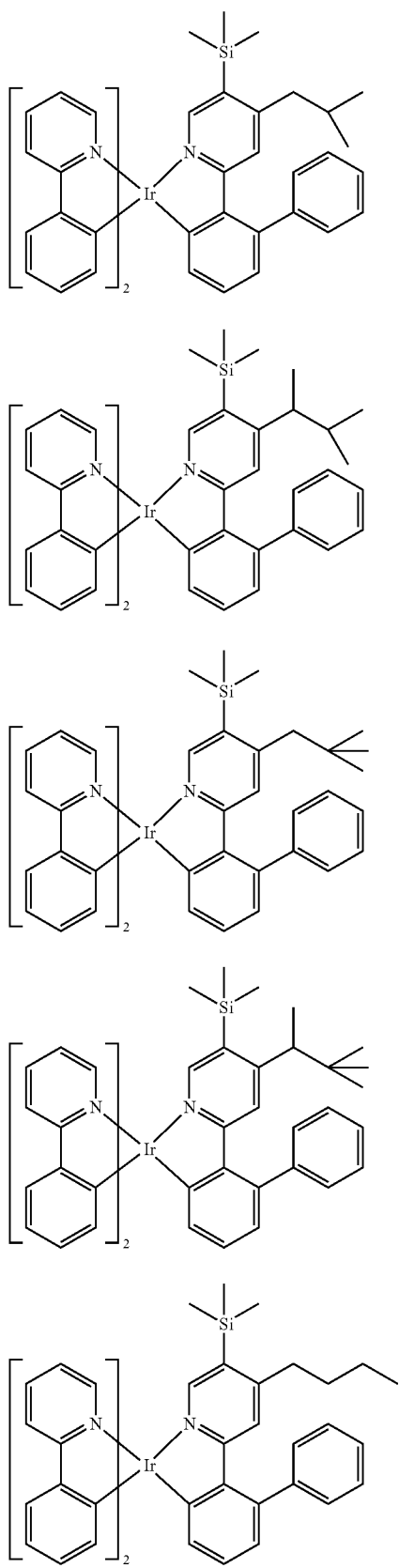
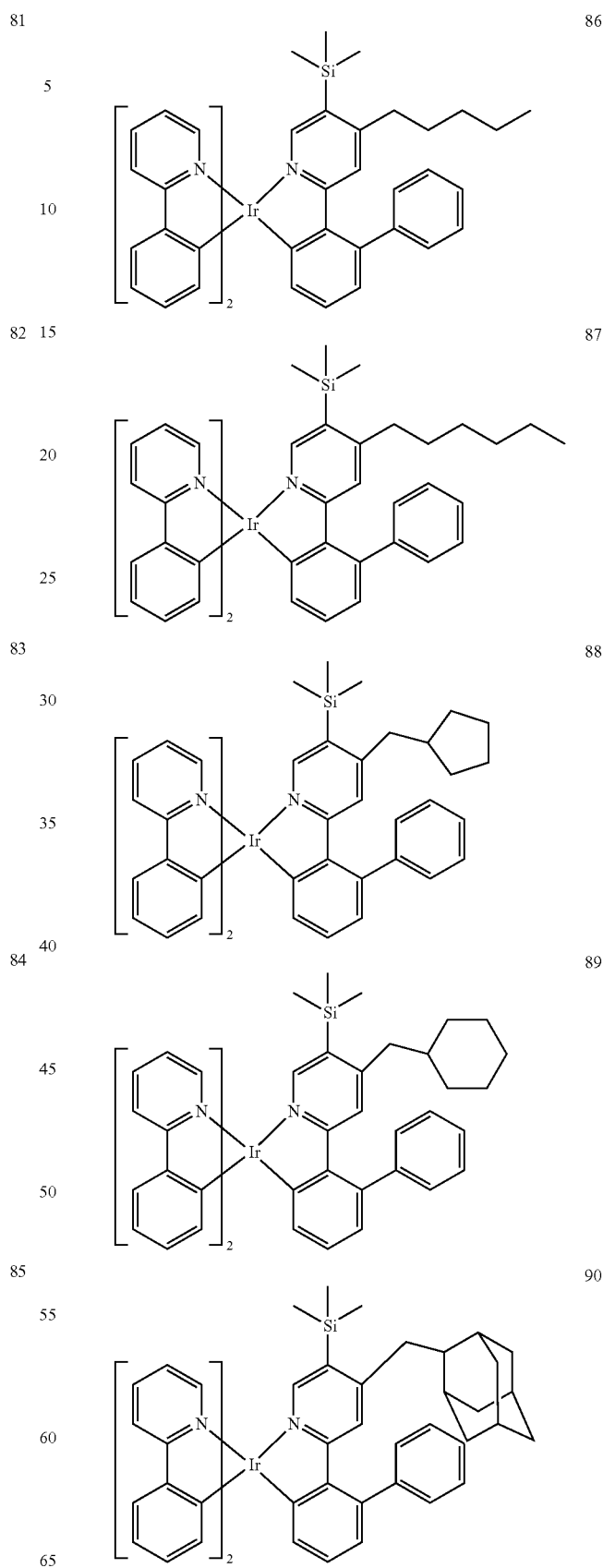

91
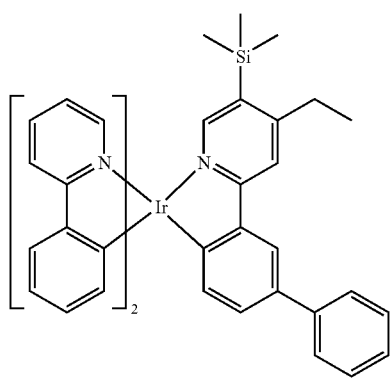
92
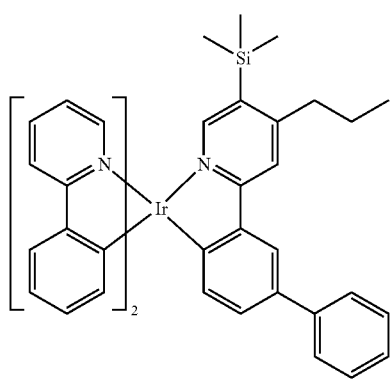
93
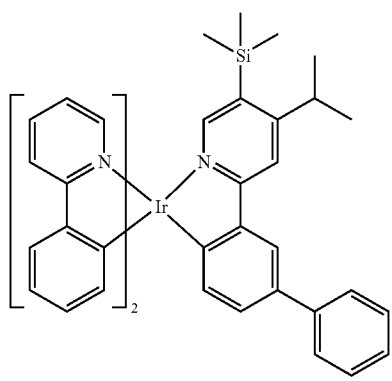
94
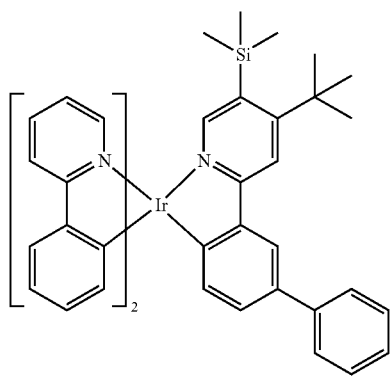
95
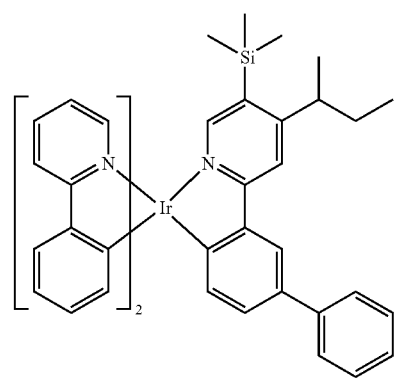
96
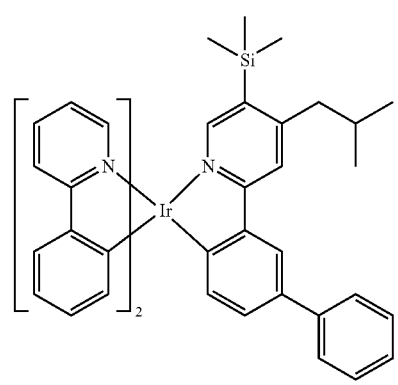
97
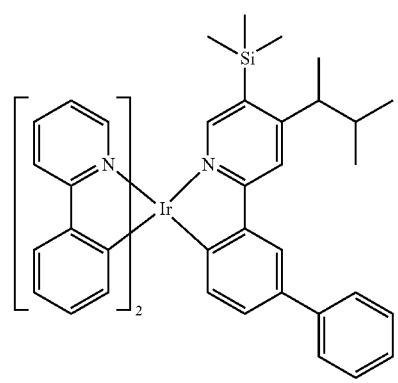
98
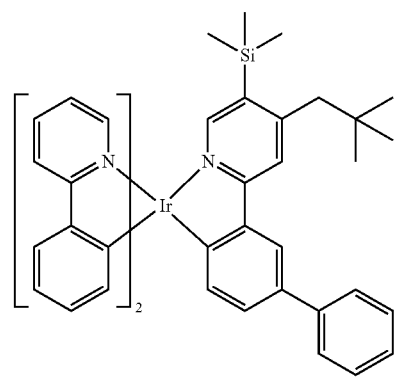

99 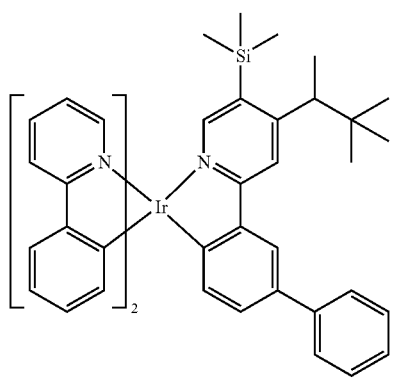
100 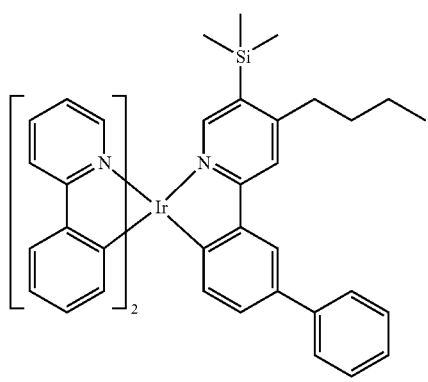
101 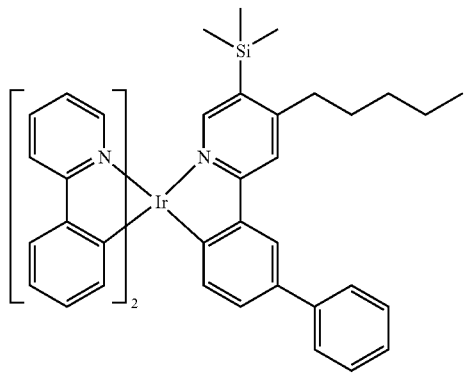
102 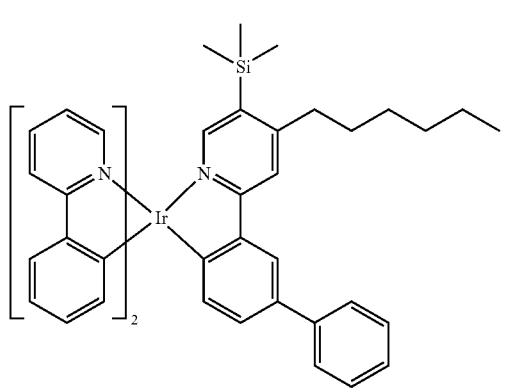
103 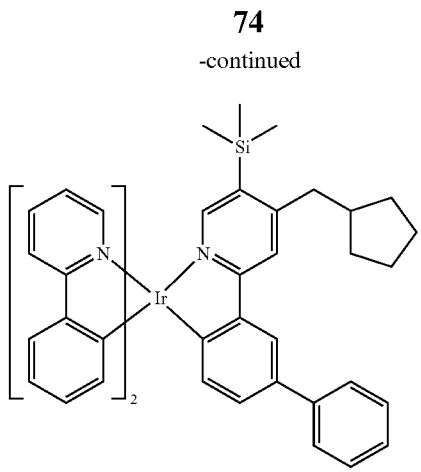
104 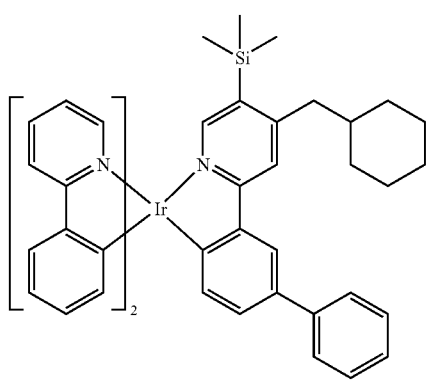
105 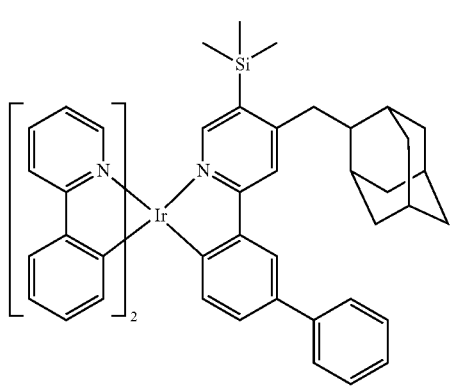
106 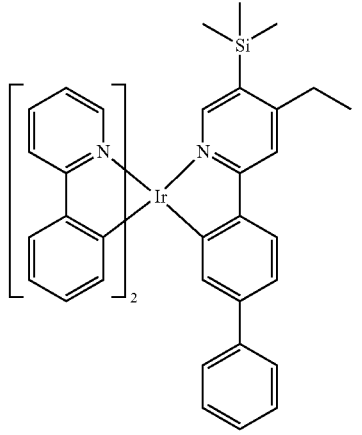

107
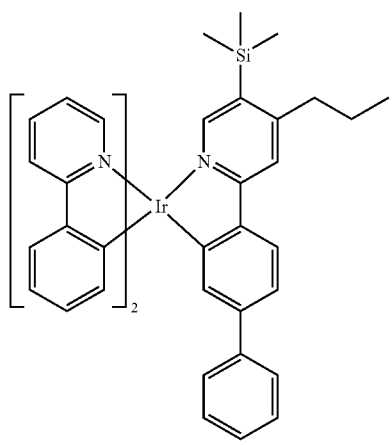
108
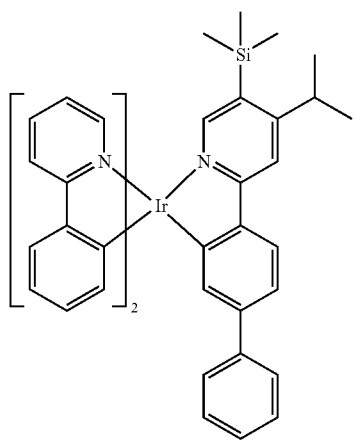
109
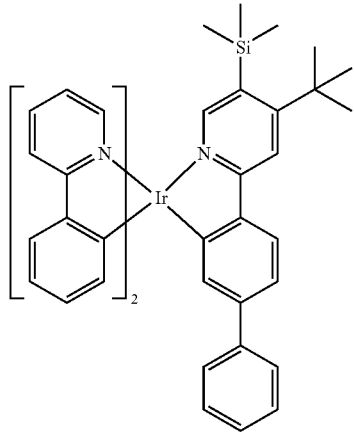
110
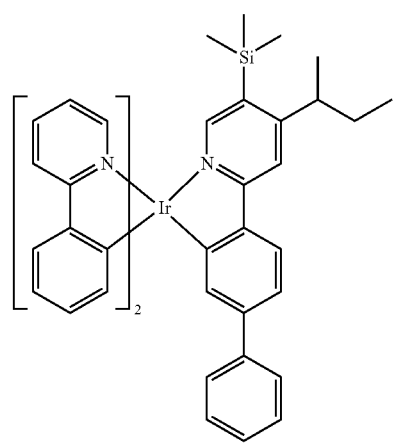
111
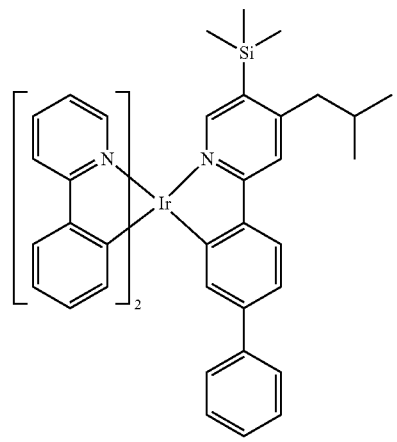
112
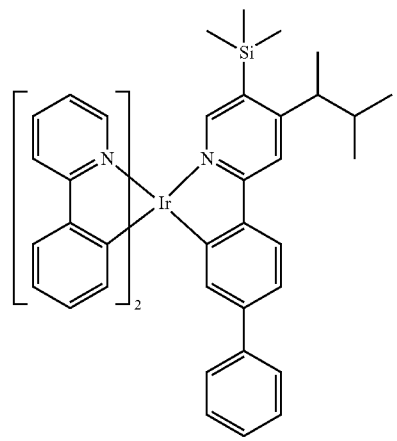

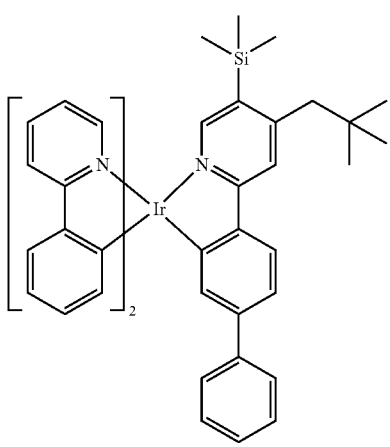
113
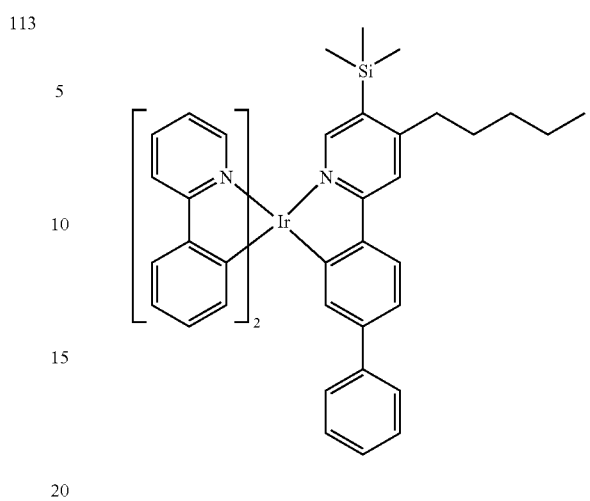
116
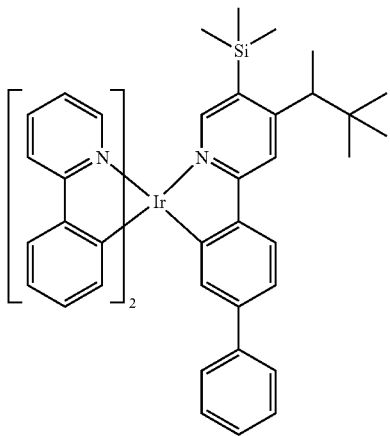
114
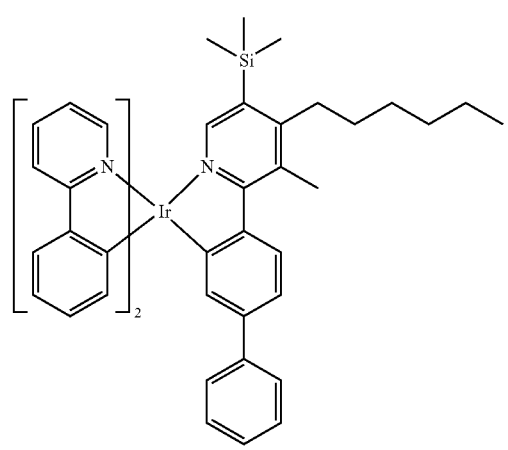
117
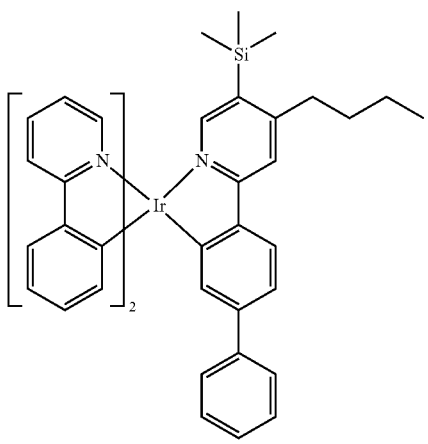
115
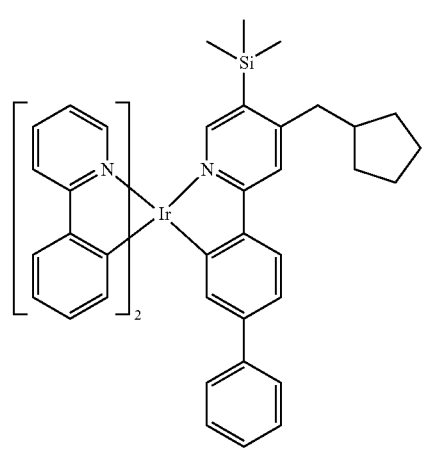
118

119
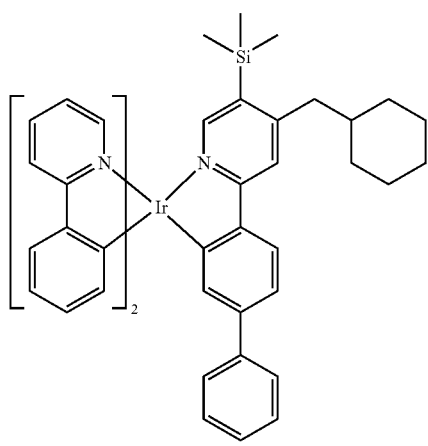
120
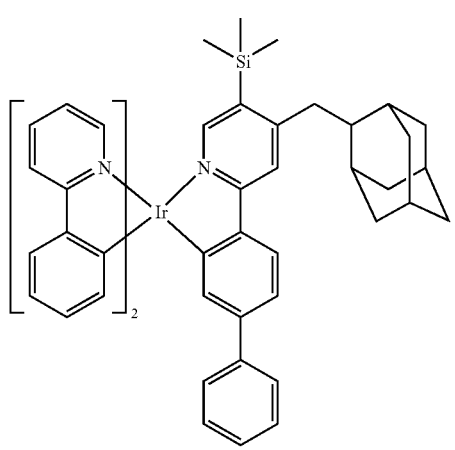
121
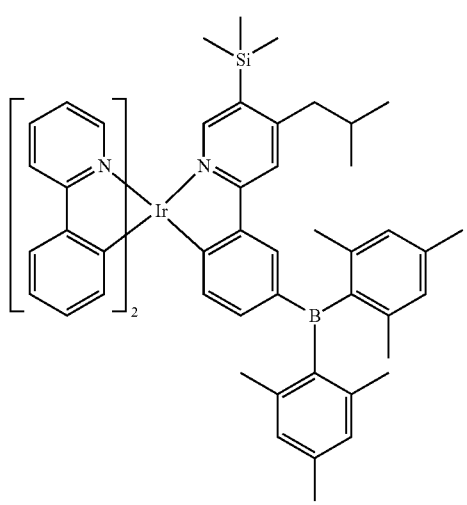
122
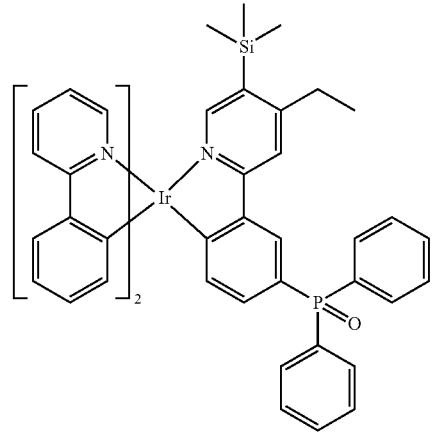
123
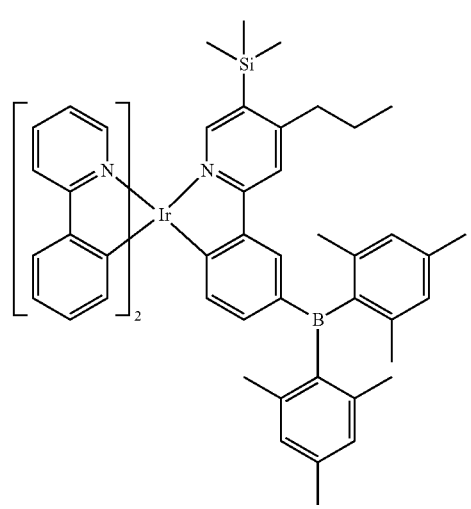
124
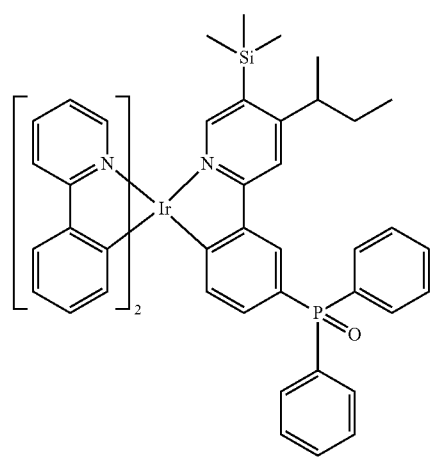

125 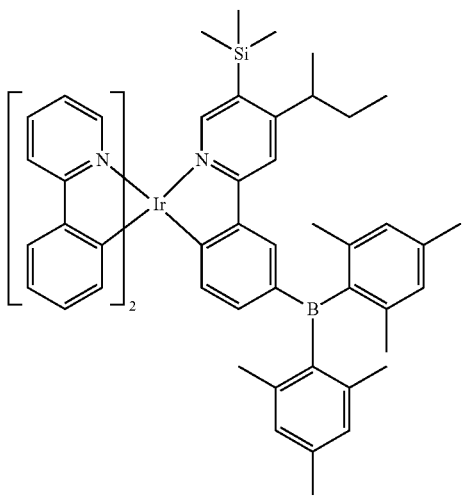
126 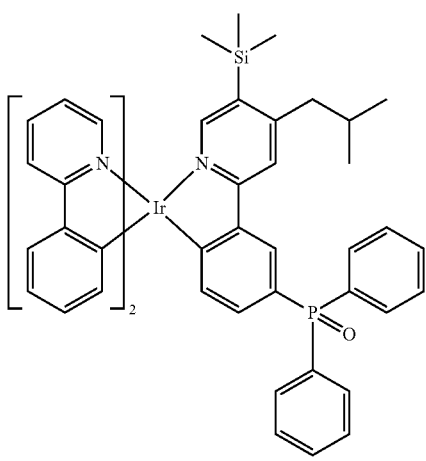
127 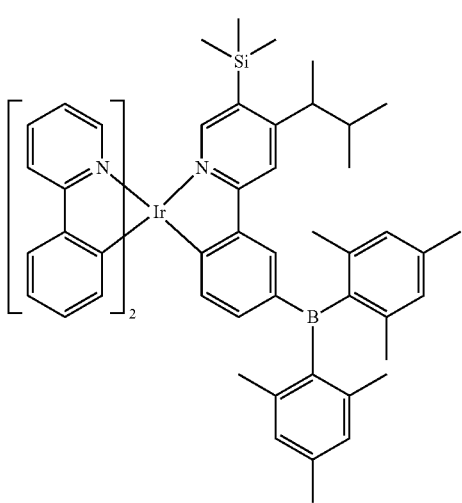
128 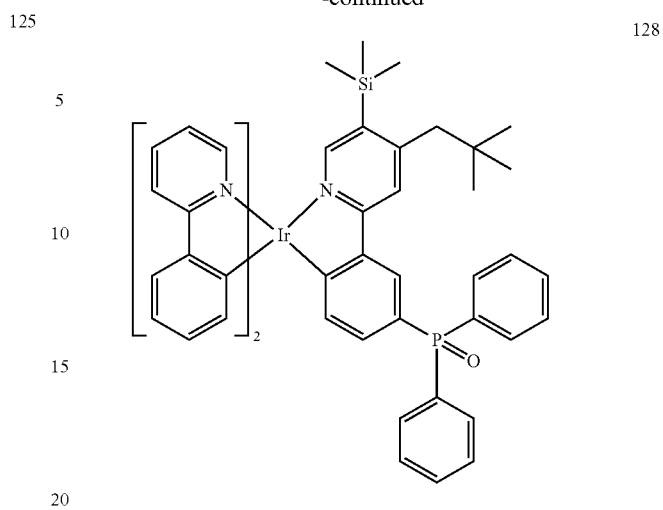
129 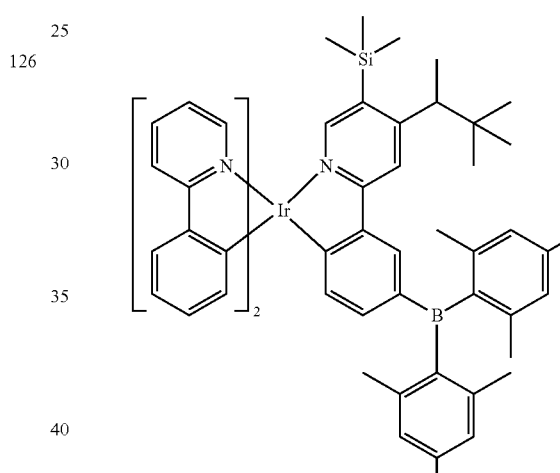
130 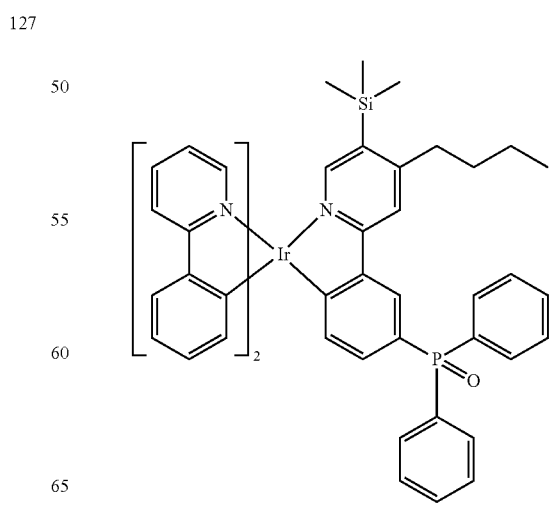

131
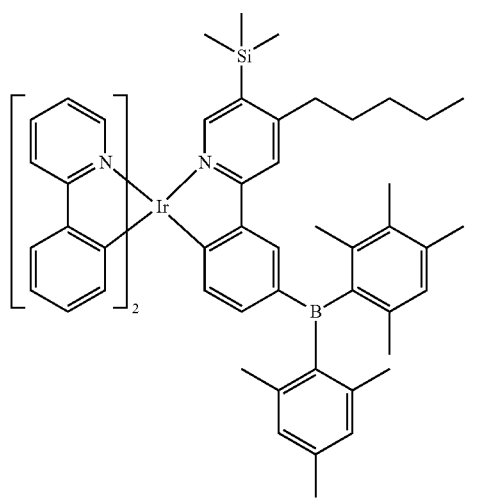
132
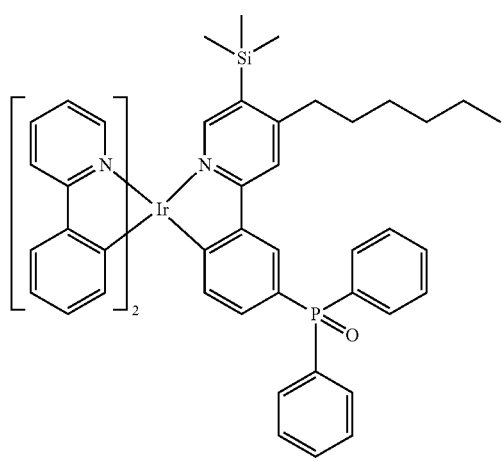
133
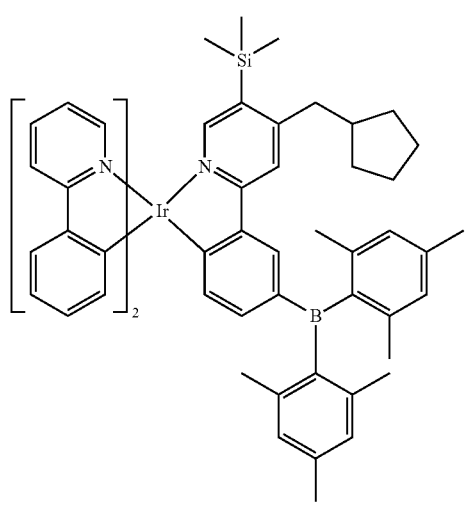
134
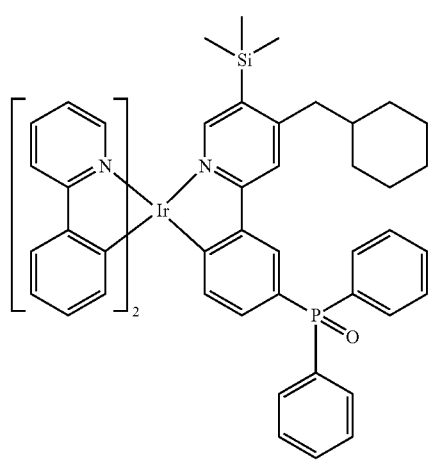
135
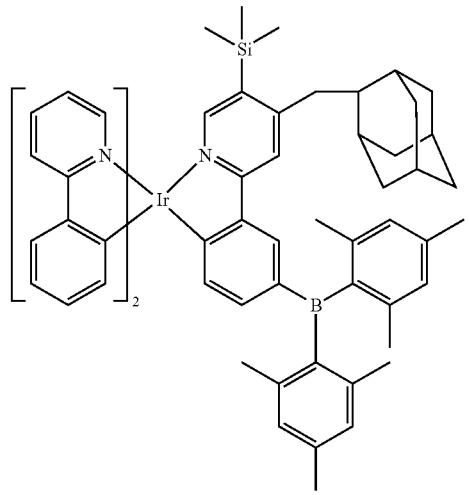
136
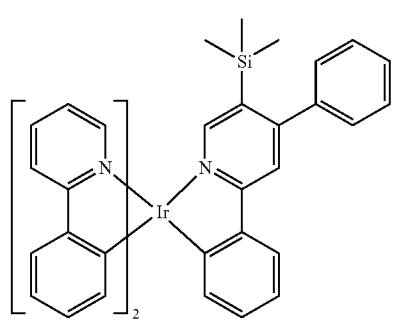
137
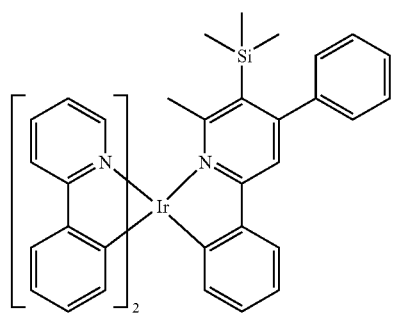

138
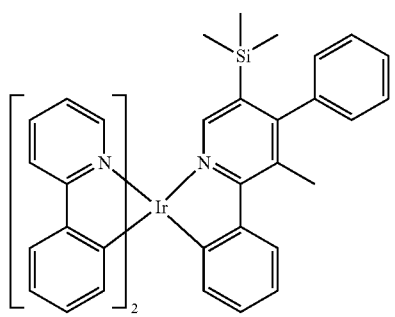
139
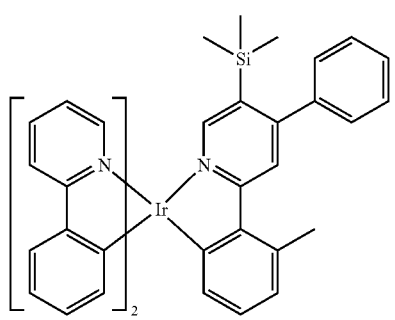
140
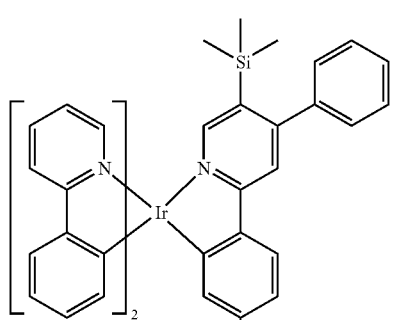
141
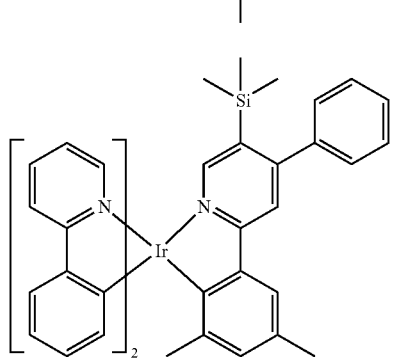
142
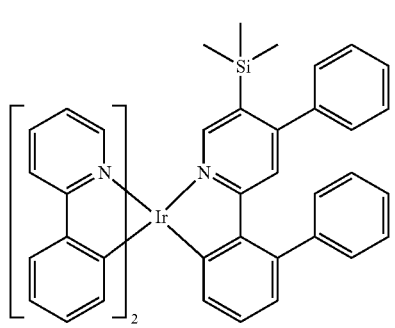
143
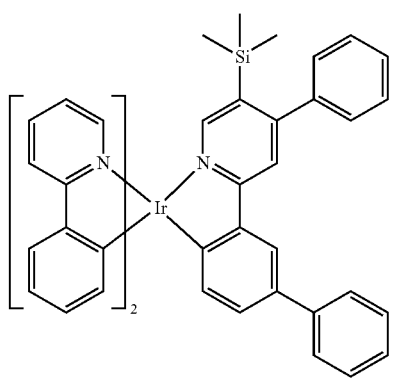
144
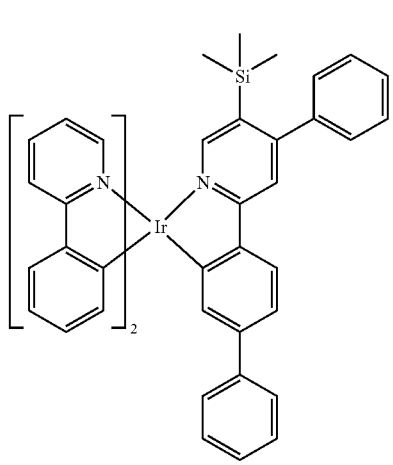
145
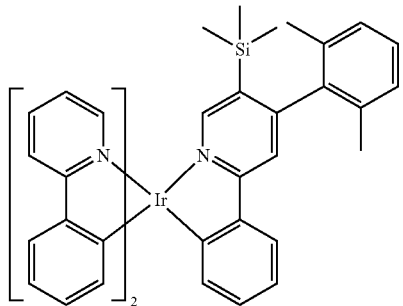
146
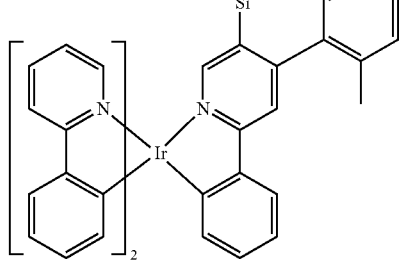

147
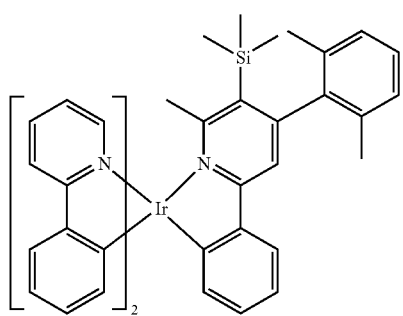
148
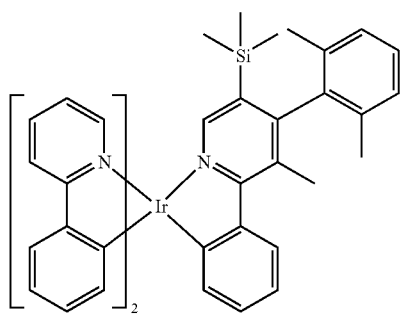
149
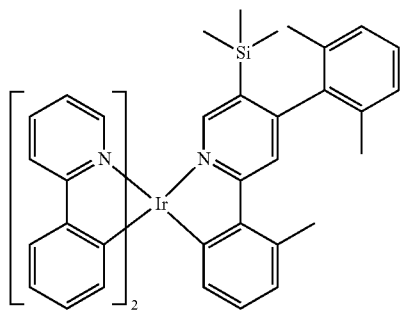
150
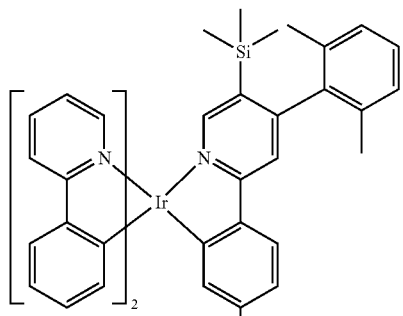
151
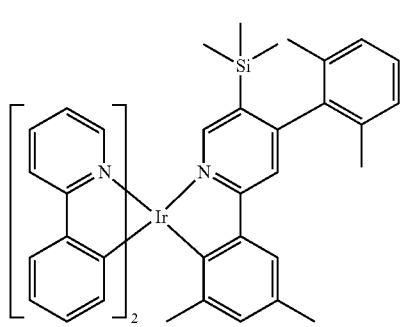
152
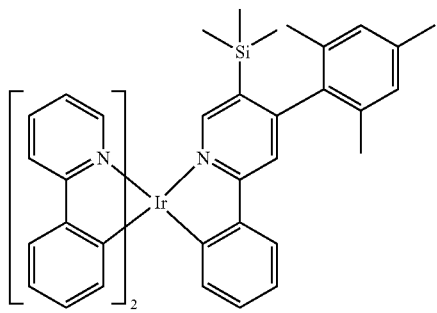
153
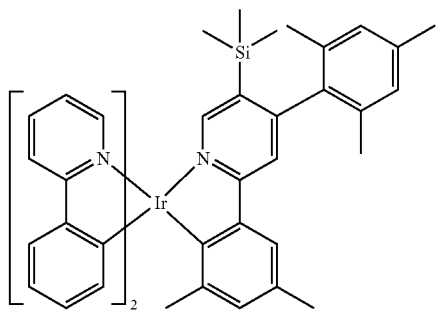
154
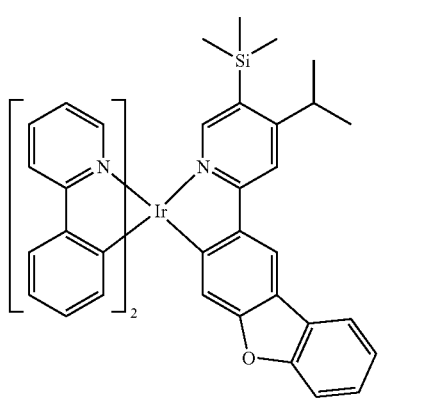
155
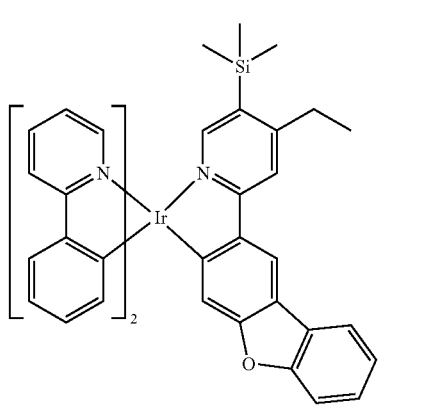

156
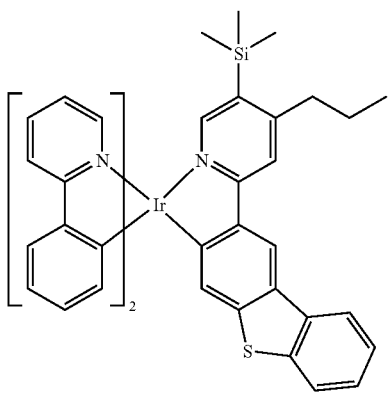
157
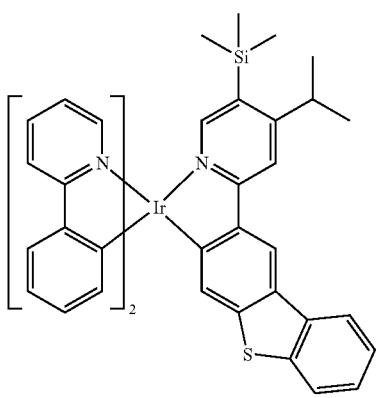
158
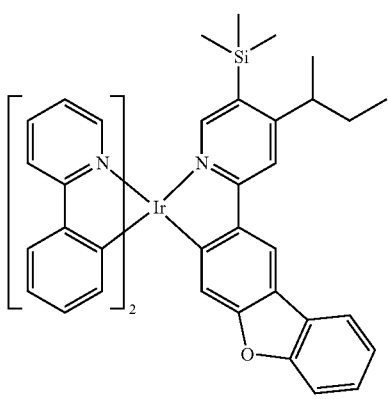
159
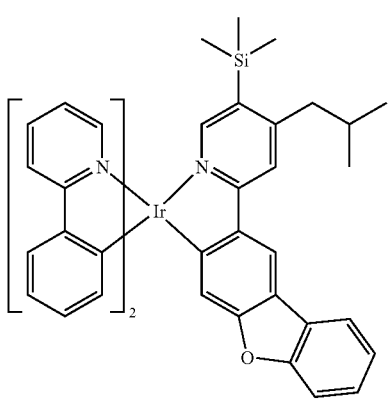
160
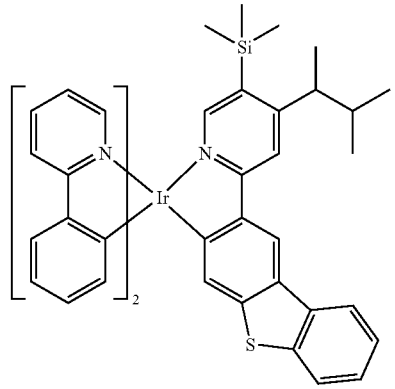
161
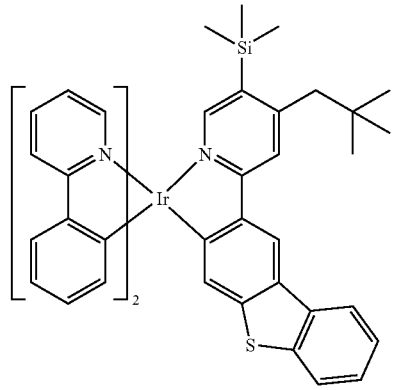
162
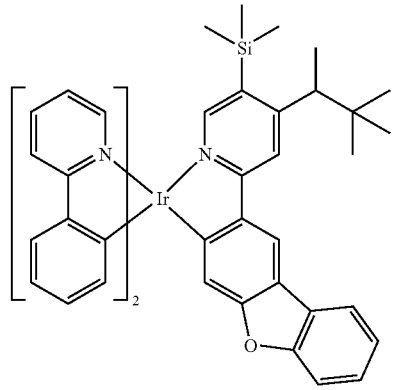
163
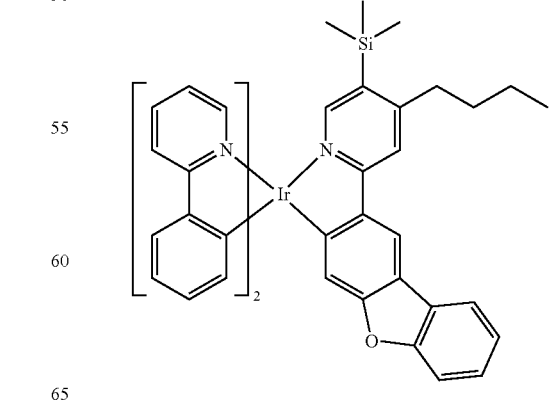

164
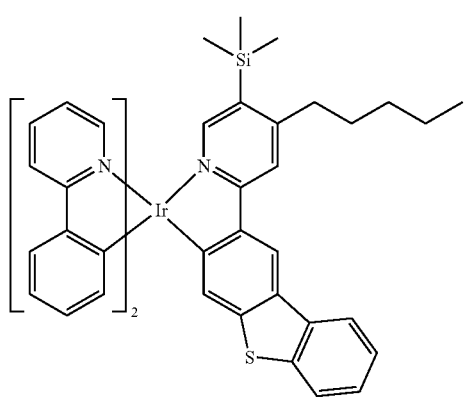
165
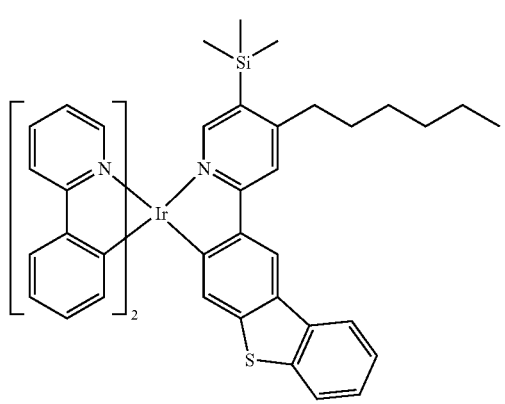
166
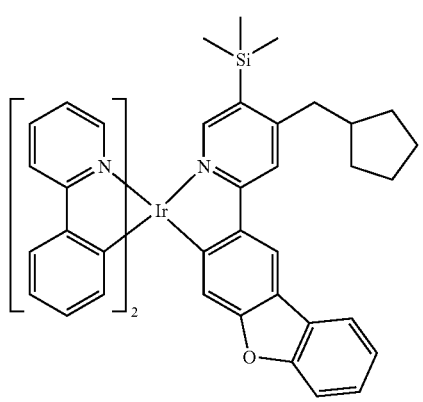
167
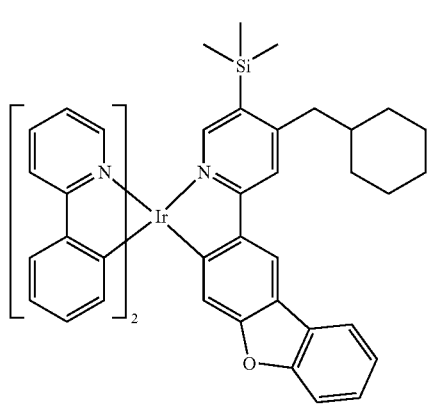
168
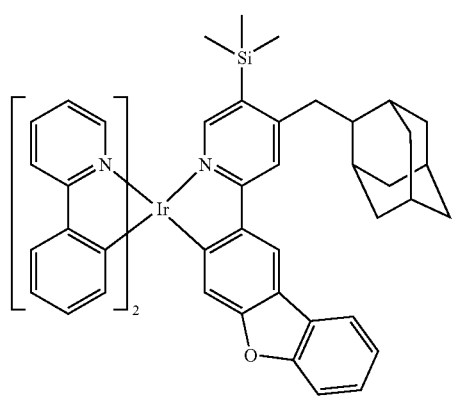
169
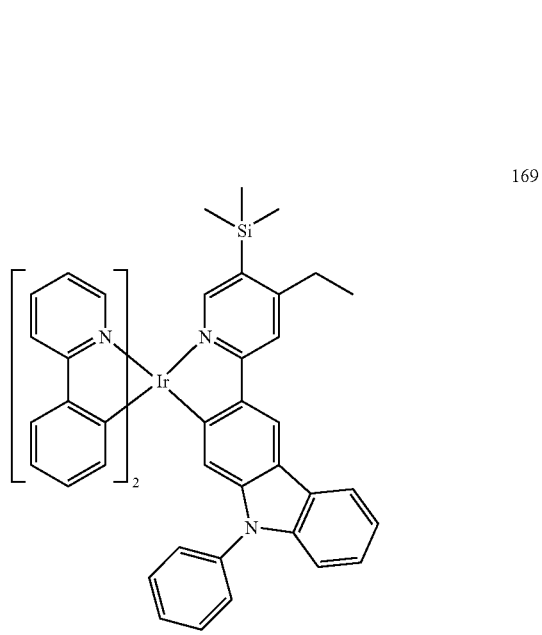
170
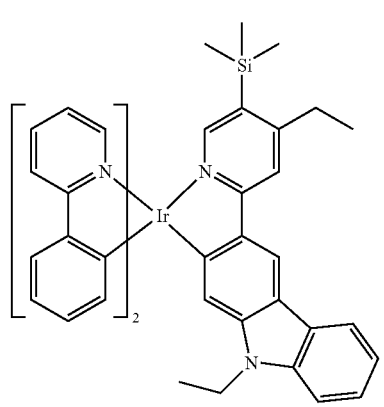

171 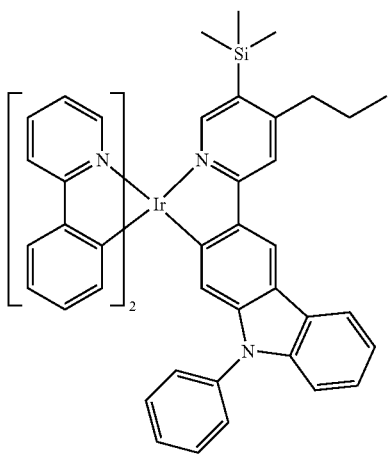
172 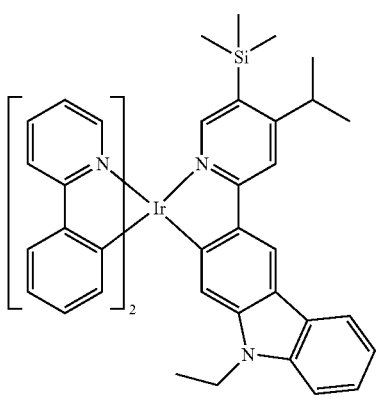
173 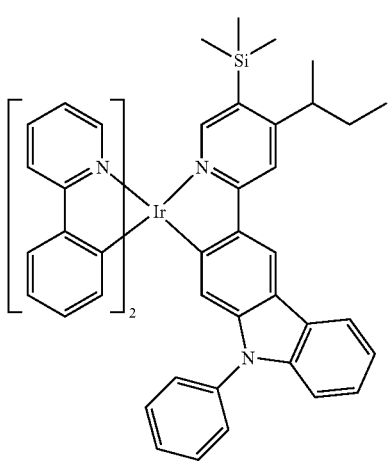
174 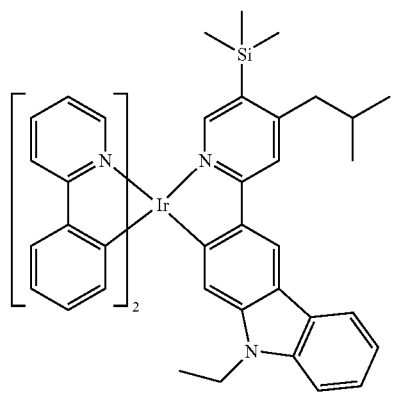
175 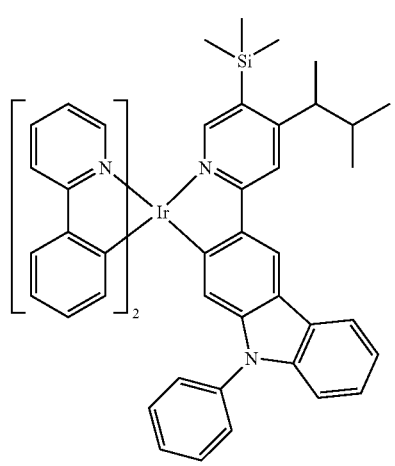
176 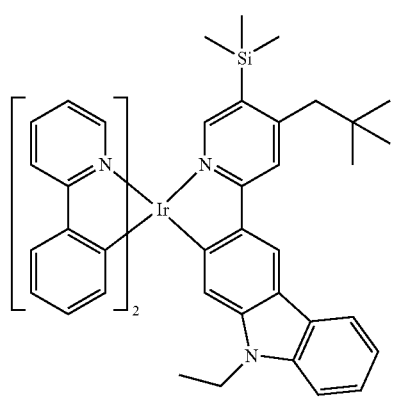

177
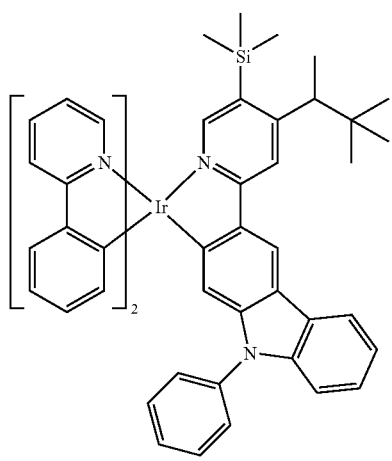
178
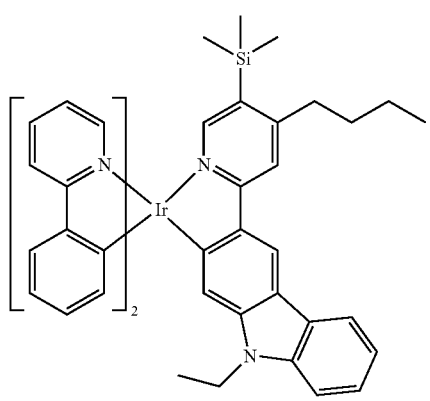
179
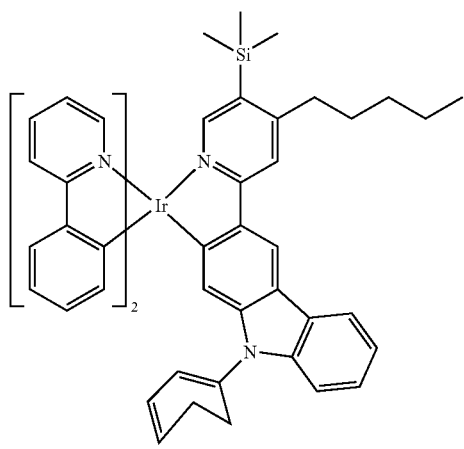
180
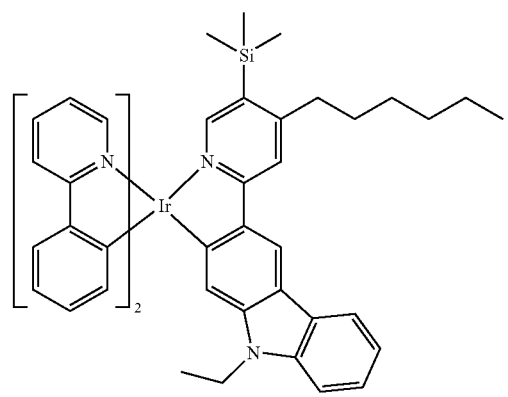
181
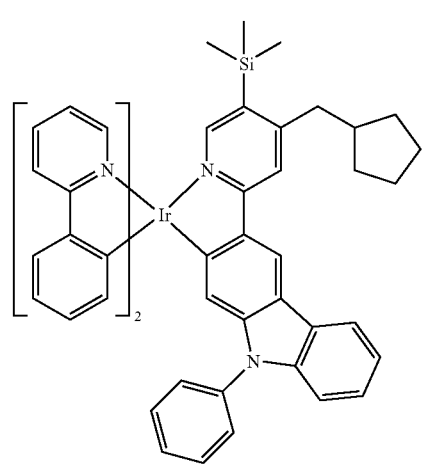
182
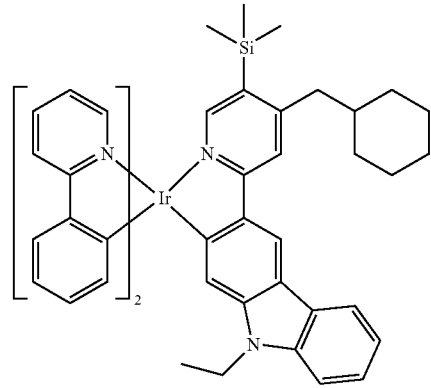

183
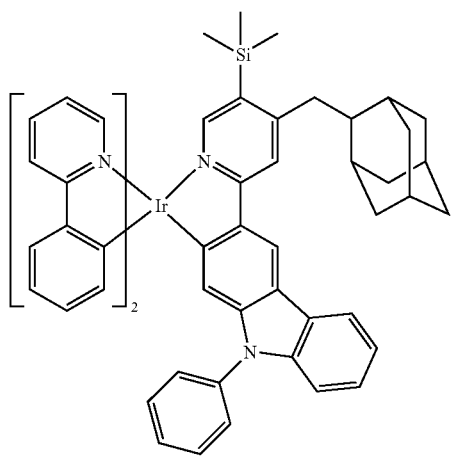
184
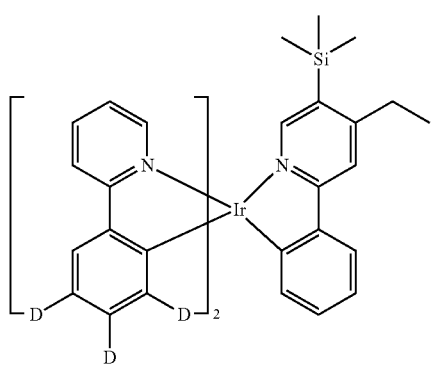
185
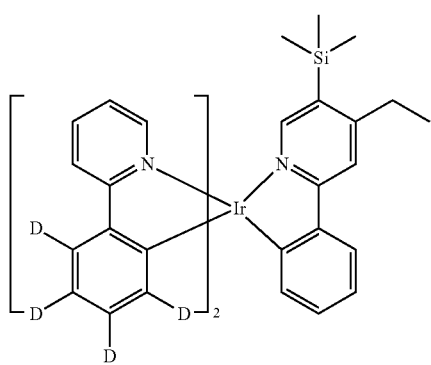
186
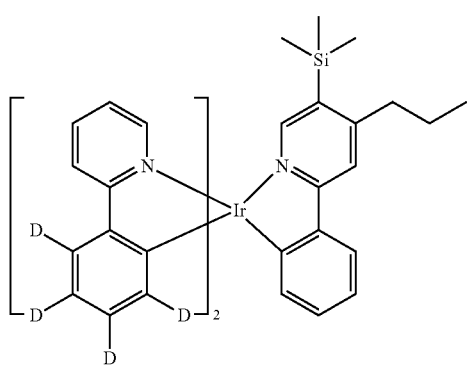
187
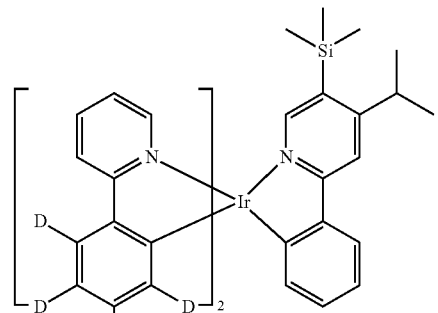
188
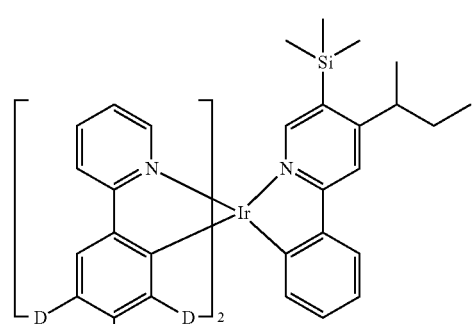
189
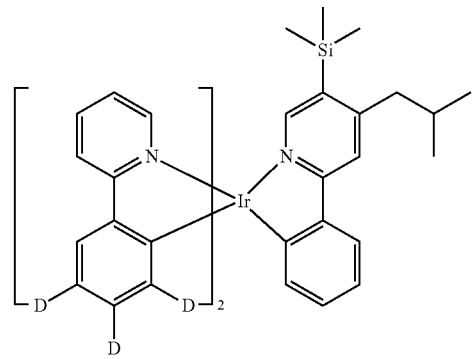
190
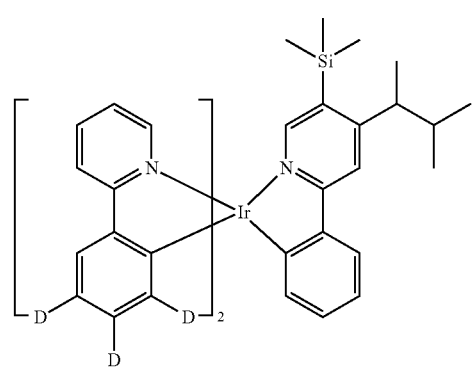

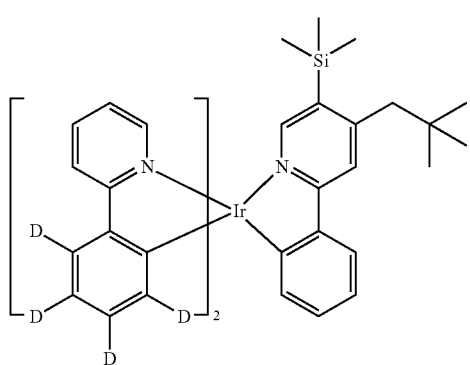
191
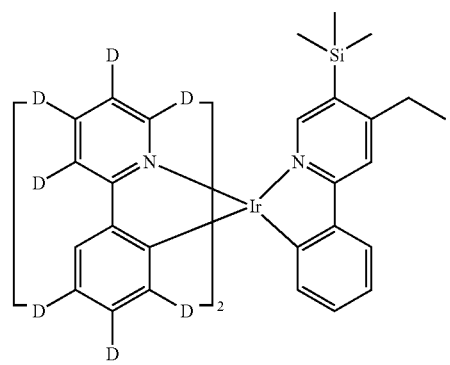
195
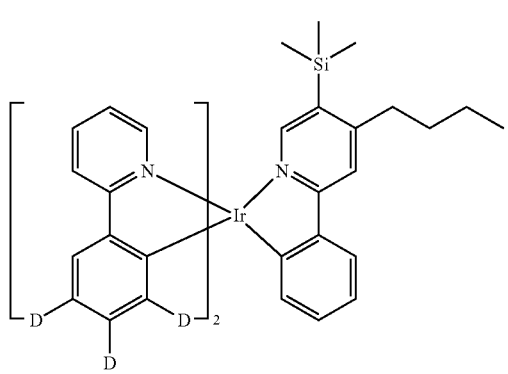
192
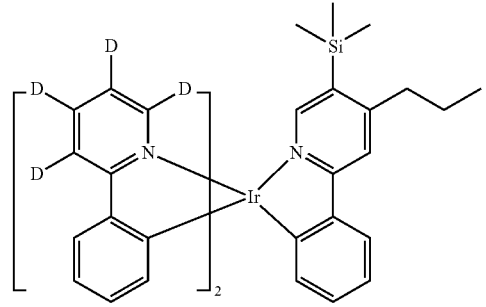
196
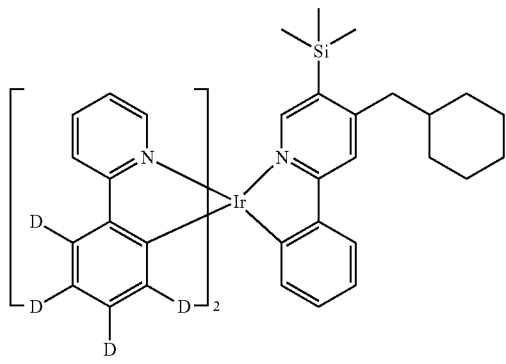
193
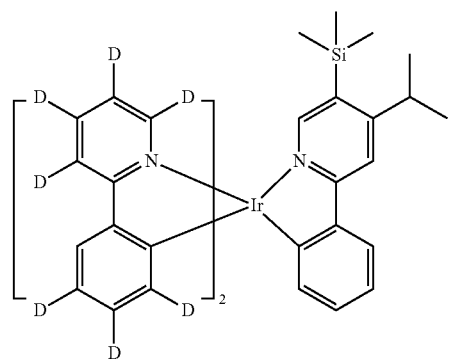
197
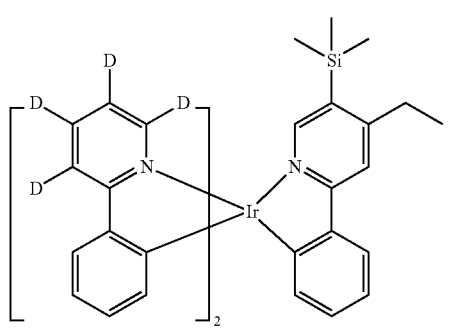
194
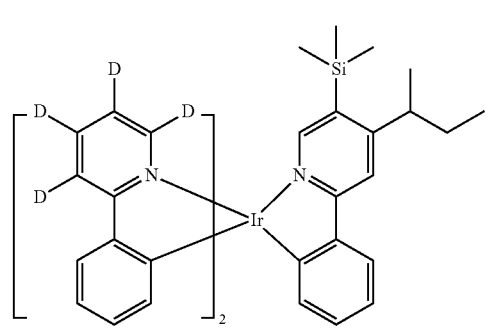
198

199
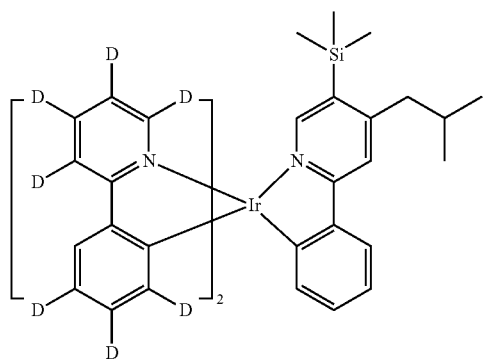
200
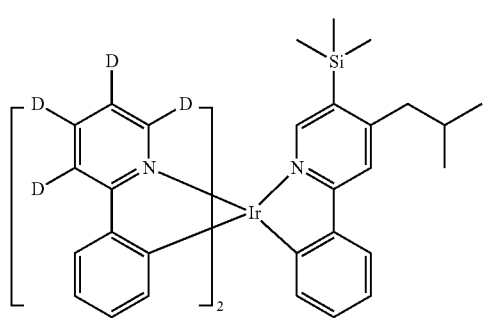
201
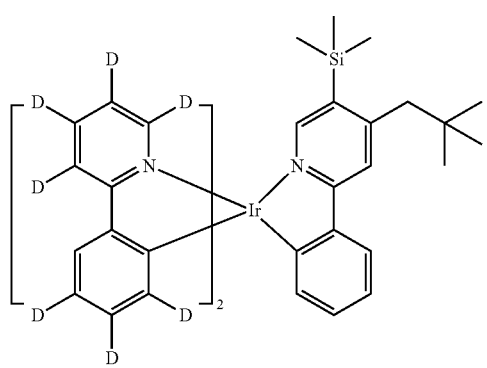
202
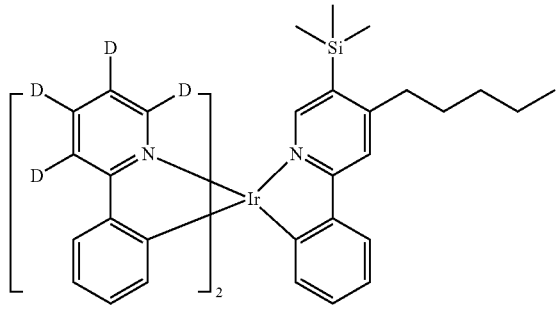
203
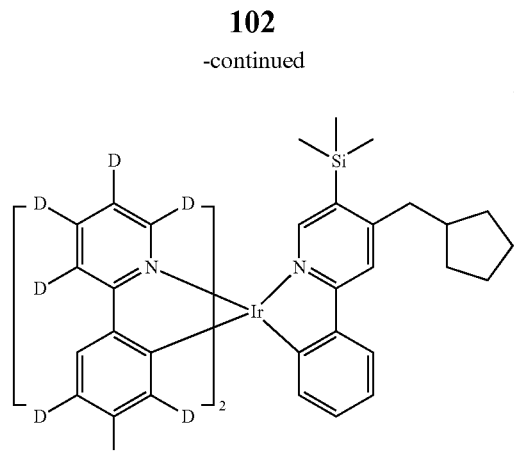
204
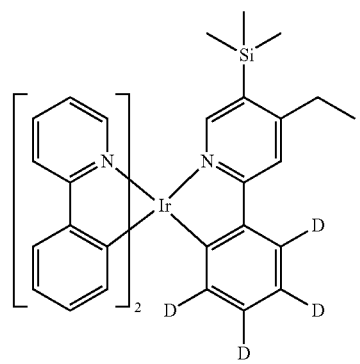
205
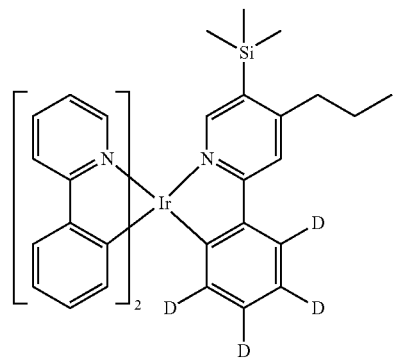
206
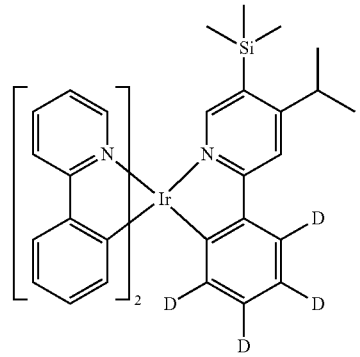

207
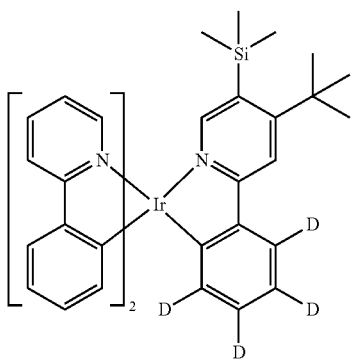
208
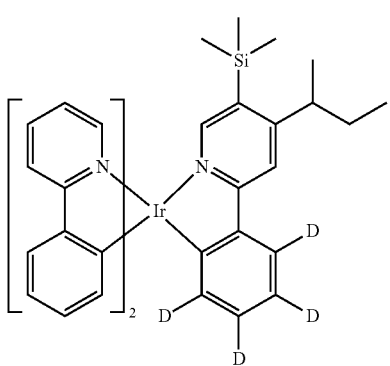
209
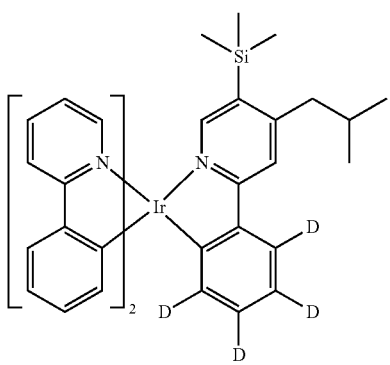
210
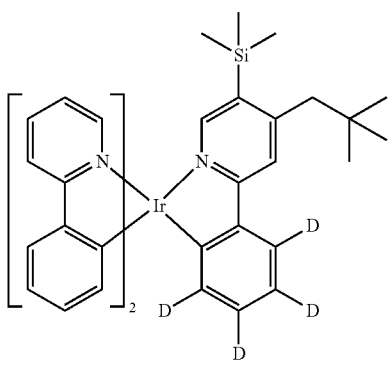
211
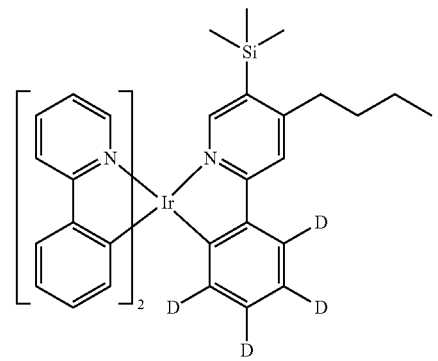
212
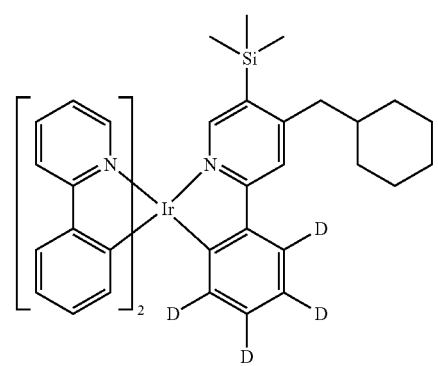
213
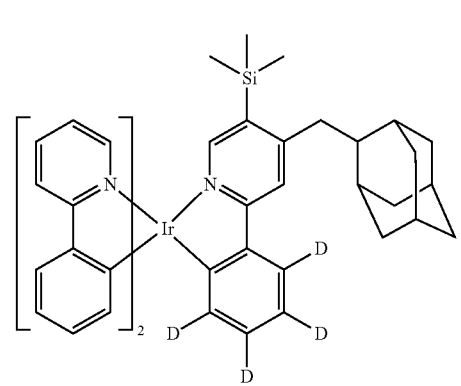
214
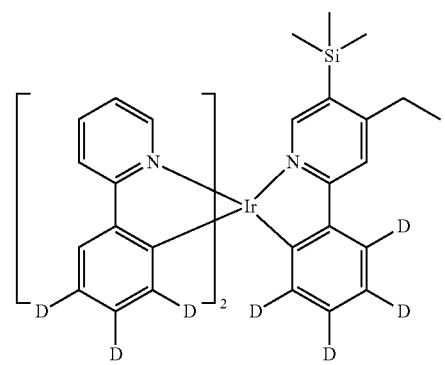

215
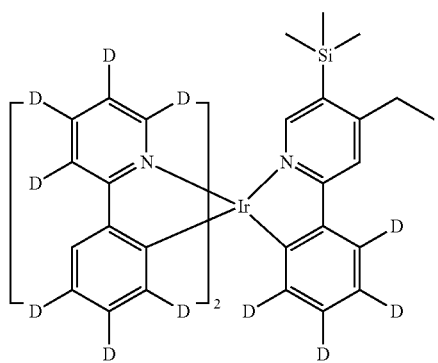
216
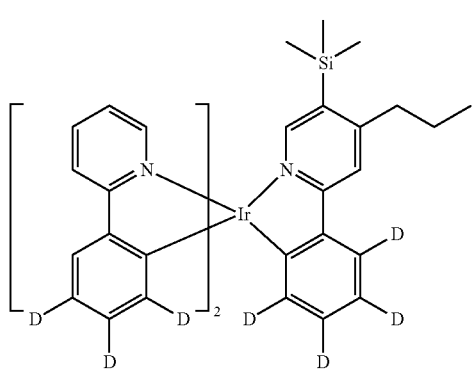
217
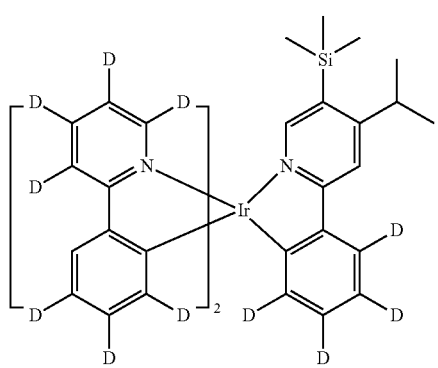
218
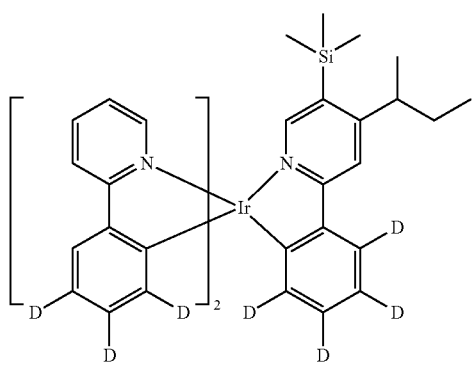
219
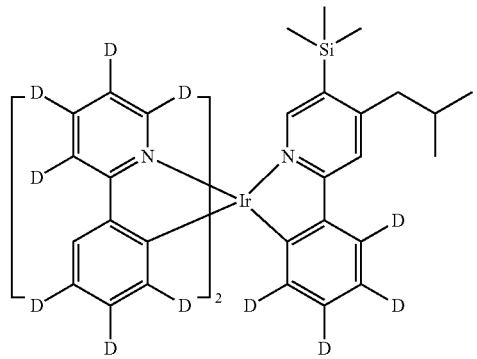
220
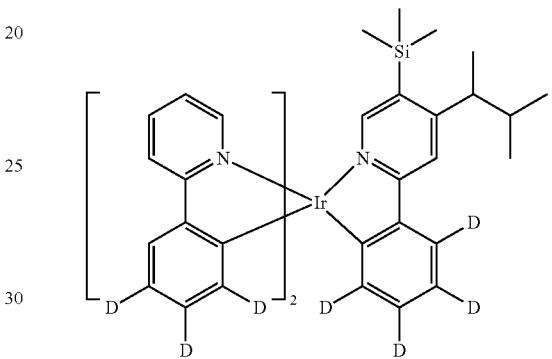
221
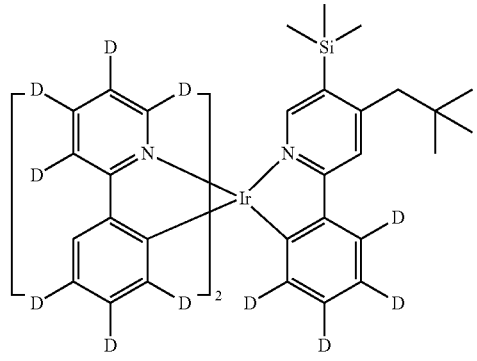
222
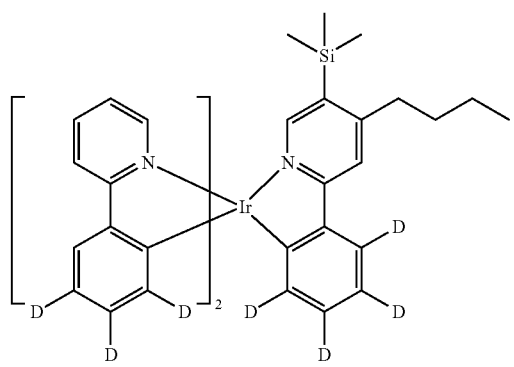

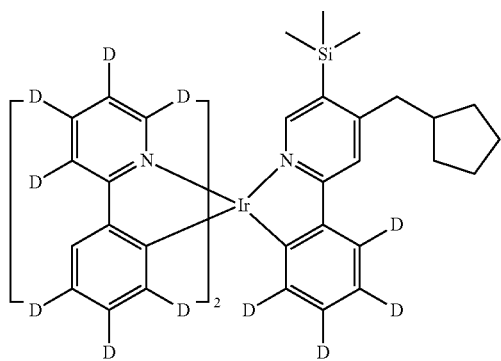
223
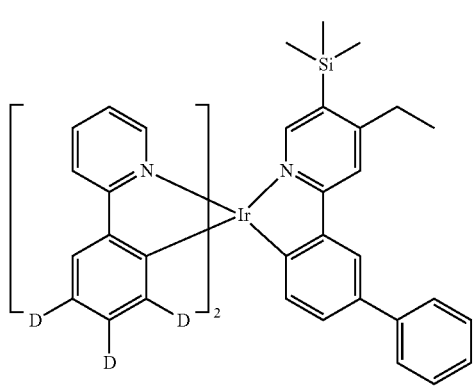
224
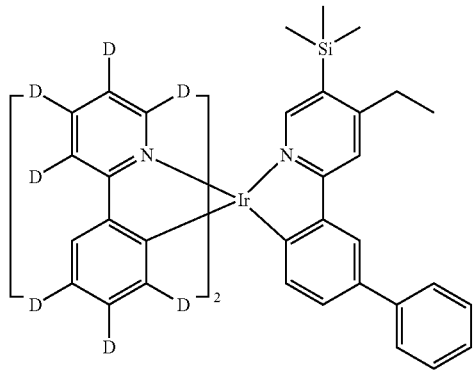
225
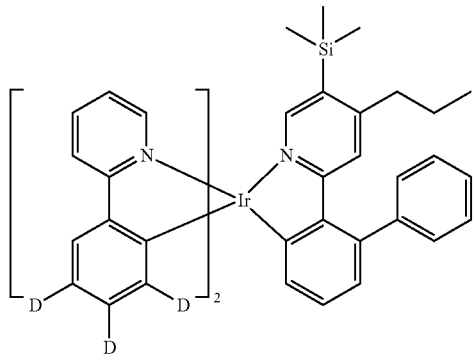
226
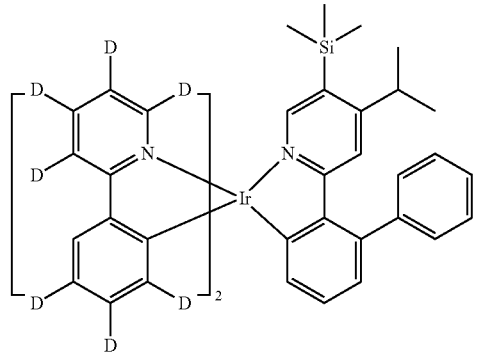
227
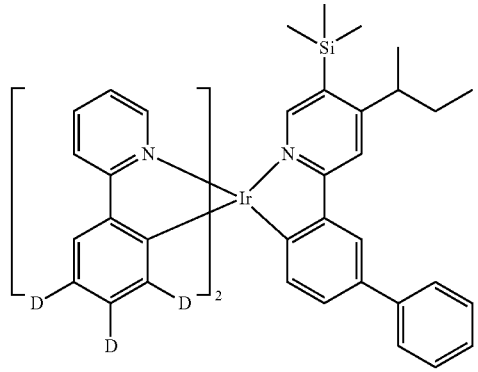
228
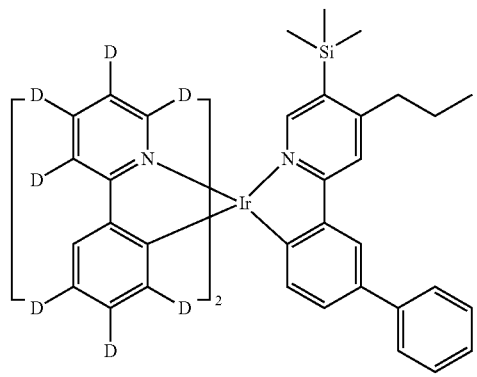
229
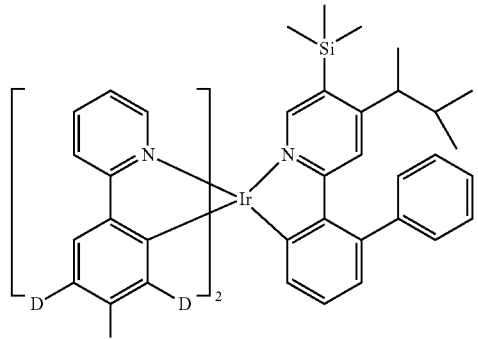
230

231 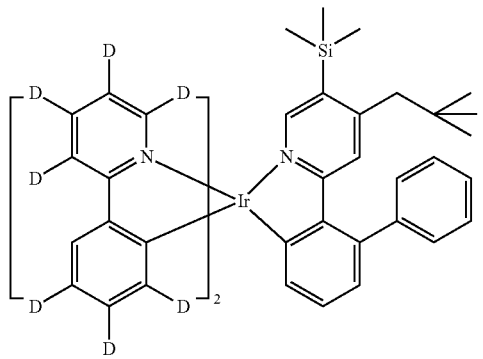
232 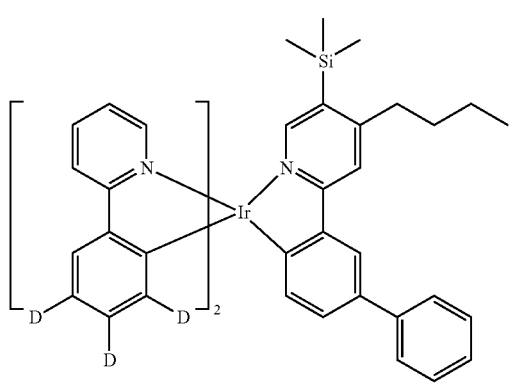
233 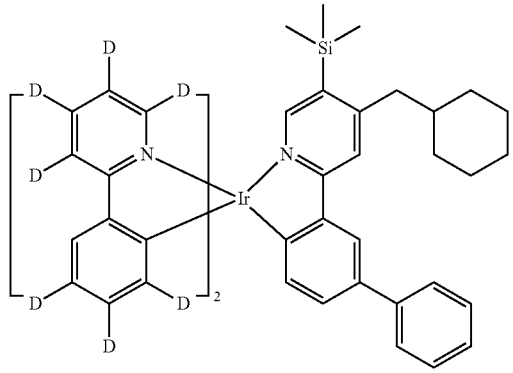
234 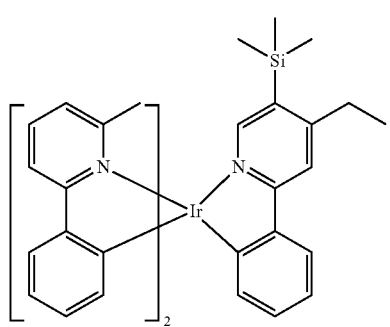
235 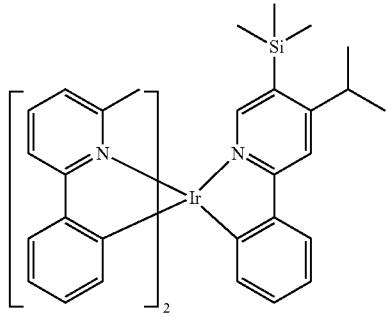
236 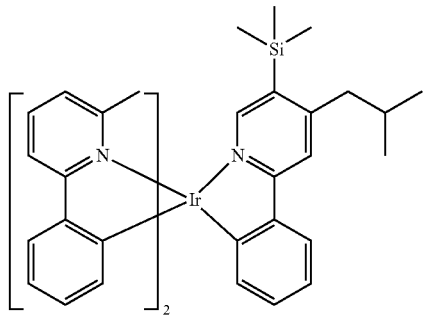
237 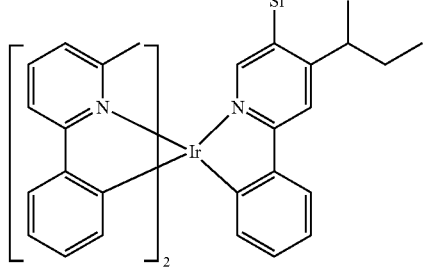
238 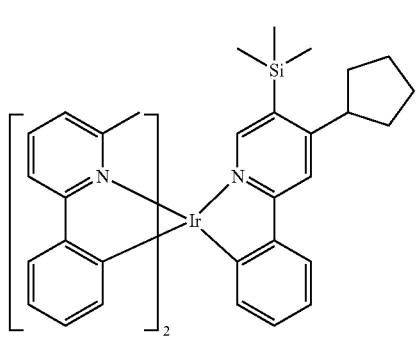
239 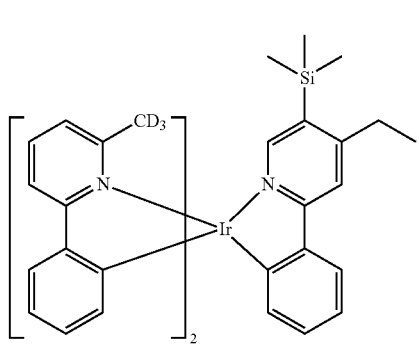

-continued
240 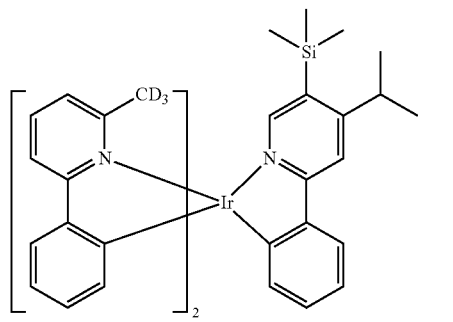
241 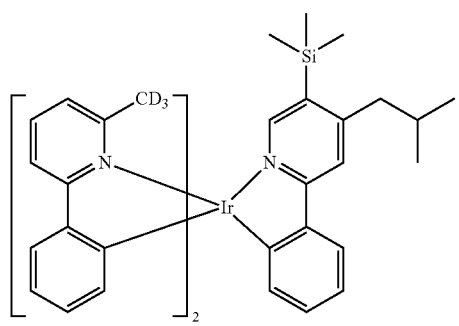
242 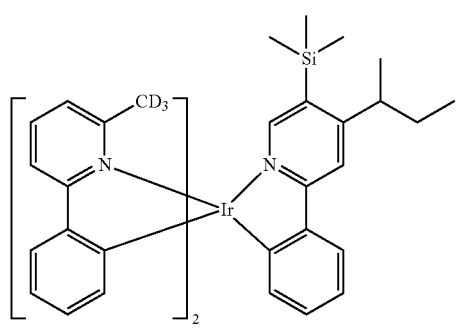
243 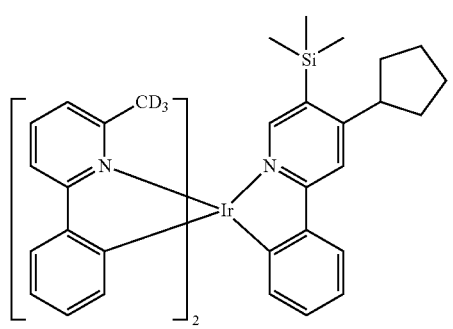
244 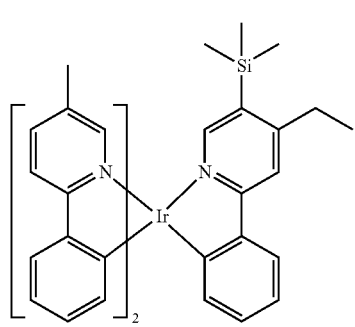
-continued
245 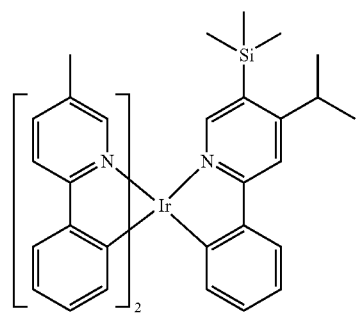
246 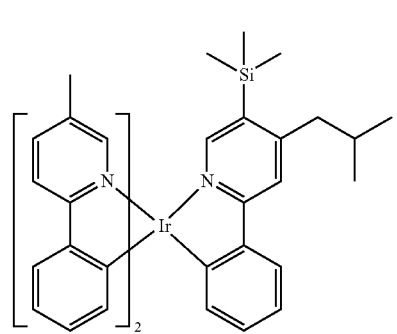
247 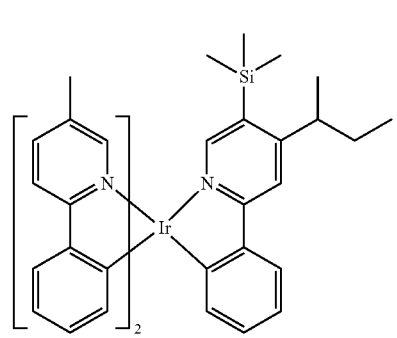
248 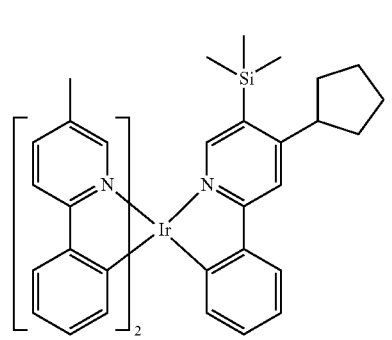
249 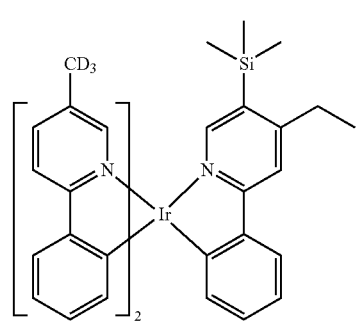

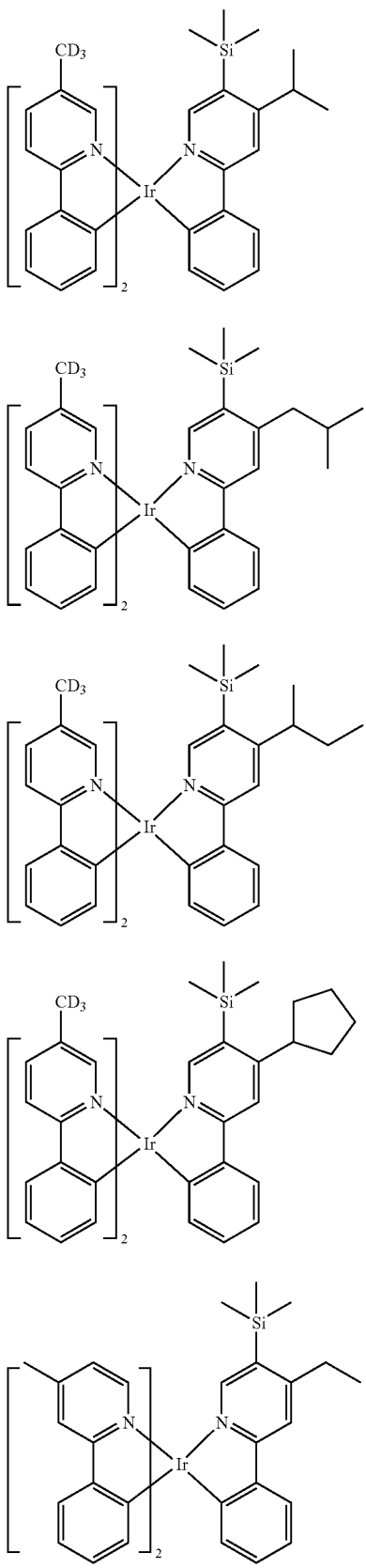
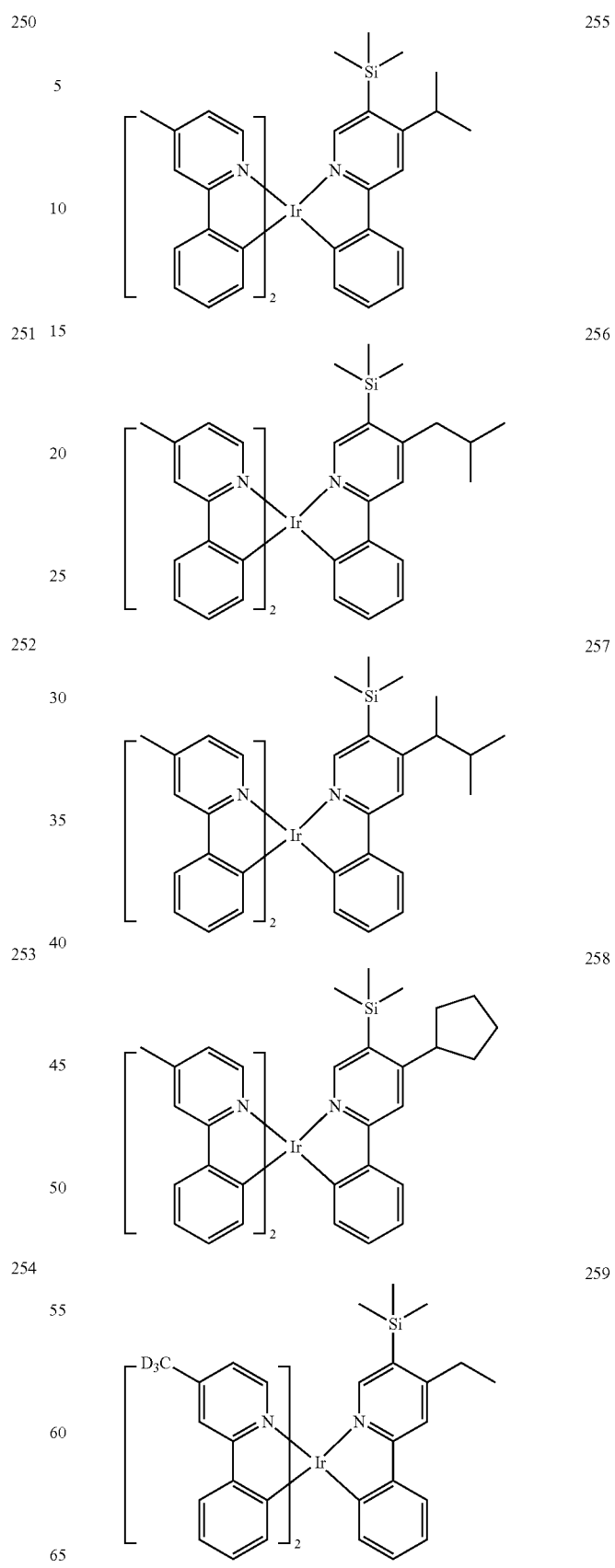

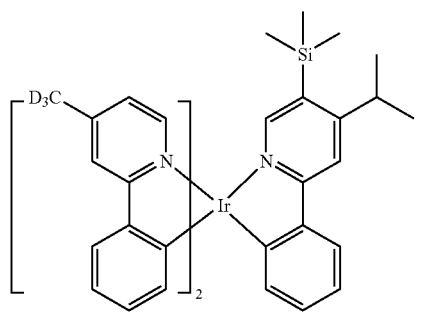
260
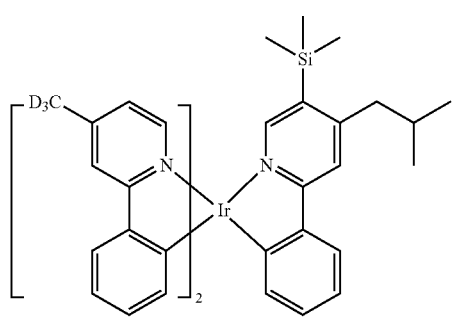
261
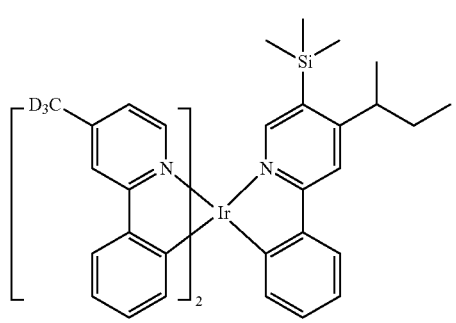
262
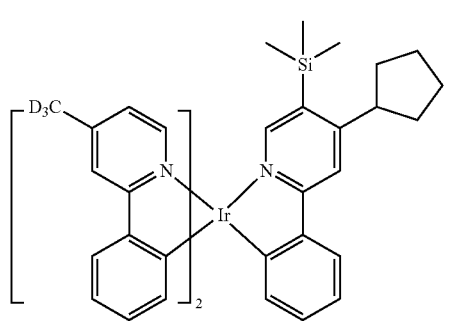
263
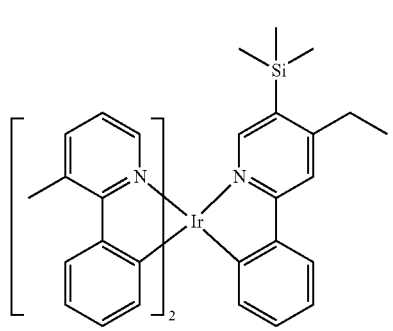
264
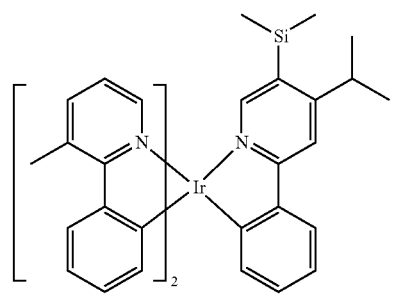
265
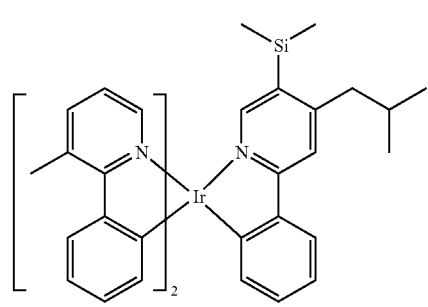
266
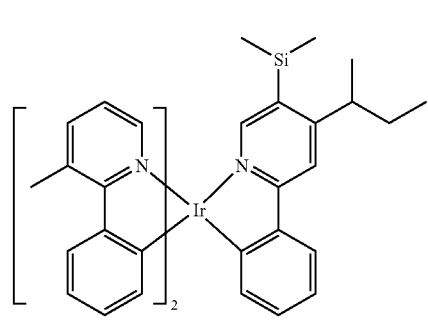
267
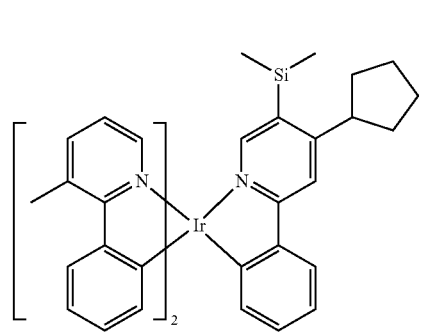
268
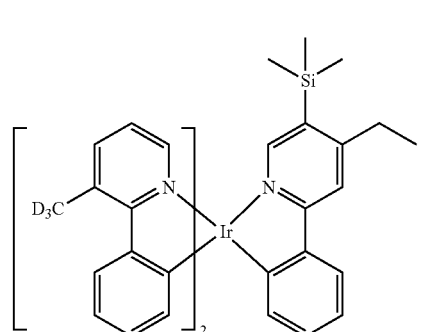
269

270
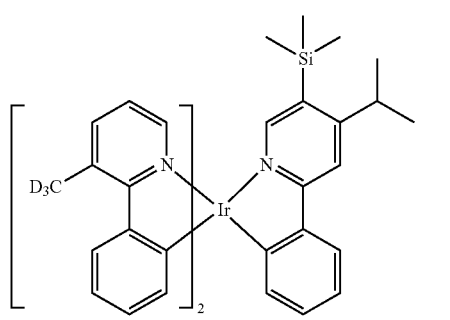
271
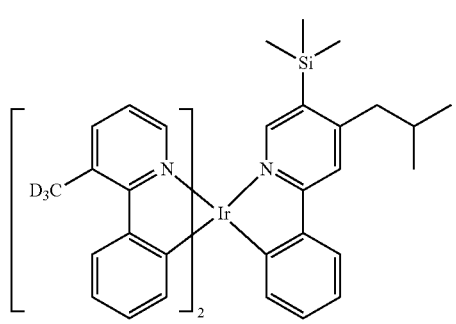
272
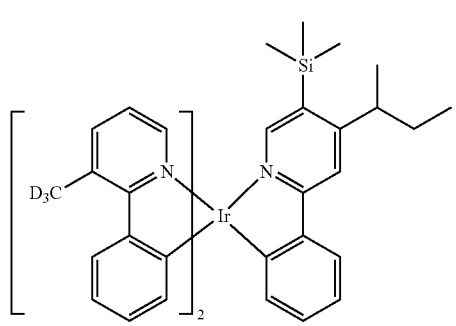
273
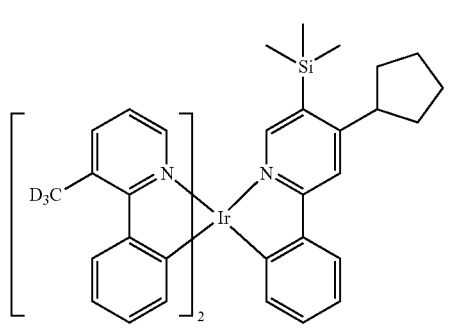
274
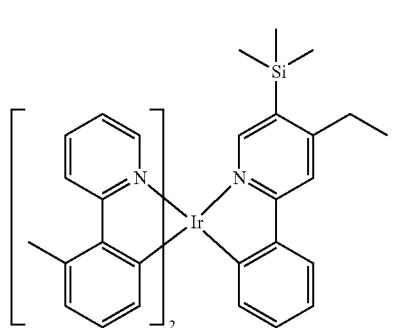
275
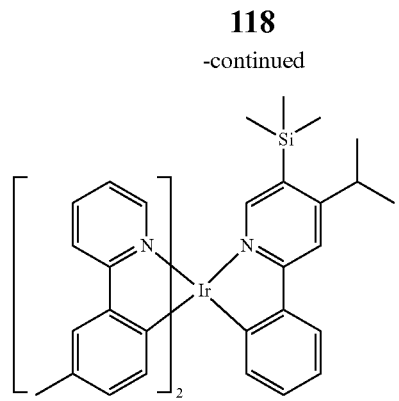
276
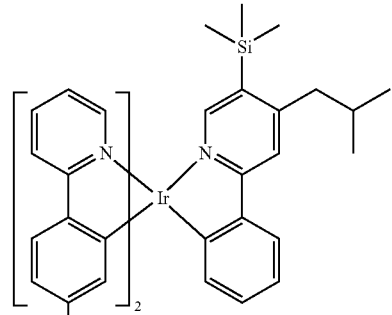
277
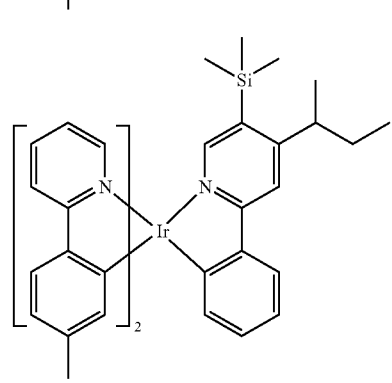
278
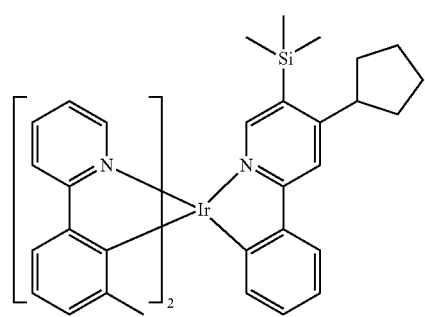
279
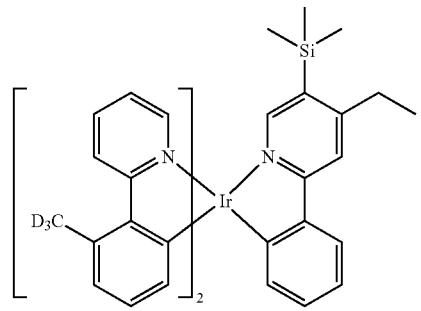

280 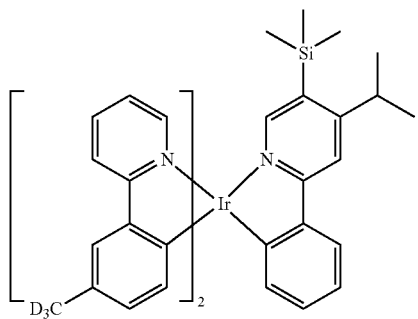
181 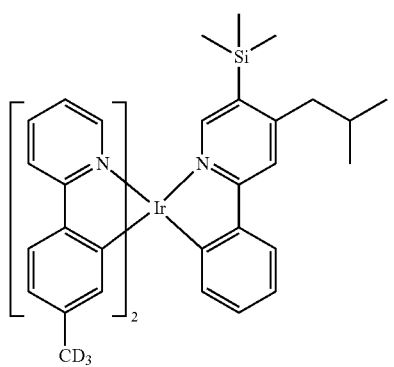
282 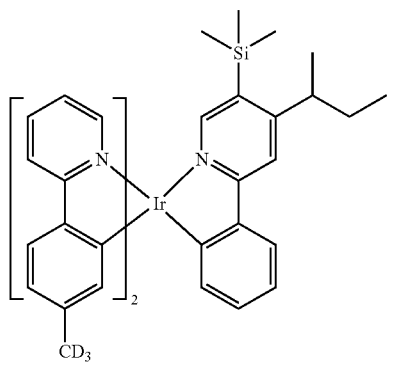
283 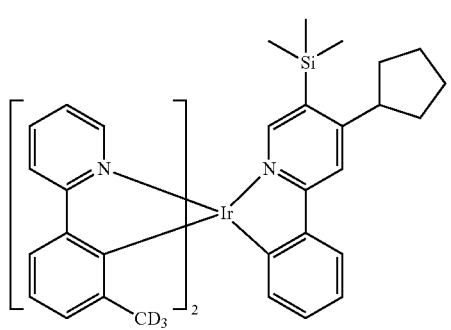
284 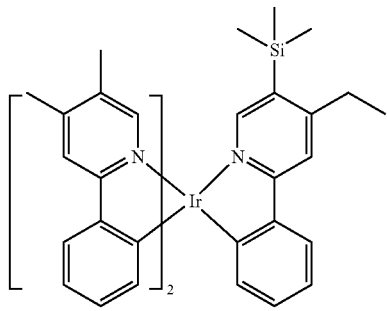
285 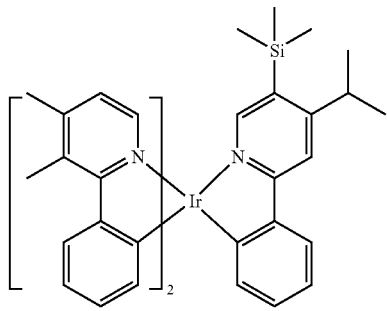
286 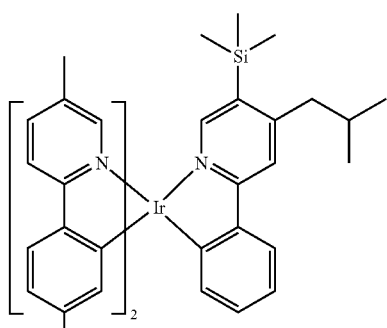
287 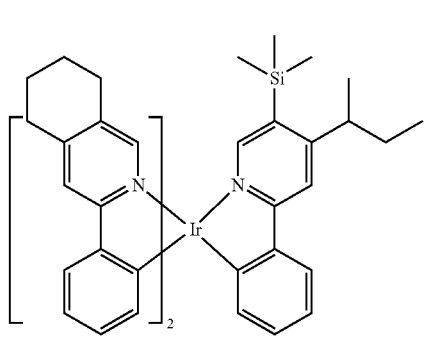
288 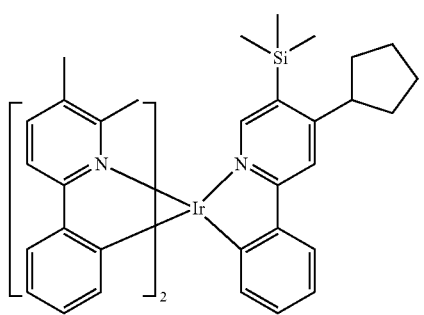

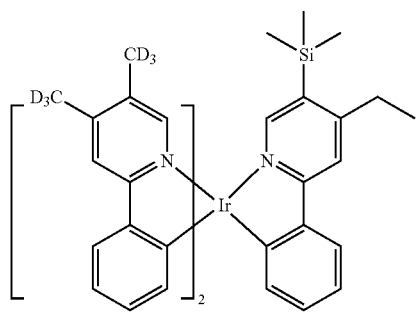
289
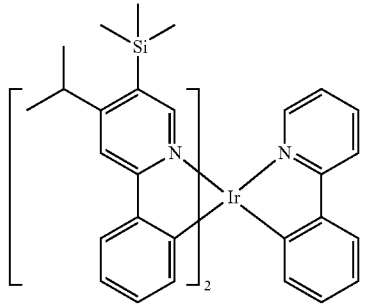
294
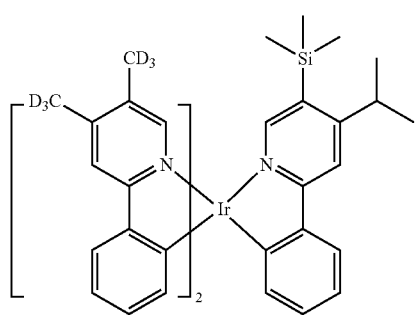
290
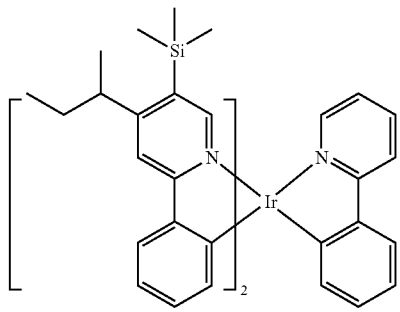
295
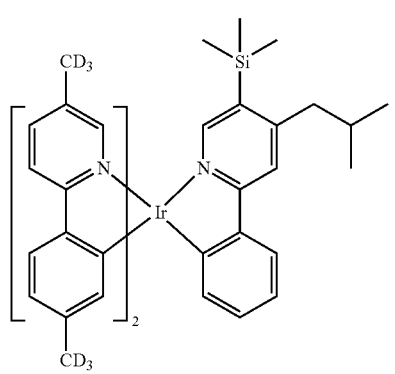
291
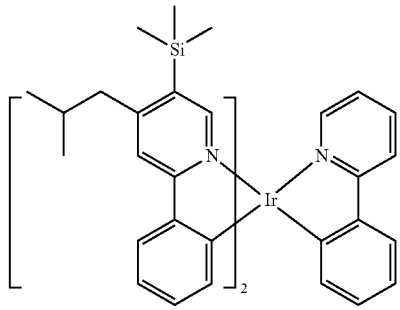
296
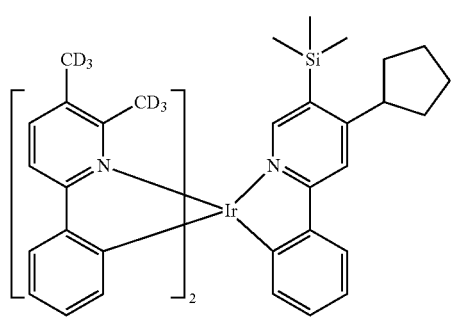
292
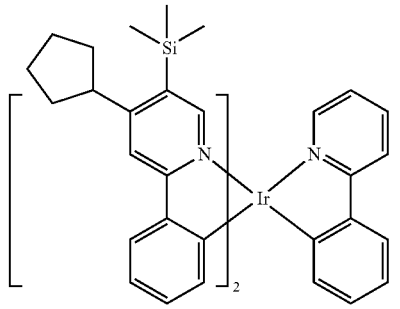
297
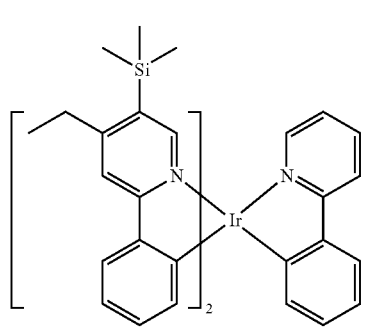
293
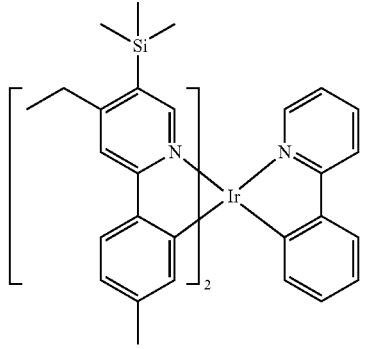
298

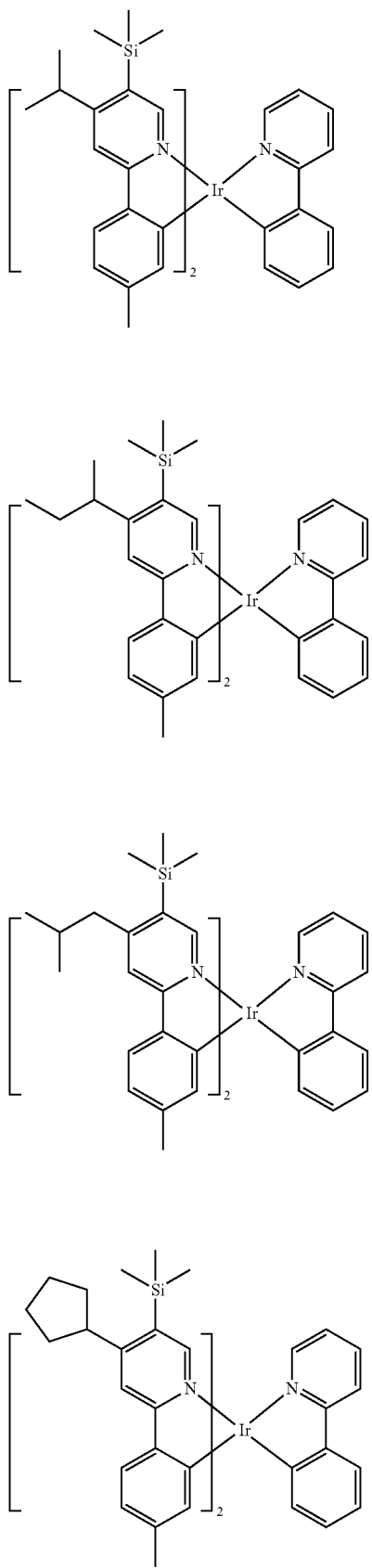
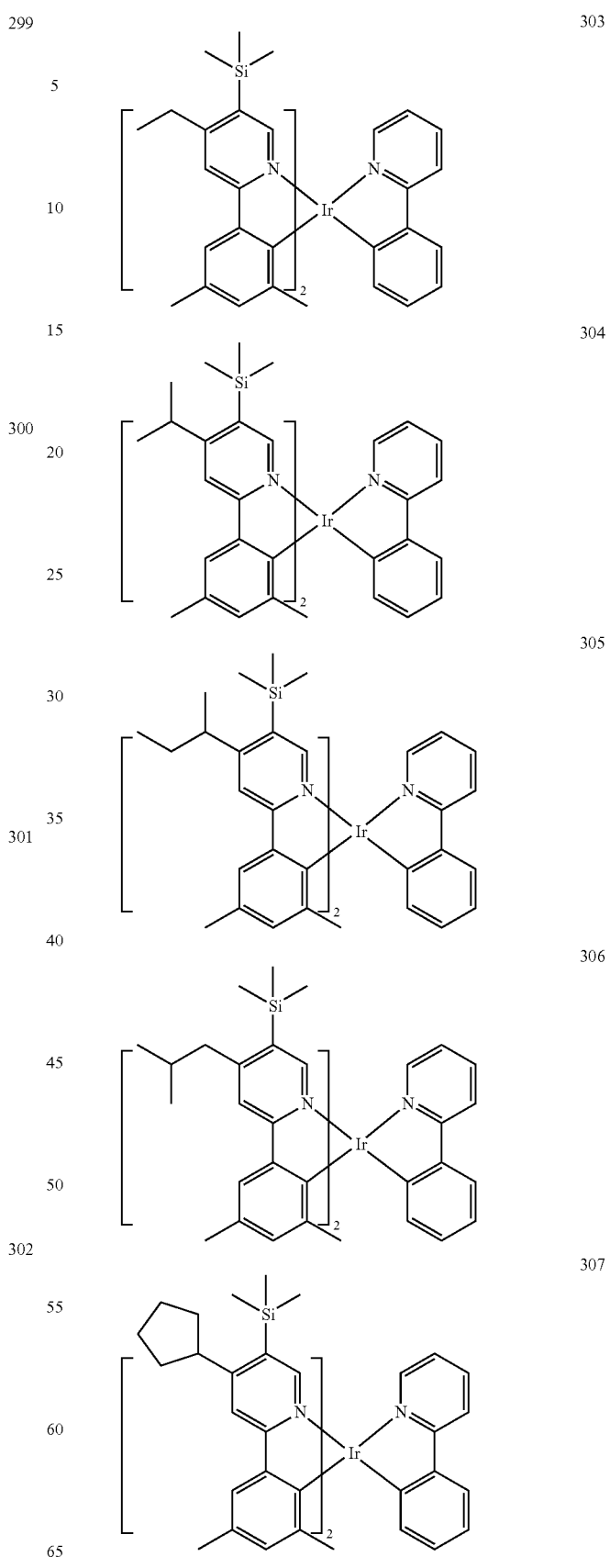

308
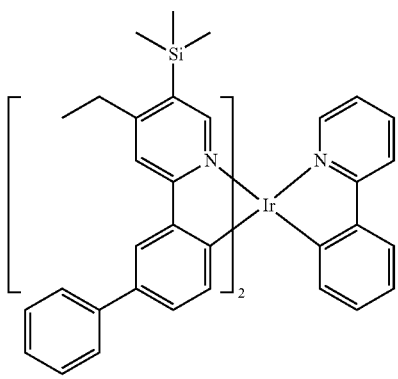
309
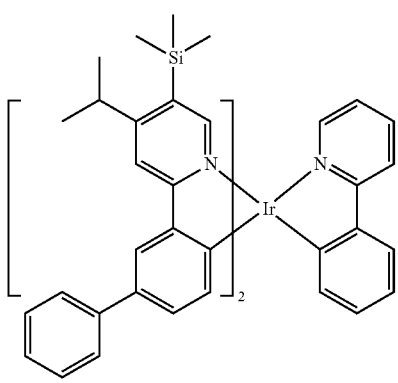
310
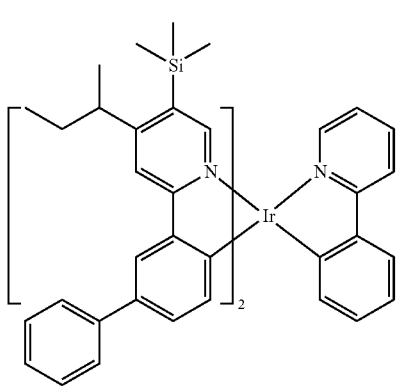
311
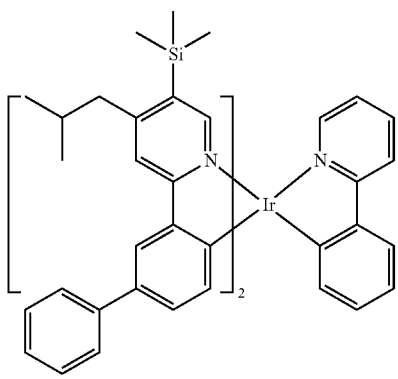
312
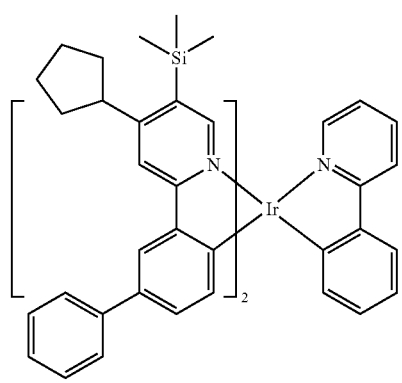
313
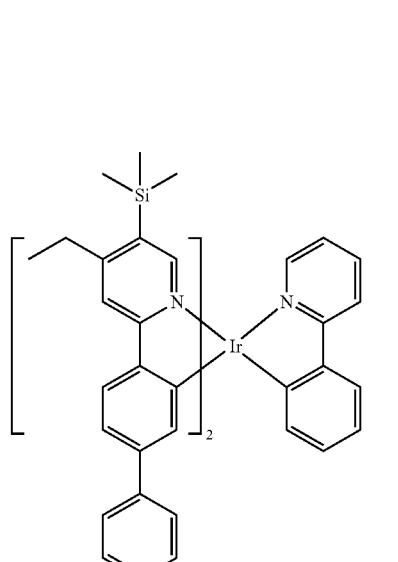
314
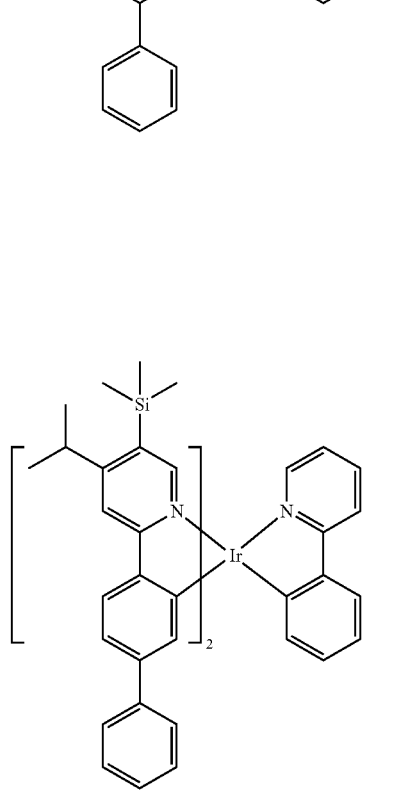

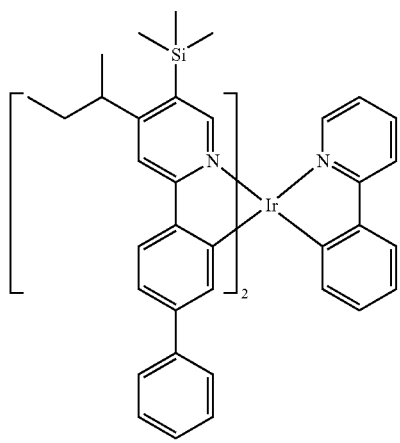
315
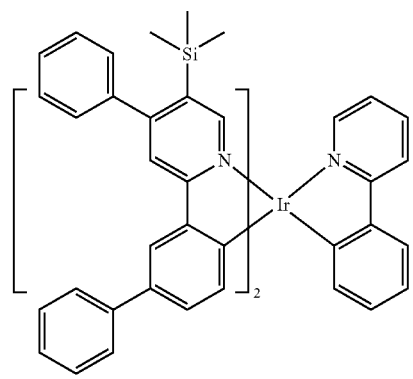
319
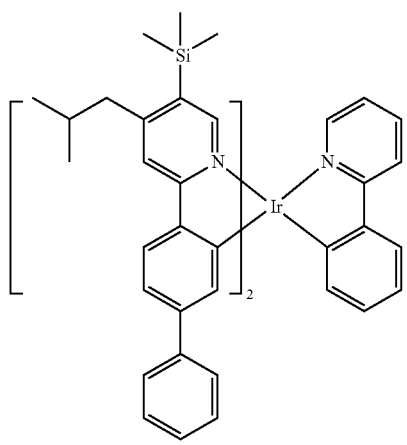
316
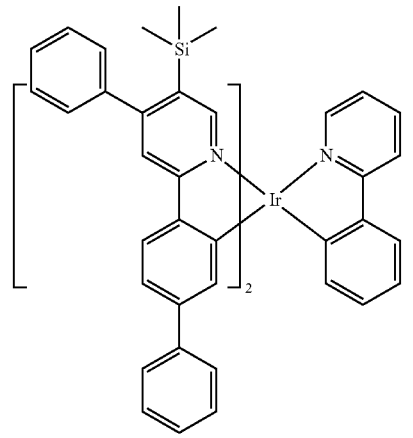
320
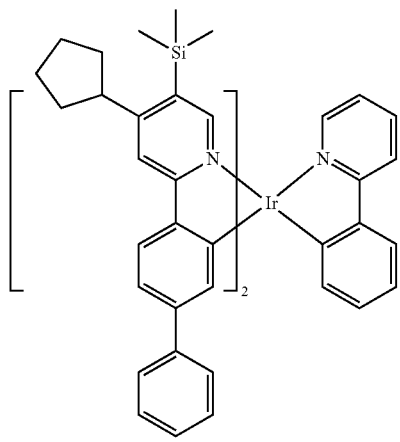
317
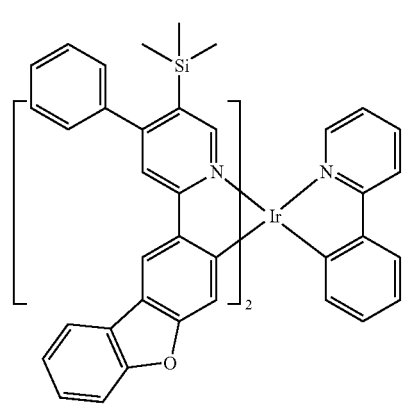
321
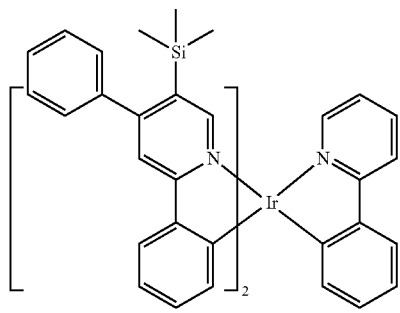
318
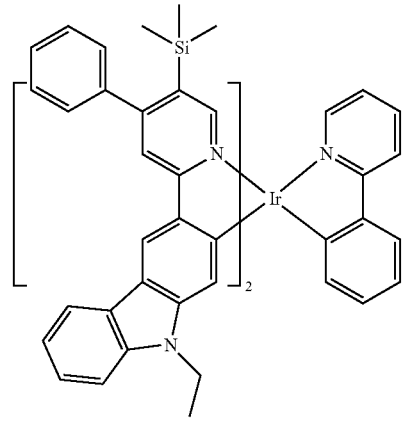
322

323
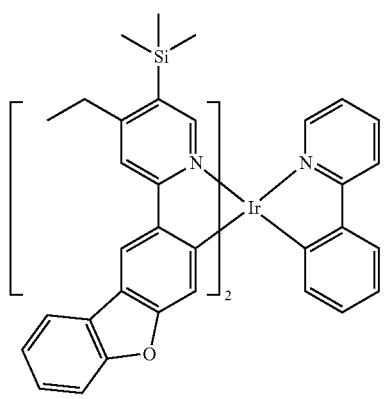
324
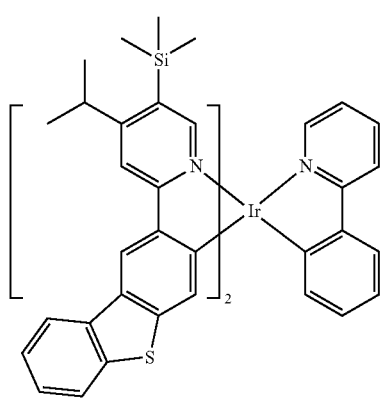
325
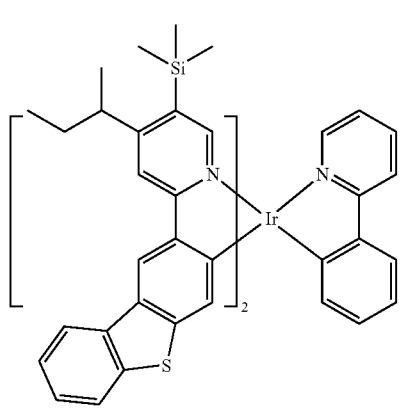
326
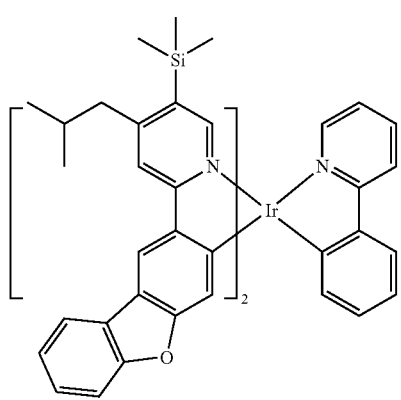
327
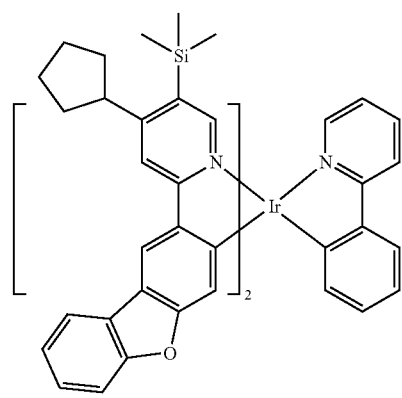
328
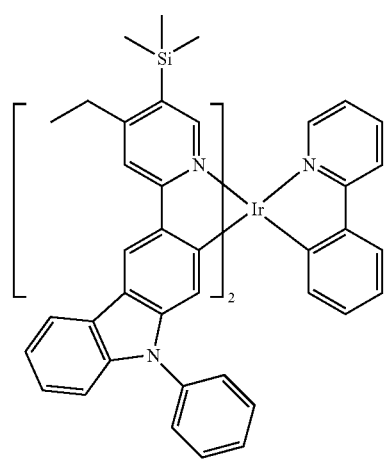
329

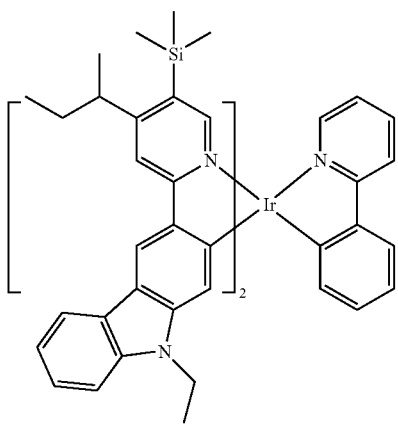
330
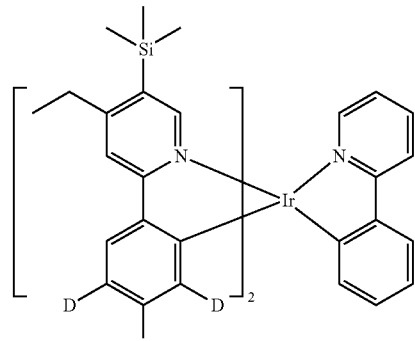
333
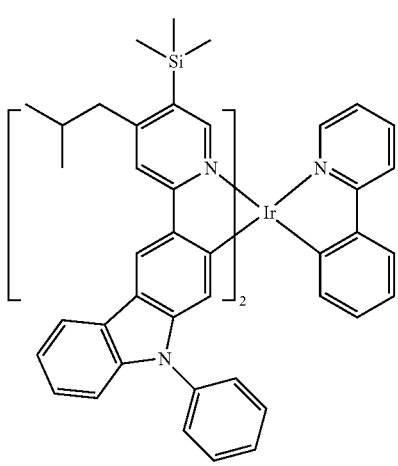
331
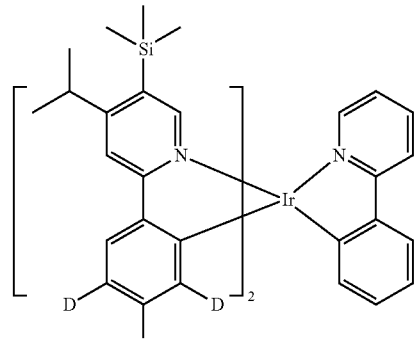
334
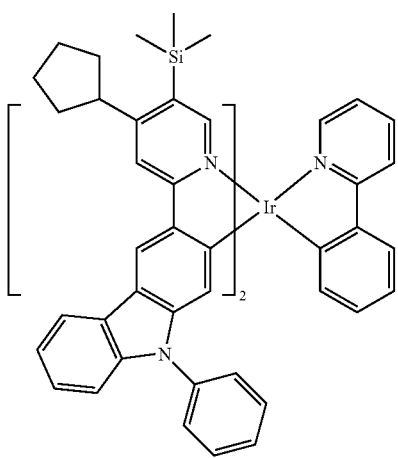
332
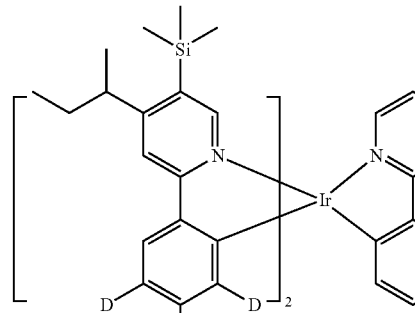
335
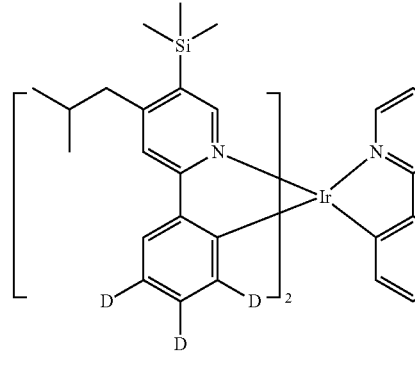
336

337 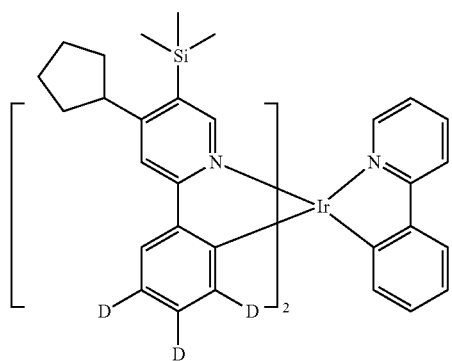
338 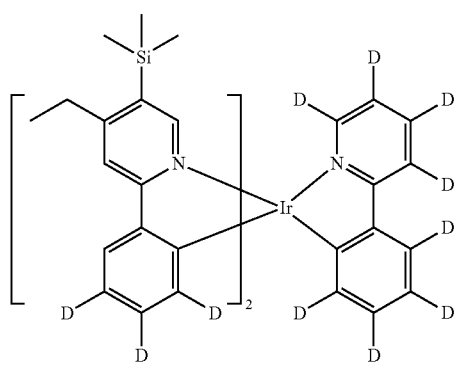
339 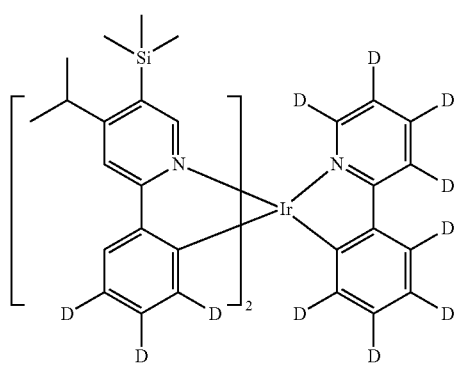
340 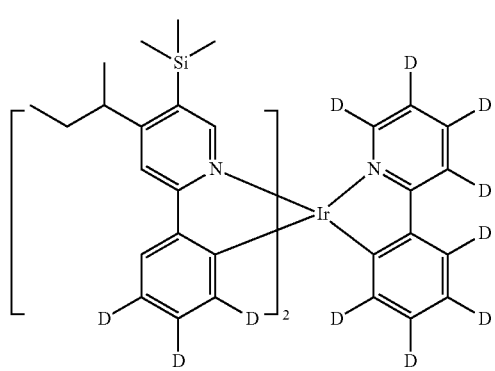
341 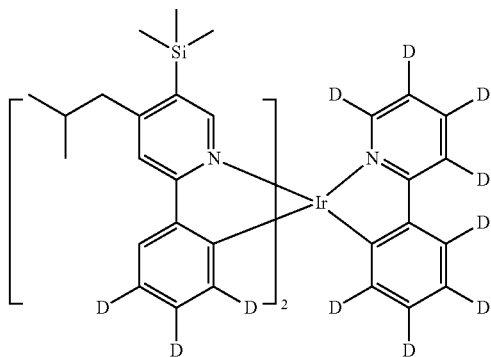
342 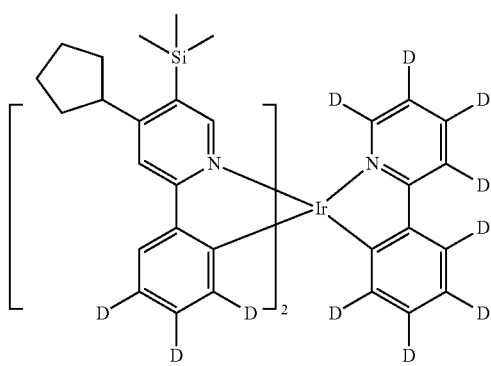
343 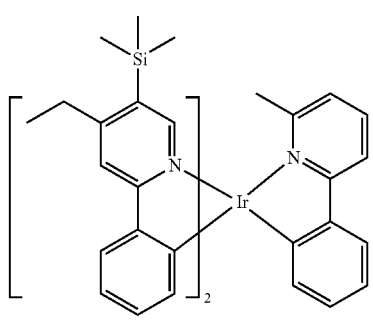
344 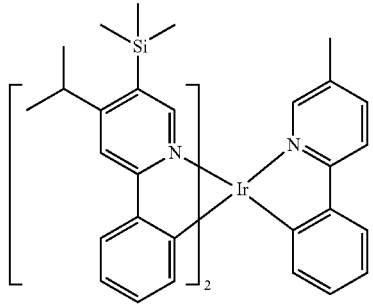

345
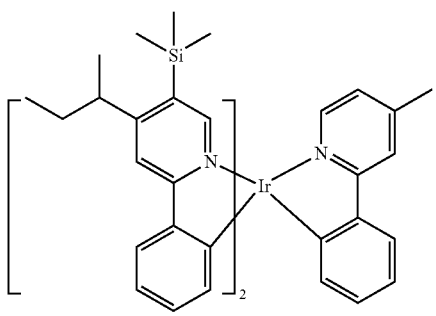
346
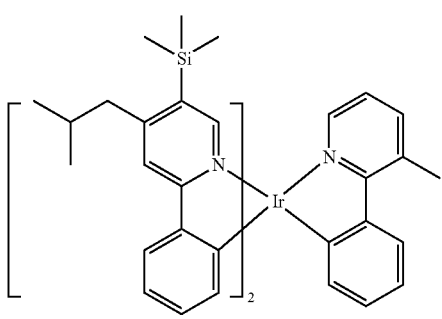
347
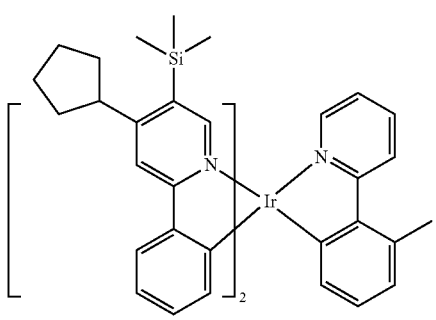
348
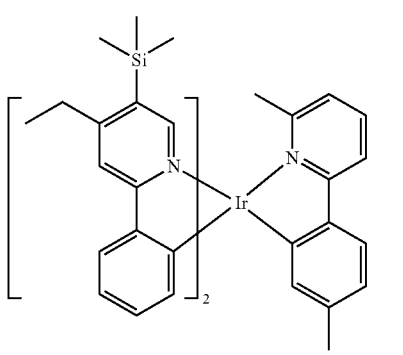
349
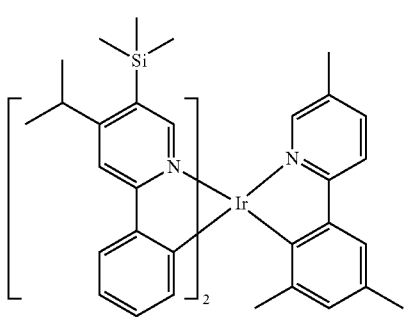
350
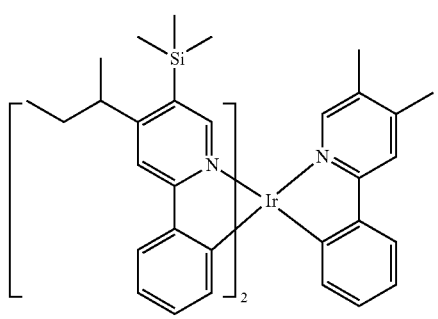
351
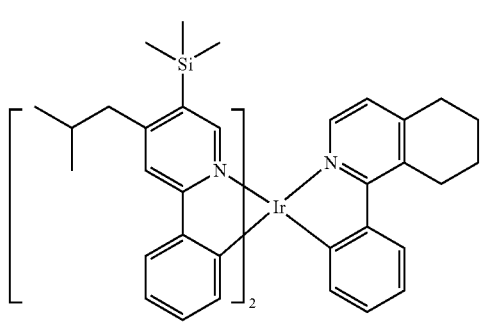
352
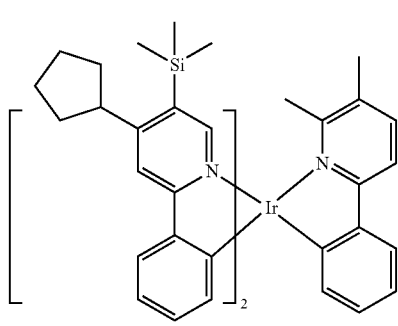
353
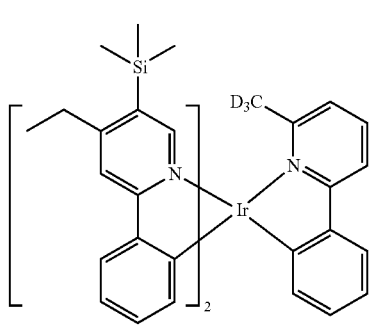
354
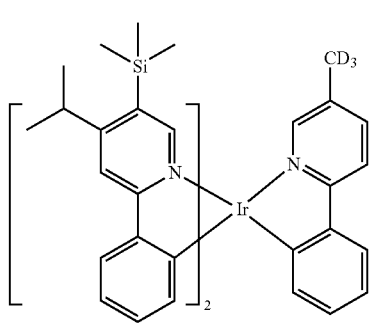

355 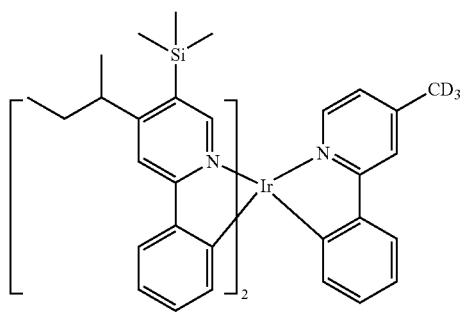
356 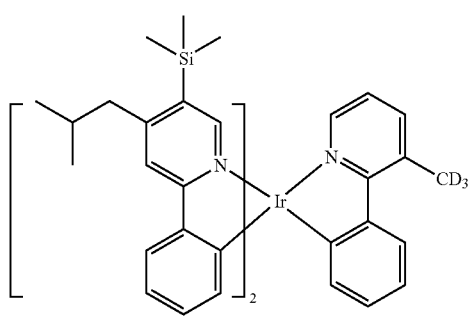
357 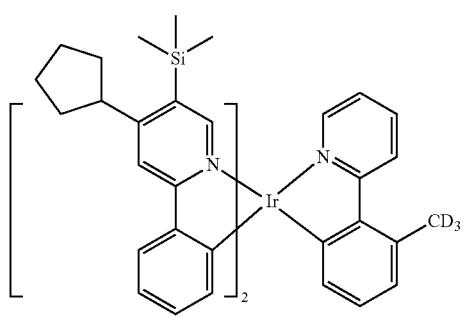
358 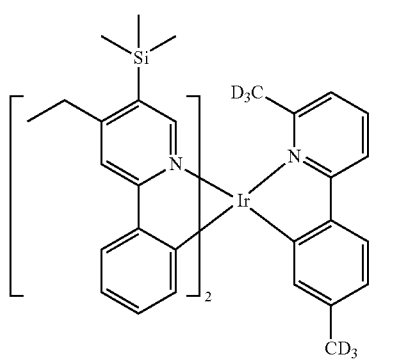
359 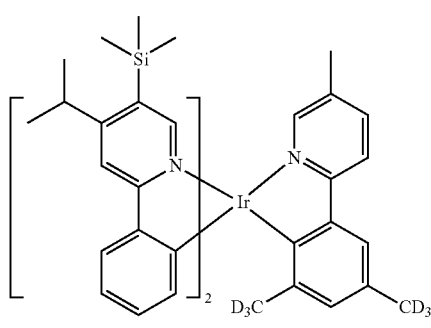
360 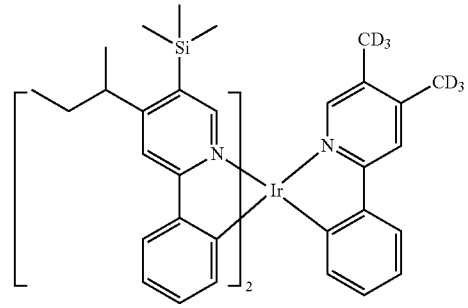
361 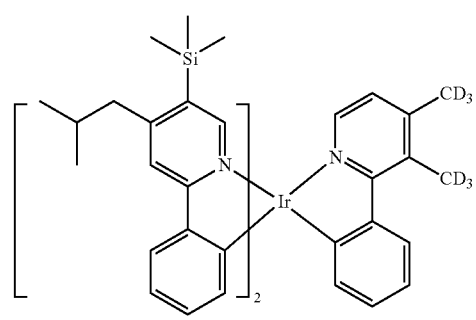
362 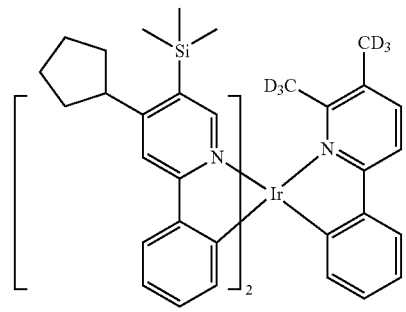
363 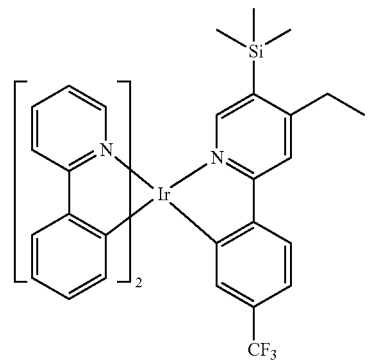

-continued
364
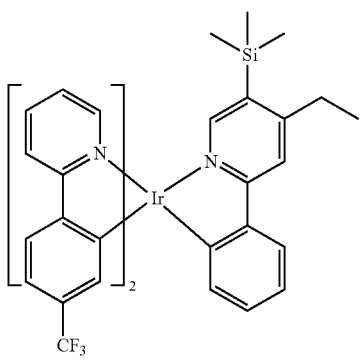
365
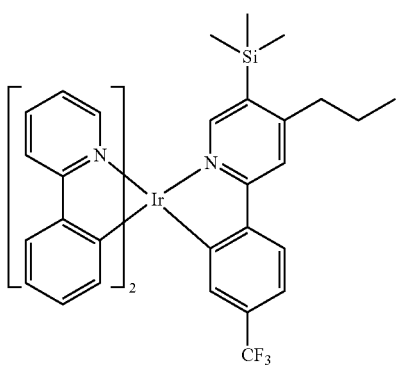
366
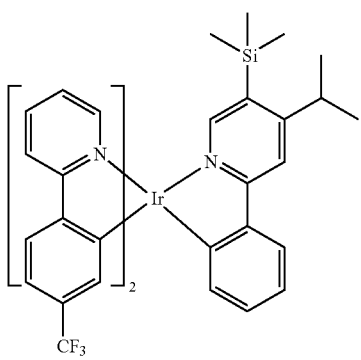
367
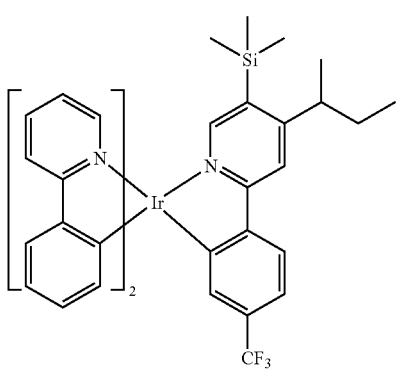
-continued
368
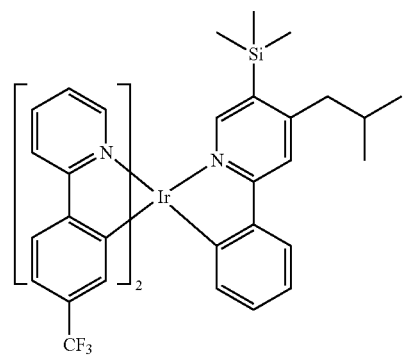
369
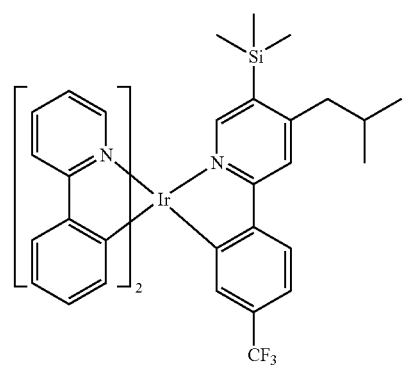
370
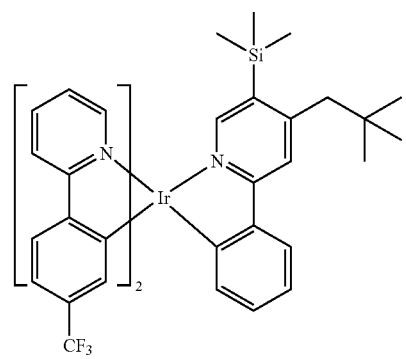
371
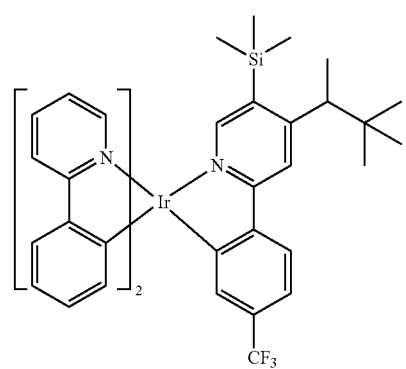

372
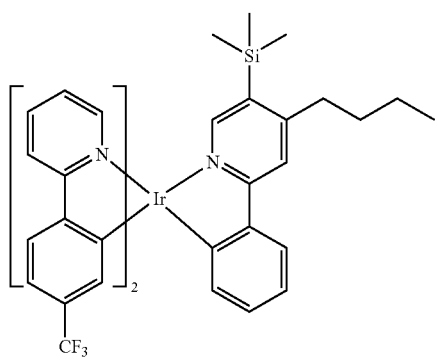
373
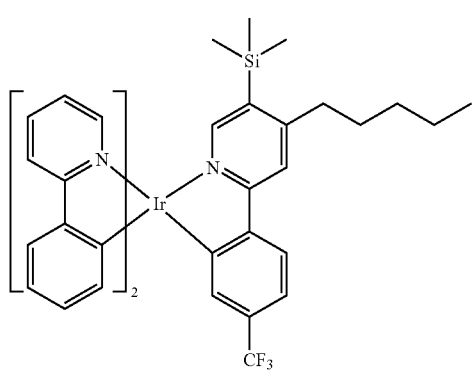
374
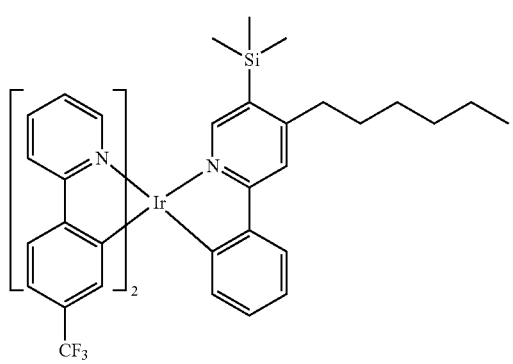
375
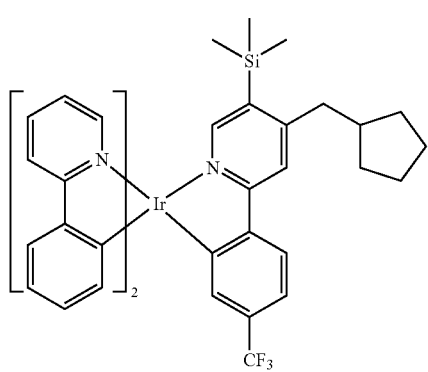
376
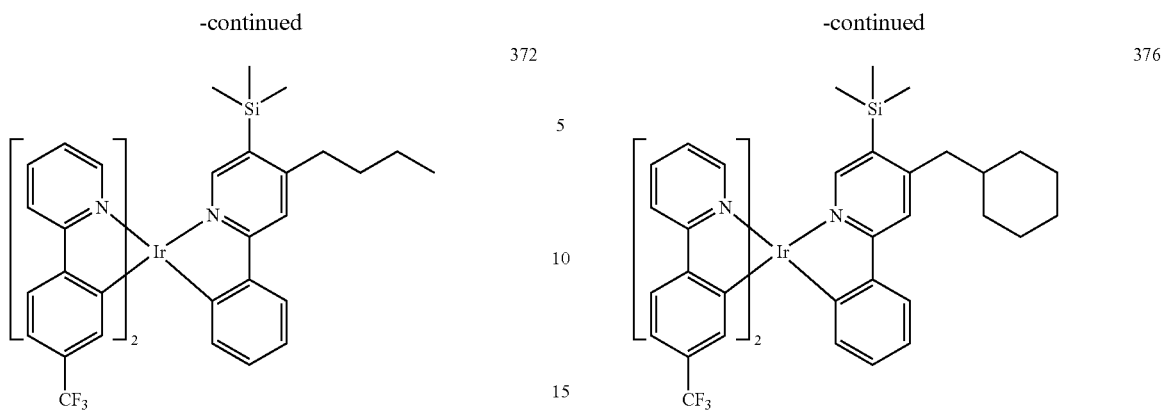
377
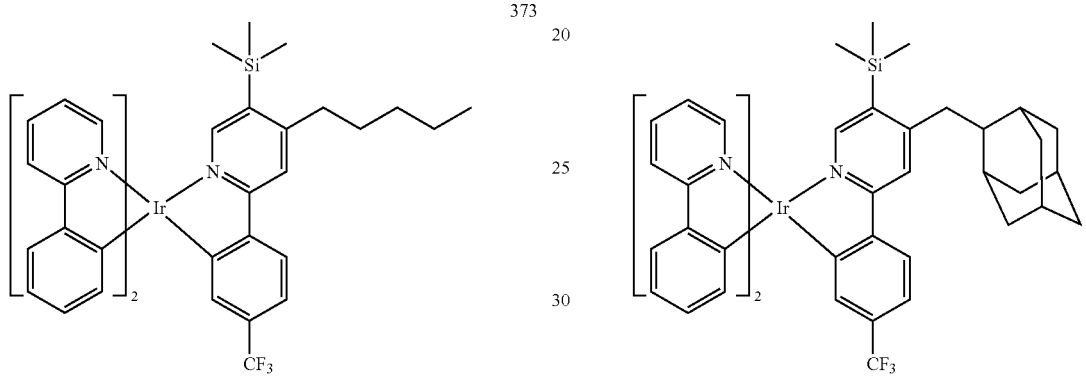
378
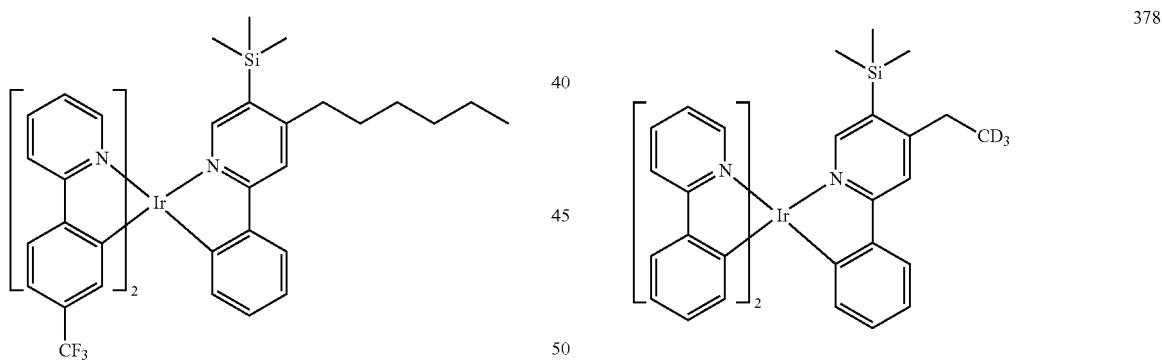
379
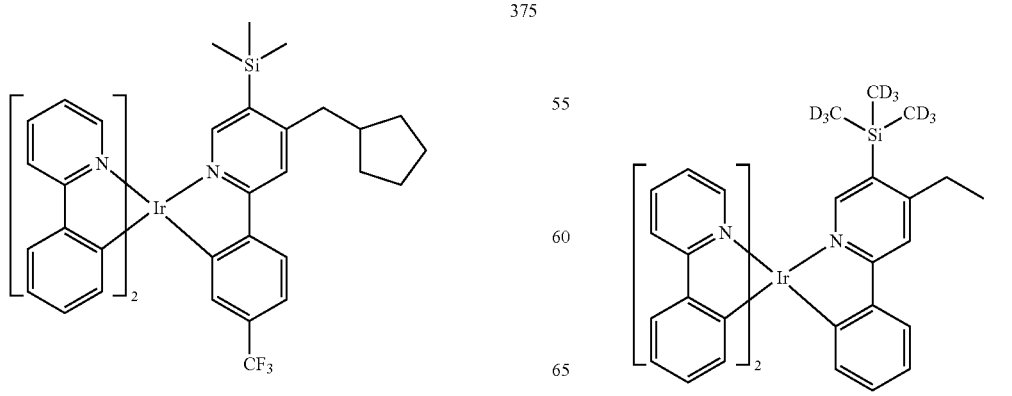

380
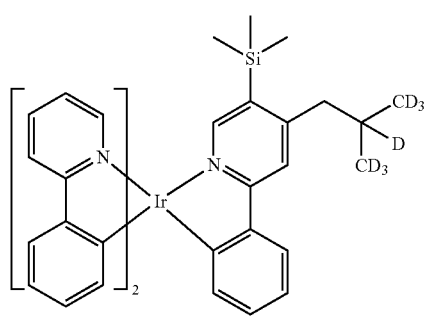
381
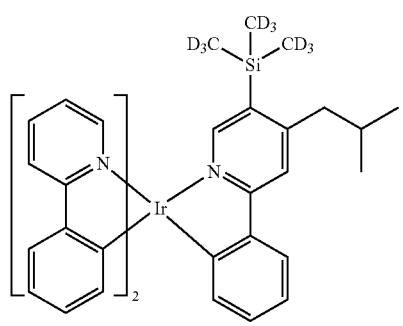
382
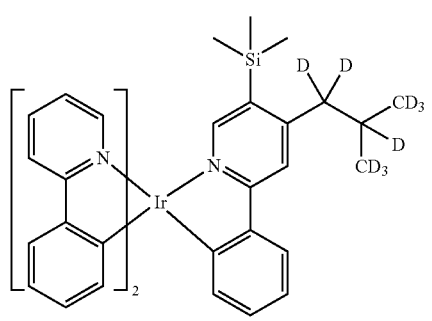
383
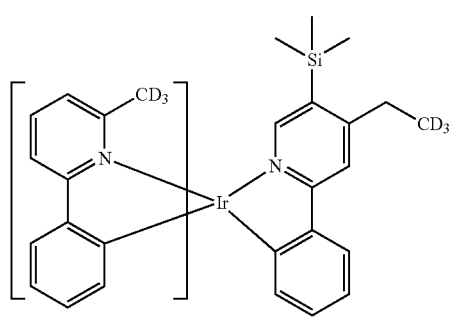
384
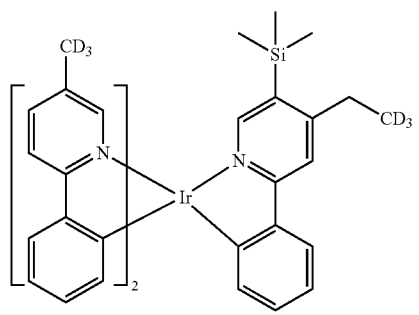
385
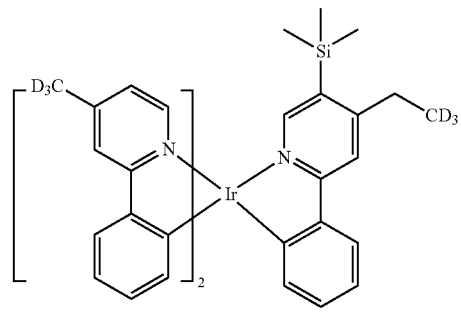
386
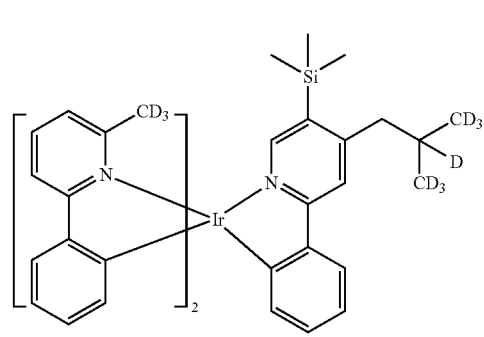
387
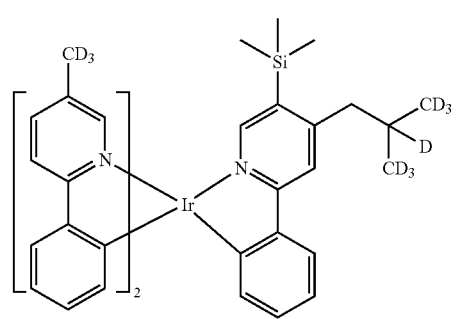
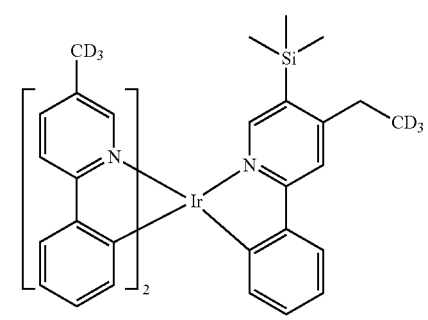

-continued

388

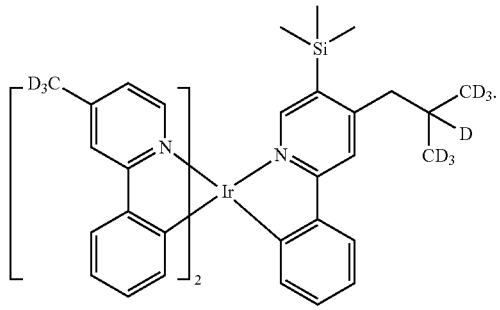

L₂ in Formula 1 is a ligand represented by Formula 2B, which is a phenyl-pyridinyl based bidentate ligand. Accordingly, the organometallic compound represented by Formula 1 has a highest occupied molecular orbital ("HOMO") energy level, lowest unoccupied molecular orbital ("LUMO") energy level, and T1 energy level which are appropriate for use as a material for an electric device, for example, a material for an organic light-emitting device. Thus, an organic light-emitting device using the organometallic compound represented by Formula 1 has excellent efficiency and lifespan characteristics.

$R_1$ to $R_3$ in Formula 2B are each independently a substituted or unsubstituted $C_1$-$C_{10}$ alkyl group and $R_{12}$ in Formula 2B is not a hydrogen and a methyl group. As such, the organometallic compound represented by Formula 1 may emit blue light, green light, or greenish blue light that is shifted toward relatively shorter wavelengths, and a device, for example, an organic light-emitting device, including the organometallic compound may have long lifespan.

In Formula 2B, a silyl group bonds to the fifth position of a pyridine ring (see Formula 2B). Due to the bonding, the organometallic compound including the ligand represented by Formula 2B has excellent heat resistance and decomposition resistance characteristics. Accordingly, a device, for example, an organic light-emitting device, including the organometallic compound has high stability during manufacturing, preserving, and/or driving, and long lifespan.

For example, HOMO, LUMO, singlet ($S_1$) and triplet ($T_1$) energy levels of some of the organometallic compounds and Compound A' were evaluated by using a density functional theory ("DFT") method of Gaussian program (structurally optimized at a level of B3LYP, 6-31 G(d,p)). Evaluation results are shown in Table 1.

TABLE 1

| Compound No. | HOMO(eV) | LUMO(eV) | $S_1$ energy level (eV) | $T_1$ energy level (eV) |
|---|---|---|---|---|
| 6 | −4.807 | −1.180 | 2.880 | 2.624 |
| 14 | −4.803 | −1.175 | 2.881 | 2.624 |
| 51 | −4.776 | −1.167 | 2.832 | 2.581 |
| 96 | −4.803 | −1.232 | 2.862 | 2.567 |
| 136 | −4.830 | −1.294 | 2.815 | 2.563 |
| 189 | −4.807 | −1.180 | 2.880 | 2.624 |
| 219 | −4.807 | −1.180 | 2.880 | 2.624 |
| 241 | −4.767 | −1.174 | 2.869 | 2.641 |

TABLE 1-continued

| Compound No. | HOMO(eV) | LUMO(eV) | $S_1$ energy level (eV) | $T_1$ energy level (eV) |
|---|---|---|---|---|
| 296 | −4.756 | −1.153 | 2.866 | 2.615 |
| A' | −4.936 | −1.567 | 2.691 | 2.498 |

Compound A'

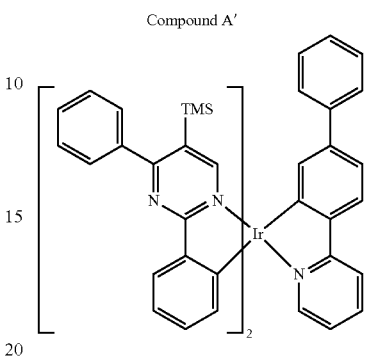

From Table 1, it is confirmed that absolute values of the HOMO energy level and LUMO energy level of Compound A' are greater than absolute values of the HOMO energy level and LUMO energy level of Compounds 6, 14, 51, 96, 136, 189, 219, 241, and 296, and $T_1$ energy value of Compound A' is smaller than $T_1$ energy values of Compounds 6, 14, 51, 96, 136, 189, 219, 241 and 296. Accordingly, the organometallic compound represented by Formula 1 provides higher charge mobility than Compound A', and thus, an electric device, for example, an organic light-emitting device, including the organometallic compound represented by Formula 1 may have excellent efficiency and lifespan characteristics. In addition, since the organometallic compound represented by Formula 1 provides a wider color reproduction range than Compound A', the use of the organometallic compound represented by Formula 1 may enable production of a high-quality organic light-emitting device.

Synthesis methods of the organometallic compound represented by Formula 1 may be understood to one of ordinary skill in the art by referring to Synthesis Examples provided.

The organometallic compound represented by Formula 1 is suitable for use in an organic layer of an organic light-emitting device, for example, for use as a dopant in an emission layer of the organic layer. Thus, another aspect provides an organic light-emitting device that includes: a first electrode; a second electrode; and an organic layer that is disposed between the first electrode and the second electrode and including an emission layer and at least one of the organometallic compound represented by Formula 1.

The organic light-emitting device may have, due to the inclusion of an organic layer including the organometallic compound represented by Formula 1, low driving voltage, high efficiency, high power, high quantum efficiency, long lifespan and excellent color coordinate.

The organometallic compound of Formula 1 may be used between a pair of electrodes of an organic light-emitting device to provide an emission layer. For example, the organometallic compound represented by Formula 1 may be included in the emission layer. In this regard, the organometallic compound may act as a dopant, and the emission layer may further include a host, wherein an amount of the organometallic compound represented by Formula 1 is less than an amount of the host.

In an embodiment, the organic layer, which includes at least one organometallic compound, may include two or more different organometallic compounds of Formula 1.

For example, the organic layer may include, as the organometallic compound, only Compound 1. In this regard, Compound 1 may be present in an emission layer of the organic light-emitting device. In some embodiments, the organic layer may include, as the organometallic compound, Compound 1 and Compound 2. In this regard, Compound 1 and Compound 2 may be present in a same layer, for example when an entirety of Compound 1 and Compound 2 are present in a same emission layer.

The first electrode may be an anode, which is a hole injection electrode, and the second electrode may be a cathode, which is an electron injection electrode; or the first electrode may be a cathode, which is an electron injection electrode, or the second electrode may be an anode, which is a hole injection electrode.

For example, the first electrode is an anode, and the second electrode is a cathode, and the organic layer includes i) a hole transport region that is disposed between the first electrode and the emission layer and includes at least one of a hole injection layer, a hole transport layer, and an electron blocking layer, and ii) an electron transport region that is disposed between the emission layer and the second electrode and includes at least one selected from a hole blocking layer, an electron transport layer, and an electron injection layer.

The term "organic layer" used herein refers to a single layer and/or a plurality of layers disposed between the first electrode and the second electrode of an organic light-emitting device. The "organic layer" may include, in addition to an organic compound, an organometallic complex including metal.

The FIGURE is a schematic view of an embodiment of an organic light-emitting device 10. Hereinafter, the structure of an organic light-emitting device according to an embodiment and a method of manufacturing an organic light-emitting device according to an embodiment will be further disclose with reference to the FIGURE. The organic light-emitting device 10 includes a first electrode 11, an organic layer 15, and a second electrode 19, which are sequentially stacked.

In the FIGURE, a substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water-proofness.

The first electrode 11 may be formed by depositing or sputtering a material for forming the first electrode on the substrate. The first electrode 11 may be an anode. The material for the first electrode 11 may be selected from materials with a high work function to allow holes be easily provided. The first electrode 11 may be a reflective electrode or a transmissive electrode. The material for the first electrode 11 may be an indium tin oxide ("ITO"), indium zinc oxide ("IZO"), tin oxide ($SnO_2$), or zinc oxide (ZnO). In some embodiments, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers. For example, the first electrode 11 may have a three-layered structure of ITO/Ag/ITO, but the structure of the first electrode 11 is not limited thereto.

An organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one of a hole injection layer, a hole transport layer, an electron blocking layer, and a buffer layer.

The hole transport region may include only either a hole injection layer or a hole transport layer. According to another embodiment, the hole transport region may have a structure of hole injection layer/hole transport layer or hole injection layer/hole transport layer/electron blocking layer, which are sequentially stacked in this stated order from the first electrode 11.

When the hole transport region includes a hole injection layer (HIL), the hole injection layer may be formed on the first electrode 11 by using any one of various methods, for example, vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2000 revolutions per minute ("rpm") to about 5000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4''-tris(N-carbazolyl)triphenylamine ("TCTA"), polyaniline/dodecylbenzenesulfonic acid ("Pani/DBSA"), poly(3,4-ethylenedioxythiophene)/poly(4-styrene-sulfonate) ("PEDOT/PSS"), polyaniline/camphor sulfonicacid ("Pani/CSA"), polyaniline/poly(4-styrenesulfonate) ("PANI/PSS"), a compound represented by Formula 201, and a compound represented by Formula 202:

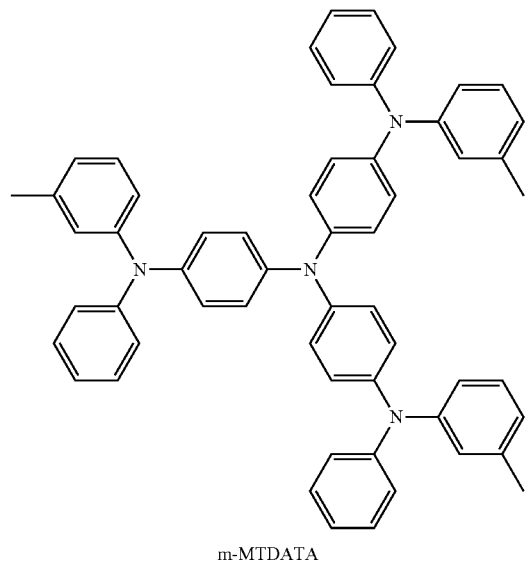

m-MTDATA

-continued
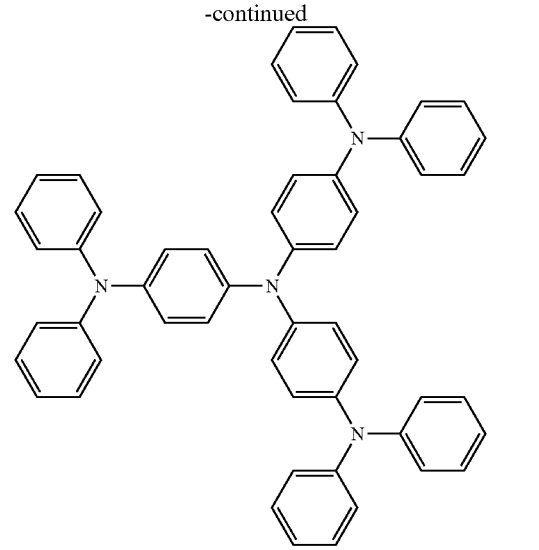
TDATA
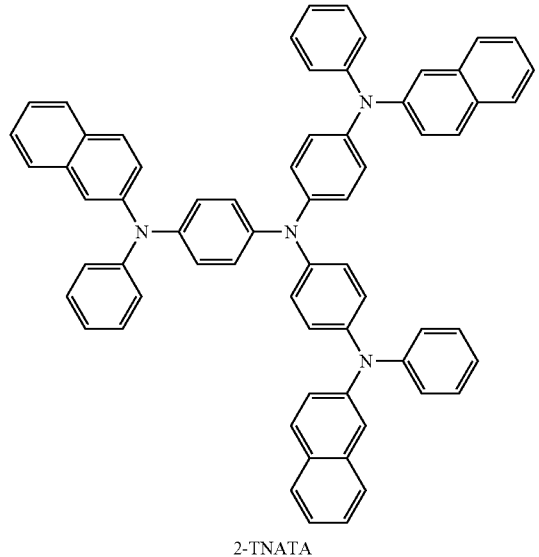
2-TNATA
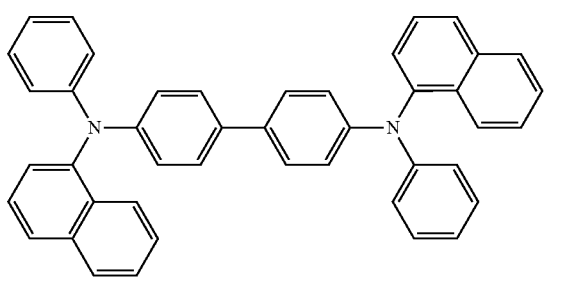
NPB
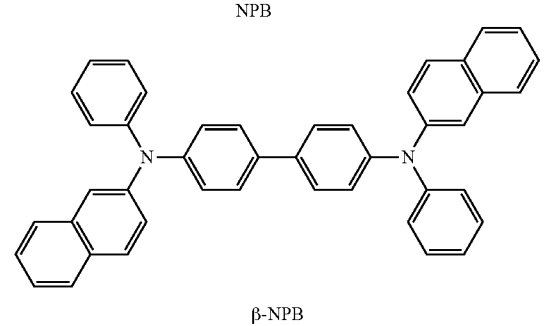
β-NPB
-continued
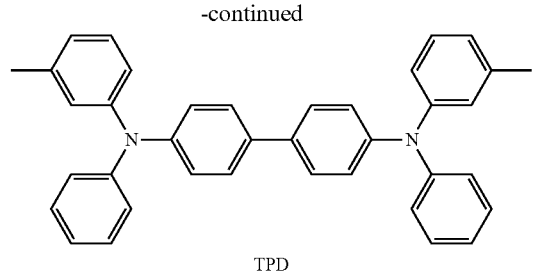
TPD
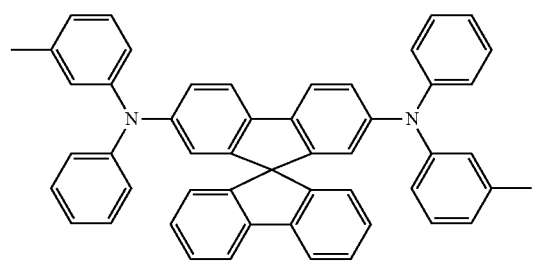
Spiro-TPD
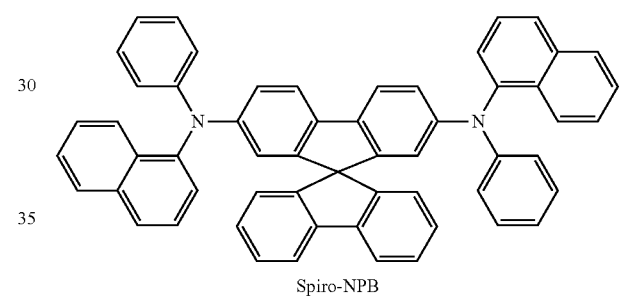
Spiro-NPB
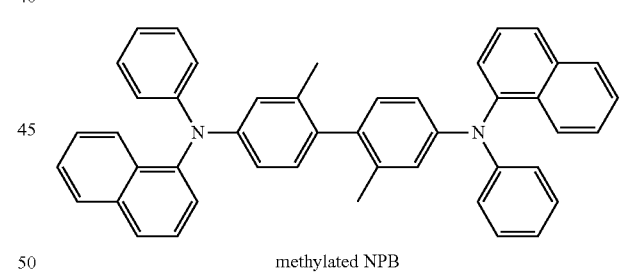
methylated NPB
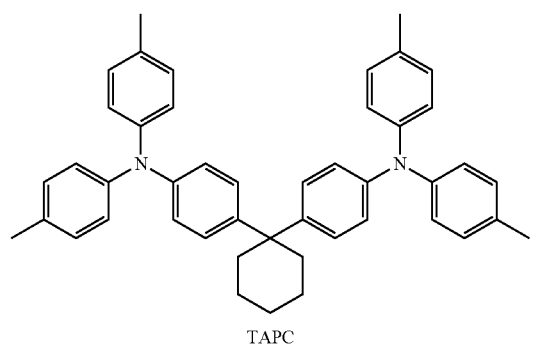
TAPC -continued

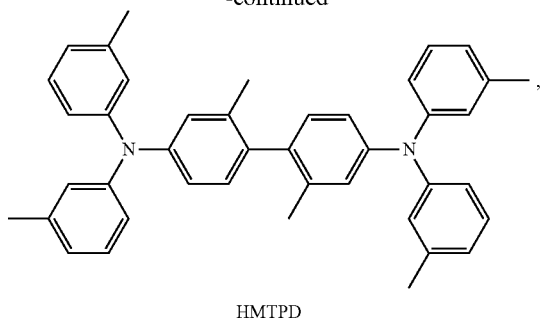

HMTPD

Formula 201

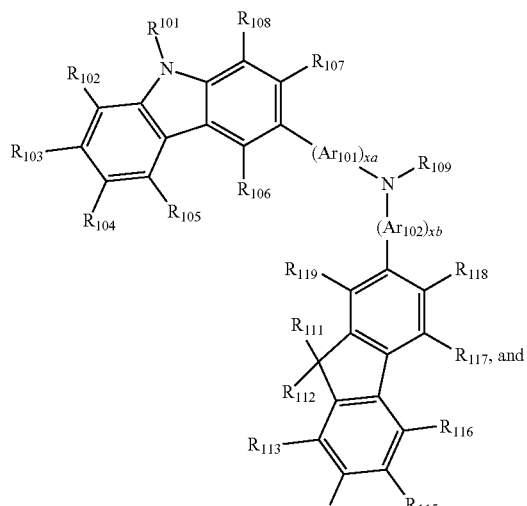

Formula 202

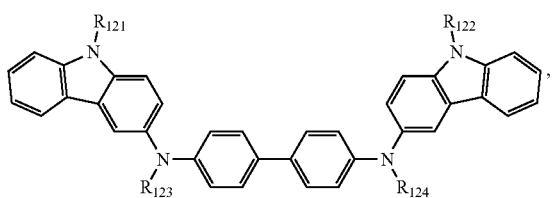

wherein $Ar_{101}$ and $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently selected from 0, 1, 2, 3, 4, and 5, and for example, may each be 0, 1, or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulas 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), and a $C_1$-$C_{10}$ alkoxy group (for example, a methoxy group, an ethoxy group, a propoxy group, a butoxy group, a pentoxy group, and so on);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from a phenyl group, a naphthyl group, an anthracenyl group and a pyridinyl group; and a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but is not limited thereto:

Formula 201A

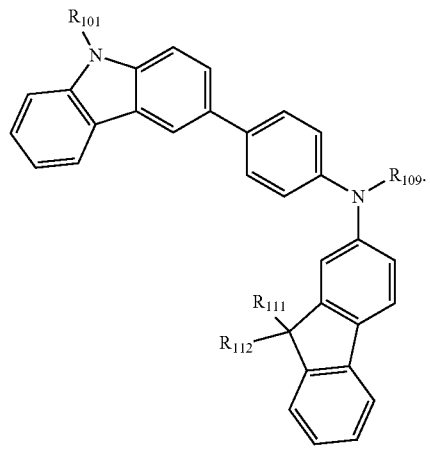

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated, but are not limited thereto.

HT1

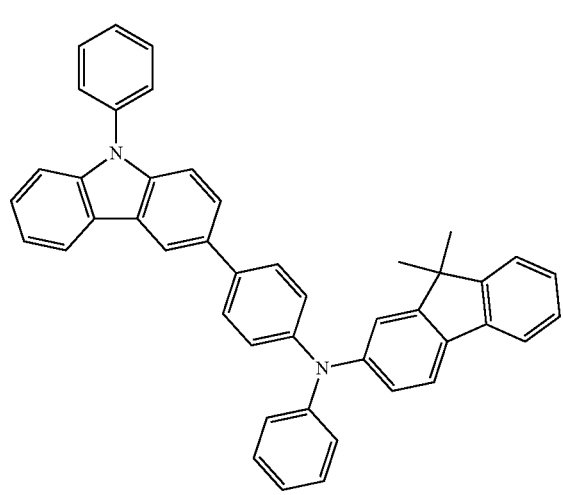

HT2

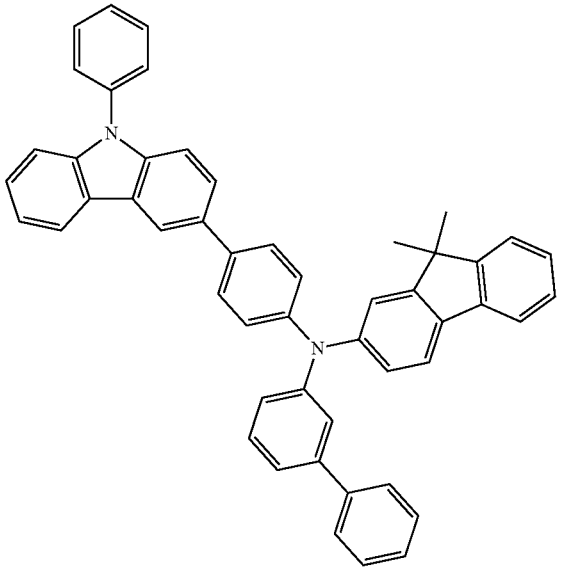

HT3

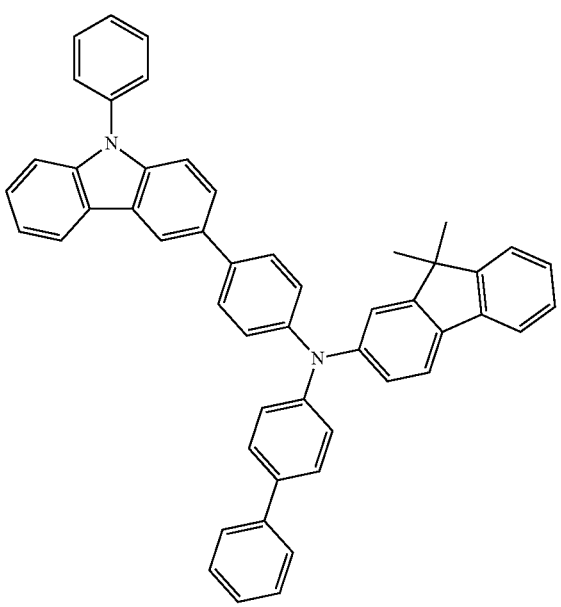

HT4
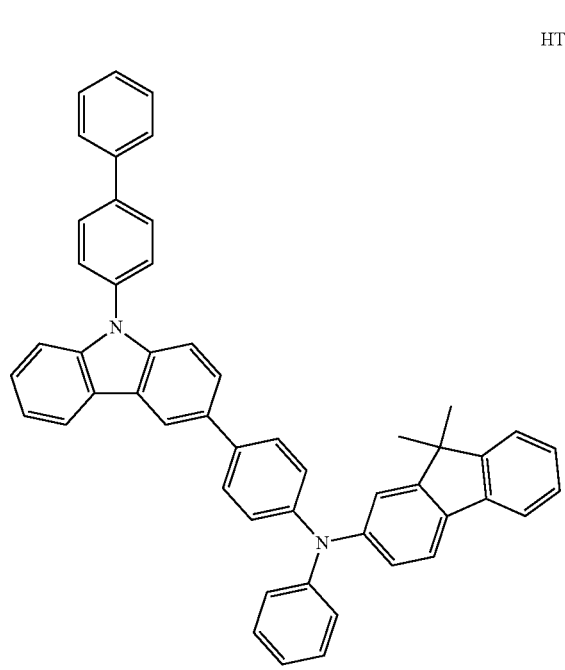
HT6
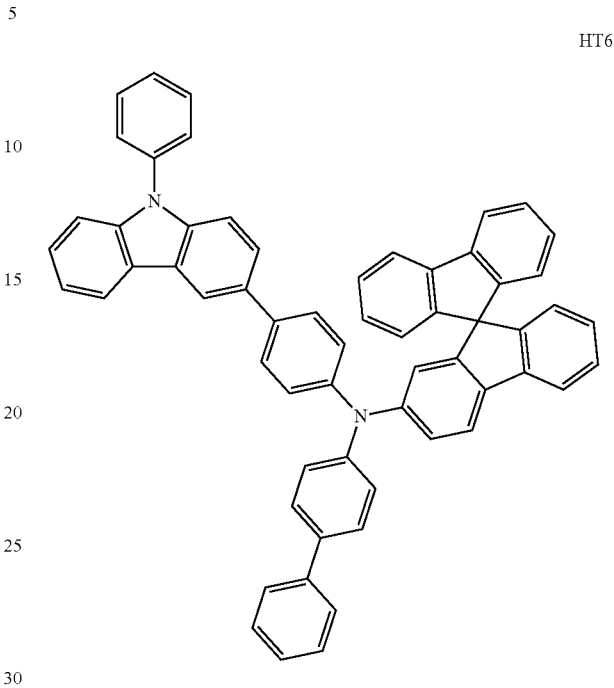
HT5
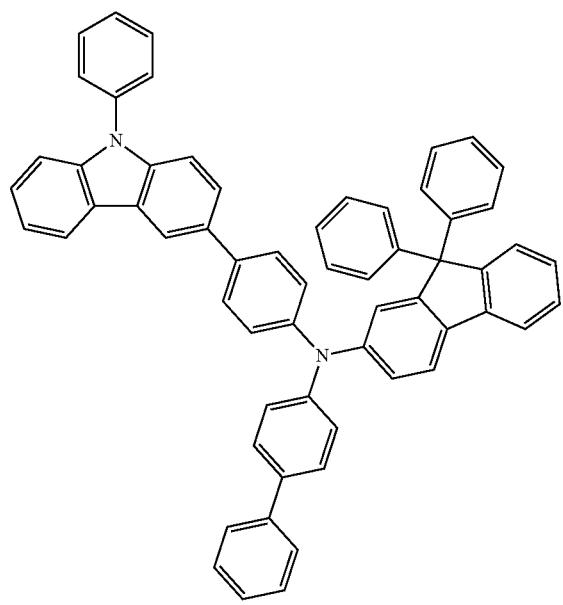
HT7

-continued
HT8
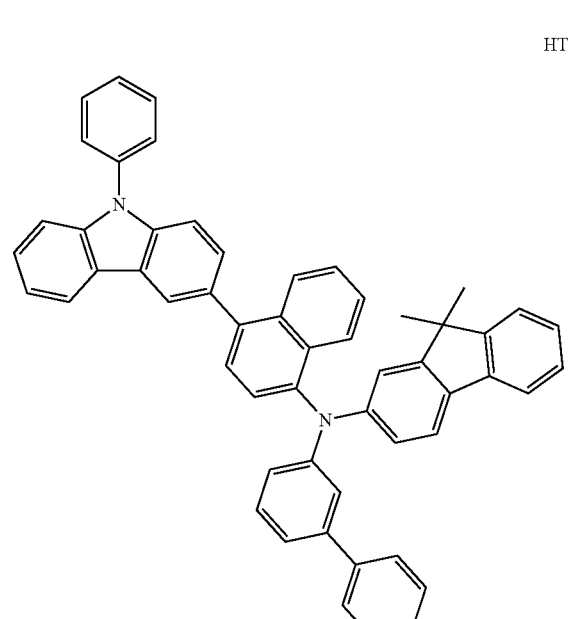
HT10
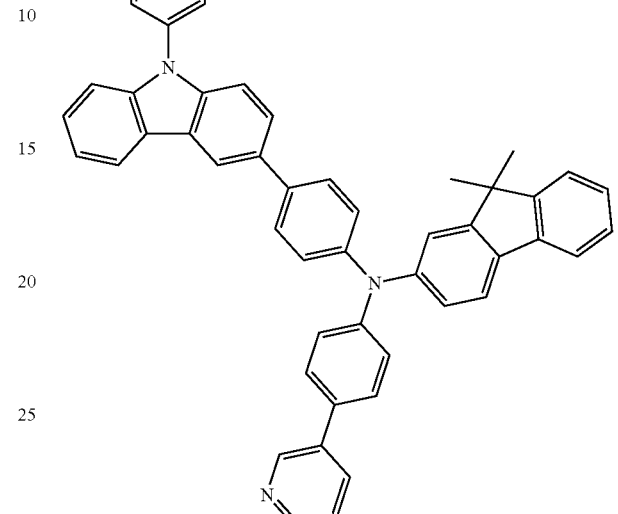
HT9
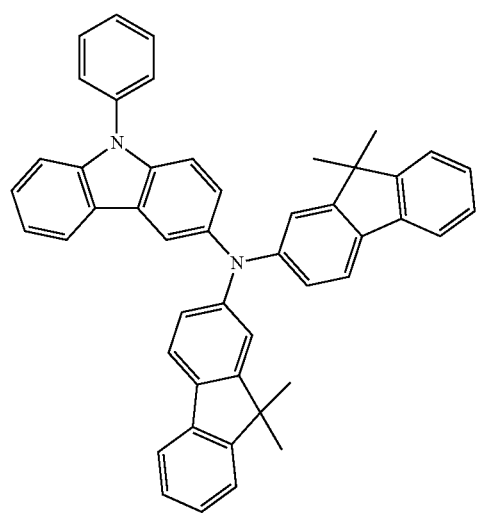
HT11
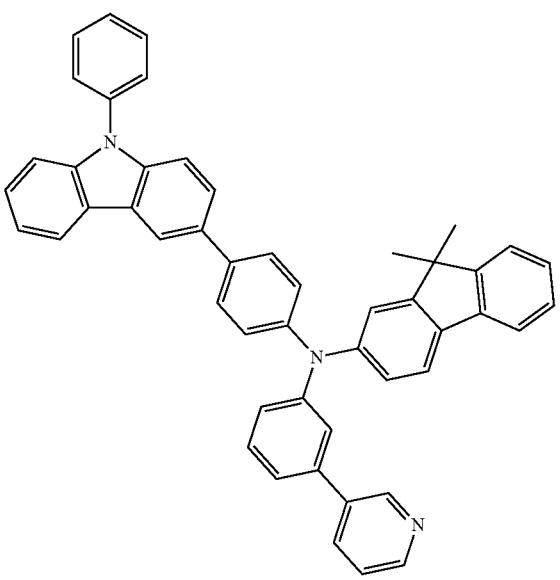

HT12
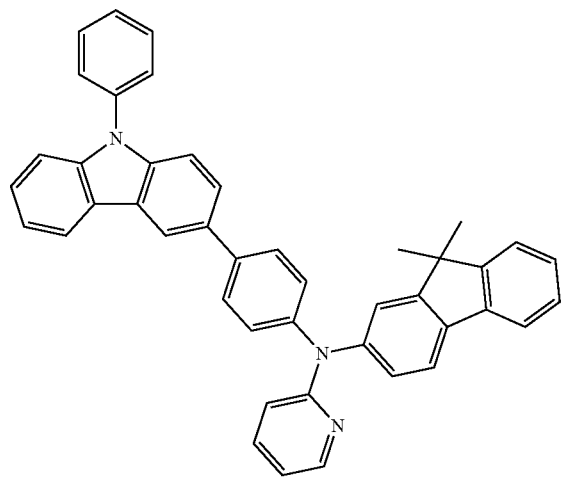
HT13
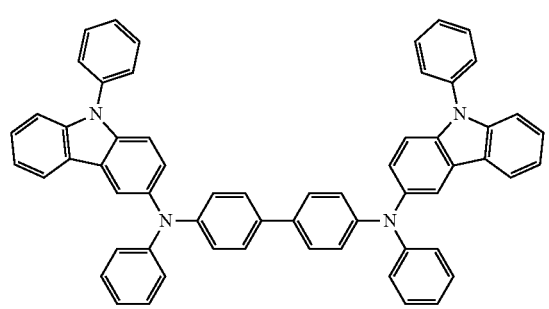
HT14
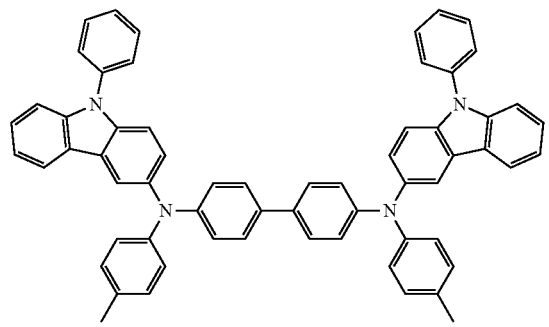
HT15
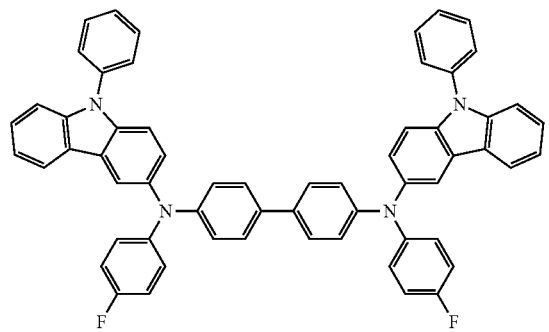
HT16
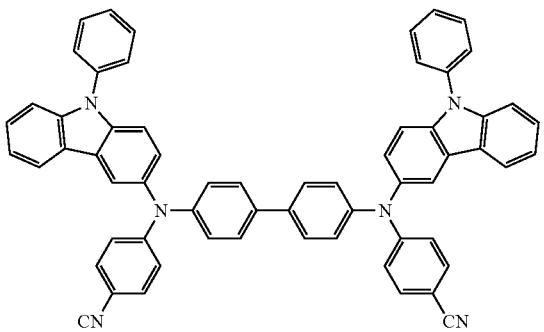
HT17
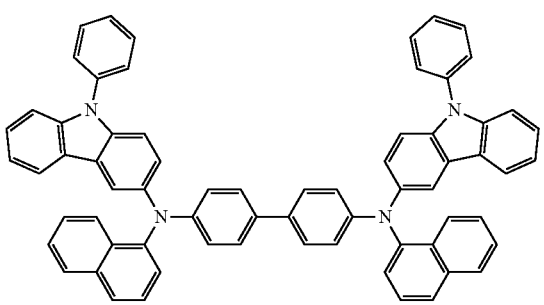
HT18
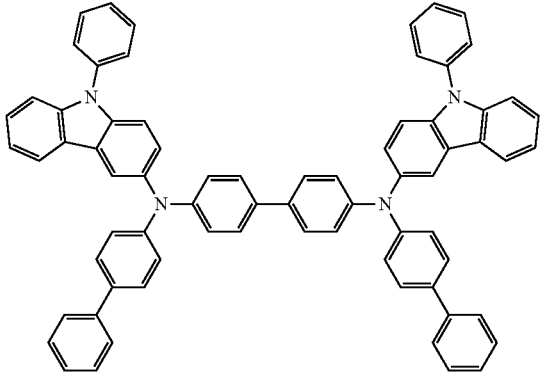
HT19
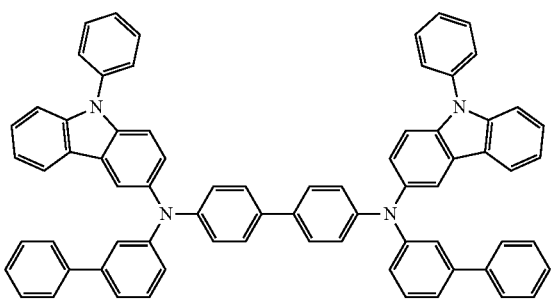

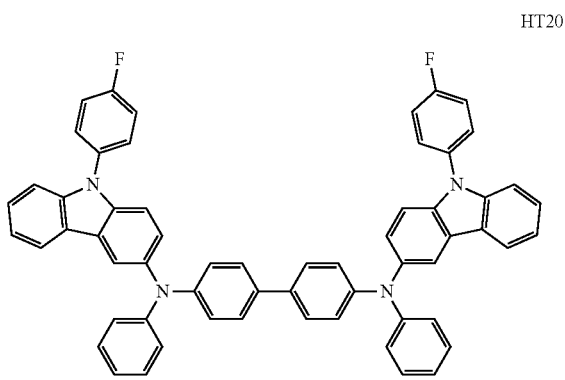

HT20

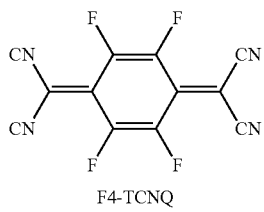

F4-TCNQ

A thickness of the hole transport region may be in a range of about 100 angstroms (Å) to about 10,000 Å, for example, about 100 Å to about 1000 Å. When the hole transport region includes both a hole injection layer and a hole transport layer, a thickness of the hole injection layer may be in a range of about 100 Å to about 10000 Å, for example, about 100 Å to about 1000 Å, and a thickness of the hole transport layer may be in a range of about 50 Å to about 2000 Å, for example about 100 Å to about 1500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethane ("TCNQ") or 2,3,5,6-tetrafluoro-tetracyano-1,4-benzoquinonedimethane ("F4-TCNQ"); a metal oxide, such as a tungsten oxide or a molybdenum oxide; and a cyano group-containing compound, such as Compound HT-D1, but are not limited thereto.

Compound HT-D1

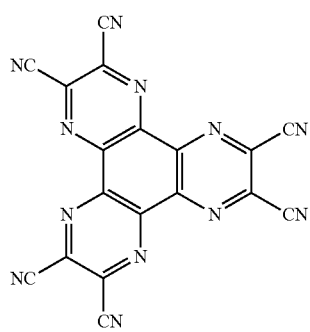

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer ("EML") may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

In an embodiment, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP, which will be explained later.

The emission layer may include a host and a dopant, and the dopant may include the organometallic compound represented by Formula 1.

The host may include at least one selected form TPBi, TBADN, AND (also referred to as "DNA"), CBP, CDBP, TCP, mCP, Compound H50, and Compound H51:

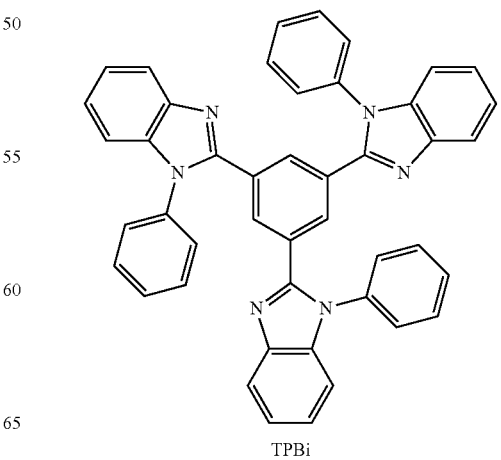

TPBi

-continued

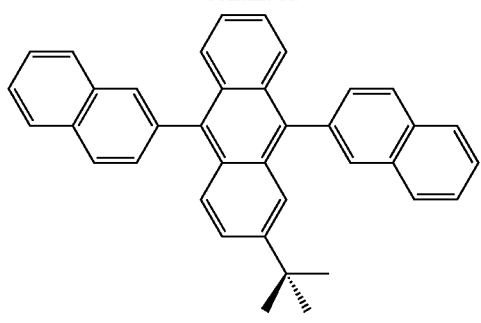

TBADN

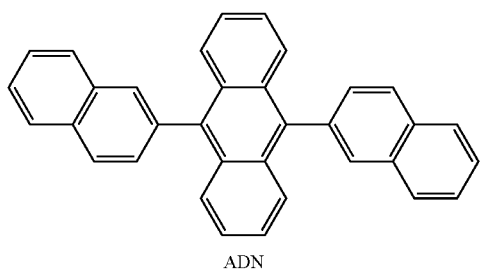

ADN

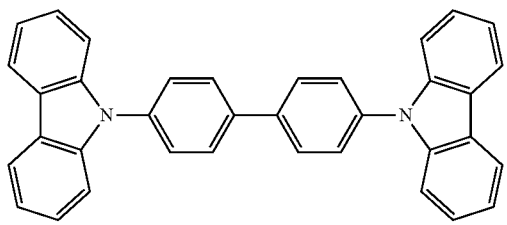

CBP

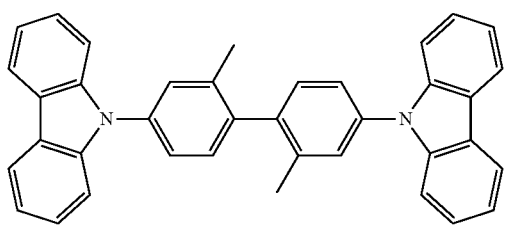

CDBP

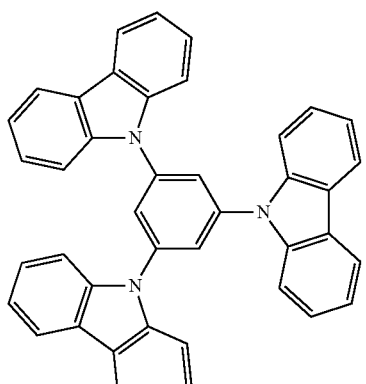

TCP

-continued

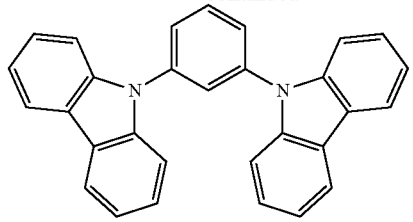

mCP

Compound H50

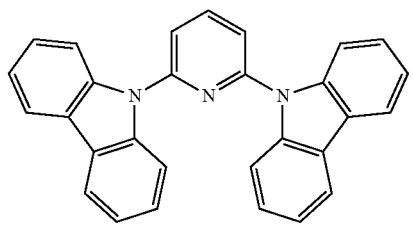

Compound H51

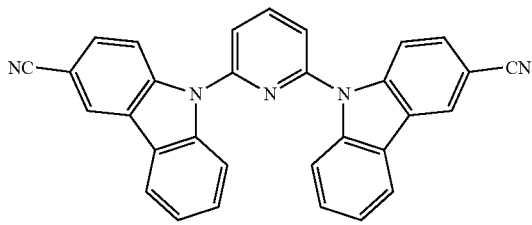

According to another embodiment, the host may further include a compound represented by Formula 301, Formula 301

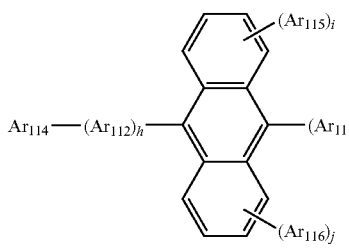

wherein $Ar_{111}$ and $Ar_{112}$ in Formula 301 may be each independently selected from
a phenylene group, a naphthylene group, a phenanthrenylene group, and a pyrenylene group; and
a phenylene group, a naphthylene group, a phenanthrenylene group, and a pyrenylene group, each substituted with at least one selected from a phenyl group, a naphthyl group, and an anthracenyl group.

$Ar_{113}$ to $Ar_{116}$ in Formula 301 may be each independently selected from
a $C_1$-$C_{10}$ alkyl group, a phenyl group, a naphthyl group, a phenanthrenyl group, and a pyrenyl group; and
a phenyl group, a naphthyl group, a phenanthrenyl group, and a pyrenyl group, each substituted with at least one selected from a phenyl group, a naphthyl group, and an anthracenyl group.

In Formula 301, g, h, i, and j in Formula 301 may be each independently selected from 0, 1, 2, 3, and 4, and may be, for example, 0, 1, or 2.

$Ar_{113}$ and $Ar_{116}$ in Formula 301 may be each independently selected from a $C_1$-$C_{10}$ alkyl group substituted with at least one selected from a phenyl group, a naphthyl group, and an anthracenyl group;

a phenyl group, a naphthyl group, an anthracenyl group, a pyrenyl, a phenanthrenyl group, and a fluorenyl group;

a phenyl group, a naphthyl group, an anthracenyl group, a pyrenyl group, a phenanthrenyl group, and a fluorenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

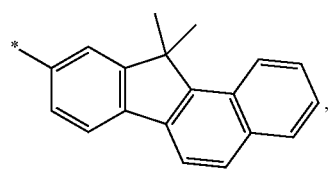 [SMILES: *c1ccc2c(c1)C(C)(C)c1c-2ccc2ccccc12]

but they are not limited thereto.

In some embodiments, the host may include a compound represented by Formula 302:

Formula 302

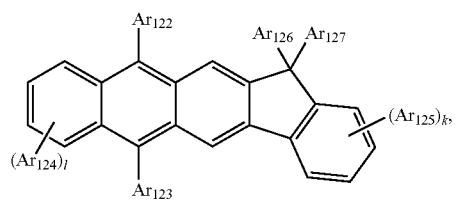

wherein $Ar_{122}$ to $Ar_{125}$ in Formula 302 are the same as described in detail in connection with $Ar_{113}$ in Formula 301.

In Formula 302, $Ar_{126}$ and $Ar_{127}$ may be each independently a $C_1$-$C_{10}$ alkyl group (for example, a methyl group, an ethyl group, or a propyl group).

In Formula 302, k and l may be each independently an integer of 0 to 4. For example, k and l may be 0, 1, or 2.

The compound represented by Formula 301 and the compound represented by Formula 302 may include Compounds H1 to H42, but are not limited thereto.

H1

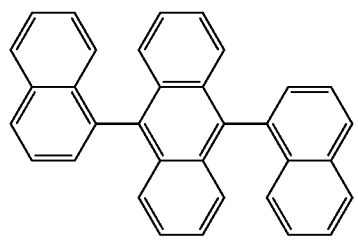

H2

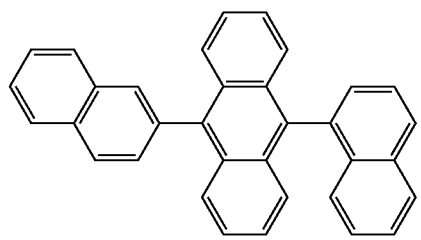

H3

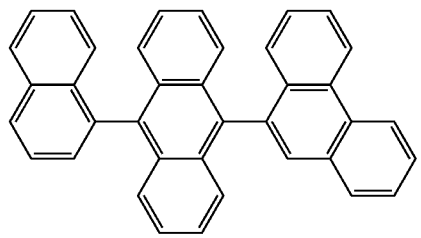

H4

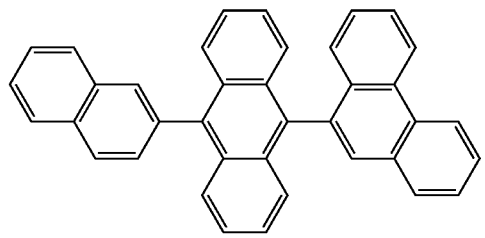

H5

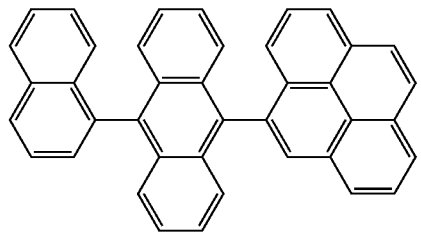

H6

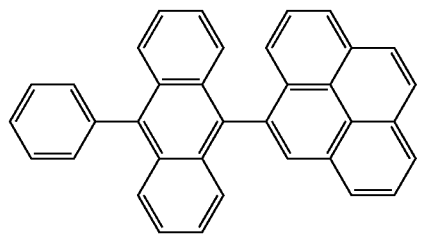

H7

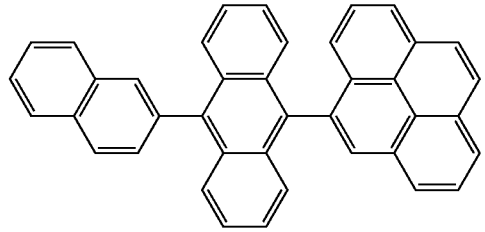

H8
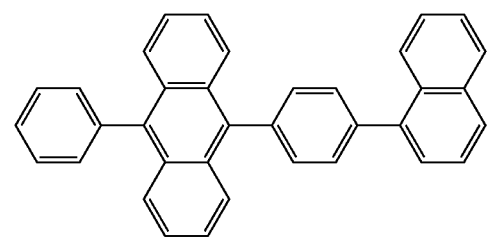
H9
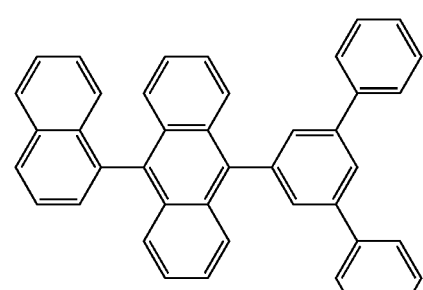
H10
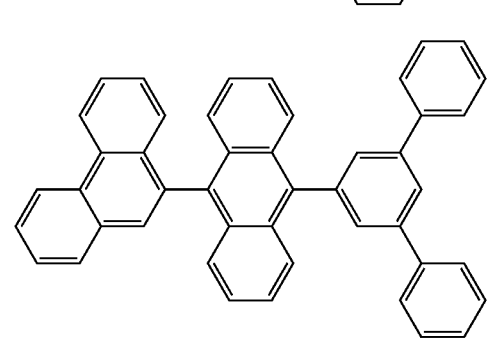
H11
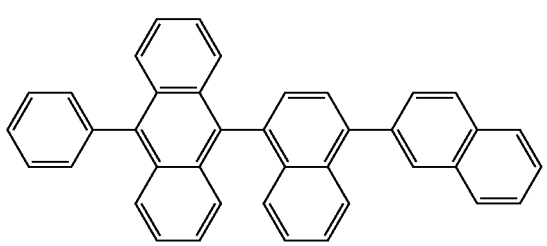
H12
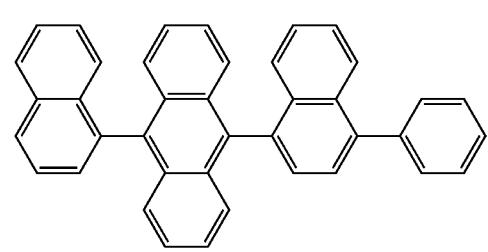
H13
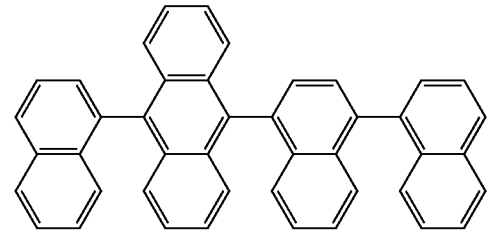
H14
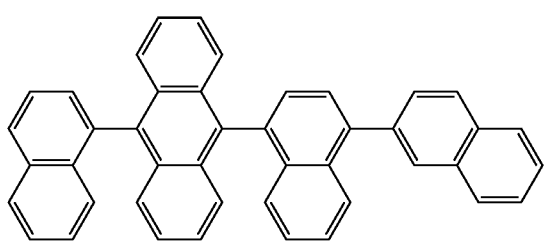
H15
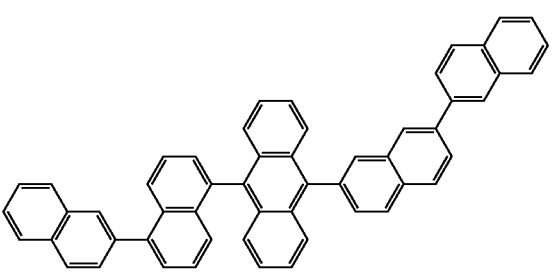
H16
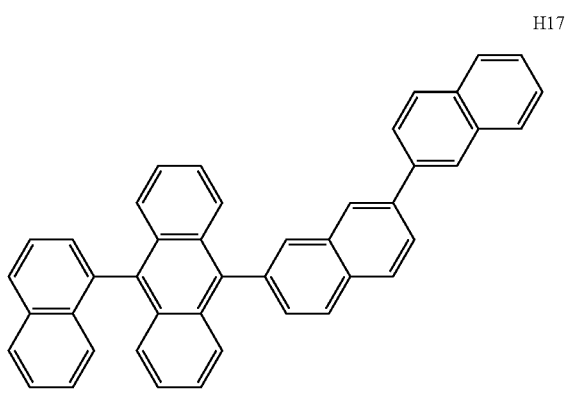
H17
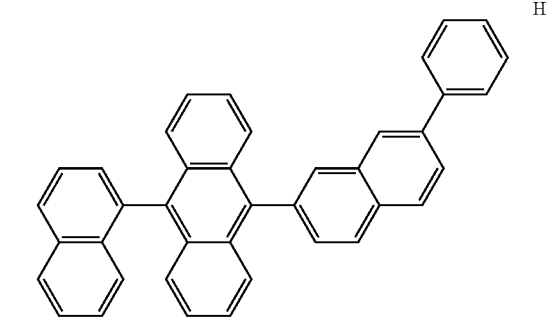
H18

H19
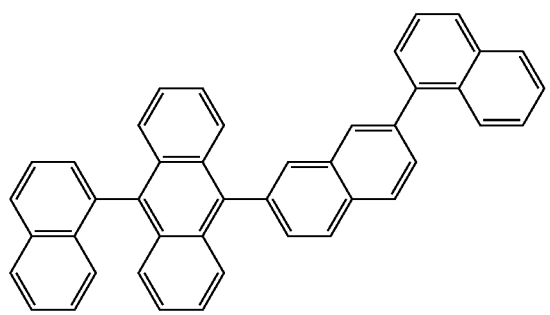
H20
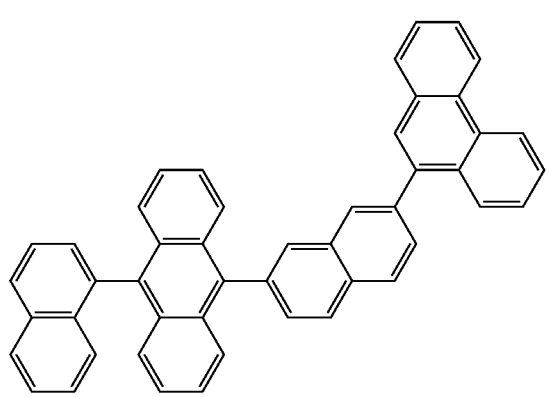
H21
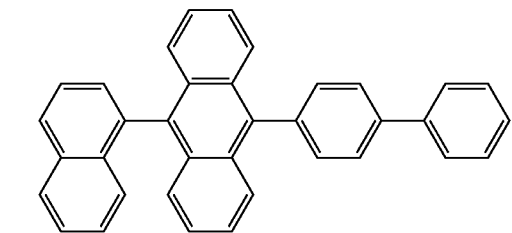
H22
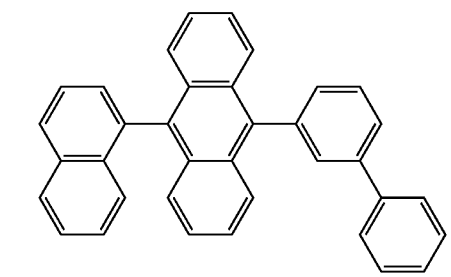
H23
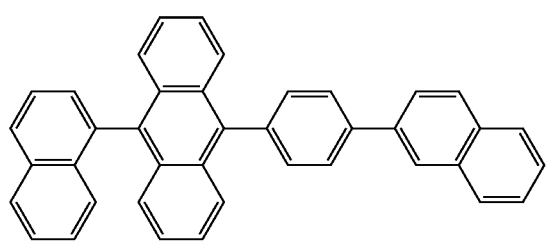
H24
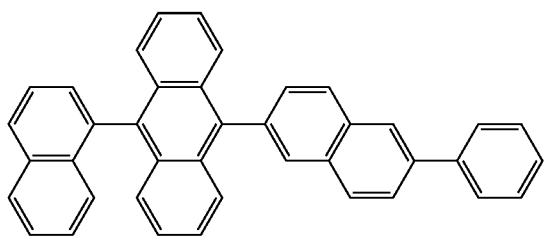
H25
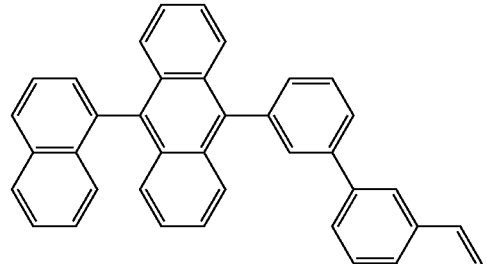
H26
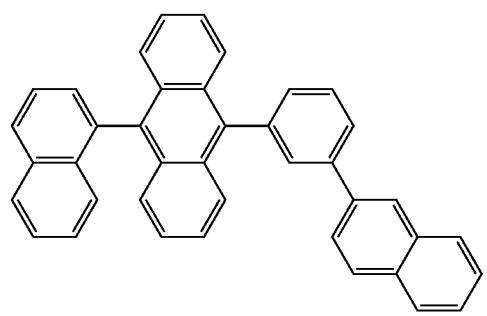
H27
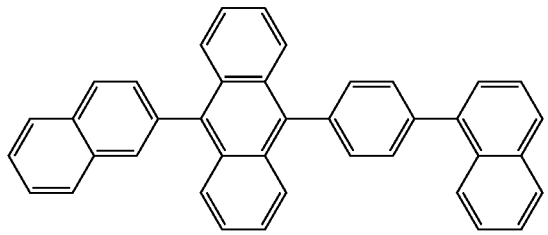
H28
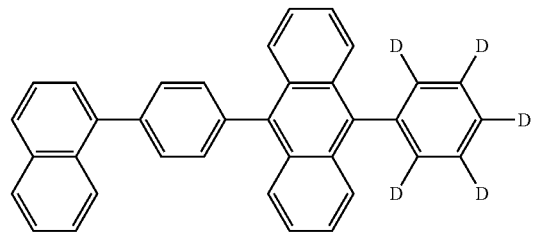
H29
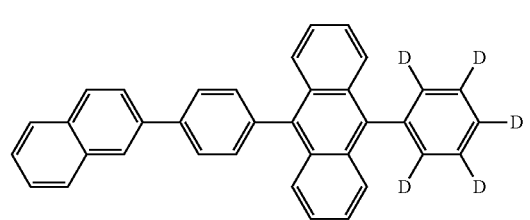

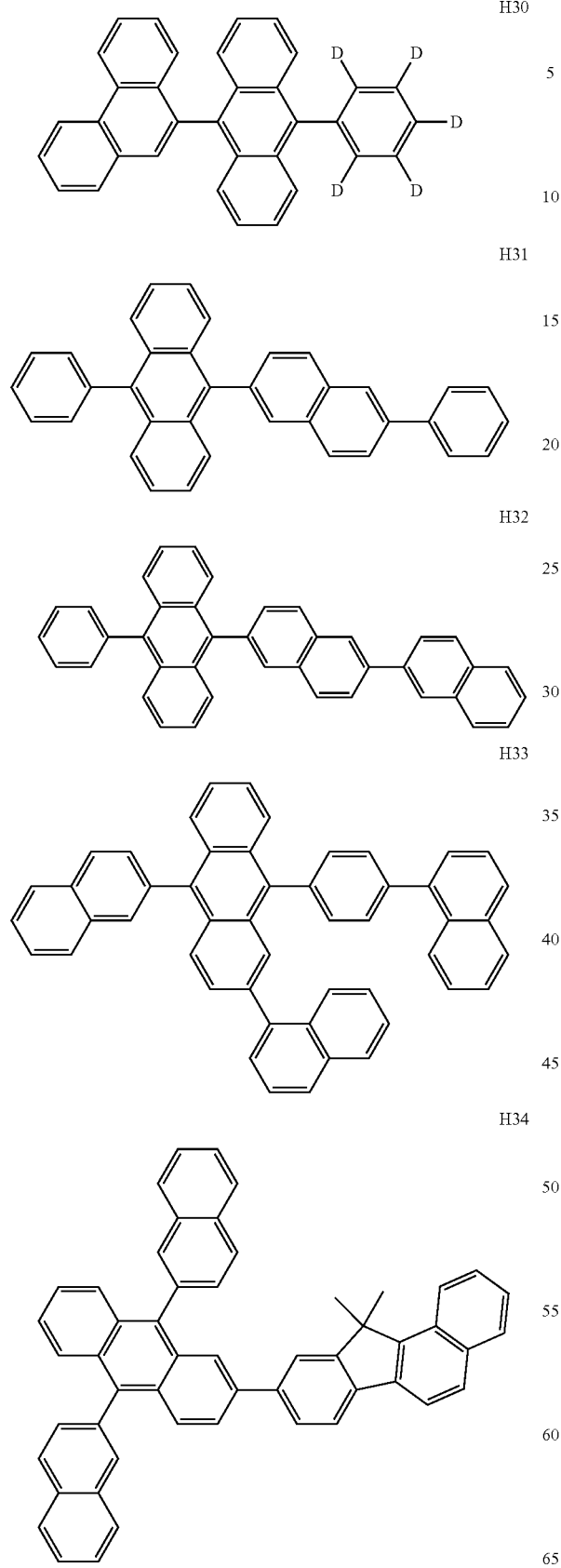
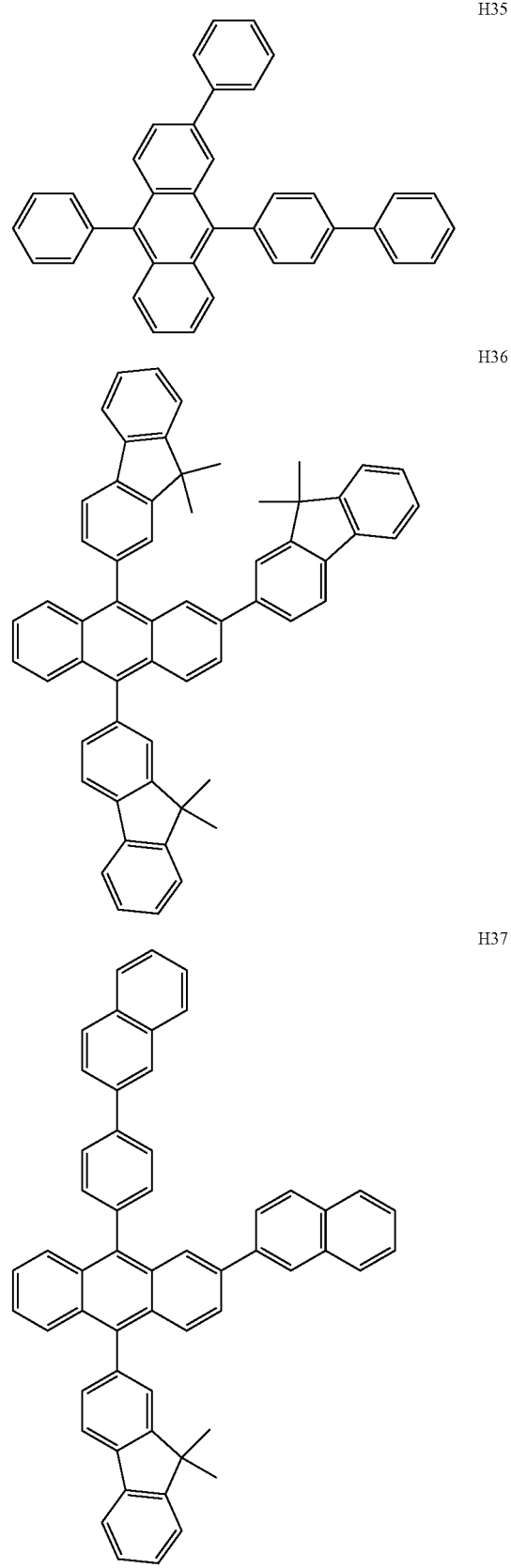

H38

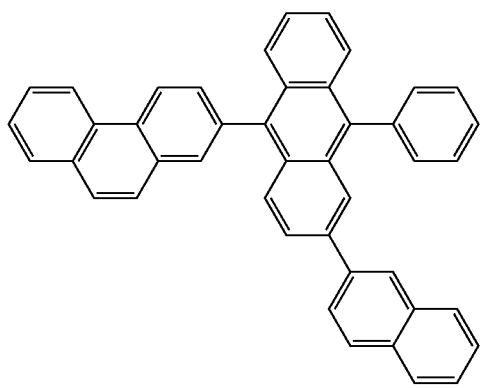

H39

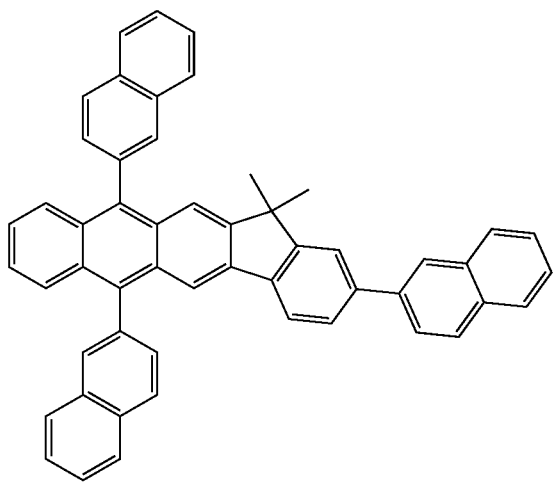

H40

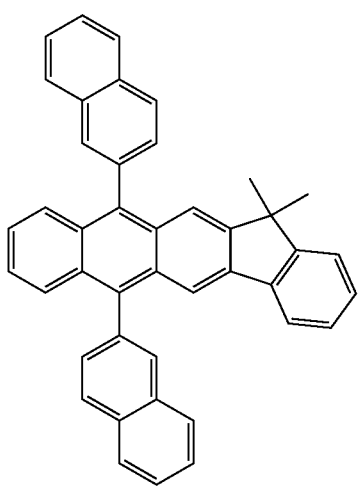

H41

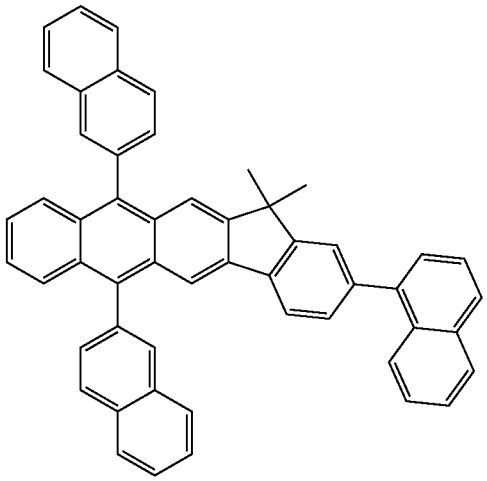

H42

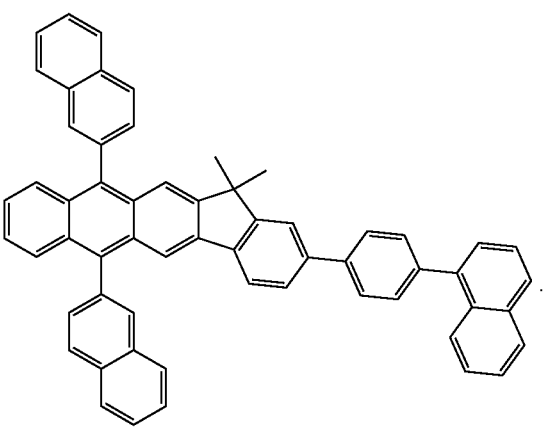

When the organic light-emitting device is a full color organic light-emitting device, the emission layer may be patterned into a red emission layer, a green emission layer, and a blue emission layer. According to another embodiment, due to a stack structure including a red emission layer, a green emission layer, and/or a blue emission layer, the emission layer may emit white light.

When the emission layer includes a host and a dopant, an amount of the dopant may be in a range of about 0.01 to about 15 parts by weight, based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP, Bphen, and Balq but is not limited thereto.

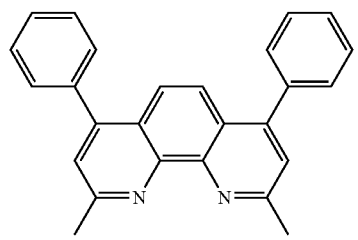

BCP

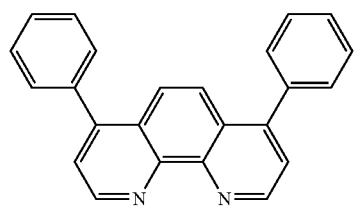

Bphen

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, Balq, TAZ, and NTAZ.

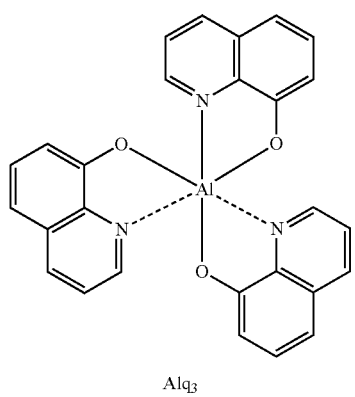

Alq$_3$

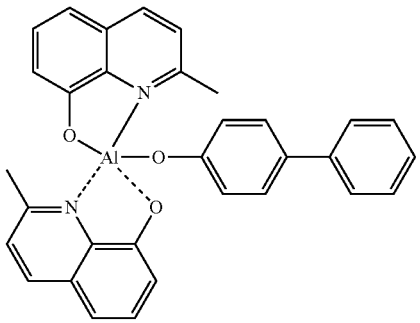

BAlq

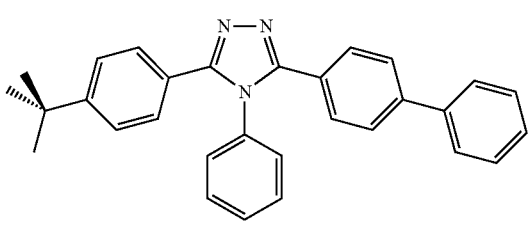

TAZ

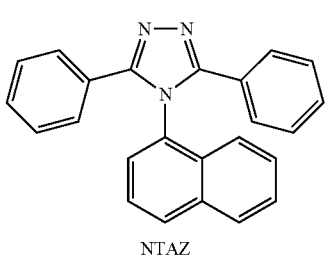

NTAZ

According to another embodiment, the electron transport layer may include at least one of ET1 and ET2, but are not limited thereto:

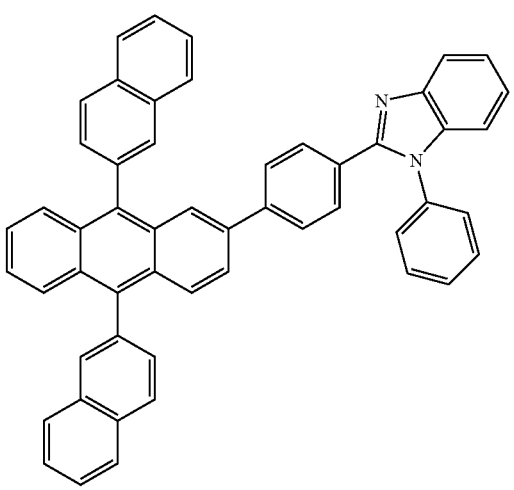

ET1

-continued

ET2

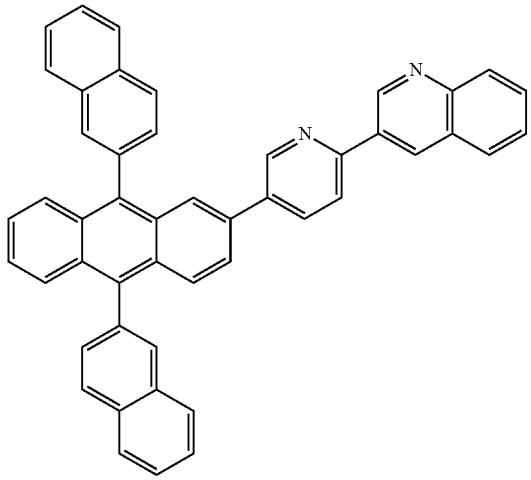

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

ET-D1

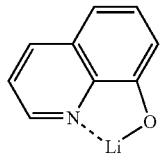

ET-D2

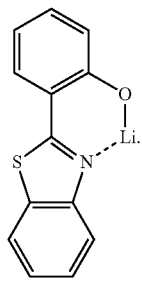

The electron transport region may include an electron injection layer ("EIL") that allows electrons to be easily provided from a second electrode 19.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or terminal of the $C_2$-$C_{60}$ alkyl group, and detailed examples thereof are an ethenyl group, a prophenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or terminal of the $C_2$-$C_{60}$ alkyl group, and detailed examples thereof are an ethynyl group, and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one hetero atom selected from N, O, P, and S as a ring-forming atom and 1 to 10 carbon atoms, and detailed examples thereof are a tetrahydrofuranyl group, and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromacity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein refers to a monovalent group having a carboncyclic aromatic system that has at least one hetero atom selected from N, O, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein can be of the formula —$OA_{102}$, wherein $A_{102}$ is the $C_6$-$C_{60}$ aryl group, and a $C_6$-$C_{60}$ arylthio group can be of the formula —$SA_{103}$, wherein $A_{103}$ is the $C_6$-$C_{60}$ aryl group.

A monovalent non-aromatic condensed polycyclic group used herein refers to a monovalent group (for example, having 8 to 60 carbon atoms) that has two or more rings condensed to each other, only carbon atoms as a ring forming atom, and non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (for example, having 1 to 60 carbon atoms) that has two or more rings condensed to each other, has a heteroatom selected from N, O P, and S, other than carbon atoms, as a ring forming atom, and has non-aromacity in the entire molecular structure. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arythio group, the substituted $C_1$-$C_{60}$ heteroaryl group, the substituted a monovalent non-aromatic condensed polycyclic group, and the substituted monovalent non-aromatic condensed heteropolycyclic group may be selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$)-B($Q_{36}$)($Q_{37}$), and —P(=O)($Q_{38}$)($Q_{39}$);

wherein $Q_1$ to $Q_9$, $Q_{11}$ to $Q_{19}$, $Q_{21}$ to $Q_{29}$, and $Q_{31}$ to $Q_{39}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that a molar equivalent of A was identical to a molar equivalent of B.

EXAMPLES

Synthesis Example 1

Synthesis of Compound 6

Synthesis of Compound A3

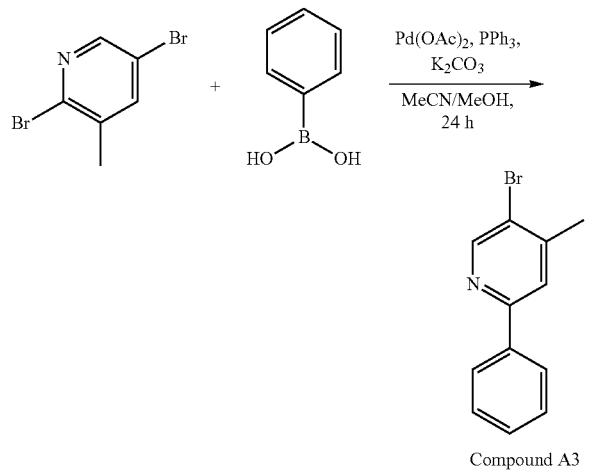

Compound A3

2,5-dibromo-4-methylpyridine (10 grams (g), 39.86 millimoles (mmol)), phenylbornic acid (5.35 g, 43.85 mmol), Pd(OAc)$_2$ (0.90 g, 3.99 mmol), PPh$_3$ (2.09 g, 7.97 mmol), and K$_2$CO$_3$ (11.02 g, 79.72 mmol) were mixed with 100 mL of acetonitrile and 50 milliliters (mL) of methanol, and then, the mixture was stirred at a temperature of 50° C. for 18 hours and cooled to room temperature and filtered. Methylenechloride ("MC") was used to separate an organic layer from the result, and an anhydrous magnesium sulfate (MgSO$_4$) was added thereto to perform dehydration and then, the result was filtered. A solvent in the obtained filtrate was removed under reduced pressure and the obtained residual was refined by column chromatography using ethylacetate ("EA") and hexane at a ratio of 3:97 to obtain 6 g (61%) of Compound A3.

Synthesis of Compound A2

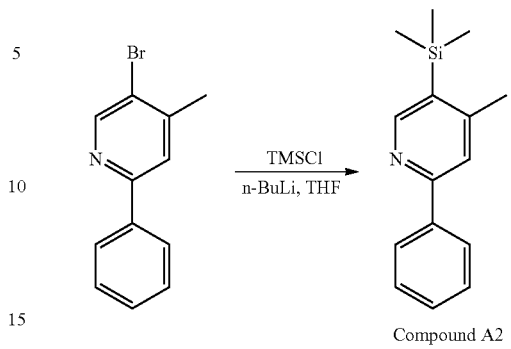

Compound A2

100 mL of tetrahydrofuran ("THF") was added to Compound A3 (6 g, 24.18 mmol), and then, the mixture was cooled to a temperature of −78° C. and n-BuLi (16.6 mL, 26.60 mmol) was slowly added thereto, and the result was stirred at a temperature of −78° C. for 1 hour. Then, TMSCl (3.38 mL, 26.60 mmol) was added thereto, and a reaction was carried out at a temperature of −78° C. for 1 hour, and then, the temperature was raised to room temperature and the reaction was carried out for 12 hours. An organic layer separated therefrom was extracted using MC, and an anhydrous magnesium sulfate was added thereto to perform dehydration. The result was filtered and a solvent in the obtained filtrate was removed under reduced pressure. The residual was purified by column chromatography using EA (ethyl acetate) and hexane at a ratio of 4:96 to obtain 4.5 g (77%) of Compound A2.

Synthesis of Compound A1

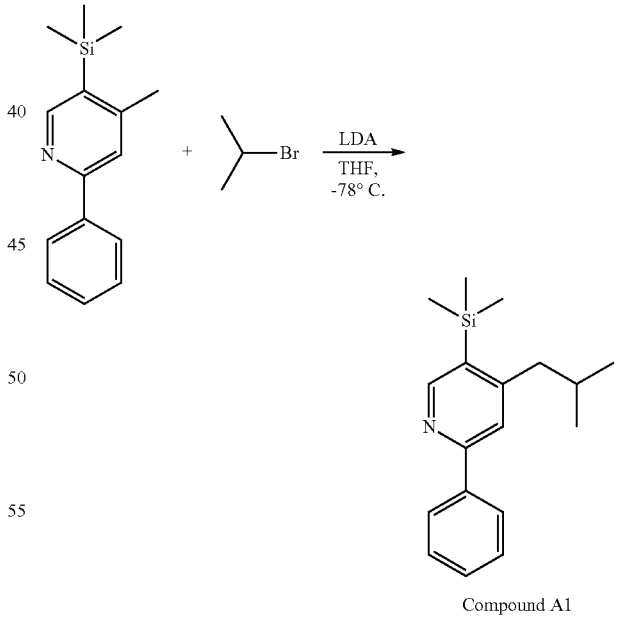

Compound A1

Compound A2 (4.27 g, 17.68 mmol) was mixed with 100 mL of THF, and then the result was cooled to a temperature of −78° C. and lithium diisopropylamide (LDA, 16 mL, 31.83 mmol) was slowly added thereto. Next, the result was stirred at a temperature of −78° C. for 1 hour to perform a reaction, and then, the temperature was raised to room temperature and then, the reaction was further carried out for 1.5 hours. Then, the temperature was dropped to a temperature of −78° C., and 2-bromopropane (2.99 mL, 31.83 mmol) was slowly added to the result and the temperature was raised to room temperature and the reaction was carried out for 12 hours. An organic layer separated therefrom was extracted using MC, and an anhydrous magnesium sulfate was added thereto to perform dehydration. The result was filtered and a solvent in the obtained filtrate was removed under reduced pressure. The residual was purified by column chromatography using EA and hexane at a ratio of 4:96 to obtain 3.73 g (74%) of Compound A1.

Synthesis of Compound M2A

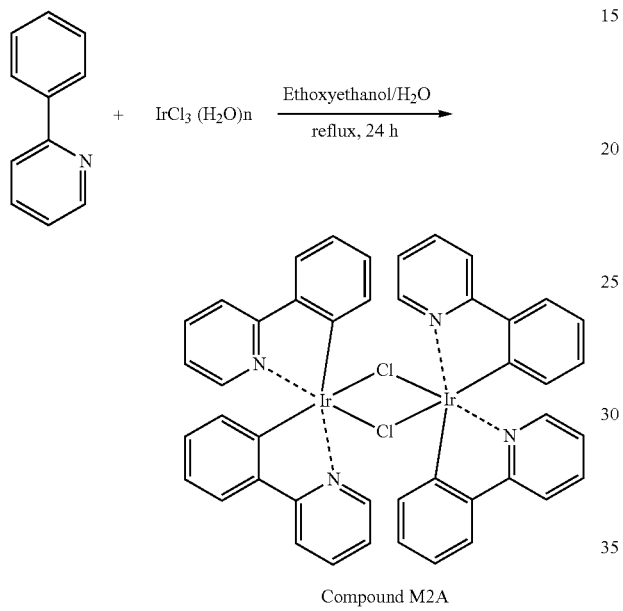

Compound M2A 2-phenylpyridine (14.66 g, 94.44 mmol) and iridium chloride (14.8 g, 41.97 mmol) were mixed with 210 mL of ethoxyethanol and 70 mL of distilled water, and then the mixture was stirred while refluxing for 24 hours to carry out the reaction, and then, the temperature was dropped to room temperature. The resultant solid was separated by filtration, and then, sufficiently, sequentially washed with water, methanol, and hexane in this stated order. The obtained solid was dried in a vacuum oven to obtain 20.2 g (90%) of Compound M2A.

Synthesis of Compound M1A

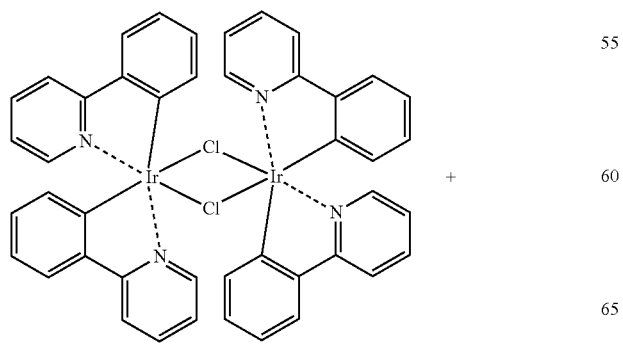

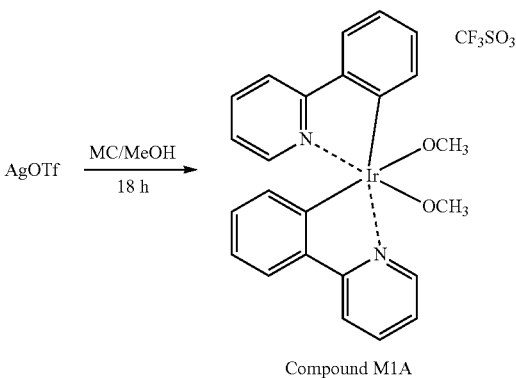

Compound M1A

Compound M2A (4.5 g, 4.20 mmol) was mixed with 60 mL of MC, and then, AgOTf (2.16 g, 8.41 mmol) dissolved in 20 mL of methanol was added thereto. Next, while being blocked from light by using an aluminum foil, the mixture was stirred at room temperature for 18 hours to carry out the reaction, and the generated solid was removed by celite filtration, and a solvent in the obtained filtrate was removed under reduced pressure. The obtained solid (Compound M1) was used for the subsequent reaction without purification.

Synthesis of Compound 6

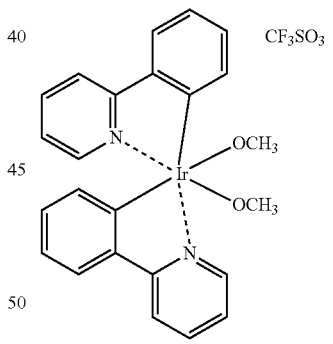

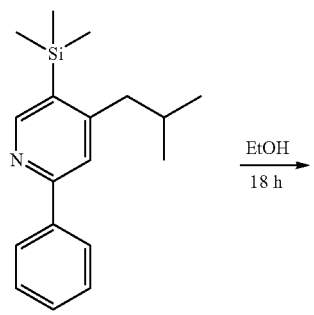

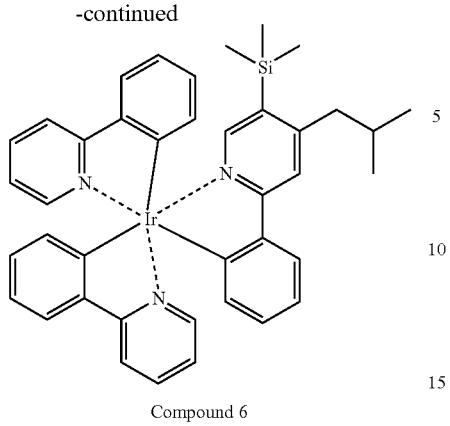

Compound 6

Compound M1A (5 g, 7 mmol) and Compound A1 (2.98 g, 10.50 mmol) were mixed with 90 mL of ethanol, and the result was stirred while refluxing for 18 hours to carry out the reaction, and then, the temperature was dropped. The resultant mixture was filtered to separate a solid, which was then sufficiently washed with ethanol and hexane, and then, column chromatography was performed thereon using MC and hexane at a ratio of 35:65 to obtain 2.1 g (38%) of Compound 6. The obtained product was confirmed by Mass and HPLC analysis.

HRMS(MALDI) calculated for $C_{40}H_{40}IrN_3Si$: m/z 783.2621. Found: 783.2625.

Synthesis Example 2

Synthesis of Compound 96

Synthesis of Compound B3 and acetonitrile and methanol were respectively used in amounts of 120 mL and 60 mL.

Synthesis of Compound B2

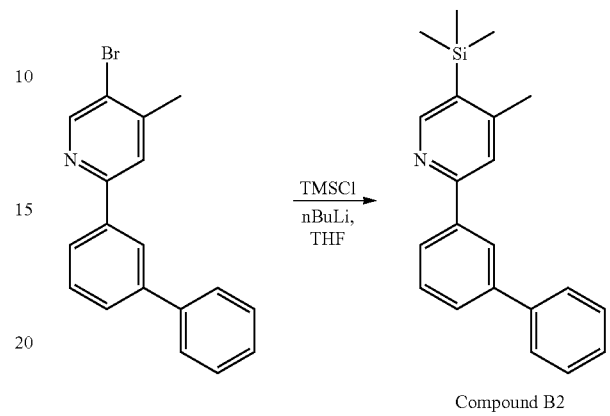

Compound B2

4.6 g (78%) of Compound B2 was prepared in the same manner as used to synthesize Compound A2 in Synthesis Example 1, except that Compound B3 (6 g, 18.51 mmol) was used instead of Compound A3 and n-BuLi was used in an amount of 12.8 mL (20.36 mmol).

Synthesis of Compound B1

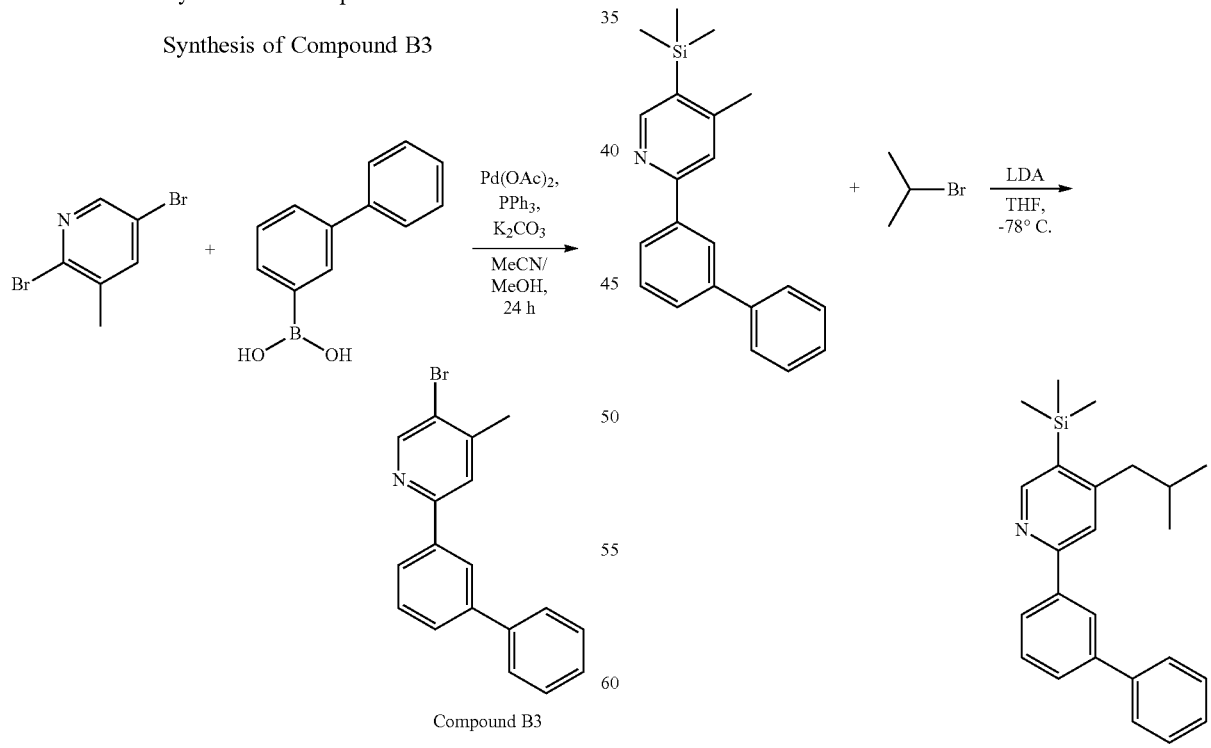

Compound B3

Compound B1

10.4 g (80%) of Compound B3 was prepared in the same manner as used to synthesize Compound A3 in Synthesis Example 1, except that [1,1-biphenyl]-3-ylboronic acid (8.68 g, 43.85 mmol) was used instead of phenylbornic acid, 3.9 g (86%) of Compound B1 was prepared in the same manner as used to synthesize Compound A1 in Synthesis Example 1, except that Compound B2 (4 g, 12.60 mmol) was used instead of Compound A2 and LDA was used in an amount of 11.34 mL (22.68 mmol).

Synthesis of Compound 96

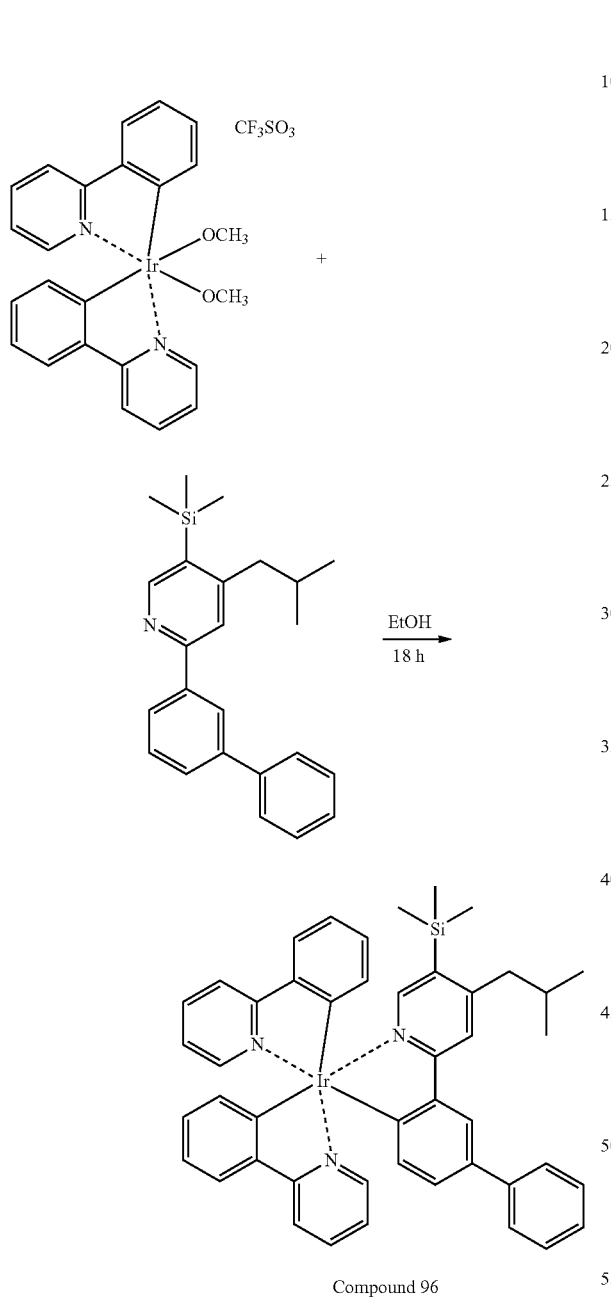

Compound 96

1.5 g (30%) of Compound 96 was prepared in the same manner as used to synthesize Compound 6 in Synthesis Example 1, except that Compound M1A (4.2 g, 5.89 mmol) and Compound B1 (3.18 g, 8.83 mmol) were used instead of Compound M1A (5 g, 7 mmol) and Compound A1 (2.98 g, 10.50 mmol), respectively. The obtained product was confirmed by Mass and HPLC analysis.

HRMS(MALDI) calculated for $C_{46}H_{44}IrN_3Si$: m/z 859.2934. Found: 859.2930.

Synthesis Example 3

Synthesis of Compound 136

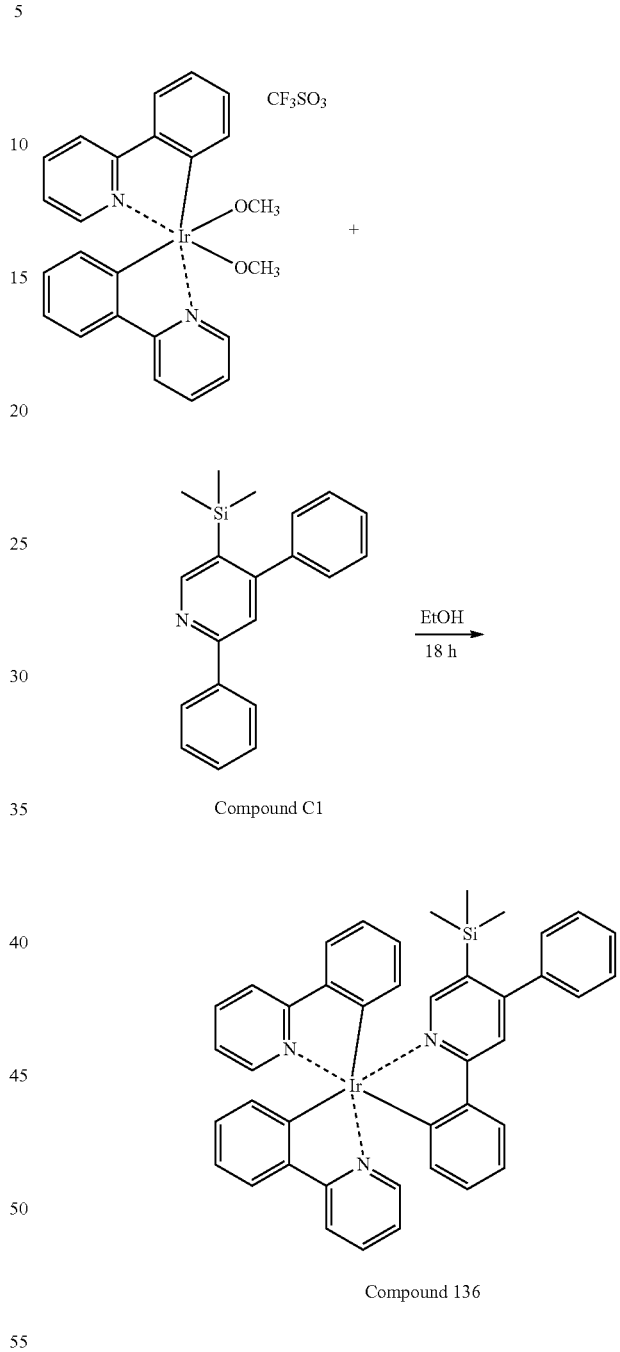

Compound 136

1.4 g (31%) of Compound 136 was prepared in the same manner as used to synthesize Compound 6 in Synthesis Example 1, except that Compound M1A (4 g, 5.60 mmol), Compound C1 (2.55 g, 8.41 mmol), and 60 mL of ethanol were used instead of Compound M1A (5 g, 7 mmol), Compound A1, and 90 mL of ethanol, respectively. The obtained product was confirmed by Mass and HPLC analysis.

HRMS(MALDI) calculated for $C_{42}H_{36}IrN_3Si$: m/z 803.2308. Found: 803.2313.

Synthesis Example 4

Synthesis of Compound 189

Synthesis of Compound M2B

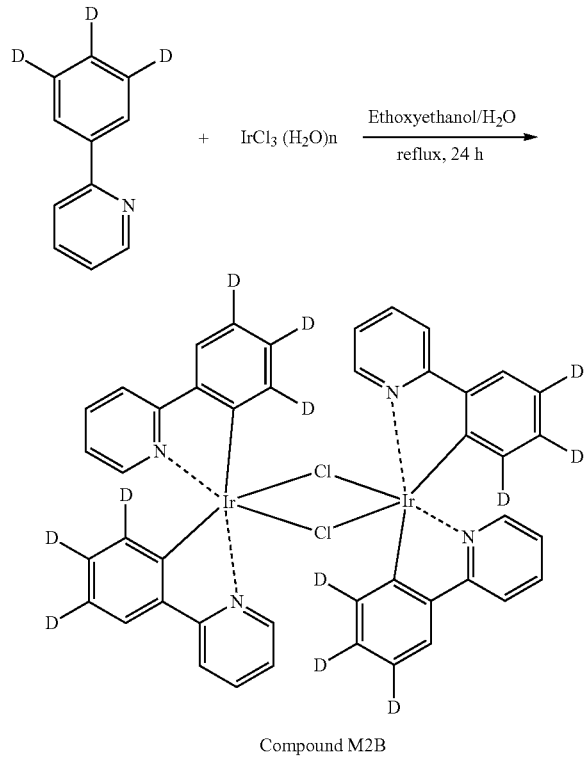

Compound M2B 14.0 g (88%) of Compound M2B was prepared in the same manner as used to synthesize Compound M2A in Synthesis Example 1, except that 2-phenyl(d5)-pyridine (10.64 g, 66.41 mmol) and iridium chloride (10.41 g, 29.52 mmol) were respectively used instead of 2-phenylpyridine (14.66 g, 94.44 mmol) and iridium chloride (14.8 g, 41.97 mmol), and ethoxyethanol and distilled water were used in amounts of 180 mL and 70 mL.

Synthesis of Compound M1B

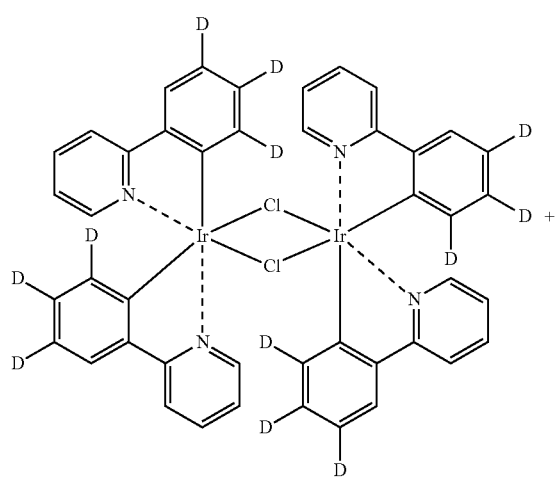

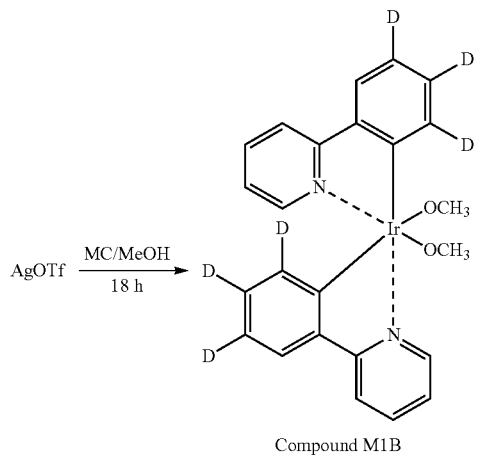

Compound M1B

Compound M1B was prepared in the same manner as used to synthesize Compound M1A in Synthesis Example 1, except that Compound M2B (4.52 g, 4.17 mmol) was used instead of Compound M2A. Compound M1B was used for the subsequent process without purification.

Synthesis of Compound 189

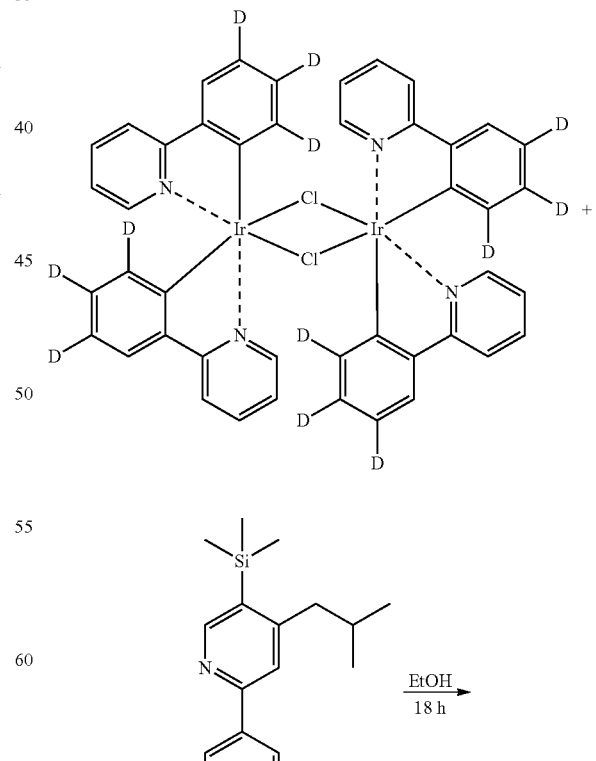

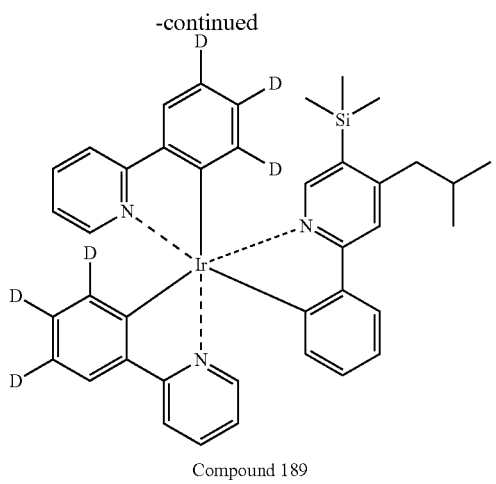

Compound 189

2.7 g (41%) of Compound 189 was prepared in the same manner as used to synthesize Compound 6 in Synthesis Example 1, except that Compound M1B (6 g, 8.34 mmol), Compound A1 (3.55 g, 12.51 mmol) and 60 mL of ethanol were used instead of Compound M1A, Compound A1 (2.98 g, 10.50 mmol) and 90 mL of ethanol, respectively. The obtained product was confirmed by Mass and HPLC analysis.

HRMS(MALDI) calculated for $C_{40}H_{34}D_6IrN_3Si$: m/z 789.2997. Found: 789.2990.

Synthesis Example 5

Synthesis of Compound 209

Synthesis of Compound D4

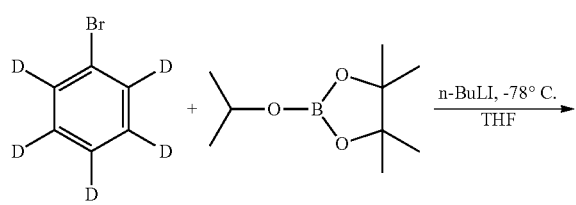

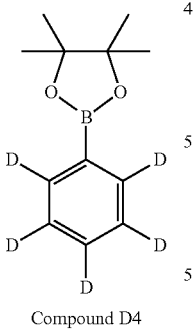

Compound D4

100 mL of THF was added to bromobenzene (d5) (10.72 g, 66.48 mmol), and then, the temperature was dropped to a temperature of −78° C., and then, n-BuLI (49.86 mL, 79.77 mmol) was slowly added thereto. Next, while the temperature was maintained at −78° C., the reaction was carried out for 30 minutes, and then, 2-isopropoxy-4,4,5,5-tetramethyl-1,3,2-dioxaborolane (16.27 mL, 79.77 mmol) was added thereto, and the temperature was raised to room temperature to carry out the reaction, and the result was stirred for 18 hours to carry out the reaction at room temperature. From the obtained mixture, an organic layer was extracted using EA, and anhydrous magnesium sulfate (MgSO4) was added thereto to perform dehydration. The result was filtered and a solvent in the obtained filtrate was removed under reduced pressure, and the residual was subjected to column chromatography using ethylacetate (EA) and hexane at a ratio of 4:96 to 11.7 g (84%) of obtain Compound D4.

Synthesis of Compound D3

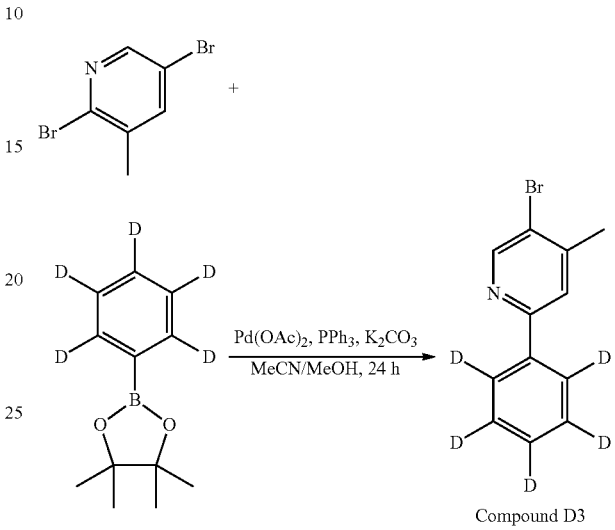

Compound D3

2,5-dibromo-4-methylpyridine (11.89 g, 47.40 mmol), Compound D4 (10.90 g, 52.14 mmol), $Pd(OAc)_2$ (1.06 g, 4.74 mmol), $PPh_3$ (2.49 g, 9.48 mmol), and KOH (5.32 g, 94.81 mmol) were mixed with 180 mL of acetonitrile, and then, at a temperature of 50° C., the mixture was stirred for 18 hours, and cooled to room temperature and filtered. From the result, an organic layer was extracted using methylenechloride ("MC"), and an anhydrous magnesium sulfate ($MgSO_4$) was added thereto to perform dehydration, and then, the result was filtered, and a solvent in the obtained filtrate was removed under reduced pressure. The residual was purified by column chromatography using ethylacetate ("EA") and hexane at a ratio of 3:97 to obtain 9.7 g (81%) of Compound D3.

Synthesis of Compound D2

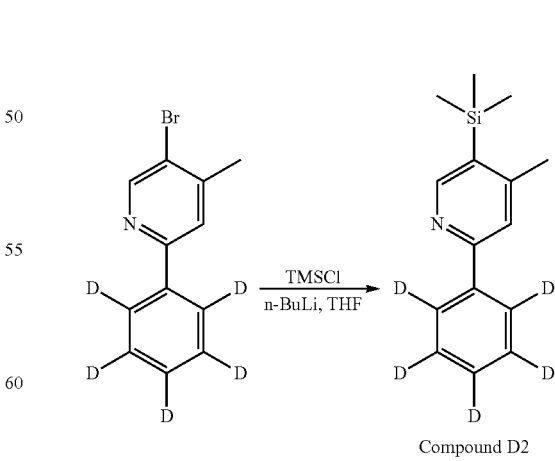

Compound D2

6.4 g (73%) of Compound D2 was prepared in the same manner as used to synthesize Compound A2 in Synthesis Example 1, except that Compound D3 (9 g, 35.55 mmol)

was used instead of Compound A3 and THF was used in an amount of 120 mL and n-BuLi was used in an amount of 24.5 mL (39.11 mmol).

Synthesis of Compound D1

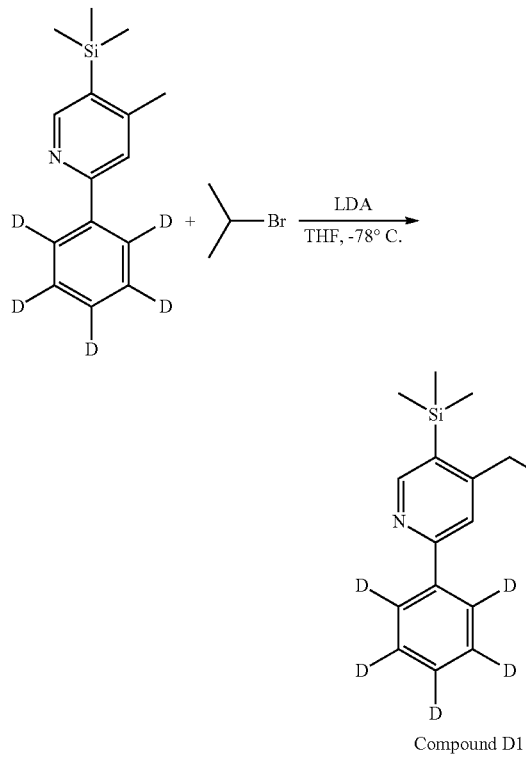

Compound D1

3.3 g (70%) of Compound D1 was prepared in the same manner as used to synthesize Compound A1 in Synthesis Example 1, except that Compound D2 (4 g, 16.23 mmol) was used instead of Compound A2 and THF was used in an amount of 70 mL and LDA was used in an amount of 14.61 mL (29.22 mmol).

Synthesis of Compound 209

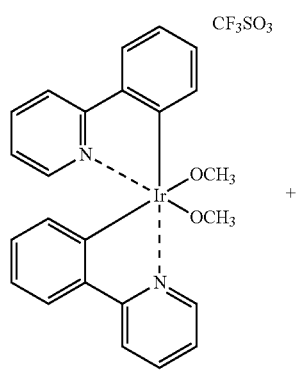

-continued

Compound 209

1.7 g (39%) of Compound 209 was prepared in the same manner as used to synthesize Compound 6 in Synthesis Example 1, except that Compound M1A (4 g, 5.61 mmol), Compound D1 (2.43 g, 8.40 mmol), and 60 mL of ethanol were used instead of Compound M1A (5 g, 7 mmol), Compound A1 (2.98 g, 10.50 mmol), and 90 mL of ethanol, respectively. The obtained product was confirmed by Mass and HPLC analysis.

HRMS(MALDI) calculated for $C_{40}H_{36}D_4IrN_3Si$: m/z 787.2872. Found: 787.2879.

Synthesis Example 6

Synthesis of Compound 241

Synthesis of Compound M2C

-continued

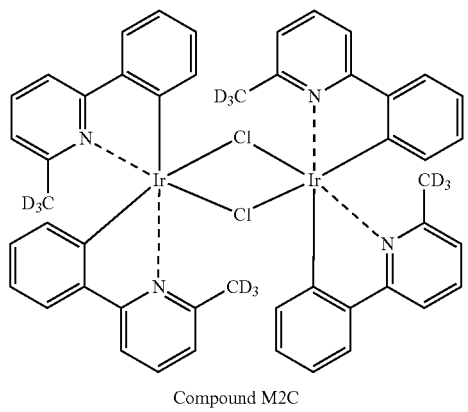

Compound M2C 9.9 g (77%) of Compound M2C was prepared in the same manner as used to synthesize Compound M2A in Synthesis Example 1, except that 2-methyl(d3)-6-phenylpyridine(2-methyl(d3)-6-phenylpyridine) (8.792 g, 51.05 mmol), iridium chloride (8 g, 22.69 mmol), 150 mL of ethoxyethanol, and 50 mL of distilled water were used instead of 2-phenylpyridine, iridium chloride (14.8 g, 41.97 mmol), 210 mL of ethoxyethanol, and 70 mL of distilled water, respectively.

Synthesis of Compound M1C

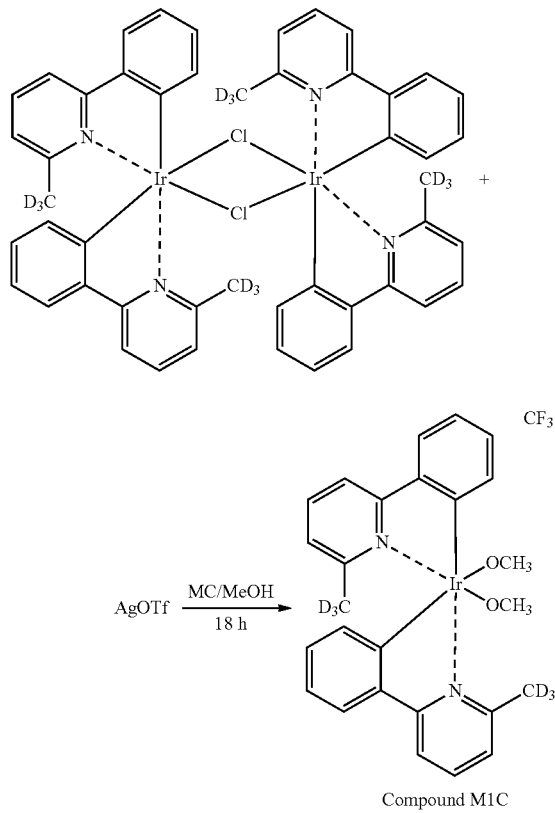

Compound M1C

Compound M1C was prepared in the same manner as used to synthesize Compound M1A in Synthesis Example 1, except that Compound M2C (4.57 g, 4.01 mmol) was used instead of Compound M2A. Compound M1C was used for the subsequent process without purification.

Synthesis of Compound 241

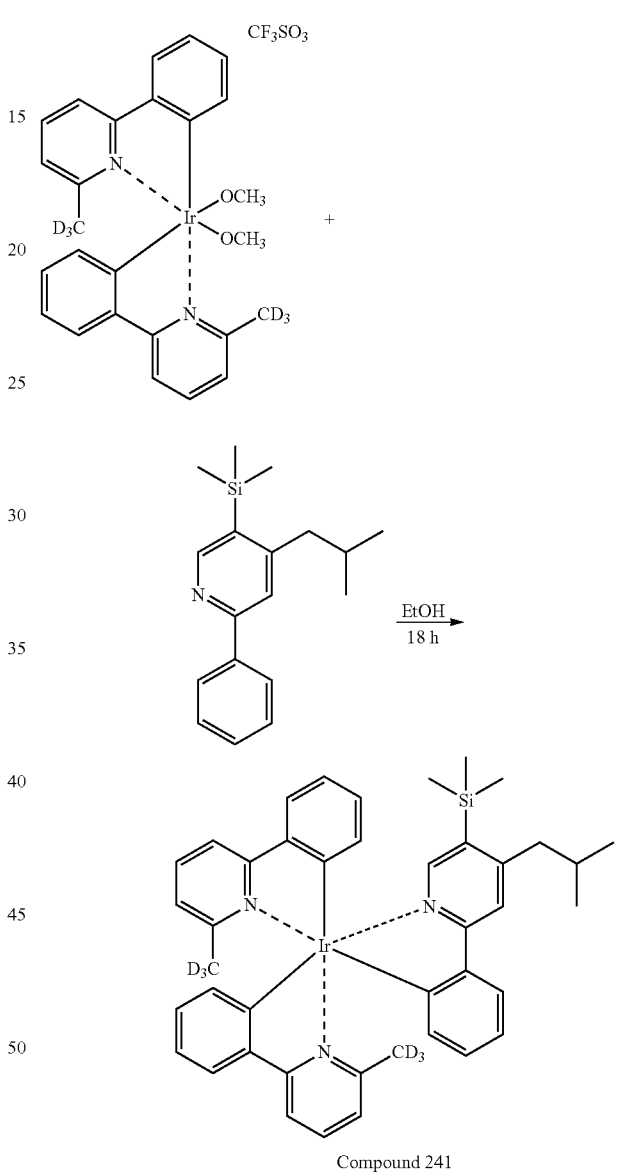

Compound 241

1.3 g (20%) of Compound 241 was prepared in the same manner as used to synthesize Compound 6 in Synthesis Example 1, except that Compound M1C (6 g, 8.02 mmol), Compound A1 (3.41 g, 12.03 mmol), and 60 mL of ethanol were used instead of Compound M1A (5 g, 7 mmol), Compound A1 (2.98 g, 10.50 mmol), and 90 mL of ethanol, respectively. The obtained product was confirmed by Mass and HPLC analysis.

HRMS(MALDI) calculated for $C_{42}H_{38}D_6IrN_3Si$: m/z 817.3310. Found: 817.3301.

Synthesis Example 7

Synthesis of Compound 296

Synthesis of Compound M2D

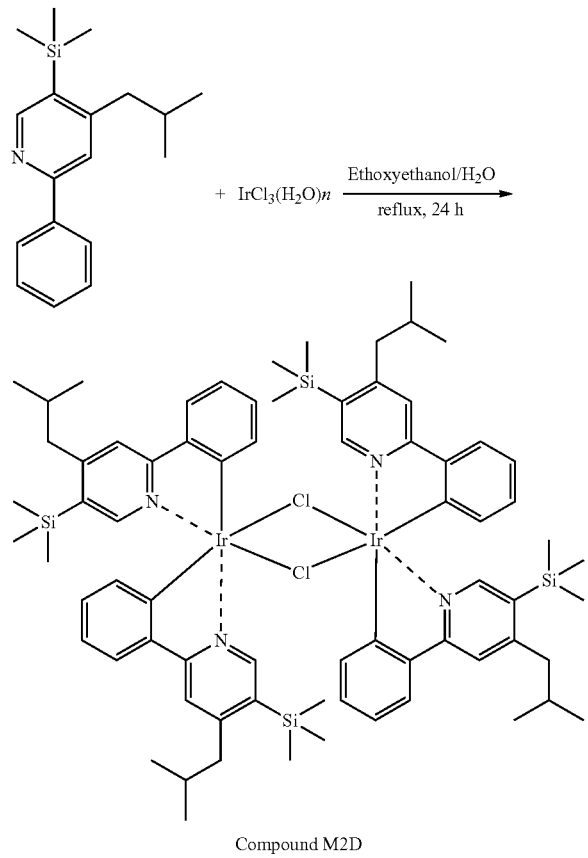

Compound M2D 7.4 g (62%) of Compound M2D was prepared in the same manner as used to synthesize Compound M2A in Synthesis Example 1, except that Compound A1 (9.66 g, 34.06 mmol), iridium chloride (5.34 g, 15.14 mmol), 150 mL of ethoxyethanol, and 50 mL of distilled water were used instead of 2-phenylpyridine, iridium chloride (14.8 g, 41.97 mmol), 210 mL of ethoxyethanol, and 70 mL of distilled water, respectively.

Synthesis of Compound M1D

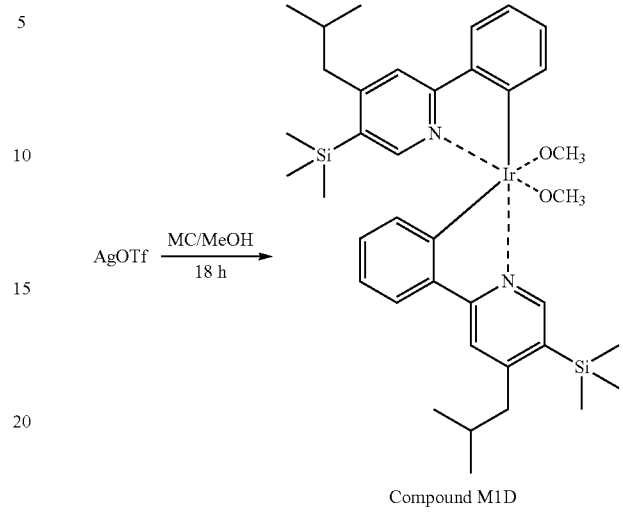

Compound M1D

Compound M1D was prepared in the same manner as used to synthesize Compound M1A in Synthesis Example 1, except that Compound M2D (4.90 g, 3.09 mmol) and AgOTf (1.59 g, 6.18 mmol) were used instead of Compound M2A and AgOTf (2.16 g, 8.41 mmol), respectively. Compound M1D was used for the subsequent reaction without purification.

Synthesis of Compound 296

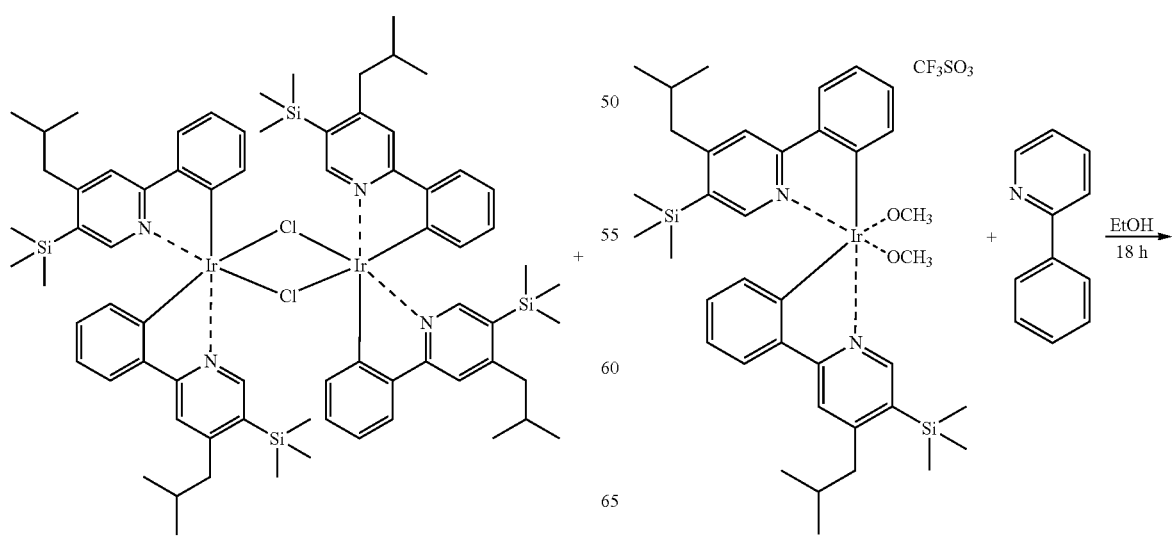

-continued

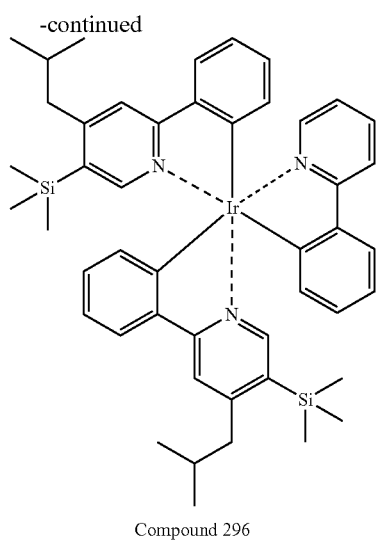

Compound 296

2.0 g (35%) of Compound 296 was prepared in the same manner as used to synthesize Compound 6 in Synthesis Example 1, except that Compound M1D (6 g, 6.18 mmol) and phenylpyridine (1.44 g, 9.28 mmol) were used instead of Compound M1A (5 g, 7 mmol) and Compound A1 (2.98 g, 10.50 mmol), respectively. The obtained product was confirmed by Mass and HPLC analysis.

HRMS(MALDI) calculated for $C_{47}H_{56}IrN_3Si_2$: m/z 911.3642. Found: 911.3648.

Comparative Synthesis Example 1

Synthesis of Comparative Compound 1

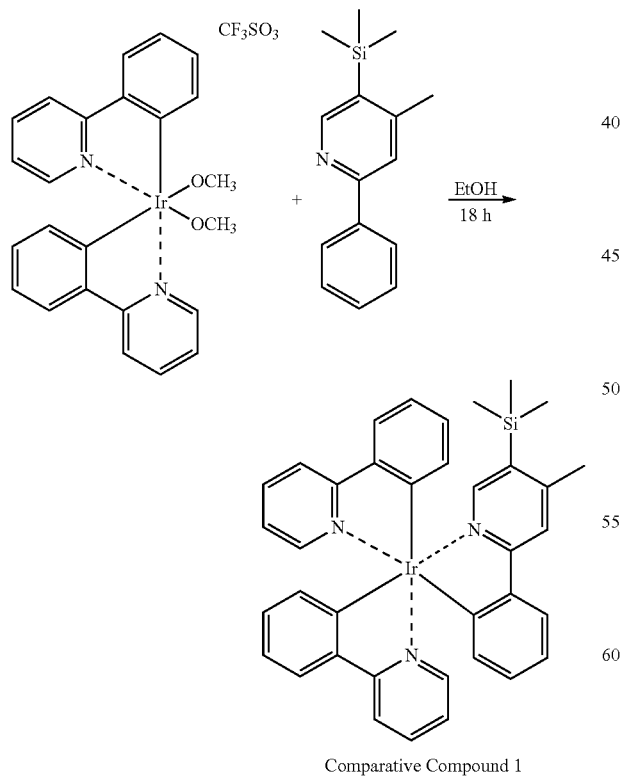

Comparative Compound 1

2.4 g (39%) of Comparative Compound 1 was prepared in the same manner as used to synthesize Compound 6 in Synthesis Example 1, except that Compound M1A (6 g, 8.41 mmol) and Compound A2 (3.0 g, 12.61 mmol) were used instead of Compound M1A (5 g, 7 mmol) and Compound A1 (2.98 g, 10.50 mmol), respectively. The obtained product was confirmed by Mass and HPLC analysis.

HRMS(MALDI) calculated for $C_{37}H_{34}IrN_3Si$: m/z 741.2151. Found: 741.2157.

Example 1

An ITO glass substrate was cut to a size of 50 mm×50 mm×0.5 mm and then, sonicated in acetone isopropyl alcohol and pure water, each for 15 minutes, and then, washed by exposure to UV ozone for 30 minutes.

Then, m-MTDATA was deposited on an ITO electrode (anode) of the glass substrate at a deposition speed of 1 Å/sec to form a hole injection layer having a thickness of 600 Å, and then, α-NPD was deposited on the hole injection layer at a deposition speed of 1 Å/sec to form a hole transport layer having a thickness of 250 Å.

Compound 6 (dopant) and CBP (host) were co-deposited on the hole transport layer at a deposition speed 0.1 Å/sec and a deposition speed of 1 Å/sec, respectively, to form an emission layer having a thickness of 400 Å.

BAlq was deposited on the emission layer at a deposition speed of 1 Å/sec to form a hole blocking layer having a thickness of 50 Å, and $Alq_3$ was deposited on the hole blocking layer to form an electron transport layer having a thickness of 300 Å, and then, LiF was deposited on the electron transport layer to form an electron injection layer having a thickness of 10 Å, and then, Al was vacuum deposited on the electron injection layer to form a second electrode (cathode) having a thickness of 1200 Å, thereby completing manufacturing of an organic light-emitting device having a structure of ITO/m-MTDATA (600 Å)/α-NPD (250 Å)/CBP+10% (Compound 6) (400 Å)/Balq (50 Å)/Alq3(300 Å) /LiF (10 Å)/Al(1200 Å).

Examples 2 to 7 and Comparative Examples 1 and 2

Organic light-emitting devices were manufactured in the same manner as in Example 1, except that in forming an emission layer, for use as a dopant, corresponding compounds shown in Table 2 were used instead of Compound 6.

Evaluation Example 1

Evaluation on Characteristics of Organic Light-Emitting Devices

The organic light-emitting devices manufactured according to Examples 1 to 7 and Comparative Examples 1 and 2 were evaluated in terms of driving voltage, efficiency, power, color purity, quantum efficiency, and lifespan ($T_{95}$). Results thereof are shown in Table 2. This evaluation was performed using a current-voltage meter (Keithley 2400) and a brightness meter (Minolta Cs-1000A), and the lifespan (T95)(at 6000 nit) was evaluated by measuring a time taken until brightness was reduced to 95% of the initial brightness of 100%.

TABLE 2

| | Dopant | Driving Voltage Voltage (V) | Efficiency (cd/A) | Power (lm/W) | CIEx | CIEy | Quantum Efficiency (%) | Lifespan (hr), (T95) |
|---|---|---|---|---|---|---|---|---|
| Ex 1 | Compound 6 | 5.0 | 49.2 | 30.9 | 0.340 | 0.605 | 19 | 250 |
| Ex 2 | Compound 96 | 4.9 | 48.7 | 31.2 | 0.342 | 0.604 | 19 | 234 |
| Ex 3 | Compound 136 | 5.2 | 52.2 | 31.5 | 0.349 | 0.605 | 19 | 190 |
| Ex 4 | Compound 189 | 5.0 | 49.9 | 31.3 | 0.340 | 0.604 | 19 | 285 |
| Ex 5 | Compound 209 | 5.0 | 49.3 | 31.0 | 0.340 | 0.605 | 19 | 270 |
| Ex 6 | Compound 241 | 4.9 | 53.1 | 34.0 | 0.338 | 0.605 | 19 | 270 |
| Ex 7 | Compound 296 | 5.1 | 52.4 | 32.3 | 0.344 | 0.604 | 19 | 260 |
| CEx 1 | Comparative Compound 1 | 5.3 | 48.5 | 28.7 | 0.344 | 0.604 | 18 | 135 |
| CEx 2 | Ir(ppy)$_3$ | 6.5 | 40.2 | 19.4 | 0.330 | 0.604 | 18 | 15 |

Ex = Example;
CEX = Comparative Example

From Table 2, it was confirmed that the organic light-emitting devices of Examples 1 to 7 had a lower driving voltage, higher efficiency, higher power, higher color purity, higher quantum efficiency, and longer lifetime than the organic light-emitting devices of Comparative Examples 1 and 2.

The organometallic compound according to embodiments has excellent electric characteristics and thermal stability. Accordingly, an organic light-emitting device including the organometallic compound may have low driving voltage, high efficiency, high power, high quantum efficiency, long lifespan, and excellent color purity.

What is claimed is:

1. An organometallic compound represented by Formula 1:

$$M(L_1)_{n1}(L_2)_{n2},$$  Formula 1 wherein M is iridium (Ir), or platinum (Pt),
wherein $L_1$ is a ligand selected from substituted and unsubstituted phenylpyridine that coordinates to M via a carbon atom of the phenyl ring and the nitrogen atom of the pyridine ring and $L_2$ is a ligand represented by Formula 2B, and wherein $L_1$ and $L_2$ in Formula 1 are different from each other,

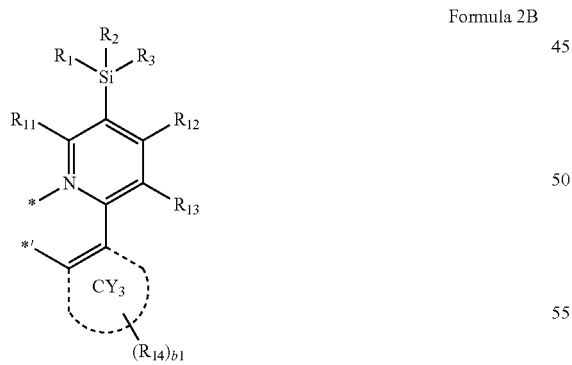

Formula 2B wherein
CY$_3$ is a benzene,
$R_1$ to $R_3$ in Formula 2B are each independently selected from:
 a $C_1$-$C_{10}$ alkyl group; and
 a $C_1$-$C_{10}$ alkyl group, which is substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group, any substituent on $L_1$, and $R_{11}$ to $R_{14}$ in Formula 2B are each independently selected from a hydrogen, a deuterium, —F, —Cl, —Br, —I, —SF$_5$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group having 8 to 60 carbon atoms, a substituted or unsubstituted monovalent non-aromatic condensed heteropolycyclic group having 1 to 60 carbon atoms, —N(Q$_1$)(Q$_2$), —Si(Q$_3$)(Q$_4$)(Q$_5$), —B(Q$_6$)(Q$_7$), and —P(=O)(Q$_8$)(Q$_9$), wherein $R_{12}$ in Formula 2B is not a hydrogen, a —CH$_3$, or a cyano group; and i) two substituents on the pyridine ring of the $L_1$, together with the pyridine ring, optionally form a 5,6,7,8-tetrahydroisoquinoline and ii) two substituents on the phenyl ring of the $L_1$, together with the phenyl ring, optionally form a dibenzofuran, a dibenzothiophene or a carbazole, at least one of $R_{11}$ to $R_{14}$ in Formula 2B are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group having 8 to 60 carbon atoms, and a substituted or unsubstituted monovalent non-aromatic condensed heteropolycyclic group having 1 to 60 carbon atoms, and b1 in Formula 2B is selected from 1, 2, 3, and 4, and wherein in Formula 1, n1 and n2 are each independently 1 or 2, with the proviso that a sum of n1 and n2 is 2 when M is Pt, or 3 when M is Ir, wherein * and *' in Formula 2B are each a binding site to M in Formula 1; and wherein at least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted a monovalent non-aromatic condensed polycyclic group having 8 to 60 carbon atoms, and the substituted monovalent non-aromatic condensed heteropolycyclic group having 1 to 60 carbon atoms is selected from:

a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_1$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group having 8 to 60 carbon atoms, a monovalent non-aromatic condensed heteropolycyclic group having 1 to 60 carbon atoms, —$N(Q_{11})(Q_{12})$, —$Si(Q_{13})(Q_{14})(Q_{15})$, —$B(Q_{16})(Q_{17})$, and —$P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, and a monovalent non-aromatic condensed heteropolycyclic group having 1 to 60 carbon atoms;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, and a monovalent non-aromatic condensed heteropolycyclic group having 1 to 60 carbon atoms, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms and a monovalent non-aromatic condensed heteropolycyclic group having 1 to 60 carbon atoms, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$;

wherein $Q_1$ to $Q_9$, $Q_{11}$ to $Q_{19}$, $Q_{21}$ to $Q_{29}$, and $Q_{31}$ to $Q_{39}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms and a monovalent non-aromatic condensed heteropolycyclic group having 1 to 60 carbon atoms.

2. The organometallic compound of claim 1, wherein $R_1$ to $R_3$ in Formula 2B are each independently selected from:

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each of which is unsubstituted; and a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, and a tert-decyl group, each of which is substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group.

3. The organometallic compound of claim 1, wherein $R_1$ to $R_3$ in Formula 2B are each independently selected from —$CH_3$, —$CH_2CH_3$, —$CD_3$, —$CD_2H$, —$CDH_2$, —$CH_2CD_3$, and —$CD_2CH_3$.

4. The organometallic compound of claim 1, wherein $R_1$ to $R_3$ in Formula 2B are identical.

5. The organometallic compound of claim 1, wherein any substituent on $L_1$, and $R_{11}$, $R_{13}$, and $R_{14}$ in Formula 2B are each independently selected from:

a hydrogen, a deuterium, —F, —Cl, —Br, —I, —$SF_5$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group, each of which is unsubstituted;

a $C_1$-$C_{20}$ alkyl group and a $C_1$-$C_{20}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms, each of which is unsubstituted;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms; and i) two substituents on the pyridine ring of the $L_1$, together with the pyridine ring, optionally form a 5,6,7,8-tetrahydroisoquinoline and ii) two substituents on the phenyl ring of the $L_1$, together with the phenyl ring, optionally form a dibenzofuran, a dibenzothiophene or a carbazole, —$N(Q_1)(Q_2)$, —$Si(Q_3)(Q_4)(Q_5)$, —$B(Q_6)(Q_7)$, and —$P(=O)(Q_8)(Q_9)$, wherein $Q_1$ to $Q_9$ are each independently selected from a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryl group substituted with at least one selected from a $C_1$-$C_{20}$ alkyl group and a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms, and at least one of $R_{11}$, $R_{13}$ and $R_{14}$ in Formula 2B are each independently selected from:

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms, each of which is unsubstituted; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms.

6. The organometallic compound of claim 1, wherein any substituent on $L_1$, and $R_{11}$, $R_{13}$, and $R_{14}$ in Formula 2B are each independently selected from:

a hydrogen, a deuterium, —F, a cyano group, a nitro group, —$SF_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and —B(Q$_6$)(Q$_7$) and —P($=$O)(Q$_8$)(Q$_9$), wherein Q$_6$ to Q$_9$ are each independently selected from:
  a $C_1$-$C_{10}$ alkyl group, a $C_1$-$C_{10}$ alkoxy group, a phenyl group, and a naphthyl group;
  a phenyl group and a naphthyl group, each substituted with at least one selected from a $C_1$-$C_{10}$ alkyl group, a phenyl group, and a naphthyl group, and at least one of R$_{11}$, R$_{13}$ and R$_{14}$ in Formula 2B are each independently selected from:
a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and
a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —CD$_3$, —CD$_2$H, —CDH$_2$, —CF$_3$, —CF$_2$H, —CFH$_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group.

7. The organometallic compound of claim 1, wherein R$_{12}$ in Formula 2B is selected from:
a $C_2$-$C_{20}$ alkyl group and a $C_2$-$C_{20}$ alkoxy group;
a methyl group and a methoxy group, each substituted with at least one selected from a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms;
a $C_2$-$C_{20}$ alkyl group and a $C_2$-$C_{20}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms; and
—N(Q$_1$)(Q$_2$), —Si(Q$_3$)(Q$_4$)(Q$_5$), —B(Q$_6$)(Q$_7$), and —P($=$O)(Q$_8$)(Q$_9$), wherein Q$_1$ to Q$_9$ are each independently selected from a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{14}$ aryl group, a $C_6$-$C_{14}$ aryl group substituted with at least one selected from a $C_1$-$C_{20}$ alkyl group and a $C_6$-$C_{14}$ aryl group, a $C_1$-$C_{14}$ heteroaryl group, a monovalent non-aromatic condensed polycyclic group having 8 to 60 carbon atoms, and a monovalent non-aromatic condensed heteropolycyclic group having 1 to 60 carbon atoms.

8. The organometallic compound of claim 1, wherein $R_{12}$ in Formula 2B is selected from:
a $C_2$-$C_{20}$ alkyl group and a $C_2$-$C_{20}$ alkoxy group;
a methyl group and a methoxy group, each substituted with at least one selected from a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;
a $C_2$-$C_{20}$ alkyl group and a $C_2$-$C_{20}$ alkoxy group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_2$-$C_{10}$ alkyl group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;
a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;
a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each of which is substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and
—B($Q_6$)($Q_7$) and —P(=O)($Q_8$)($Q_9$), wherein $Q_6$ to $Q_9$ are each independently selected from:
a $C_1$-$C_{20}$ alkyl group, a $C_1$-$C_{20}$ alkoxy group, a phenyl group, a naphthyl group, a pyridinyl group, a pyrimidinyl group, a triazinyl group, and a carbazolyl group; and
a phenyl group and a naphthyl group, each substituted with at least one selected from a $C_1$-$C_{20}$ alkyl group, a phenyl group, and a naphthyl group.

9. The organometallic compound of claim 1, wherein $R_{12}$ in Formula 2B is selected from:
an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group;

a methyl group and a methoxy group, each substituted with at least one selected from a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each of which is substituted with at least one selected from a deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group.

10. The organometallic compound of claim 1, wherein any substituent on $L_1$, and $R_{11}$, $R_{13}$, and $R_{14}$ in Formula 2B are each independently selected from a hydrogen, a deuterium, —F, a cyano group, a nitro group, —$SF_5$, —$CH_3$, —$CD_3$, —$CD_2H$, —$CDH_2$, —$CF_3$, —$CF_2H$, —$CFH_2$, a group represented by Formulas 9-1 to 9-17, and a group represented by Formulas 10-1 to 10-16, $R_{12}$ in Formula 2B is selected from the group represented by Formulas 9-1 to 9-17 and groups represented by Formulas 10-1 to 10-16, and at least one of $R_{11}$ to $R_{14}$ are each independently selected from Formulae 10-1 to 10-9:

Formula 9-1

Formula 9-2

Formula 9-3

Formula 9-4

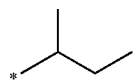

Formula 9-5

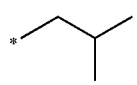

Formula 9-6

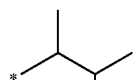

Formula 9-7

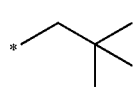

Formula 9-8

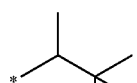

Formula 9-9

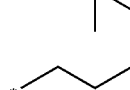

Formula 9-10

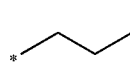

Formula 9-11

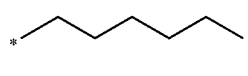

Formula 9-12

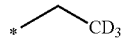

Formula 9-13

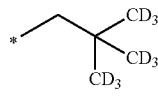

Formula 9-14

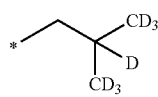

Formula 9-15

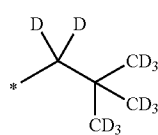

Formula 9-16

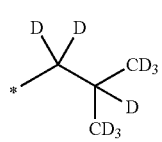

Formula 9-17

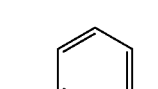

Formula 10-1

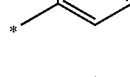

Formula 10-2

-continued

Formula 10-3
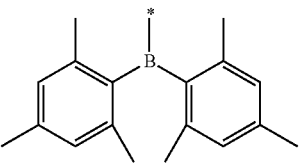

Formula 10-4

Formula 10-5

Formula 10-6

Formula 10-7

Formula 10-8

Formula 10-9

Formula 10-10

Formula 10-11

Formula 10-12

Formula 10-13

Formula 10-14

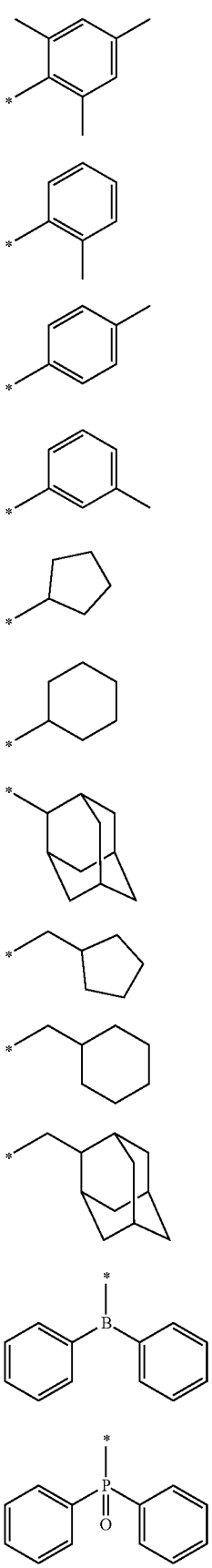

-continued

Formula 10-15
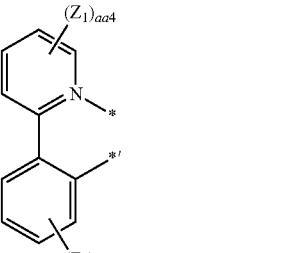

Formula 10-16
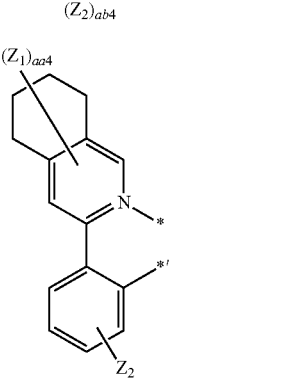

11. The organometallic compound of claim 1, wherein $L_1$ is a ligand represented by Formula 2-1 or 2-112:

Formula 2-1
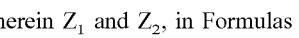

Formula 2-112
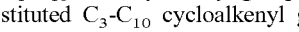

wherein $Z_1$ and $Z_2$, in Formulas 2-1 and 2-112 are each independently selected from a hydrogen, a deuterium, —F, —Cl, —Br, —I, —SF$_5$, a hydroxyl group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, $-B(Q_6)(Q_7)$, and $-P(=O)(Q_8)(Q_9)$, wherein $Q_1$ to $Q_9$ are each independently selected from a hydrogen, a deuterium, $-F$, $-C_1$, $-Br$, $-I$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, aa4 and ab4 are each independently selected from, 1, 2, 3, and 4,

* and *' indicate binding sites to M, and wherein at least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, a substituted monovalent non-aromatic condensed polycyclic group having 8 to 60 carbon atoms, and a substituted monovalent non-aromatic condensed heteropolycyclic group having 1 to 60 carbon atoms is selected from:

a deuterium, $-F$, $-Cl$, $-Br$, $-I$, $-CD_3$, $-CD_2H$, $-CDH_2$, $-CF_3$, $-CF_2H$, $-CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, $-F$, $-Cl$, $-Br$, $-I$, $-CD_3$, $-CD_2H$, $-CDH_2$, $-CF_3$, $-CF_2H$, $-CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_1$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group having 8 to 60 carbon atoms, a monovalent condensed heteropolycyclic group having 1 to 60 carbon atoms, $-N(Q_{11})(Q_{12})$, $-Si(Q_{13})(Q_{14})(Q_{15})$, $-B(Q_{16})(Q_{17})$, and $-P(=O)(Q_{18})(Q_{19})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, and a monovalent non-aromatic condensed heteropolycyclic group having 1 to 60 carbon atoms;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, and a monovalent non-aromatic condensed heteropolycyclic group having 1 to 60 carbon atoms, each substituted with at least one selected from a deuterium, $-F$, $-Cl$, $-Br$, $-I$, $-CD_3$, $-CD_2H$, $-CDH_2$, $-CF_3$, $-CF_2H$, $-CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, a monovalent non-aromatic condensed heteropolycyclic group having 1 to 60 carbon atoms, $-N(Q_{21})(Q_{22})$, $-Si(Q_{23})(Q_{24})(Q_{25})$, $-B(Q_{26})(Q_{27})$, and $-P(=O)(Q_{28})(Q_{29})$; and $-N(Q_{31})(Q_{32})$, $-Si(Q_{33})(Q_{34})(Q_{35})$, $-B(Q_{36})(Q_{37})$, and $-P(=O)(Q_{38})(Q_{39})$;

wherein $Q_{11}$ to $Q_{19}$, $Q_{21}$ to $Q_{29}$, and $Q_{31}$ to $Q_{39}$ are each independently selected from a hydrogen, a deuterium, $-F$, $-Cl$, $-Br$, $-I$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms and a monovalent non-aromatic condensed heteropolycyclic group having 1 to 60 carbon atoms.

12. The organometallic compound of claim 1, wherein $L_1$ in Formula 1 is selected from ligands represented by Formulas 2-1(1) to 2-1(18):

Formula 2-1(1)
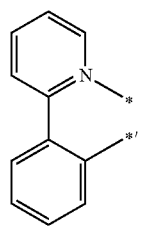
Formula 2-1(2)
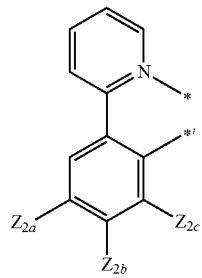
Formula 2-1(3)
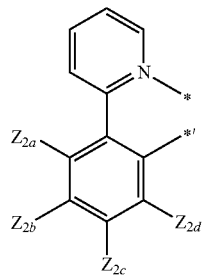
Formula 2-1(4)
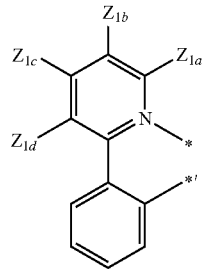
Formula 2-1(5)
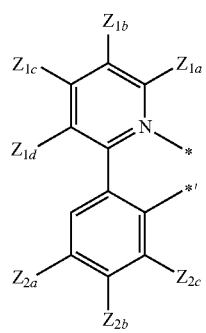
Formula 2-1(6)
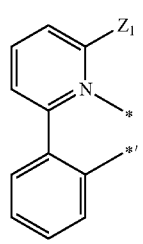
Formula 2-1(7)
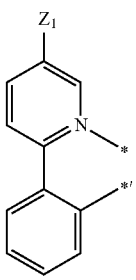
Formula 2-1(8)
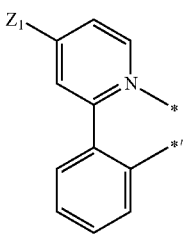
Formula 2-1(9)
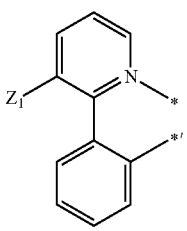
Formula 2-1(10)
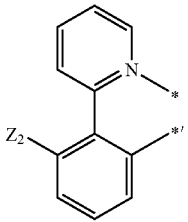
Formula 2-1(11)
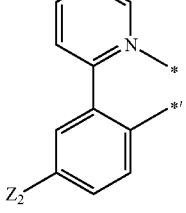
Formula 2-1(12)
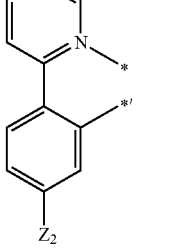

Formula 2-1(13)

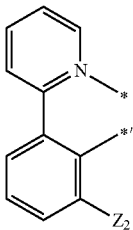

Formula 2-1(14)

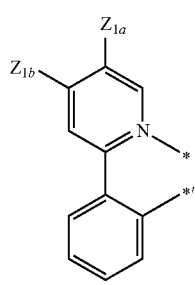

Formula 2-1(15)

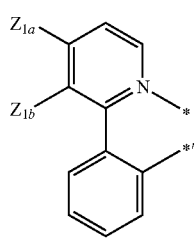

Formula 2-1(16)

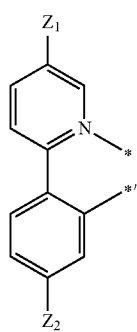

Formula 2-1(17)

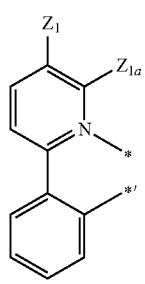

Formula 2-1(18)

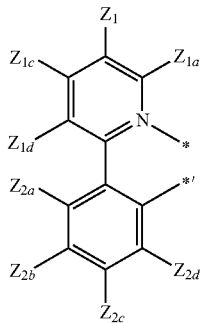

wherein in Formulas 2-1(1) to 2-1(18), $Z_1$, $Z_{1a}$, $Z_{1b}$, $Z_{1c}$, $Z_{1d}$, $Z_2$, $Z_{2a}$, $Z_{2b}$, $Z_{2c}$, and $Z_{2d}$ are each independently selected from a deuterium, —F, —Cl, —Br, —I, —SF$_5$, a hydroxyl group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group having 8 to 60 carbon atoms, a substituted or unsubstituted monovalent non-aromatic condensed heteropolycyclic group having 1 to 60 carbon atoms, —N($Q_1$)($Q_2$), —Si($Q_3$)($Q_4$)($Q_5$), —B($Q_6$)($Q_7$), and —P(=O)($Q_8$)($Q_9$), wherein $Q_1$ to $Q_9$ are each independently selected from a hydrogen, a deuterium, —F, —C$_1$, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms and a monovalent non-aromatic condensed heteropolycyclic group having 1 to 60 carbon atoms, wherein * and *' indicate binding sites to M, and wherein at least one of substituents of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group having 8 to 60 carbon atoms, and the substituted monovalent non-aromatic condensed heteropolycyclic group having 1 to 60 carbon atoms is selected from:

a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_1$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group having 8 to 60 carbon atoms, a monovalent non-aromatic condensed heteropolycyclic group having 1 to 60 carbon atoms, —$N(Q_{11})(Q_{12})$, —$Si(Q_{13})(Q_{14})(Q_{15})$, —$B(Q_{16})(Q_{17})$, and —$P(=O)(Q_{18})(Q_{19})$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, and a monovalent non-aromatic condensed heteropolycyclic group having 1 to 60 carbon atoms;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, and a monovalent non-aromatic condensed heteropolycyclic group having 1 to 60 carbon atoms, each substituted with at least one selected from a deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms, a monovalent non-aromatic condensed heteropolycyclic group having 1 to 60 carbon atoms, —$N(Q_{21})(Q_{22})$, —$Si(Q_{23})(Q_{24})(Q_{25})$, —$B(Q_{26})(Q_{27})$, and —$P(=O)(Q_{28})(Q_{29})$; and —$N(Q_{31})(Q_{32})$, —$Si(Q_{33})(Q_{34})(Q_{35})$, —$B(Q_{36})(Q_{37})$, and —$P(=O)(Q_{38})(Q_{39})$);

wherein $Q_{11}$ to $Q_{19}$, $Q_{21}$ to $Q_{29}$, and $Q_{31}$ to $Q_{39}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group having 8 to 60 carbon atoms and a monovalent non-aromatic condensed heteropolycyclic group having 1 to 60 carbon atoms.

13. The organometallic compound of claim 12, wherein $Z_1$, $Z_2$, $Z_{1a}$, $Z_{1b}$, $Z_{1c}$, $Z_{1d}$, $Z_{2a}$, $Z_{2b}$, $Z_{2c}$, and $Z_{2d}$ in Formulas 2-1(1) to 2-1(8) are each independently selected from:

a deuterium, —F, a cyano group, a nitro group, —$SF_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, and a pentoxy group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, and a pentoxy group, each substituted with at least one selected from a deuterium, —F, —$CD_3$, —$CD_2H$, —$CDH_2$, —$CF_3$, —$CF_2H$, —$CFH_2$, a cyano group, a nitro group, and a $C_1$-$C_{10}$ alkyl group; and a group represented by one of Formulas 10-1 to 10-16:

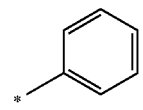

Formula 10-1

-continued
Formula 10-2
Formula 10-3
Formula 10-4
Formula 10-5
Formula 10-6
Formula 10-7
Formula 10-8
Formula 10-9
Formula 10-10
Formula 10-11
Formula 10-12
Formula 10-13
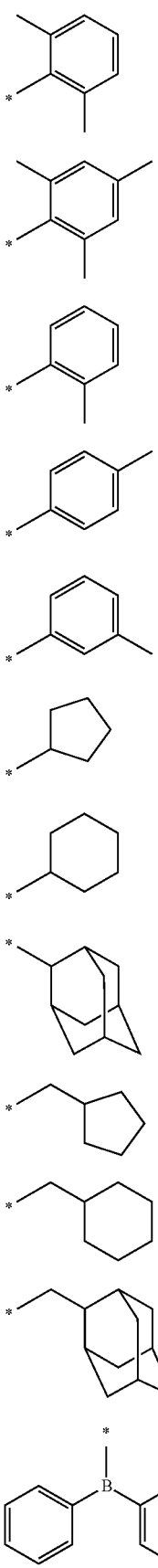
-continued
Formula 10-14
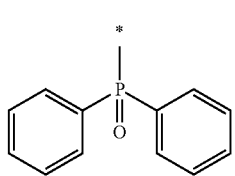
Formula 10-15
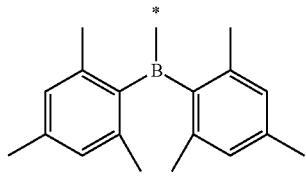
Formula 10-16
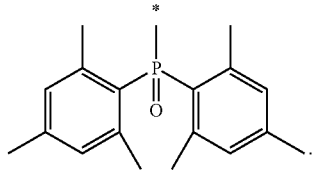
14. The organometallic compound of claim 1, wherein $L_2$ is selected from ligands represented by Formulas 2B-1 to 2B-7, 2B-11 and 2B-12:
Formula 2B-1
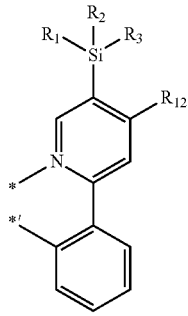
Formula 2B-2
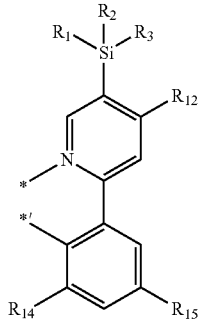

-continued

Formula 2B-3

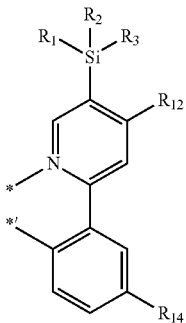

Formula 2B-4

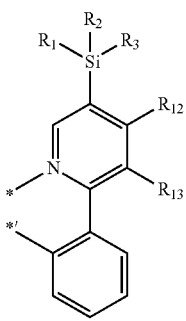

Formula 2B-5

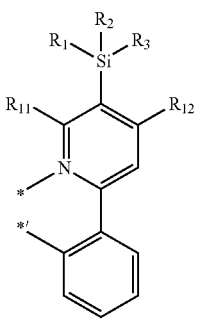

Formula 2B-6

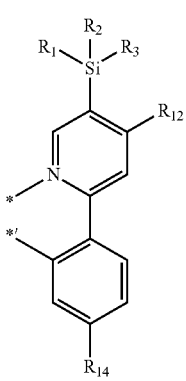

-continued

Formula 2B-7

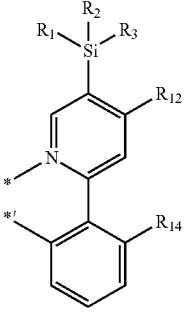

Formula 2B-11

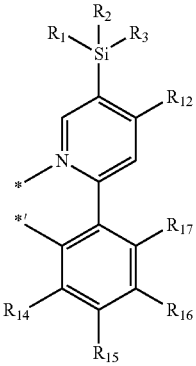

Formula 2B-12

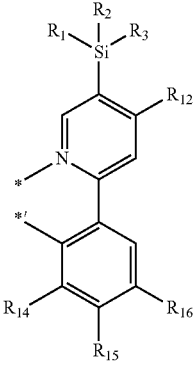

wherein Formulas 2B-1 to 2B-7, 2B-11 and 2B-12,
$R_1$ to $R_3$ are each independently selected from:
a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, and a tert-pentyl group, each of which is unsubstituted; and
a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, and a tert-pentyl group, each substituted with at least one selected from a deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, and a $C_1$-$C_{10}$ alkyl group,
$R_{11}$ and $R_{13}$ to $R_{17}$ are each independently selected from:
a deuterium, —F, a cyano group, a nitro group, —SF$_5$, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each of which is unsubstituted;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and $B(Q_6)(Q_7)$ and —$P(=O)(Q_8)(Q_9)$, wherein $Q_6$ to $Q_9$ are each independently selected from:

a $C_1$-$C_{10}$ alkyl group, a $C_1$-$C_{10}$ alkoxy group, a phenyl group, and a naphthyl group; and a phenyl group and a naphthyl group, each substituted with at least one selected from a $C_1$-$C_{10}$ alkyl group, a phenyl group, and a naphthyl group, and wherein $R_{12}$ is selected from:

an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each of which is unsubstituted;

a methyl group and a methoxy group, each substituted with at least one selected from a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, an ethoxy group, a propoxy group, a butoxy group, a pentoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, and $R_{12}$ in Formulae 2B-1 and 2B-5, at least one of $R_{11}$, $R_{14}$ and $R_{15}$ in Formula 2B-2, at least one of $R_{11}$ and $R_{14}$ in Formulae 2B-3, 2B-6 and 2B-7, at least one of $R_{11}$ and $R_{13}$ in Formula 2B-4, at least one of $R_{11}$, $R_{14}$, $R_{15}$, $R_{16}$ and $R_{17}$ in Formula 2B-11 and at least one of $R_{11}$, $R_{14}$, $R_{15}$ and $R_{16}$ in Formula 2B-12 are each independently selected from:

a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group; and a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group, each substituted with at least one selected from a deuterium, —F, —$CD_3$, —$CD_2H$, —$CDH_2$, —$CF_3$, —$CF_2H$, —$CFH_2$, a cyano group, a nitro group, a $C_1$-$C_{10}$ alkyl group, a $C_1$-$C_{10}$ alkoxy group, a cyclopentyl group, a cyclohexyl group, a cycloheptyl group, a cyclooctyl group, an adamantanyl group, a norbornenyl group, a cyclopentenyl group, a cyclohexenyl group, a cycloheptenyl group, a phenyl group, a naphthyl group, a pyridinyl group, and a pyrimidinyl group.

15. The organometallic compound of claim 1, wherein n2 in Formula 1 is 1.

16. The organometallic compound of claim 1, wherein
in Formula 1, M is Ir and the sum of n1 and n2 is 3; or M is Pt and the sum of n1 and n2 is 2, and the organometallic compound is neutral.

17. The organometallic compound of claim 1, being one of Compounds 76 to 120, 136 to 153, 224 to 233, and 308 to 320:

76
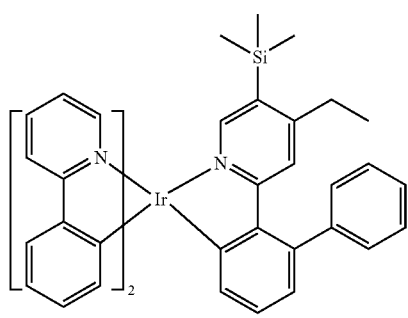

77
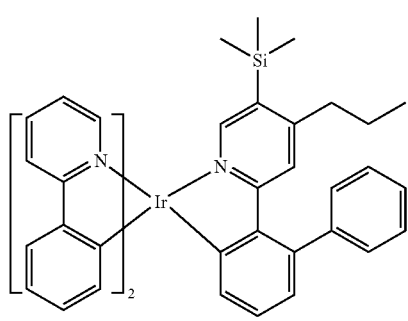

78
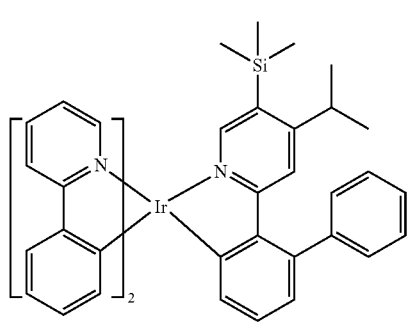

79
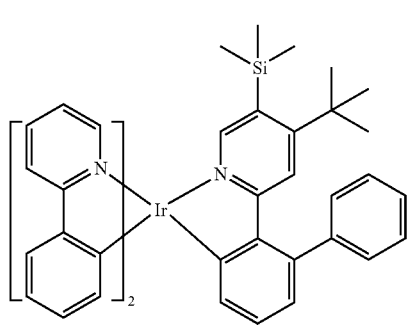

80
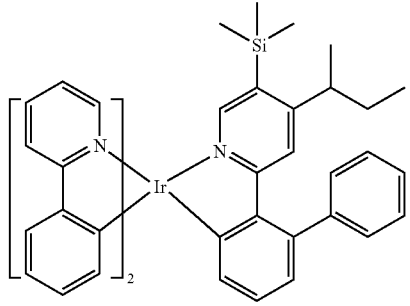

81
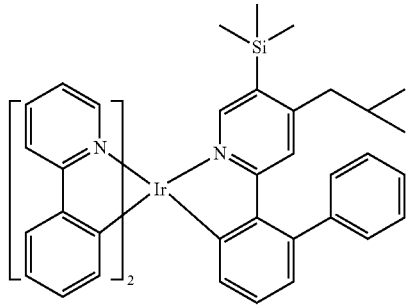

82
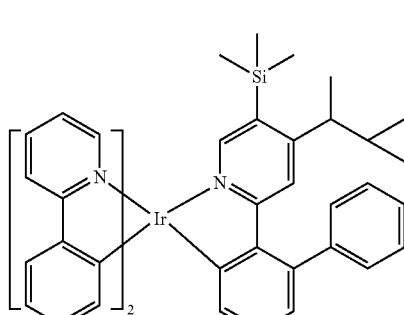

83
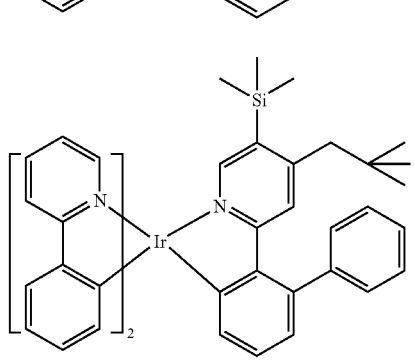

84
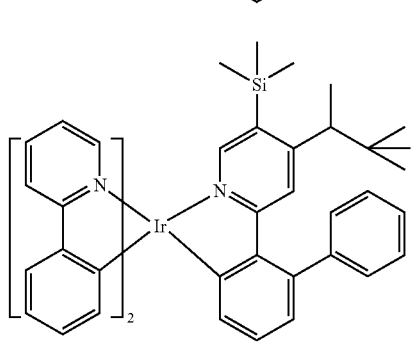

85
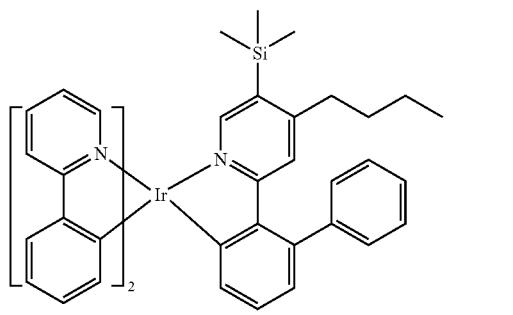
86
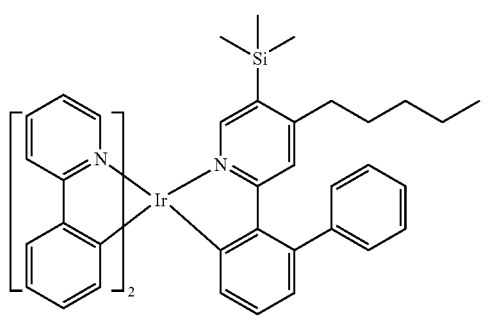
87
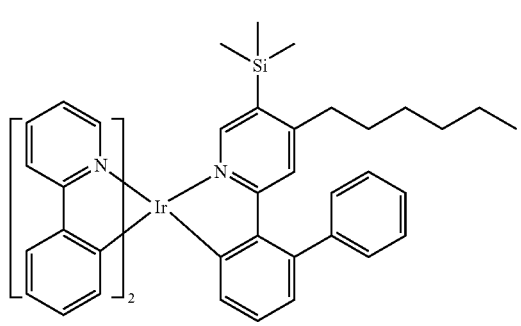
88
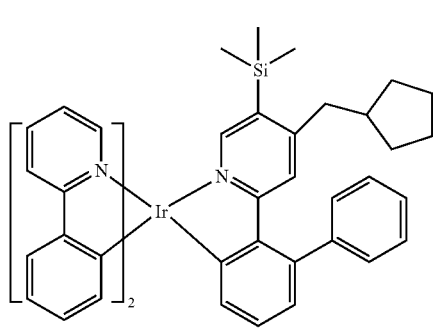
89
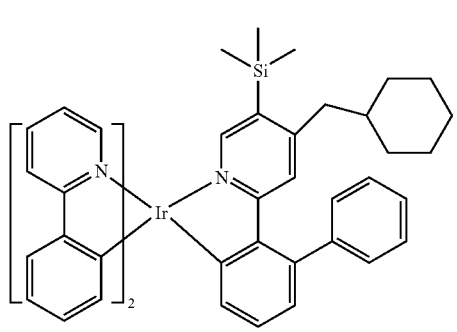
90
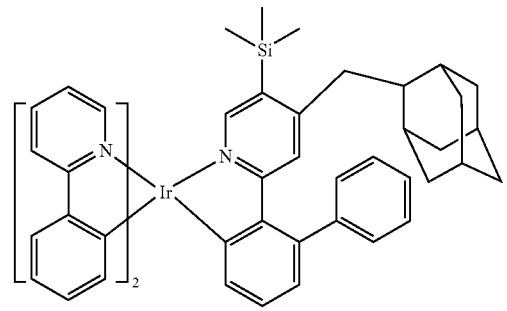
91
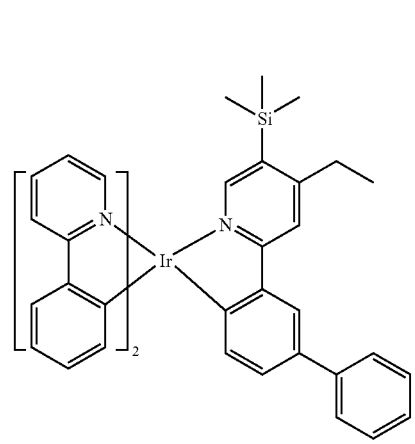
92
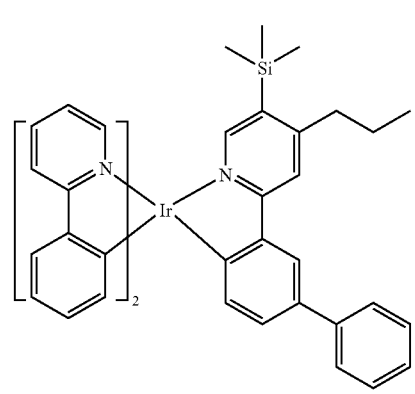
93
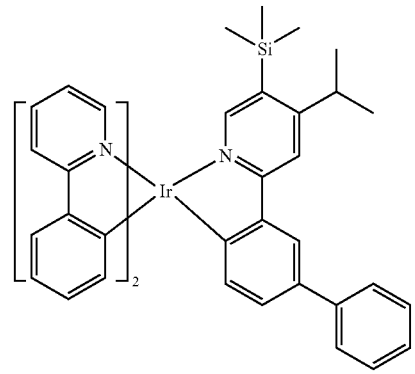

94
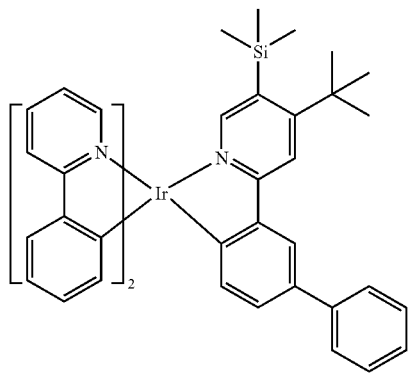
95
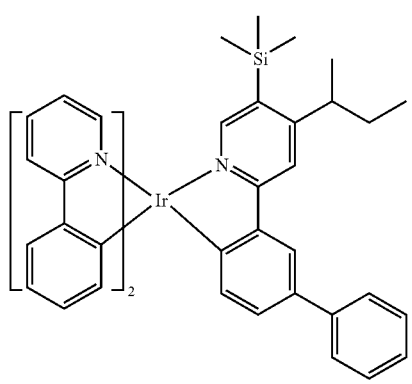
96
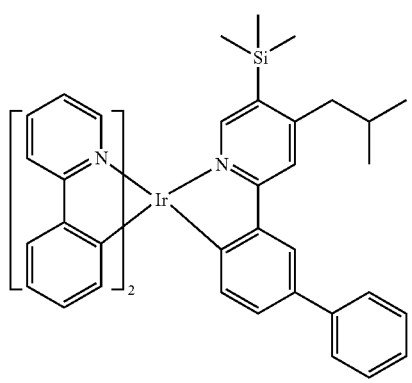
97
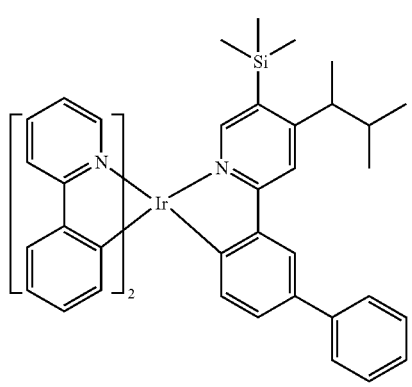
98
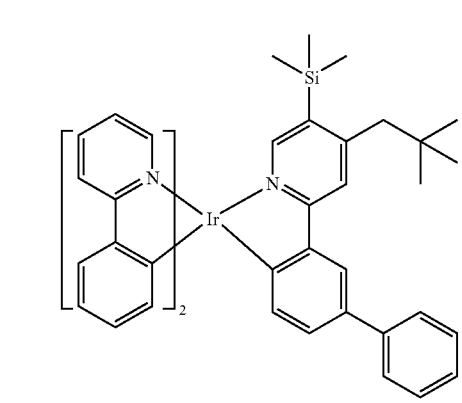
99
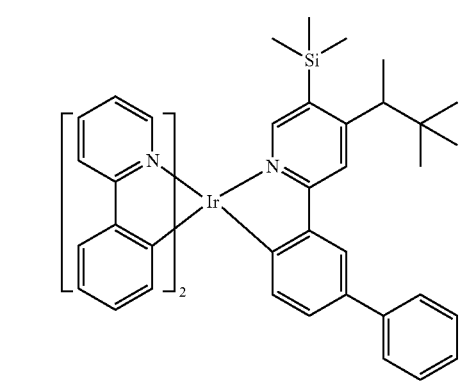
100
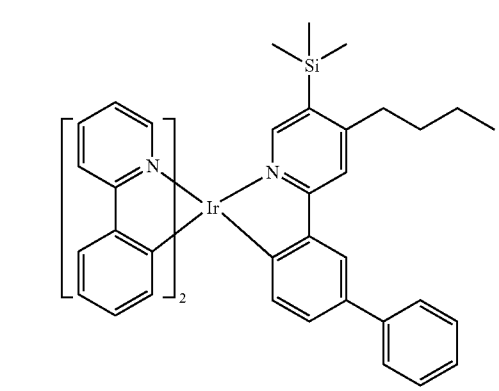
101
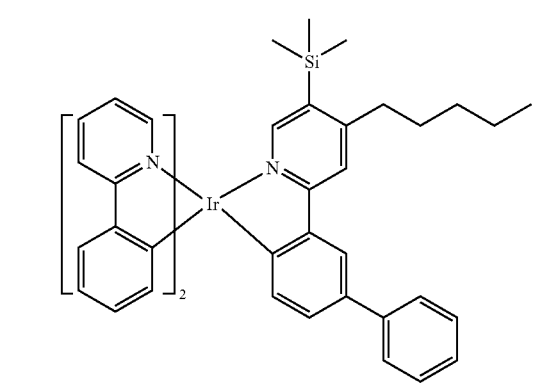

235
-continued
102
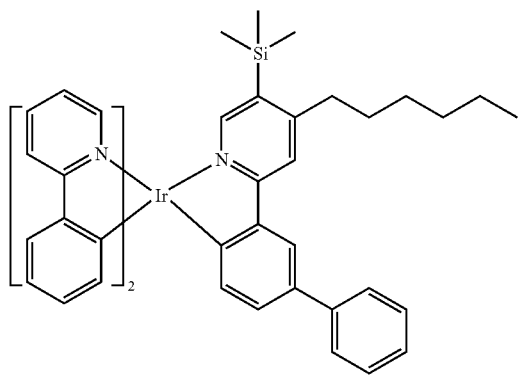
103
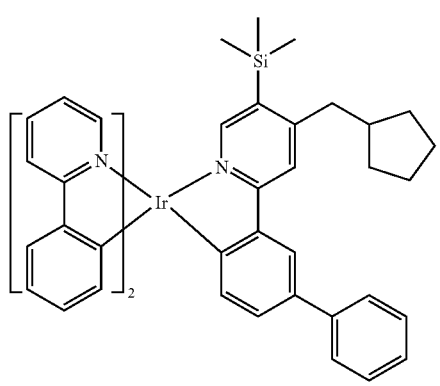
104
105
236
-continued
106
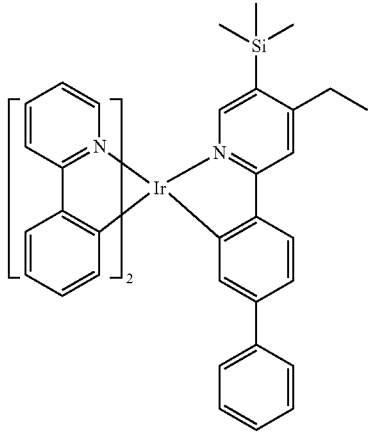
107
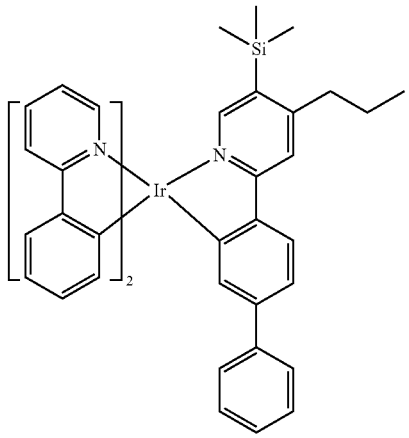
108
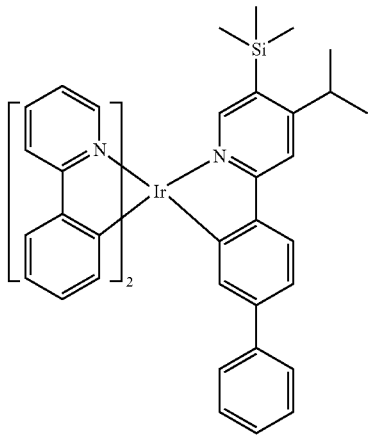

109
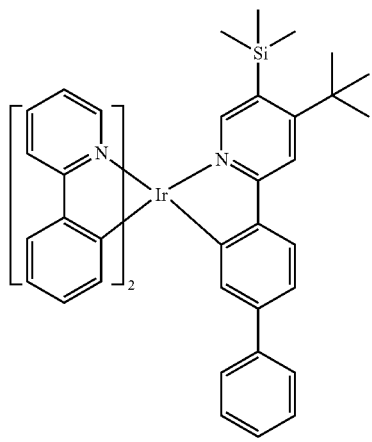
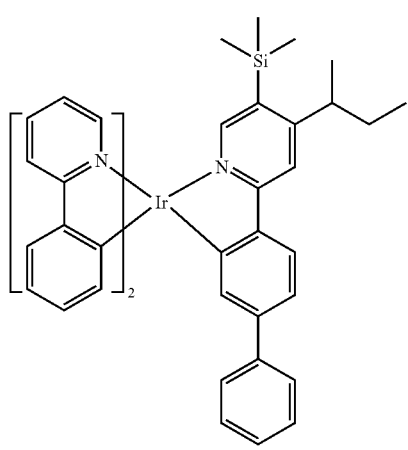
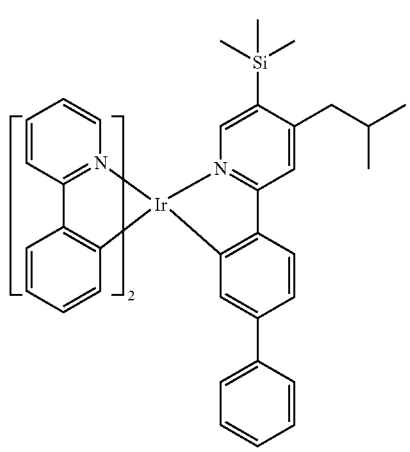
112
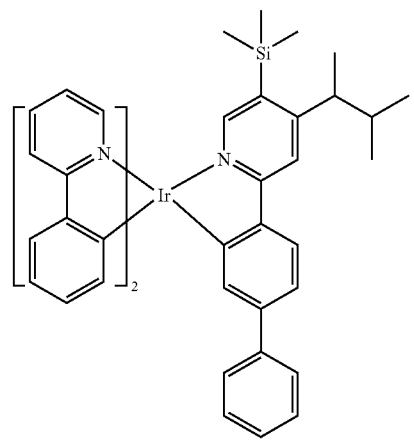
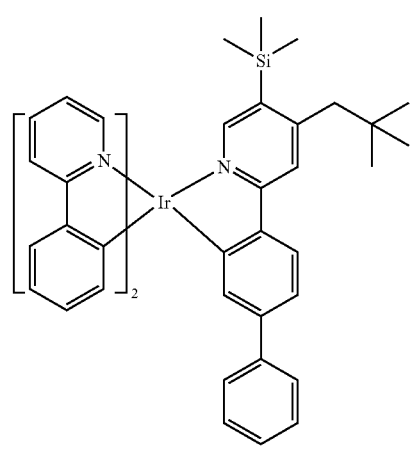
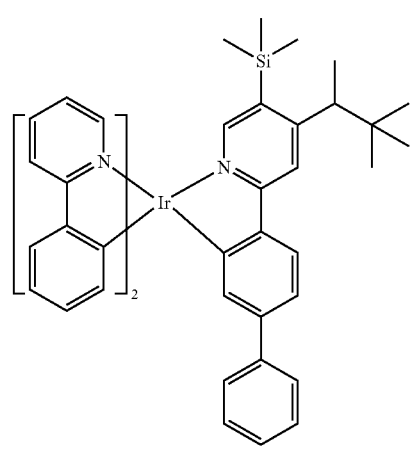

-continued
115
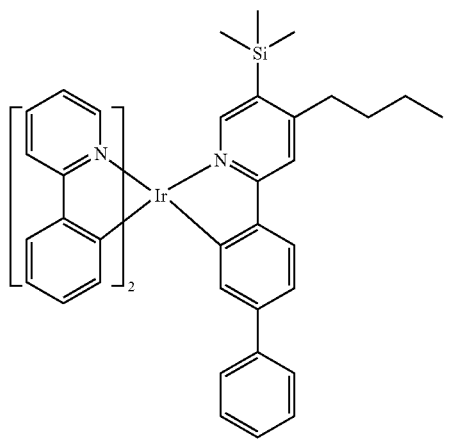
116
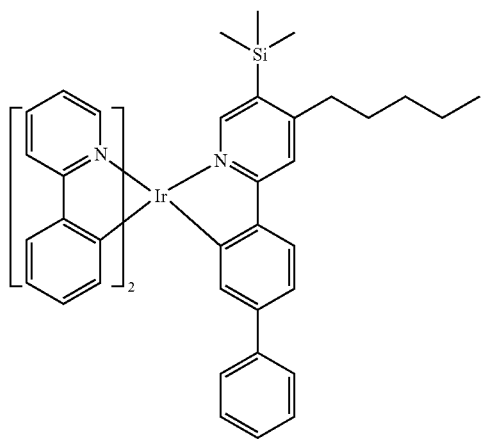
117
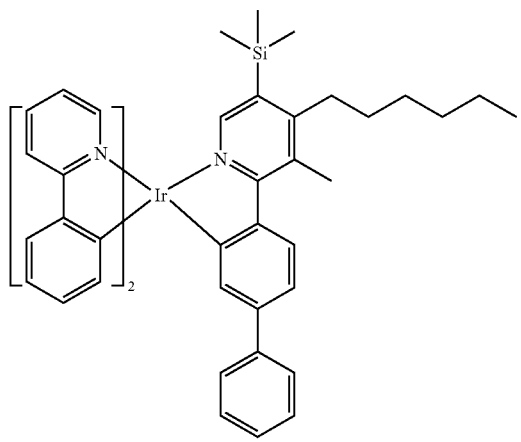
-continued
118
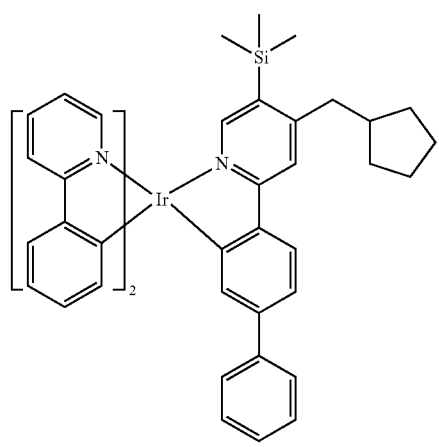
119
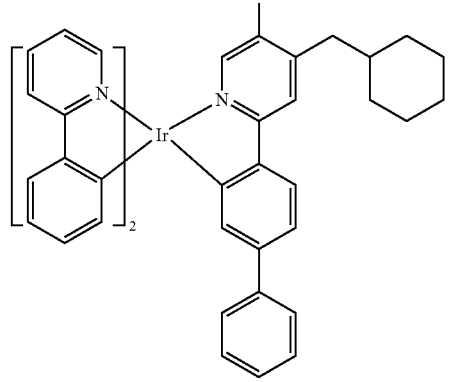
120
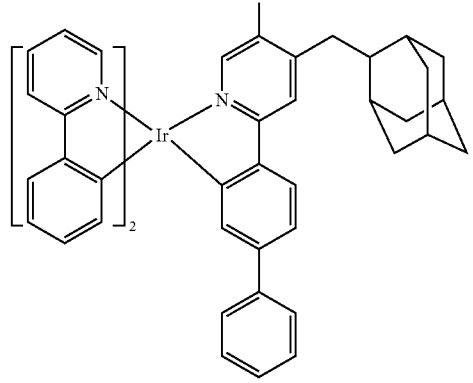
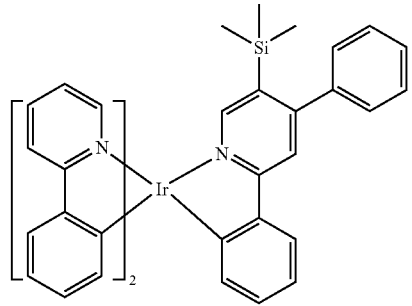

241
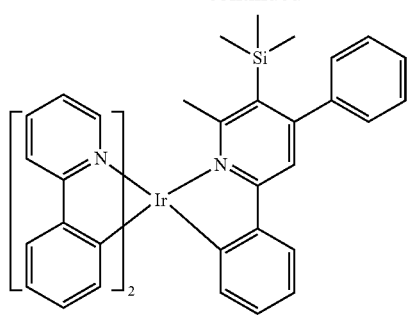
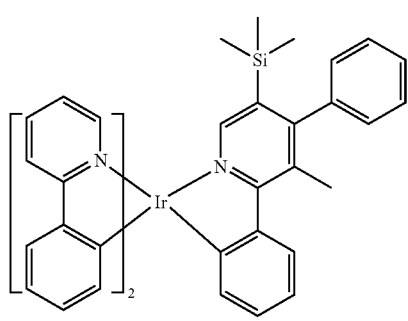
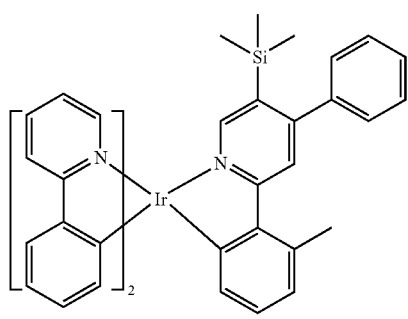
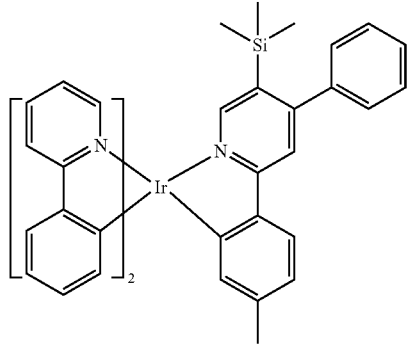
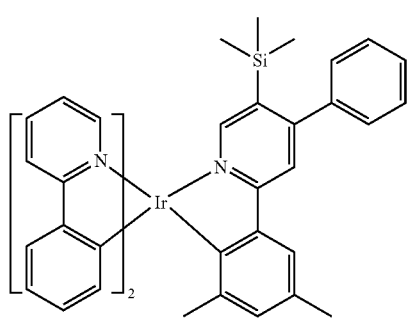
141
242
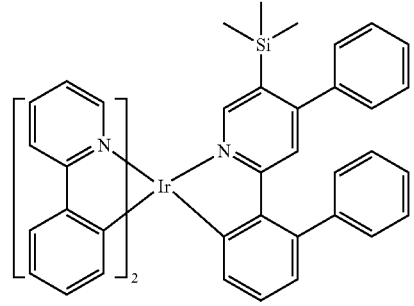
142
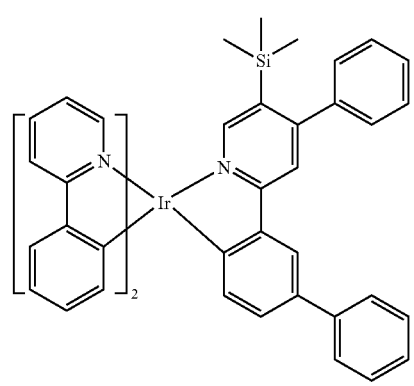
143
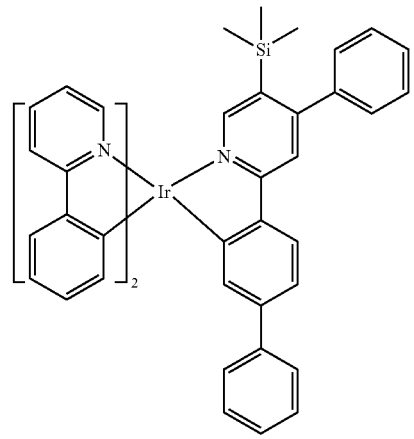
144
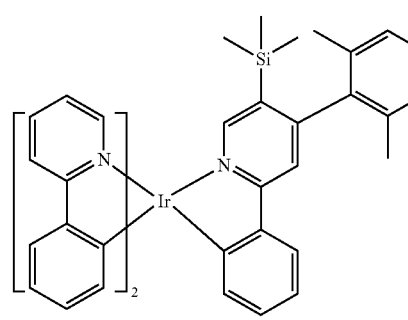
145

146 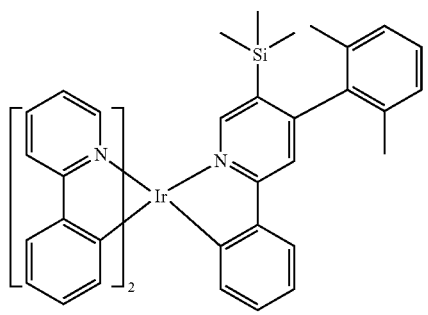
147 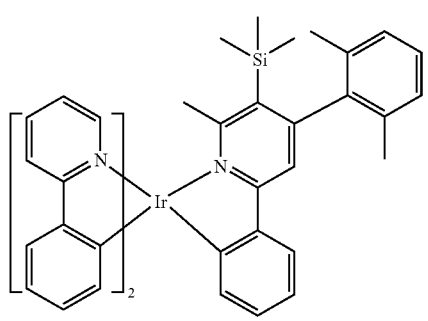
148 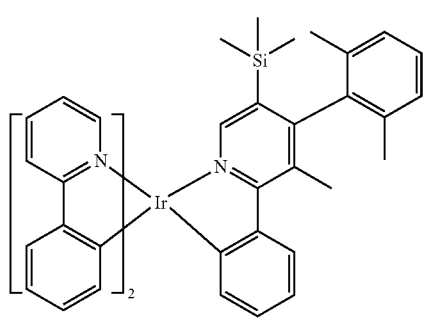
149 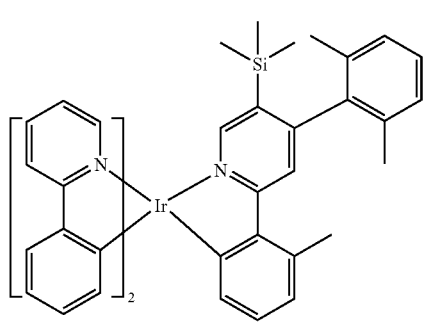
150 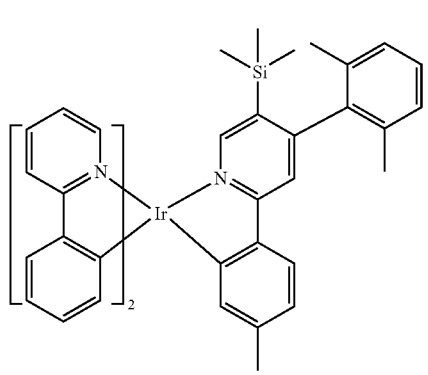
151 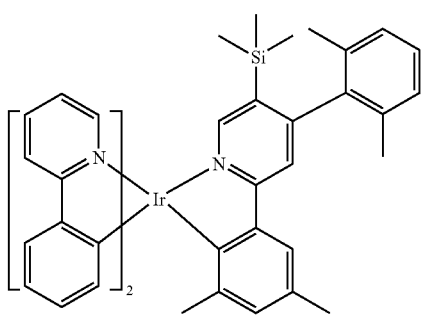
152, 153 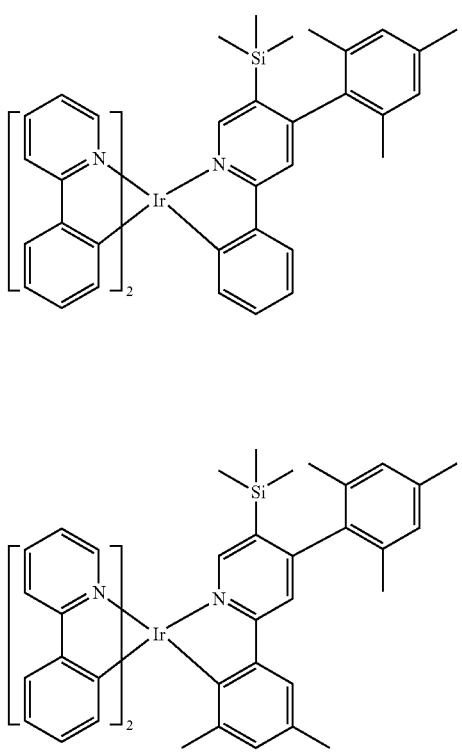
224 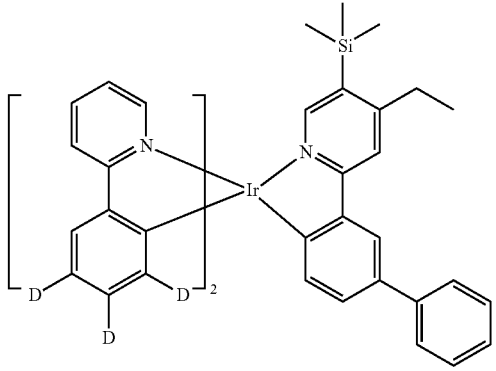

225
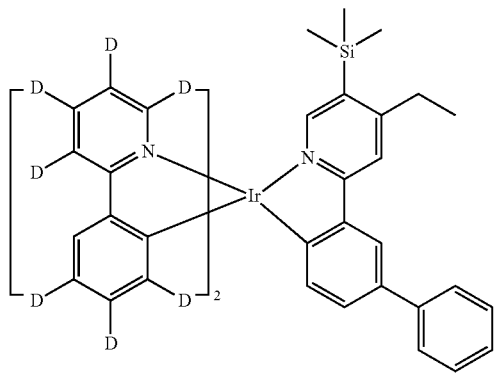
226
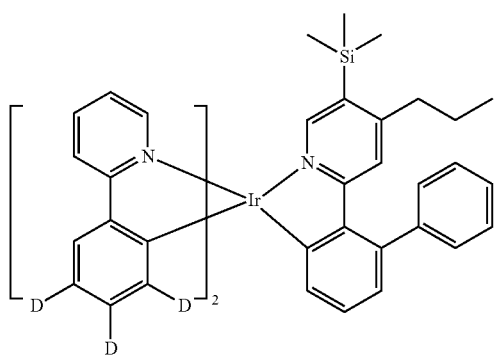
227
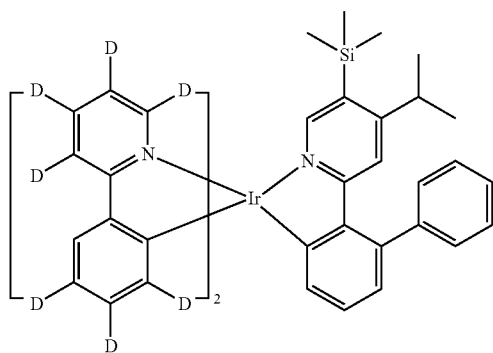
228
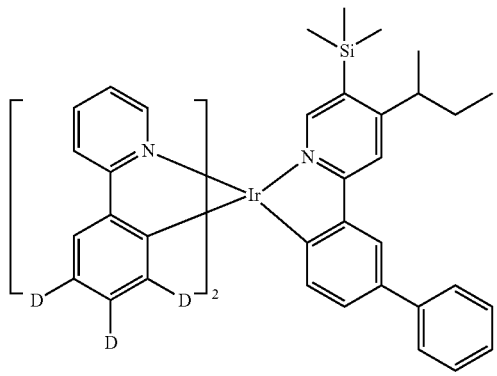
229
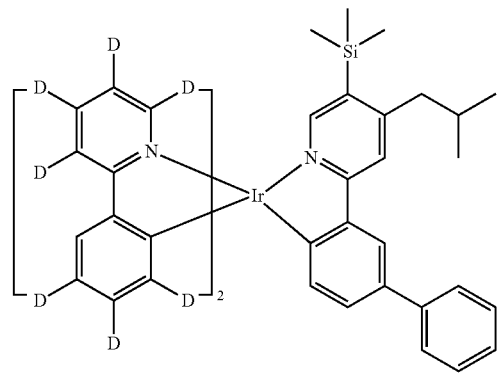
230
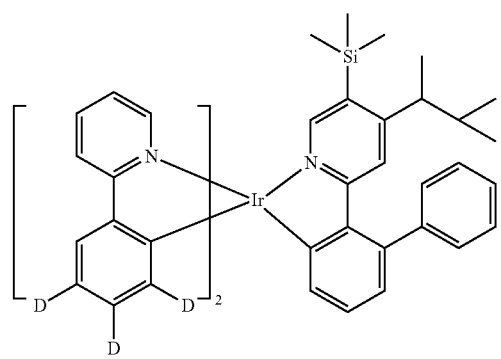
231
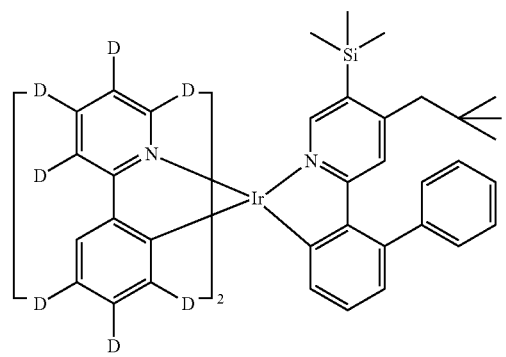
232
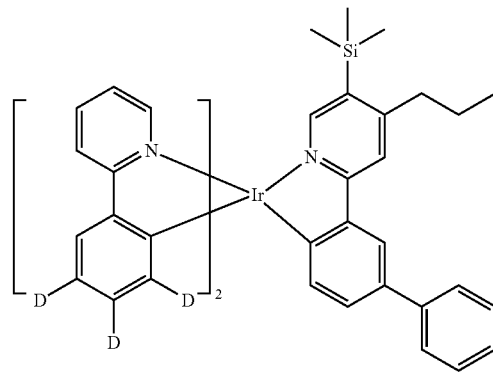

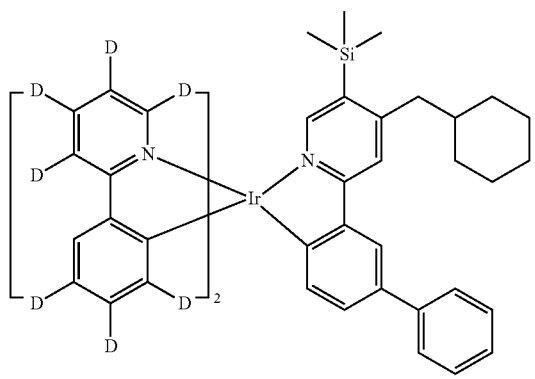
233
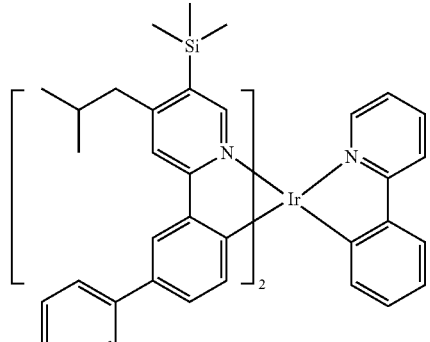
311
308
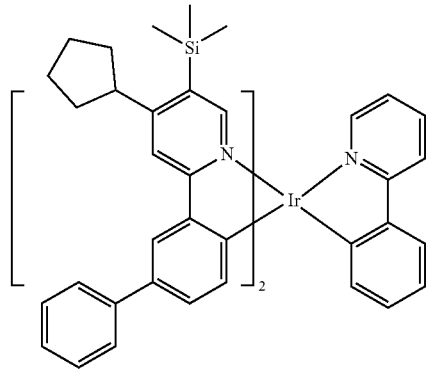
312
309
313
310
314
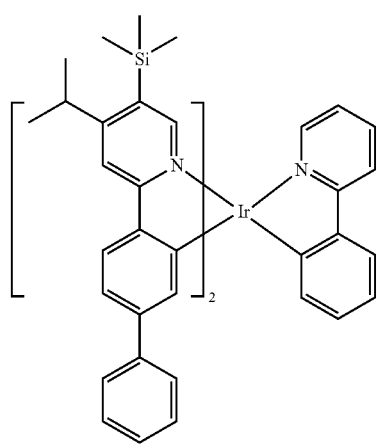

315

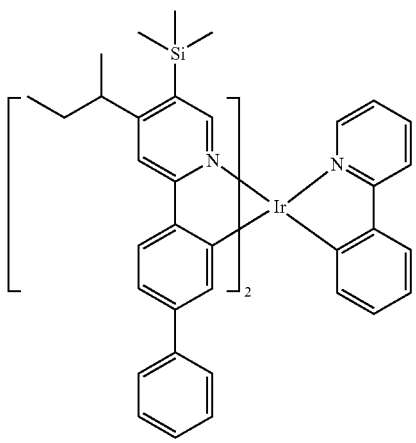

316

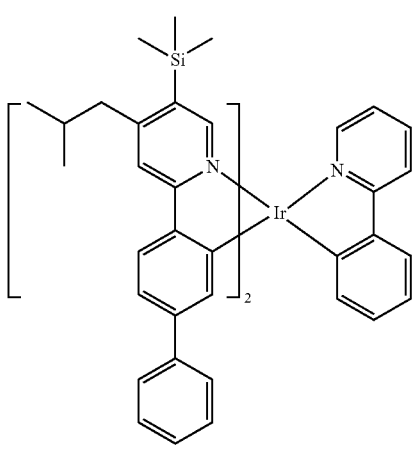

317

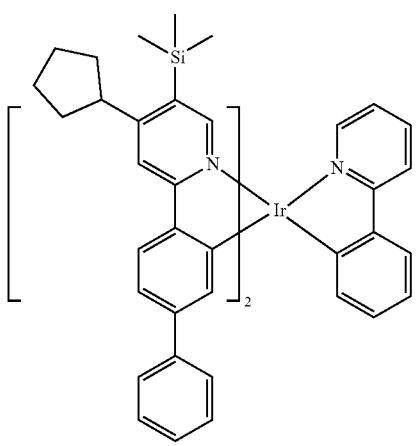

318

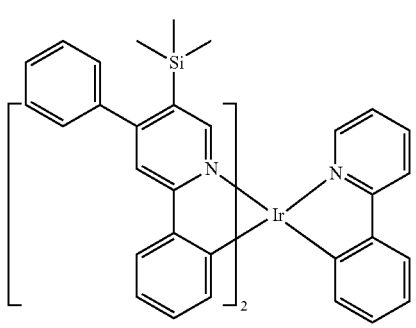

319

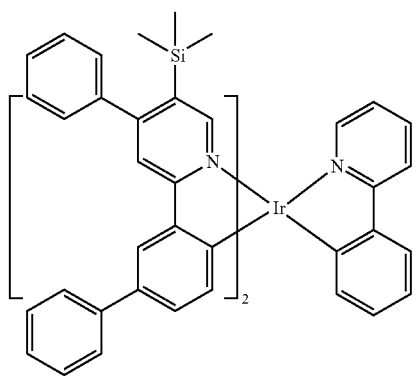

320

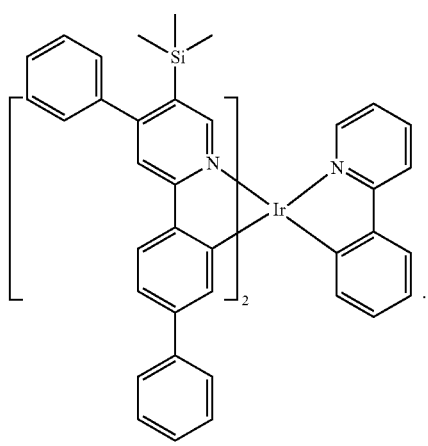

18. An organic light-emitting device comprising: a first electrode; a second electrode; and an organic layer that is disposed between the first electrode and the second electrode and which comprises an emission layer, wherein the organic layer comprises the organometallic compound of claim 1.

19. The organic light-emitting device of claim 18, wherein the first electrode is an anode, and the second electrode is a cathode, the organic layer comprises a hole transport region that is disposed between the first electrode and the emission layer and comprises at least one of a hole injection layer, a hole transport layer, and an electron blocking layer, and an electron transport region that is disposed between the emission layer and the second electrode and comprises at least one selected from a hole blocking layer, an electron transport layer, and an electron injection layer.

20. The organic light-emitting device of claim 18, wherein the organometallic compound is comprised in the emission layer, and wherein the emission layer further comprises a host, and an amount of the organometallic compound is less than an amount of the host.

* * * * *